US006812045B1

(12) United States Patent
Nikoonahad et al.

(10) Patent No.: US 6,812,045 B1
(45) Date of Patent: Nov. 2, 2004

(54) METHODS AND SYSTEMS FOR DETERMINING A CHARACTERISTIC OF A SPECIMEN PRIOR TO, DURING, OR SUBSEQUENT TO ION IMPLANTATION

(75) Inventors: Mehrdad Nikoonahad, Menlo Park, CA (US); Ady Levy, Sunnyvale, CA (US); Kyle A. Brown, Irvine, CA (US); Gary Bultman, Los Altos, CA (US); Dan Wack, Los Altos, CA (US); John Fielden, Los Altos, CA (US)

(73) Assignee: KLA-Tencor, Inc., San Jose, CA (US)

( * ) Notice: Subject to any disclaimer, the term of this patent is extended or adjusted under 35 U.S.C. 154(b) by 256 days.

(21) Appl. No.: 09/956,842

(22) Filed: Sep. 20, 2001

Related U.S. Application Data
(60) Provisional application No. 60/234,323, filed on Sep. 20, 2000.

(51) Int. Cl.[7] .............................................. H01L 21/66
(52) U.S. Cl. .......................................... 438/14; 438/15
(58) Field of Search .......................... 356/72, 601, 508, 356/484, 369; 438/14–16; 355/27

(56) References Cited

U.S. PATENT DOCUMENTS

| | | | |
|---|---|---|---|
| 3,946,484 A | 3/1976 | Aronstein et al. |
| 4,232,063 A | 11/1980 | Rosler et al. |
| 4,247,203 A | 1/1981 | Levy et al. |
| 4,347,001 A | 8/1982 | Levy et al. |
| 4,378,159 A | 3/1983 | Galbraith |
| 4,448,532 A | 5/1984 | Joseph et al. |
| 4,511,800 A | 4/1985 | Harbeke et al. |
| 4,532,650 A | 7/1985 | Wihl et al. |
| 4,555,798 A | 11/1985 | Broadbent, Jr. et al. |
| 4,556,317 A | 12/1985 | Sandland et al. |

(List continued on next page.)

FOREIGN PATENT DOCUMENTS

| | | |
|---|---|---|
| EP | 0 993 019 | 4/2000 |
| EP | 1 022 093 | 7/2000 |
| EP | 1 061 358 | 12/2000 |
| EP | 1 061 571 | 12/2000 |
| EP | 1 065 567 | 1/2001 |
| EP | 1 066 925 | 1/2001 |
| EP | 1 069 609 | 1/2001 |
| EP | 1 071 128 | 1/2001 |

(List continued on next page.)

OTHER PUBLICATIONS

McNeil et al., "Scatterometry Applied to Microelectronics Processing," Microlithography World, Nov./Dec. 1992, pp. 16–22.

Raymond et al., "Metrology of subwavelength photoresist gratings using optical scatterometry," J. Vac. Sci. Technol. B 13(4), Jul./Aug. 1995, pp. 1484–1495.

Wittekoek et al., "In–process Image Detecting Technique for Determination of Overlay, and Image Quality for ASM–L Wafer Stepper," SPIE vol. 1674 Optical/Laser Microlithography V (1992), pp. 594–608.

*Primary Examiner*—John F. Neibling
*Assistant Examiner*—Olivia T. Luk
(74) *Attorney, Agent, or Firm*—Ann Marie Mewherter; Conley Rose, P.C.

(57) ABSTRACT

Methods and systems for monitoring semiconductor fabrication processes are provided. A system may include a stage configured to support a specimen and coupled to a measurement device. The measurement device may include an illumination system and a detection system. The illumination system and the detection system may be configured such that the system may be configured to determine multiple properties of the specimen. For example, the system may be configured to determine multiple properties of a specimen including, but not limited to, a characteristic of a specimen prior to, during, or subsequent to ion implantation. In this manner, a measurement device may perform multiple optical and/or non-optical metrology and/or inspection techniques.

52 Claims, 23 Drawing Sheets

U.S. PATENT DOCUMENTS

| | | |
|---|---|---|
| 4,559,450 A | 12/1985 | Robinson et al. |
| 4,571,685 A | 2/1986 | Kamoshida |
| 4,578,589 A | 3/1986 | Aitken |
| 4,579,455 A | 4/1986 | Levy et al. |
| 4,579,463 A | 4/1986 | Rosencwaig et al. |
| 4,587,432 A | 5/1986 | Aitken |
| 4,599,558 A | 7/1986 | Castellano, Jr. et al. |
| 4,601,576 A | 7/1986 | Galbraith |
| 4,618,938 A | 10/1986 | Sandland et al. |
| 4,619,529 A | 10/1986 | Iuchi et al. |
| 4,631,416 A | 12/1986 | Trutna, Jr. |
| 4,633,504 A | 12/1986 | Wihl |
| 4,641,967 A | 2/1987 | Pecen |
| 4,644,172 A | 2/1987 | Sandland et al. |
| 4,645,929 A | 2/1987 | Criegern et al. |
| 4,710,030 A | 12/1987 | Tauc et al. |
| 4,733,091 A | 3/1988 | Robinson et al. |
| 4,743,767 A | 5/1988 | Plumb et al. |
| 4,750,822 A | 6/1988 | Rosencwaig et al. |
| 4,766,324 A | 8/1988 | Saadat et al. |
| 4,770,536 A | 9/1988 | Golberstein |
| 4,805,123 A | 2/1989 | Specht et al. |
| 4,807,994 A | 2/1989 | Felch et al. |
| 4,812,756 A | 3/1989 | Curtis et al. |
| 4,818,110 A | 4/1989 | Davidson |
| 4,842,683 A | 6/1989 | Cheng et al. |
| 4,845,558 A | 7/1989 | Tsai et al. |
| 4,854,710 A | 8/1989 | Opsal et al. |
| 4,877,326 A | 10/1989 | Chadwick et al. |
| 4,898,471 A | 2/1990 | Vaught et al. |
| 4,899,055 A | 2/1990 | Adams |
| 4,905,170 A | 2/1990 | Forouhi et al. |
| 4,912,326 A | 3/1990 | Naito |
| 4,926,489 A | 5/1990 | Danielson et al. |
| 4,999,014 A | 3/1991 | Gold et al. |
| 4,999,578 A | 3/1991 | Ohashi et al. |
| 5,023,424 A | 6/1991 | Vaught |
| 5,042,951 A | 8/1991 | Gold et al. |
| 5,043,589 A | 8/1991 | Smedt et al. |
| 5,047,648 A | 9/1991 | Fishkin et al. |
| 5,074,669 A | 12/1991 | Opsal |
| 5,076,692 A | 12/1991 | Neukermans et al. |
| 5,112,129 A | 5/1992 | Davidson et al. |
| 5,114,235 A | 5/1992 | Suda et al. |
| 5,181,080 A | 1/1993 | Fanton et al. |
| 5,182,455 A | 1/1993 | Muraki |
| 5,182,610 A | 1/1993 | Shibata |
| 5,189,481 A | 2/1993 | Jann et al. |
| 5,189,494 A | 2/1993 | Muraki |
| 5,215,619 A | 6/1993 | Cheng et al. |
| 5,264,912 A | 11/1993 | Vaught et al. |
| 5,316,984 A | 5/1994 | Leourx |
| 5,327,221 A | 7/1994 | Saitoh et al. |
| 5,340,992 A | 8/1994 | Matsugu et al. |
| 5,344,491 A | 9/1994 | Katou |
| 5,355,212 A | 10/1994 | Wells et al. |
| 5,393,624 A | 2/1995 | Ushijima |
| 5,401,316 A | 3/1995 | Shiraishi et al. |
| 5,412,473 A | 5/1995 | Rosencwaig et al. |
| 5,414,514 A | 5/1995 | Smith et al. |
| 5,438,313 A | 8/1995 | Henderson et al. |
| 5,438,413 A * | 8/1995 | Mazor et al. ............... 356/508 |
| 5,485,091 A | 1/1996 | Verkuil |
| 5,516,608 A | 5/1996 | Hobbs et al. |
| 5,517,312 A | 5/1996 | Finarov |
| 5,520,769 A | 5/1996 | Barrett et al. |
| 5,537,669 A | 7/1996 | Evans et al. |
| 5,563,702 A | 10/1996 | Emery et al. |
| 5,565,979 A | 10/1996 | Gross |
| 5,572,598 A | 11/1996 | Wihl et al. |
| 5,574,278 A | 11/1996 | Poirier |
| 5,581,350 A | 12/1996 | Chen et al. |
| 5,594,247 A | 1/1997 | Verkuil et al. |
| 5,596,406 A | 1/1997 | Rosencwaig et al. |
| 5,596,411 A | 1/1997 | Fanton et al. |
| 5,604,344 A | 2/1997 | Finarov |
| 5,604,585 A | 2/1997 | Johnson et al. |
| 5,608,526 A | 3/1997 | Piwonka-Corle et al. |
| 5,614,060 A | 3/1997 | Hanawa |
| 5,619,548 A | 4/1997 | Koppel |
| 5,633,747 A | 5/1997 | Nikoonahad |
| 5,641,969 A | 6/1997 | Cooke et al. |
| 5,644,223 A | 7/1997 | Verkuil |
| 5,650,731 A | 7/1997 | Fung et al. |
| 5,652,654 A | 7/1997 | Asimopoulos |
| 5,666,196 A | 9/1997 | Ishii et al. |
| 5,682,242 A | 10/1997 | Eylon |
| 5,684,393 A | 11/1997 | Ryat |
| 5,689,614 A | 11/1997 | Gronet et al. |
| 5,695,568 A | 12/1997 | Sinha et al. |
| 5,699,156 A | 12/1997 | Carver |
| 5,703,692 A | 12/1997 | McNeil et al. |
| 5,712,707 A | 1/1998 | Ausschnitt et al. |
| 5,730,642 A | 3/1998 | Sandhu et al. |
| 5,737,072 A | 4/1998 | Emery et al. |
| 5,740,226 A | 4/1998 | Komiya et al. |
| 5,747,813 A | 5/1998 | Norton et al. |
| 5,748,318 A | 5/1998 | Maris et al. |
| 5,754,297 A | 5/1998 | Nulman |
| 5,757,507 A | 5/1998 | Ausschnitt et al. |
| 5,764,365 A | 6/1998 | Finarov |
| 5,767,693 A | 6/1998 | Verkuil |
| 5,770,099 A | 6/1998 | Rice et al. |
| 5,771,094 A | 6/1998 | Carter et al. |
| 5,783,342 A | 7/1998 | Yamashita et al. |
| 5,798,529 A | 8/1998 | Wagner |
| 5,798,829 A | 8/1998 | Vaez-Iravani |
| 5,798,837 A | 8/1998 | Aspnes et al. |
| 5,801,390 A | 9/1998 | Shiraishi |
| 5,805,290 A | 9/1998 | Ausschnitt et al. |
| 5,822,055 A | 10/1998 | Tsai et al. |
| 5,825,482 A | 10/1998 | Nikoonahad et al. |
| 5,831,865 A | 11/1998 | Berezin et al. |
| 5,844,684 A | 12/1998 | Maris et al. |
| 5,849,136 A | 12/1998 | Mintz et al. |
| 5,859,424 A | 1/1999 | Norton et al. |
| 5,859,964 A | 1/1999 | Wang et al. |
| 5,864,394 A | 1/1999 | Jordan, III et al. |
| 5,866,437 A | 2/1999 | Chen et al. |
| 5,867,590 A | 2/1999 | Eylon |
| 5,872,633 A | 2/1999 | Holzapfel et al. |
| 5,877,859 A | 3/1999 | Aspnes et al. |
| 5,882,165 A | 3/1999 | Maydan et al. |
| 5,883,374 A | 3/1999 | Mathews |
| 5,883,710 A | 3/1999 | Nikoonahad et al. |
| 5,886,355 A | 3/1999 | Bright et al. |
| 5,887,085 A | 3/1999 | Otsuka |
| 5,889,593 A | 3/1999 | Bareket |
| 5,896,294 A | 4/1999 | Chow et al. |
| 5,900,939 A | 5/1999 | Aspnes et al. |
| 5,910,011 A | 6/1999 | Cruse |
| 5,910,842 A | 6/1999 | Piwonka-Corle et al. |
| 5,914,784 A | 6/1999 | Ausschnitt et al. |
| 5,917,588 A | 6/1999 | Addiego |
| 5,917,594 A | 6/1999 | Norton |
| 5,920,076 A | 7/1999 | Burgin et al. |
| 5,923,423 A * | 7/1999 | Sawatari et al. ............ 356/484 |
| 5,926,690 A | 7/1999 | Toprac et al. |
| 5,930,138 A | 7/1999 | Lin et al. |
| 5,935,338 A | 8/1999 | Lei et al. |
| 5,935,397 A | 8/1999 | Masterson |

| | | |
|---|---|---|
| 5,943,122 A | 8/1999 | Holmes |
| 5,955,661 A | 9/1999 | Samsavar et al. |
| 5,959,735 A | 9/1999 | Maris et al. |
| 5,959,812 A | 9/1999 | Rothermel |
| 5,963,314 A | 10/1999 | Worster et al. |
| 5,963,783 A | 10/1999 | Lowell et al. |
| 5,964,643 A | 10/1999 | Birang et al. |
| 5,966,312 A | 10/1999 | Chen |
| 5,968,691 A | 10/1999 | Yoshioka et al. |
| 5,973,323 A | 10/1999 | Adler et al. |
| 5,973,787 A | 10/1999 | Aspnes et al. |
| 5,976,310 A | 11/1999 | Levy |
| 5,978,074 A | 11/1999 | Opsal et al. |
| 5,982,482 A | 11/1999 | Nelson et al. |
| 5,985,497 A | 11/1999 | Phan et al. |
| 6,008,906 A | 12/1999 | Maris |
| 6,012,966 A | 1/2000 | Ban et al. |
| 6,020,214 A | 2/2000 | Watanabe et al. |
| 6,020,957 A | 2/2000 | Rosengaus et al. |
| 6,023,338 A | 2/2000 | Bareket |
| 6,025,918 A | 2/2000 | Maris |
| 6,038,029 A | 3/2000 | Finarov |
| 6,039,848 A | 3/2000 | Moslehi et al. |
| 6,040,198 A | 3/2000 | Komiya et al. |
| 6,045,433 A | 4/2000 | Dvir et al. |
| 6,046,094 A | 4/2000 | Jost et al. |
| 6,052,185 A | 4/2000 | Banet et al. |
| 6,052,188 A | 4/2000 | Fluckiger et al. |
| 6,052,478 A | 4/2000 | Wihl et al. |
| 6,060,715 A | 5/2000 | England et al. |
| 6,064,517 A | 5/2000 | Chuang et al. |
| 6,072,147 A | 6/2000 | Koshiishi et al. |
| 6,072,178 A | 6/2000 | Mizuno |
| 6,072,320 A | 6/2000 | Verkuil |
| 6,074,518 A | 6/2000 | Imafuku et al. |
| 6,077,756 A | 6/2000 | Lin et al. |
| 6,078,045 A | 6/2000 | Maul et al. |
| 6,078,386 A | 6/2000 | Tsai et al. |
| 6,079,256 A | 6/2000 | Bareket |
| 6,080,287 A | 6/2000 | Drewery et al. |
| 6,081,325 A | 6/2000 | Leslie et al. |
| 6,083,363 A | 7/2000 | Ashtiani et al. |
| 6,084,679 A | 7/2000 | Steffan et al. |
| 6,086,737 A | 7/2000 | Patonay et al. |
| 6,089,181 A | 7/2000 | Suemasa et al. |
| 6,093,625 A | 7/2000 | Wagner et al. |
| 6,097,205 A | 8/2000 | Liberman et al. |
| 6,097,555 A | 8/2000 | Lehmann et al. |
| 6,099,705 A | 8/2000 | Chen et al. |
| 6,101,971 A | 8/2000 | Denholm et al. |
| 6,103,014 A | 8/2000 | Lei et al. |
| 6,107,629 A | 8/2000 | Benninghoven et al. |
| 6,108,087 A | 8/2000 | Nikoonahad et al. |
| 6,110,287 A | 8/2000 | Arai et al. |
| 6,112,697 A | 9/2000 | Sharan et al. |
| 6,114,216 A | 9/2000 | Yieh et al. |
| 6,122,046 A | 9/2000 | Almogy |
| 6,124,924 A | 9/2000 | Feldman et al. |
| 6,128,089 A | 10/2000 | Ausschnitt et al. |
| 6,141,103 A | 10/2000 | Pinaton et al. |
| 6,153,886 A | 11/2000 | Hagiwara et al. |
| 6,157,032 A | 12/2000 | Into |
| 6,159,073 A | 12/2000 | Wiswesser et al. |
| 6,166,801 A * | 12/2000 | Dishon et al. ............... 355/27 |
| 6,172,349 B1 | 1/2001 | Katz et al. |
| 6,174,743 B1 * | 1/2001 | Pangrle et al. ............... 438/14 |
| 6,175,416 B1 | 1/2001 | Maris et al. |
| 6,175,421 B1 | 1/2001 | Fuchs et al. |
| 6,175,645 B1 | 1/2001 | Elyasaf et al. |
| 6,177,330 B1 | 1/2001 | Yasuda |
| 6,178,257 B1 | 1/2001 | Alumot et al. |
| 6,179,709 B1 | 1/2001 | Redeker et al. |
| 6,184,984 B1 | 2/2001 | Lee et al. |
| 6,188,478 B1 | 2/2001 | Fuchs et al. |
| 6,191,605 B1 | 2/2001 | Miller et al. |
| 6,191,846 B1 * | 2/2001 | Opsal et al. ............... 356/72 |
| 6,191,855 B1 | 2/2001 | Maris |
| 6,199,157 B1 | 3/2001 | Dov et al. |
| 6,201,601 B1 | 3/2001 | Vaez-Iravani et al. |
| 6,201,998 B1 | 3/2001 | Lin et al. |
| 6,201,999 B1 | 3/2001 | Jevtic |
| 6,204,917 B1 | 3/2001 | Smedt |
| 6,208,418 B1 | 3/2001 | Maris |
| 6,208,421 B1 | 3/2001 | Maris et al. |
| 6,208,751 B1 | 3/2001 | Almogy |
| 6,211,961 B1 | 4/2001 | Maris |
| 6,212,691 B1 | 4/2001 | Heberer |
| 6,215,551 B1 | 4/2001 | Nikoonahad et al. |
| 6,224,638 B1 | 5/2001 | Jevtic et al. |
| 6,250,143 B1 | 6/2001 | Bindell et al. |
| 6,255,189 B1 | 7/2001 | Muller et al. |
| 6,256,097 B1 | 7/2001 | Wagner |
| 6,258,610 B1 * | 7/2001 | Blatchford et al. ............ 438/14 |
| 6,266,144 B1 * | 7/2001 | Li ............... 356/401 |
| 6,301,011 B1 | 10/2001 | Fung et al. |
| 6,320,666 B1 * | 11/2001 | Opsal et al. ............... 356/601 |
| 6,383,824 B1 * | 5/2002 | Lensing ............... 438/14 |
| 6,388,253 B1 | 5/2002 | Su |
| 6,408,048 B2 * | 6/2002 | Opsal et al. ............... 378/89 |
| 6,421,124 B1 | 7/2002 | Matsumoto et al. |
| 6,451,621 B1 * | 9/2002 | Rangarajan et al. ............ 438/14 |
| 6,452,685 B2 * | 9/2002 | Opsal et al. ............... 356/601 |
| 6,462,817 B1 * | 10/2002 | Strocchia-Rivera ......... 356/369 |
| 6,462,818 B1 | 10/2002 | Bareket |
| 6,476,920 B1 | 11/2002 | Scheiner et al. |
| 6,486,492 B1 | 11/2002 | Su |
| 6,486,954 B1 | 11/2002 | Mieher et al. |
| 2001/0017619 A1 | 8/2001 | Hirose et al. |
| 2001/0052257 A1 | 12/2001 | Magerle |
| 2002/0018217 A1 | 2/2002 | Weber-Grabau et al. |
| 2002/0149782 A1 | 10/2002 | Raymond |
| 2002/0158193 A1 | 10/2002 | Sezginer et al. |
| 2002/0192577 A1 | 12/2002 | Fay et al. |

FOREIGN PATENT DOCUMENTS

| | | |
|---|---|---|
| EP | 1 072 894 | 1/2001 |
| EP | 1 072 967 | 1/2001 |
| EP | 1 081 489 | 3/2001 |
| EP | 1 081 741 | 3/2001 |
| EP | 1 081 742 | 3/2001 |
| EP | 1 083 424 | 3/2001 |
| EP | 1 093 017 | 4/2001 |
| WO | 98/57358 | 12/1998 |
| WO | 99/02970 | 1/1999 |
| WO | 99/03133 | 1/1999 |
| WO | 99/23449 | 5/1999 |
| WO | 99/25004 | 5/1999 |
| WO | 99/31490 | 6/1999 |
| WO | 99/38002 | 7/1999 |
| WO | 99/39183 | 8/1999 |
| WO | 99/41434 | 8/1999 |
| WO | 99/45340 | 9/1999 |
| WO | 99/54926 | 10/1999 |
| WO | 99/59182 | 11/1999 |
| WO | 99/59200 | 11/1999 |
| WO | 99/60614 | 11/1999 |
| WO | 99/65056 | 12/1999 |
| WO | 99/67626 | 12/1999 |
| WO | 00/00873 | 1/2000 |
| WO | 00/00874 | 1/2000 |
| WO | 00/02037 | 1/2000 |
| WO | 00/02229 | 1/2000 |

| | | | | | | |
|---|---|---|---|---|---|---|
| WO | 00/03234 | 1/2000 | | WO | 00/70332 | 11/2000 |
| WO | 00/03421 | 1/2000 | | WO | 00/70646 | 11/2000 |
| WO | 00/07226 | 2/2000 | | WO | 00/77500 | 12/2000 |
| WO | 00/15870 | 3/2000 | | WO | 01/03145 | 1/2001 |
| WO | 00/17907 | 3/2000 | | WO | 01/09566 | 2/2001 |
| WO | 00/18543 | 4/2000 | | WO | 01/13098 | 2/2001 |
| WO | 00/26609 | 5/2000 | | WO | 01/14925 | 3/2001 |
| WO | 00/26613 | 5/2000 | | WO | 02/15238 | 2/2002 |
| WO | 00/26646 | 5/2000 | | WO | 02/25723 | 3/2002 |
| WO | 00/28577 | 5/2000 | | WO | 02/069390 | 9/2002 |
| WO | 00/60657 | 10/2000 | | | | |
| WO | 00/68673 | 11/2000 | | | | |

\* cited by examiner-

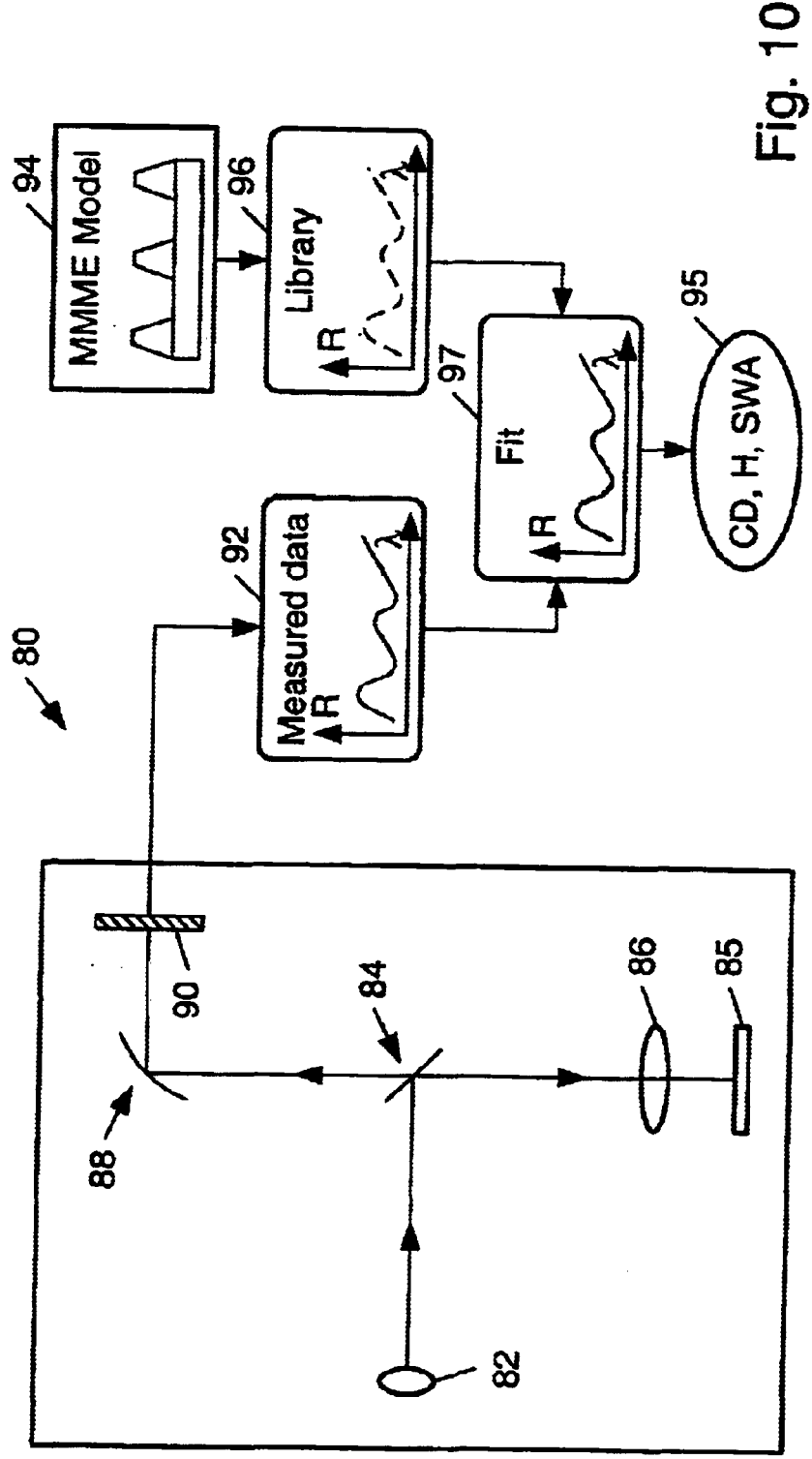

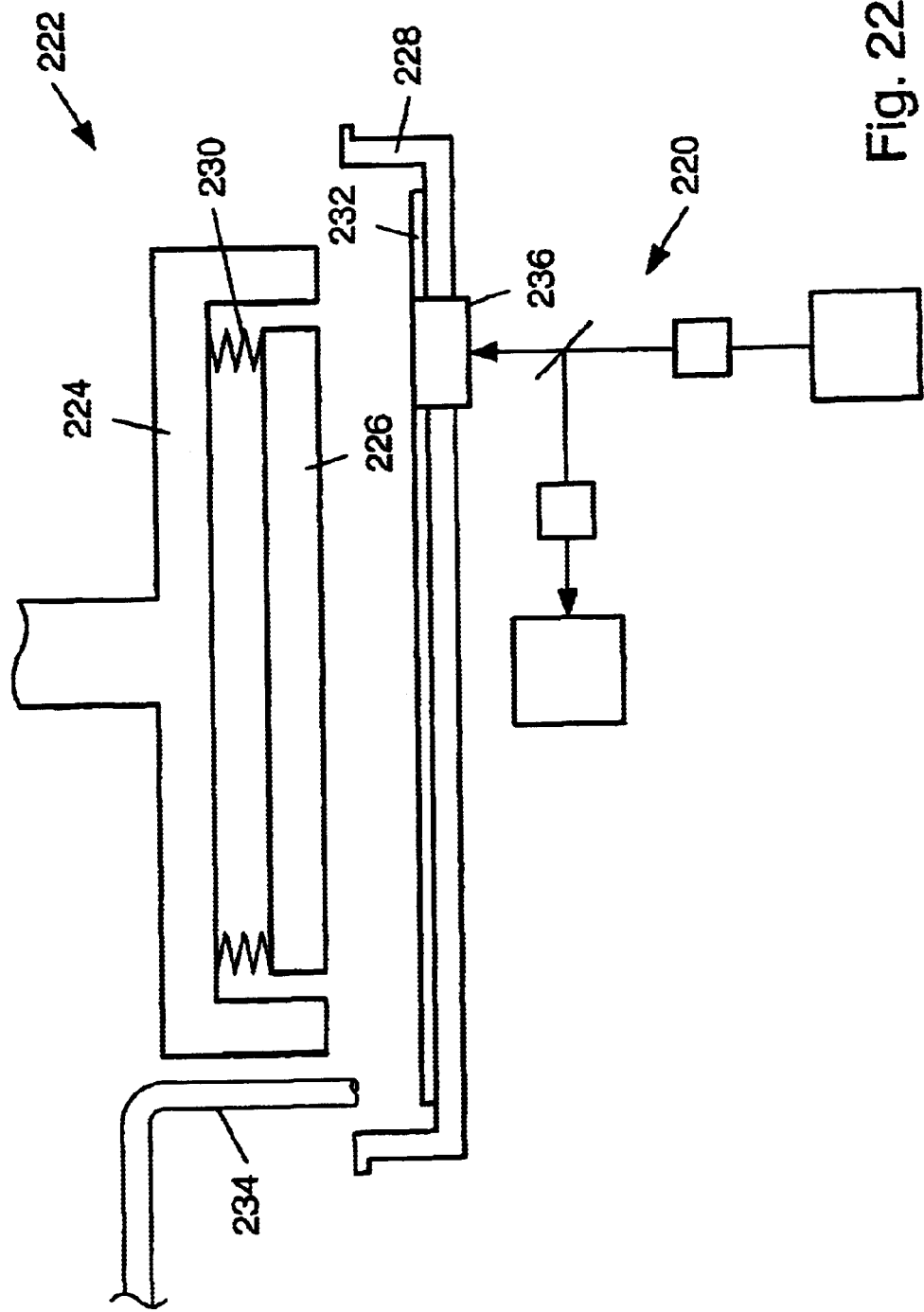

METHODS AND SYSTEMS FOR DETERMINING A CHARACTERISTIC OF A SPECIMEN PRIOR TO, DURING, OR SUBSEQUENT TO ION IMPLANTATION

PRIORITY CLAIM

This application claims priority to U.S. Provisional Application No. 60/234,323 entitled "Methods and Systems for Semiconductor Fabrication Processes," filed Sep. 20, 2000.

BACKGROUND OF THE INVENTION

1. Field of the Invention

This invention generally relates to methods and systems for semiconductor fabrication processes. Certain embodiments relate to a method and a system for evaluating and/or controlling a semiconductor fabrication process by determining at least two properties of a specimen.

2. Description of the Related Art

Fabrication of semiconductor devices such as logic and memory devices typically includes a number of processes that may be used to form various features and multiple levels or layers of semiconductor devices on a surface of a semiconductor wafer or another appropriate substrate. For example, lithography is a process that typically involves transferring a pattern to a resist arranged on a surface of a semiconductor wafer. Additional examples of semiconductor fabrication processes may include chemical-mechanical polishing, etch, deposition, ion implantation, plating, and cleaning. Semiconductor devices are significantly smaller than a typical semiconductor wafer or substrate, and an array of semiconductor devices may be formed on a semiconductor wafer. After processing is complete, the semiconductor wafer may be separated into individual semiconductor devices.

Semiconductor fabrication processes, however, are among the most sophisticated and complex processes used in manufacturing. In order to perform efficiently, semiconductor fabrication processes may require frequent monitoring and careful evaluation. For example, semiconductor fabrication processes may introduce a number of defects (e.g., non-uniformities) into a semiconductor device. As an example, defects may include contamination introduced to a wafer during a semiconductor fabrication process by particles in process chemicals and/or in a clean room environment. Such defects may adversely affect the performance of the process to an extent that overall yield of the fabrication process may be reduced below acceptable levels. Therefore, extensive monitoring and evaluation of semiconductor fabrication processes may typically be performed to ensure that the process is within design tolerance and to increase the overall yield of the process. Ideally, extensive monitoring and evaluation of the process may take place both during process development and during process control of semiconductor fabrication processes.

As features sizes of semiconductor devices continue to shrink, a minimum feature size that may be fabricated may often be limited by the performance characteristics of a semiconductor fabrication process. Examples of performance characteristics of a semiconductor fabrication process include, but are not limited to, resolution capability, across chip variations, and across wafer variations. In optical lithography, for example, performance characteristics such as resolution capability of a lithography process may be limited by the quality of the resist application, the performance of the resist material, the performance of the exposure tool, and the wavelength of light used to expose the resist. The ability to resolve a minimum feature size, however, may also be strongly dependent on other critical parameters of the lithography process such as a temperature of a post exposure bake process and an exposure dose of an exposure process. As such, controlling the parameters of processes that may be critical to the resolution capability of a semiconductor fabrication process such as a lithography process is becoming increasingly important to the successful fabrication of semiconductor devices.

As the dimensions of semiconductor devices continue to shrink with advances in semiconductor materials and processes, the ability to examine microscopic features and to detect microscopic defects has also become increasingly important to the successful fabrication of semiconductor devices. Significant research has been focused on increasing the resolution limit of metrology and/or inspection tools used to examine microscopic features and defects. There are several disadvantages, however, in using the currently available methods and systems for metrology and/or inspection of specimens fabricated by semiconductor fabrication processes. For example, multiple stand-alone metrology/inspection systems may be used for metrology and/or inspection of specimens fabricated by such processes. As used herein, "stand-alone metrology/inspection system" may generally refer a system that is not coupled to a process tool and is operated independently of any other process tools and/or metrology/inspection systems. Multiple metrology/inspection systems, however, may occupy a relatively large amount of clean room space due to the footprints of each of the metrology and/or inspection systems.

In addition, testing time and process delays associated with measuring and/or inspecting a specimen with multiple metrology/inspection systems may increase the overall cost of manufacturing and the manufacturing time for fabricating a semiconductor device. For example, process tools may often be idle while metrology and/or inspection of a specimen is performed such that the process may be evaluated before additional specimens are processed thereby increasing manufacturing delays. Furthermore, if processing problems can not be detected before additional wafers have been processed, wafers processed during this time may need to be scrapped, which increases the overall cost of manufacturing. Additionally, buying multiple metrology/inspection systems increases the cost of fabrication.

In an additional example, for in situ metrology and/or inspection using multiple currently available systems, determining a characteristic of a specimen during a process may be difficult if not impossible. For example, measuring and/or inspecting a specimen with multiple currently available systems during a lithography process may introduce a delay time between or after process steps of the process. If the delay time is relatively long, the performance of the resist may be adversely affected, and the overall yield of semiconductor devices may be reduced. As such, there may also be limitations on process enhancement, control, and yield of semiconductor fabrication processes due to the limitations associated with metrology and/or inspection using multiple currently available systems. Process enhancement, control, and yield may also be limited by an increased potential for contamination associated with metrology and/or inspection using multiple currently available metrology/inspection systems. In addition, there may be practical limits to using multiple metrology/inspection systems in semiconductor manufacturing processes. In an example, for in situ metrology and/or inspection using multiple currently available systems, integrating multiple metrology/inspection systems into a process tool or a cluster tool may be difficult due to the availability of space within the tool.

SUMMARY OF THE INVENTION

An embodiment relates to a system that may be configured to determine at least two properties of a specimen. The system may include a stage configured to support the specimen. The system may also include a measurement device coupled to the stage. The measurement device may include an illumination system configured to direct energy toward a surface of the specimen. The measurement device may also include a detection system coupled to the illumination system. The detection system may be configured to detect energy propagating from the surface of the specimen. The measurement device may also be configured to generate one or more output signals in response to the detected energy. The system may also include a processor coupled to the measurement device. The processor may be configured to determine at least a first property and a second property of the specimen from the one or more output signals.

In an embodiment, the first property may include a critical dimension of the specimen. The second property may include overlay misregistration of the specimen. In addition, the processor may be configured to determine a third and/or a fourth property of the specimen from the one or more output signals. For example, a third property of the specimen may include a presence of defects on the specimen, and the fourth property of the specimen may include a flatness measurement of the specimen. In an embodiment, the measurement device may include a non-imaging scatterometer, a scatterometer, a spectroscopic scatterometer, a reflectometer, a spectroscopic reflectometer, an ellipsometer, a spectroscopic ellipsometer, a bright field imaging device, a dark field imaging device, a bright field and dark field imaging device, a bright field non-imaging device, a dark field non-imaging device, a bright field and dark field non-imaging device, a coherence probe microscope, an interference microscope, an optical profilometer, or any combination thereof. In this manner, the measurement device may be configured to function as a single measurement device or as multiple measurement devices. Because multiple measurement devices may be integrated into a single measurement device of the system, optical elements of a first measurement device, for example, may also be optical elements of a second measurement device.

In an embodiment, the processor may include a local processor coupled to the measurement device and/or a remote controller computer coupled to the local processor. The local processor may be configured to at least partially process the one or more output signals. The remote controller computer may be configured to receive the at least partially processed one or more output signals from the local processor. In addition, the remote controller computer may be configured to determine at least the first property and the second property of the specimen from the at least partially processed one or more output signals. Furthermore, the remote controller computer may be configured to determine the third property and/or the fourth property of the specimen from the at least partially processed one or more output signals. In an additional embodiment, the remote controller computer may be coupled to a process tool such as a semiconductor fabrication process tool. In this manner, the remote controller computer may be further configured to alter a parameter of one or more instruments coupled to the semiconductor fabrication process tool in response to at least the determined first or second property of the specimen using an in situ control technique, a feedback control technique, or a feedforward control technique.

An additional embodiment relates to a method for determining at least two properties of a specimen. The method may include disposing a specimen upon a stage. The stage may be coupled to a measurement device. The measurement device may include an illumination system and a detection system. In addition, the method may include directing energy toward a surface of the specimen. The method may also include detecting energy propagating from the surface of the specimen. The method may further include generating one or more output signals in response to the detected energy. Furthermore, the method may include processing the one or more output signals to determine at least a first property and a second property of the specimen.

In an embodiment, the first property may include a critical dimension of the specimen. The second property may include overlay misregistration of the specimen. In addition, the method may further include processing the one or more output signals to determine a third and/or a fourth property of the specimen. For example, a third and a fourth property of the specimen may include a presence of defects on the specimen and a flatness measurement of the specimen. In an additional embodiment, a semiconductor device may be fabricated by the method. For example, the method may include forming a portion of a semiconductor device upon the specimen.

In an embodiment, processing the one or more output signals to determine at least a first property and a second property of the specimen may include at least partially processing the one or more output signals using a local processor. The local processor may be coupled to the measurement device. Processing the one or more output signals may also include sending the partially processed one or more output signals from the local processor to a remote controller computer. In addition, processing the one or more output signals may include further processing the partially processed one or more output signals using the remote controller computer. In an additional embodiment, the remote controller computer may be coupled to a process tool such as a semiconductor fabrication process tool. In this manner, the method may include altering a parameter of one or more instruments coupled to the process tool using the remote controller computer in response to at least the determined first or second property of the specimen. Altering the parameter of the instruments may include using an in situ control technique, a feedback control technique, or a feedforward control technique.

Additional embodiments relate to a computer-implemented method for controlling a system configured to determine at least two properties of a specimen. The system may include a measurement device. In this manner, controlling the system may include controlling the measurement device. In addition, the measurement device may include an illumination system and a detection system. The measurement device may also be coupled to a stage. Controlling the measurement device may include controlling the illumination system to direct energy toward a surface of the specimen. Additionally, controlling the measurement device may include controlling the detection system to detect energy propagating from the surface of the specimen. The method may further include generating one or more output signals in response to the detected energy. The computer-implemented method may further include processing the one or more output signals to determine at least a first property and a second property of the specimen. For example, the first property may include a critical dimension of the specimen. Furthermore, the second property may include overlay misregistration of the specimen. The computer-implemented method may also include processing the one or more output signals to determine a third and/or fourth properties of the specimen. In an example, the third and fourth properties of the specimen may include a presence of defects on the specimen and a flatness measurement of the specimen.

An embodiment relates to a system configured to determine at least two properties of a specimen. The system may include a stage configured to support the specimen. The system may also include a measurement device coupled to the stage. The measurement device may include an illumination system configured to direct energy toward a surface of the specimen. The measurement device may also include a detection system coupled to the illumination system. The detection system may be configured to detect energy propagating from the surface of the specimen. The measurement device may also be configured to generate one or more output signals in response to the detected energy. The system may also include a processor coupled to the measurement device. The processor may be configured to determine at least a first property and a second property of the specimen from the one or more output signals.

In an embodiment, the first property may include a presence of defects on specimen. The second property may include a thin film characteristic of the specimen. In addition, the processor may be configured to determine other properties of the specimen from the one or more output signals. In an embodiment, the measurement device may include a non-imaging scatterometer, a scatterometer, a spectroscopic scatterometer, a reflectometer, a spectroscopic reflectometer, an ellipsometer, a spectroscopic ellipsometer, a beam profile ellipsometer, a bright field imaging device, a dark field imaging device, a bright field and dark field imaging device, a bright field non-imaging device, a dark field non-imaging device, a bright field and dark field non-imaging device, a double dark field device, a dual beam spectrophotometer, a coherence probe microscope, an interference microscope, an optical profilometer, or any combination thereof. In this manner, the measurement device may be configured to function as a single measurement device or as multiple measurement devices. Because multiple measurement devices may be integrated into a single measurement device of the system, optical elements of a first measurement device, for example, may also be optical elements of a second measurement device.

In an embodiment, the processor may include a local processor coupled to the measurement device and a remote controller computer coupled to the local processor. The local processor may be configured to at least partially process the one or more output signals. The remote controller computer may be configured to receive the at least partially processed one or more output signals from the processor. In addition, the remote controller computer may be configured to determine at least the first property and the second property of the specimen from the at least partially processed one or more output signals. Furthermore, the remote controller computer may be configured to determine additional properties of the specimen from the at least partially processed one or more output signals. In an additional embodiment, the remote controller computer may be coupled to a process tool such as a semiconductor fabrication process tool. In this manner, the remote controller computer may be further configured to alter a parameter of one or more instruments coupled to the process tool in response to at least the determined first or second property of the specimen using an in situ control technique, a feedback control technique, or a feedforward control technique.

An additional embodiment relates to a method for determining at least two properties of a specimen. The method may include disposing a specimen upon a stage. The stage may be coupled to a measurement device. The measurement device may include an illumination system and a detection system. In addition, the method may include directing energy toward a surface of the specimen. The method may also include detecting energy propagating from the surface of the specimen. The method may further include generating one or more output signals in response to the detected energy. Furthermore, the method may include processing the one or more output signals to determine at least a first property and a second property of the specimen.

In an embodiment, the first property may include a presence of defects on specimen. The second property may include a thin film characteristic of the specimen. In addition, the processor may be configured to determine other properties of the specimen from the one or more output signals. In an additional embodiment, a semiconductor device may be fabricated by the method. For example, the method may include forming a portion of a semiconductor device upon a specimen.

In an embodiment, processing the one or more output signals to determine at least a first property and a second property of the specimen may include at least partially processing the one or more output signals using a local processor. The local processor may be coupled to the measurement device. Processing the one or more output signals may also include sending the partially processed one or more output signals from the local processor to a remote controller computer. In addition, processing the one or more output signals may include further processing the partially processed one or more output signals using the remote controller computer. In an additional embodiment, the remote controller computer may be coupled to a process tool such as a semiconductor fabrication process tool. In this manner, the method may include altering a parameter of one or more instruments coupled to the process tool using the remote controller computer in response to at least the determined first or second property of the specimen. Altering the parameter of the instruments may include using an in situ control technique, a feedback control technique, or a feedforward control technique.

Additional embodiments relate to a computer-implemented method for controlling a system configured to determine at least two properties of a specimen. The system may include a measurement device. In this manner, controlling the system may include controlling the measurement device. In addition, the measurement device may include an illumination system and a detection system. The measurement device may also be coupled to a stage. Controlling the measurement device may include controlling the illumination system to direct energy toward a surface of the specimen. Additionally, controlling the measurement device may include controlling the detection system to detect energy propagating from the surface of the specimen. The method may also include generating one or more output signals in response to the detected energy. The computer-implemented method may further include processing the one or more output signals to determine at least a first property and a second property of the specimen. For example, the first property may include a presence of defects on specimen. The second property may include a thin film characteristic of the specimen. In addition, the processor may be configured to determine other properties of the specimen from the one or more output signals.

An embodiment relates to a system configured to determine at least two properties of a specimen. The system may include a stage configured to support the specimen. The system may also include a measurement device coupled to the stage. The measurement device may include an illumination system configured to direct energy toward a surface of the specimen. The measurement device may also include a detection system coupled to the illumination system. The detection system may be configured to detect energy propagating from the surface of the specimen. The measurement device may also be configured to generate one or more output signals in response to the detected energy. The system may also include a processor coupled to the measurement device. The processor may be configured to determine at least a first property and a second property of the specimen from the one or more output signals.

In an embodiment, the first property may include a presence of defects on specimen. The second property may include a critical dimension of the specimen. In addition, the processor may be configured to determine other properties of the specimen from the one or more output signals. In an embodiment, the measurement device may include a non-imaging scatterometer, a scatterometer, a spectroscopic scatterometer, a reflectometer, a spectroscopic reflectometer, an ellipsometer, a spectroscopic ellipsometer, a bright field imaging device, a dark field imaging device, a bright field and dark field imaging device, a bright field non-imaging device, a dark field non-imaging device, a bright field and dark field non-imaging device, a coherence probe microscope, an interference microscope, an optical profilometer, or any combination thereof. In this manner, the measurement device may be configured to function as a single measurement device or as multiple measurement devices. Because multiple measurement devices may be integrated into a single measurement device of the system, optical elements of a first measurement device, for example, may also be optical elements of a second measurement device.

In an embodiment, the processor may include a local processor coupled to the measurement device and a remote controller computer coupled to the local processor. The local processor may be configured to at least partially process the one or more output signals. The remote controller computer may be configured to receive the at least partially processed one or more output signals from the processor. In addition, the remote controller computer may be configured to determine at least the first property and the second property of the specimen from the at least partially processed one or more output signals. Furthermore, the remote controller computer may be configured to determine additional properties of the specimen from the at least partially processed one or more output signals. In an additional embodiment, the remote controller computer may be coupled to a process tool such as a semiconductor fabrication process tool. In this manner, the remote controller computer may be further configured to alter a parameter of one or more instruments coupled to the process tool in response to at least the determined first or second property of the specimen using an in situ control technique, a feedback control technique, and/or a feedforward control technique.

An additional embodiment relates to a method for determining at least two properties of a specimen. The method may include disposing a specimen upon a stage. The stage may be coupled to a measurement device. The measurement device may include an illumination system and a detection system. In addition, the method may include directing energy toward a surface of the specimen using the illumination system. The method may also include detecting energy propagating firm the surface of the specimen using the detection system. The method may further include generating one or more output signals in response to the detected energy. Furthermore, the method may include processing the one or more output signals to determine at least a first property and a second property of the specimen.

In an embodiment, the first property may include a presence of defects on specimen. The second property may include a critical dimension of the specimen. In addition, the processor may be configured to determine other properties of the specimen from the one or more output signals. In an additional embodiment, a semiconductor device may be fabricated by the method. For example, the method may include forming a portion of a semiconductor device upon a specimen such as a semiconductor substrate.

In an embodiment, processing the one or more output signals to determine at least a first property and a second property of the specimen may include at least partially processing the one or more output signals using a local processor. The local processor may be coupled to the measurement device. Processing the one or more output signals may also include sending the partially processed one or more output signals from the local processor to a remote controller computer. In addition, processing the one or more output signals may include further processing the partially processed one or more output signals using the remote controller computer. In an additional embodiment, the remote controller computer may be coupled to a process tool such as a semiconductor fabrication process tool. In this manner, the method may include altering a parameter of one or more instruments coupled to the process tool using the remote controller computer in response to at least the determined first or second property of the specimen. Altering the parameter of the instruments may include using an in situ control technique, a feedback control technique, and/or a feedforward control technique.

Additional embodiments relate to a computer-implemented method for controlling a system configured to determine at least two properties of a specimen. The system may include a measurement device. In this manner, controlling the system may include controlling the measurement device. In addition, the measurement device may include an illumination system and a detection system. The measurement device may also be coupled to a stage. Controlling the measurement device may include controlling the illumination system to direct energy toward a surface of the specimen. Additionally, controlling the measurement device may include controlling the detection system to detect energy propagating from the surface of the specimen. The method may also include generating one or more output signals in response to the detected energy. The computer-implemented method may further include processing the one or more output signals to determine at least a first property and a second property of the specimen. For example, the first property may include a presence of defects on specimen. The second property may include a critical dimension of the specimen. In addition, the processor may be configured to determine other properties of the specimen from the one or more output signals.

An embodiment relates to a system configured to determine at least two properties of a specimen. The system may include a stage configured to support the specimen. The system may also include a measurement device coupled to the stage. The measurement device may include an illumination system configured to direct energy toward a surface of the specimen. The measurement device may also include a detection system coupled to the illumination system. The detection system may be configured to detect energy propagating from the surface of the specimen. The measurement device may also be configured to generate one or more output signals in response to the detected energy. The system may also include a processor coupled to the measurement device. The processor may be configured to determine at least a first property and a second property of the specimen from the one or more output signals.

In an embodiment, the first property may include a critical dimension of the specimen. The second property may include a thin film characteristic of the specimen. In addition, the processor may be configured to determine other properties of the specimen from the one or more output signals. In an embodiment, the measurement device may include a non-imaging scatterometer, a scatterometer, a spectroscopic scatterometer, a reflectometer, a spectroscopic reflectometer, an ellipsometer, a spectroscopic ellipsometer, a beam profile ellipsometer, a dual beam spectrophotometer, a bright field imaging device, a dark field imaging device, a bright field and dark field imaging device, a bright field and/or dark field non-imaging device, a coherence probe microscope, an interference microscope, an optical profilometer, or any combination thereof. In this manner, the measurement device may be configured to function as a single measurement device or as multiple measurement devices. Because multiple measurement devices may be integrated into a single measurement device of the system, optical elements of a first measurement device, for example, may also be optical elements of a second measurement device.

In an embodiment, the processor may include a local processor coupled to the measurement device and/or a remote controller computer coupled to the local processor. The local processor may be configured to at least partially process the one or more output signals. The remote controller computer may be configured to receive the at least partially processed one or more output signals from the local processor. In addition, the remote controller computer may be configured to determine at least the first property and the second property of the specimen from the at least partially processed one or more output signals. Furthermore, the remote controller computer may be configured to determine additional properties of the specimen from the at least partially processed one or more output signals. In an additional embodiment, the remote controller computer may be coupled to a process tool such as a semiconductor fabrication process tool. In this manner, the remote controller computer may be further configured to alter a parameter of one or more instruments coupled to the process tool in response to at least the determined first or second property of the specimen using an in situ control technique, a feedback control technique, and/or a feedforward control technique.

An additional embodiment relates to a method for determining at least two properties of a specimen. The method may include disposing a specimen upon a stage. The stage may be coupled to a measurement device. The measurement device may include an illumination system and a detection system. In addition, the method may include directing energy toward a surface of the specimen using the illumination system. The method may also include detecting energy propagating from the surface of the specimen using the detection system. The method may further include generating one or more output signals in response to the detected energy. Furthermore, the method may include processing the one or more output signals to determine at least a first property and a second property of the specimen.

In an embodiment, the first property may include a critical dimension of the specimen. The second property may include a thin film characteristic of the specimen. In addition, the processor may be configured to determine other properties of the specimen from the one or more output signals. In an additional embodiment, a semiconductor device may be fabricated by the method. For example, the method may include forming a portion of a semiconductor device upon a specimen such as a semiconductor substrate.

In an embodiment, processing the one or more output signals to determine at least a first property and a second property of the specimen may include at least partially processing the one or more output signals using a local processor. The local processor may be coupled to the measurement device. Processing the one or more output signals may also include sending the partially processed one or more output signals from the local processor to a remote controller computer. In addition, processing the one or more output signals may include further processing the partially processed one or more output signals using the remote controller computer. In an additional embodiment, the remote controller computer may be coupled to a process tool such as a semiconductor fabrication process tool. In this manner, the method may include altering a parameter of one or more instruments coupled to the process tool using the remote controller computer in response to at least the determined first or second property of the specimen. Altering the parameter of the instruments may include using an in situ control technique, a feedback control technique, and/or a feedforward control technique.

Additional embodiments relate to a computer-implemented method for controlling a system configured to determine at least two properties of a specimen. The system may include a measurement device. In this manner, controlling the system may include controlling the measurement device. In addition, the measurement device may include an illumination system and a detection system. The measurement device may also be coupled to a stage. Controlling the measurement device may include controlling the illumination system to direct energy toward a surface of the specimen. Additionally, controlling the measurement device may include controlling the detection system to detect energy propagating from the surface of the specimen. The method may also include generating one or more output signals in response to the detected energy. The computer-implemented method may further include processing the one or more output signals to determine at least a first property and a second property of the specimen. For example, the first property may include a critical dimension of the specimen. The second property may include a thin film characteristic of the specimen. In addition, the processor may be configured to determine other properties of the specimen from the one or more output signals.

An embodiment relates to a system configured to determine at least three properties of a specimen. The system may include a stage configured to support the specimen. The system may also include a measurement device coupled to the stage. The measurement device may include an illumination system configured to direct energy toward a surface of the specimen. The measurement device may also include a detection system coupled to the illumination system. The detection system may be configured to detect energy propagating from the surface of the specimen. The measurement device may also be configured to generate one or more output signals in response to the detected energy. The system may also include a processor coupled to the measurement device. The processor may be configured to determine at least a first property, a second property and a third property of the specimen from the one or more output signals.

In an embodiment, the first property may include a critical dimension of the specimen. The second property may include a presence of defects on the specimen. The third property may include a thin film characteristic of the specimen. In addition, the processor may be configured to determine other properties of the specimen from the one or more output signals. In an embodiment, the measurement device may include a non-imaging scatterometer, a scatterometer, a spectroscopic scatterometer, a reflectometer, a spectroscopic reflectometer, an ellipsometer, a spectroscopic ellipsometer, a beam profile ellipsometer, a bright field imaging device, a dark field imaging device, a bright field and dark field imaging device, a bright field and/or dark field non-imaging device, a coherence probe microscope, an interference microscope, an optical profilometer, a dual beam spectrophotometer, or any combination thereof. In this manner, the measurement device may be configured to function as a single measurement device or as multiple measurement devices. Because multiple measurement devices may be integrated into a single measurement device of the system, optical elements of a first measurement device, for example, may also be optical elements of a second measurement device.

In an embodiment, the processor may include a local processor coupled to the measurement device and/or a remote controller computer coupled to the local processor. The local processor may be configured to at least partially process the one or more output signals. The remote controller computer may be configured to receive the at least partially processed one or more output signals from the processor. In addition, the remote controller computer may be configured to determine at least the first property, the second property and the third property of the specimen from the at least partially processed one or more output signals. Furthermore, the remote controller computer may be configured to determine additional properties of the specimen from the at least partially processed one or more output signals. In an additional embodiment, the remote controller computer may be coupled to a process tool such as a semiconductor fabrication process tool. In this manner, the remote controller computer may be further configured to alter a parameter of one or more instruments coupled to the semiconductor fabrication process tool in response to at least the determined first, second, or third property of the specimen using an in situ control technique, a feedback control technique, and/or a feedforward control technique.

An additional embodiment relates to a method for determining at least three properties of a specimen. The method may include disposing a specimen upon a stage. The stage may be coupled to a measurement device. The measurement device may include an illumination system and a detection system. In addition, the method may include directing energy toward a surface of the specimen using the illumination system. The method may also include detecting energy propagating from the surface of the specimen using the detection system. The method may further include generating one or more output signals in response to the detected energy. Furthermore, the method may include processing the one or more output signals to determine at least a first property, a second property, and a third property of the specimen.

In an embodiment, the first property may include a critical dimension of the specimen. The second property may include a presence of defects on the specimen. The third property may include a thin film characteristic of the specimen. In addition, the processor may be configured to determine other properties of the specimen from the one or more output signals. In an additional embodiment, a semiconductor device may be fabricated by the method. For example, the method may include forming a portion of a semiconductor device upon a specimen such as a semiconductor substrate.

In an embodiment, processing the one or more output signals to determine at least a first property, a second property and a third property of the specimen may include at least partially processing the one or more output signals using a local processor. The local processor may be coupled to the measurement device. Processing the one or more output signals may also include sending the partially processed one or more output signals from the local processor to a remote controller computer. In addition, processing the one or more output signals may include further processing the partially processed one or more output signals using the remote controller computer. In an additional embodiment, the remote controller computer may be coupled to a process tool such as a semiconductor fabrication process tool. In this manner, the method may include altering a parameter of one or more instruments coupled to the process tool using the remote controller computer in response to at least the determined first or second property of the specimen. Altering the parameter of the instruments may include using an in situ control technique, a feedback control technique, and/or a feedforward control technique.

Additional embodiments relate to a computer-implemented method for controlling a system configured to determine at least three properties of a specimen. The system may include a measurement device. In this manner, controlling the system may include controlling the measurement device. In addition, the measurement device may include an illumination system and a detection system. The measurement device may also be coupled to a stage. Controlling the measurement device may include controlling the illumination system to direct energy toward a surface of the specimen. Additionally, controlling the measurement device may include controlling the detection system to detect energy propagating from the surface of the specimen. The method may also include generating one or more output signals in response to the detected energy. The computer-implemented method may further include processing the one or more output signals to determine at least a first property, a second property and a third property of the specimen. For example, the first property may include a critical dimension of the specimen. The second property may include a presence of defects on the specimen. The third property may include a thin film characteristic of the specimen. In addition, the processor may be configured to determine other properties of the specimen from the one or more output signals.

An embodiment relates to a system configured to determine at least two properties of a specimen. The system may include a stage configured to support the specimen. The system may also include a measurement device coupled to the stage. The measurement device may include an illumination system configured to direct energy toward a surface of the specimen. The measurement device may also include a detection system coupled to the illumination system. The detection system may be configured to detect energy propagating from the surface of the specimen. The measurement device may also be configured to generate one or more output signals in response to the detected energy. The system may also include a processor coupled to the measurement device. The processor may be configured to determine at least a first property and a second property of the specimen from the one or more output signals.

In an embodiment, the first property may include a presence of macro defects on the specimen. The second property may a presence of micro defects on the specimen. In addition, the processor may be configured to determine other properties of the specimen from the one or more output signals. In an embodiment, the measurement device may include a non-imaging scatterometer, a scatterometer, a spectroscopic scatterometer, a reflectometer, a spectroscopic reflectometer, an ellipsometer, a spectroscopic ellipsometer, a bright field imaging device, a dark field imaging device, a bright field and dark field imaging device, a bright field and/or dark field non-imaging device, a double dark field device, a coherence probe microscope, an interference microscope, an optical profilometer, or any combination thereof. In this manner, the measurement device may be configured to, function as a single measurement device or as multiple measurement devices. Because multiple measurement devices may be integrated into a single measurement device of the system, optical elements of a first measurement device, for example, may also be optical elements of a second measurement device.

In an embodiment, the processor may include a local processor coupled to the measurement device or a remote controller computer coupled to the local processor. The local processor may be configured to at least partially process the one or more output signals. The remote controller computer may be configured to receive the at least partially processed one or more output signals from the processor. In addition, the remote controller computer may be configured to determine at least the first property and the second property of the specimen from the at least partially processed one or more output signals. Furthermore, the remote controller computer may be configured to determine additional properties of the specimen from the at least partially processed one or more output signals. In an additional embodiment, the remote controller computer may be coupled to a process tool such as a semiconductor fabrication process tool. In this manner, the remote controller computer may be further configured to alter a parameter of one or more instruments coupled to the process tool in response to at least the determined first or second property of the specimen using an in situ control technique, a feedback control technique, and/or a feedforward control technique.

An additional embodiment relates to a method for determining at least two properties of a specimen. The method may include disposing a specimen upon a stage. The stage may be coupled to a measurement device. The measurement device may include an illumination system and a detection system. In addition, the method may include directing energy toward a surface of the specimen using the illumination system The method may also include detecting energy propagating from the surface of the specimen using the detection system. The method may also include generating one or more output signals in response to the detected energy. Furthermore, the method may include processing the one or more output signals to determine at least a first property and a second property of the specimen.

In an embodiment, the first property may include a presence of macro defects on the specimen. The second property may be a presence of micro defects on the specimen. In addition, the processor may be configured to determine other properties of the specimen from the one or more output signals. In an additional embodiment, a semiconductor device may be fabricated by the method. For example, the method may include forming a portion of a semiconductor device upon a specimen such as a semiconductor substrate.

In an embodiment, processing the one or more output signals to determine at least a first property and a second property of the specimen may include at least partially processing the one or more output signals using a local processor. The local processor may be coupled to the measurement device. Processing the one or more output signals may also include sending the partially processed one or more output signals from the local processor to a remote controller computer. In addition, processing the one or more output signals may include further processing the partially processed one or more output signals using the remote controller computer. In an additional embodiment, the remote controller computer may be coupled to a process tool such as a semiconductor fabrication process tool. In this manner, the method may include altering a parameter of one or more instruments coupled to the process tool using the remote controller computer in response to at least the determined first or second property of the specimen. Altering the parameter of the instruments may include using an in situ control technique, a feedback control technique, and/or a feedforward control technique.

Additional embodiments relate to a computer-implemented method for controlling a system configured to determine at least two properties of a specimen. The system may include a measurement device. In this manner, controlling the system may include controlling the measurement device. In addition, the measurement device may include an illumination system and a detection system. The measurement device may also be coupled to a stage. Controlling the measurement device may include controlling the illumination system to direct energy toward a surface of the specimen. Additionally, controlling the measurement device may include controlling the detection system to detect energy propagating from the surface of the specimen. The method may also include generating one or more output signals in response to the detected energy. The computer-implemented method may further include processing the one or more output signals to determine at least a first property and a second property of the specimen. For example, the first property may include a presence of macro defects on the specimen. The second property may be a presence of micro defects on the specimen. In addition, the processor may be configured to determine other properties of the specimen from the one or more output signals.

An embodiment relates to a system configured to determine at least three properties of a specimen. The system may include a stage configured to support the specimen. The system may also include a measurement device coupled to the stage. The measurement device may include an illumination system configured to direct energy toward a surface of the specimen. The measurement device may also include a detection system coupled to the illumination system. The detection system may be configured to detect energy propagating from the surface of the specimen. The measurement device may also be configured to generate one or more output signals in response to the detected energy. The system may also include a processor coupled to the measurement device. The processor may be configured to determine at least a first property, a second property and a third property of the specimen from the one or more output signals.

In an embodiment, the first property may include a flatness measurement of the specimen. The second property may include a presence of defects on the specimen. The third property may include a thin film characteristic of the specimen. In addition, the processor may be configured to determine other properties of the specimen from the one or more output signals. In an embodiment, the measurement device may include a non-imaging scatterometer, a scatterometer, a spectroscopic scatterometer, a reflectometer, a spectroscopic reflectometer, an ellipsometer, a spectroscopic ellipsometer, a beam profile ellipsometer, a bright field and/or dark field imaging device, a bright field and/or dark field non-imaging device, a double dark field device, a coherence probe microscope, an interference microscope, an interferometer, an optical profilometer, a dual beam spectrophotometer, or any combination thereof. In this manner, the measurement device may be configured to function as a single measurement device or as multiple measurement devices. Because multiple measurement devices may be integrated into a single measurement device of the system, optical elements of a first measurement device, for example, may also be optical elements of a second measurement device.

In an embodiment, the processor may include a local processor coupled to the measurement device and a remote controller computer coupled to the local processor. The local processor may be configured to at least partially process the one or more output signals. The remote controller computer may be configured to receive the at least partially processed one or more output signals from the processor. In addition, the remote controller computer may be configured to determine at least the first property, the second property and the third property of the specimen from the at least partially processed one or more output signals. Furthermore, the remote controller computer may be configured to determine additional properties of the specimen from the at least partially processed one or more output signals. In an additional embodiment, the remote controller computer may be coupled to a process tool such as a semiconductor fabrication process tool. In this manner, the remote controller computer may be further configured to alter a parameter of one or more instruments coupled to the process tool in response to at least the determined first second or third property of the specimen using an in situ control technique, a feedback control technique, and/or a feedforward control technique.

An additional embodiment relates to a method for determining at least three properties of a specimen. The method may include disposing a specimen upon a stage. The stage may be coupled to a measurement device. The measurement device may include an illumination system and a detection system. In addition, the method may include directing energy toward a surface of the specimen using the illumination system. The method may also include detecting energy propagating from the surface of the specimen using the detection system. The method may further include generating one or more output signals in response to the detected energy. Furthermore, the method may include processing the one or more output signals to determine at least a first property, a second property, and a third property of the specimen.

In an embodiment, the first property may include a flatness measurement of the specimen. The second property may include a presence of defects on the specimen. The third property may include a thin film characteristic of the specimen. In addition, the processor may be configured to determine other properties of the specimen from the one or more output signals. In an additional embodiment, a semiconductor device may be fabricated by the method. For example, the method may include forming a portion of a semiconductor device upon a specimen such as a semiconductor substrate.

In an embodiment, processing the one or more output signals to determine at least a first property, a second property and a third property of the specimen may include at least partially processing the one or more output signals using a local processor. The local processor may be coupled to the measurement device. Processing the one or more output signals may also include sending the partially processed one or more output signals from the local processor to a remote controller computer. In addition, processing the one or more output signals may include further processing the partially processed one or more output signals using the remote controller computer. In an additional embodiment, the remote controller computer may be coupled to a process tool such as a semiconductor fabrication process tool. In this manner, the method may include altering a parameter of one or more instruments coupled to the process tool using the remote controller computer in response to at least the determined first or second property of the specimen. Altering the parameter of the instruments may include using an in situ control technique, a feedback control technique, and/or a feedforward control technique.

Additional embodiments relate to a computer-implemented method for controlling a system configured to determine at least three properties of a specimen. The system may include a measurement device. In this manner, controlling the system may include controlling the measurement device. In addition, the measurement device may include an illumination system and a detection system. The measurement device may also be coupled to a stage. Controlling the measurement device may include controlling the illumination system to direct energy toward a surface of the specimen. Additionally, controlling the measurement device may include controlling the detection system to detect energy propagating from the surface of the specimen. The method may also include generating one or more output signals in response to the detected energy. The computer-implemented method may further include processing the one or more output signals to determine at least a first property, a second property and a third property of the specimen. For example, the first property may include a flatness measurement of the specimen. The second property may include a presence of defects on the specimen. The third property may include a thin film characteristic of the specimen. In addition, the processor may be configured to determine other properties of the specimen from the one or more output signals.

An embodiment relates to a system configured to determine at least two properties of a specimen. The system may include a stage configured to support the specimen. The system may also include a measurement device coupled to the stage. The measurement device may include an illumination system configured to direct energy toward a surface of the specimen. The measurement device may also include a detection system coupled to the illumination system. The detection system may be configured to detect energy propagating from the surface of the specimen. The measurement device may also be configured to generate one or more output signals in response to the detected energy. The system may also include a processor coupled to the measurement device. The processor may be configured to determine at least a first property and a second property of the specimen from the detected light.

In an embodiment, the first property may include overlay misregistration of the specimen. The second property may include a flatness measurement of the specimen. In addition, the processor may be configured to determine other properties of the specimen from the one or more output signals. In an embodiment, the measurement device may include a non-imaging scatterometer, a scatterometer, a spectroscopic scatterometer, a reflectometer, a spectroscopic reflectometer, a spectroscopic ellipsometer, a beam profile ellipsometer, a bright field imaging device, a dark field imaging device, a bright field and dark field imaging device, a coherence probe microscope, an interference microscope, an interferometer, an optical profilometer, a dual beam spectrophotometer, or any combination thereof. In this manner, the measurement device may be configured to function as a single measurement device or as multiple measurement devices. Because multiple measurement devices may be integrated into a single measurement device of the system, optical elements of a first measurement device, for example, may also be optical elements of a second measurement device.

In an embodiment, the processor may include a local processor coupled to the measurement device and a remote controller computer coupled to the local processor. The local processor may be configured to at least partially process the one or more output signals. The remote controller computer may be configured to receive the at least partially processed one or more output signals from the processor. In addition, the remote controller computer may be configured to determine at least the first property and the second property of the specimen from the at least partially processed one or more output signals. Furthermore, the remote controller computer may be configured to determine additional properties of the specimen from the at least partially processed one or more output signals. In an additional embodiment, the remote controller computer may be coupled to a process tool such as a semiconductor fabrication process tool. In this manner, the remote controller computer may be further configured to alter a parameter of one or more instruments coupled to the process tool in response to at least the determined first or second property of the specimen using an in situ control technique, a feedback control technique, and/or a feedforward control technique.

An additional embodiment relates to a method for determining at least two properties of a specimen. The method may include disposing a specimen upon a stage. The stage may be coupled to a measurement device. The measurement device may include an illumination system and a detection system. In addition, the method may include directing energy toward a surface of the specimen using the illumination system. The method may also include detecting energy propagating from the surface of the specimen using the detection system. The method may further include generating one or more output signals in response to the detected energy. Furthermore, the method may include processing the one or more output signals to determine at least a first property and a second property of the specimen.

In an embodiment, the first property may include overlay misregistration of the specimen. The second property may include a flatness measurement of the specimen. In addition, the processor may be configured to determine other properties of the specimen from the one or more output signals. In an additional embodiment, a semiconductor device may be fabricated by the method. For example, the method may include forming a portion of a semiconductor device upon a specimen such as a semiconductor substrate.

In an embodiment, processing the one or more output signals to determine at least a first property and a second property of the specimen may include at least partially processing the one or more output signals using a local processor. The local processor may be coupled to the measurement device. Processing the one or more output signals may also include sending the partially processed one or more output signals from the local processor to a remote controller computer. In addition, processing the one or more output signals may include further processing the partially processed one or more output signals using the remote controller computer. In an additional embodiment, the remote controller computer may be coupled to a process tool such as a semiconductor fabrication process tool. In this manner, the method may include altering a parameter of one or more instruments coupled to the process tool using the remote controller computer in response to at least the determined first or second property of the specimen. Altering the parameter of the instruments may include using an in situ control technique, a feedback control technique, and/or a feedforward control technique.

Additional embodiments relate to a computer-implemented method for controlling a system configured to determine at least two properties of a specimen. The system may include a measurement device. In this manner, controlling the system may include controlling the measurement device. In addition, the measurement device may include an illumination system and a detection system. The measurement device may also be coupled to a stage. Controlling the measurement device may include controlling the illumination system to direct energy toward a surface of the specimen. Additionally, controlling the measurement device may include controlling the detection system to detect energy propagating from the surface of the specimen. The method may also include generating one or more output signals in response to the detected energy. The computer-implemented method may further include processing the one or more output signals to determine at least a first property and a second property of the specimen. For example, the first property may include overlay misregistration of the specimen. The second property may include a flatness measurement of the specimen. In addition, the processor may be configured to determine other properties of the specimen from the one or more output signals.

An embodiment relates to a system configured to determine at least two properties of a specimen. The system may include a stage configured to support the specimen. The system may also include a measurement device coupled to the stage. The measurement device may include an illumination system configured to direct energy toward a surface of the specimen. The measurement device may also include a detection system coupled to the illumination system. The detection system may be configured to detect energy propagating from the surface of the specimen. The measurement device may also be configured to generate one or more output signals in response to the detected energy. The system may also include a processor coupled to the measurement device. The processor may be configured to determine at least a first property and a second property of the specimen from the one or more output signals.

In an embodiment, the first property may include a characteristic of an implanted region of the specimen. The second property may include a presence of defects on the specimen. In addition, the processor may be configured to determine other properties of the specimen from the one or more output signals. In an embodiment, the measurement device may include a modulated optical reflectometer, an X-ray reflectance device, an eddy current device, a photoacoustic device, a spectroscopic ellipsometer, a spectroscopic reflectometer, a dual beam spectrophotometer, a non-imaging scatterometer, a scatterometer, a spectroscopic scatterometer, a reflectometer, an ellipsometer, a non-imaging bright field device, a non-imaging dark field device, a non-imaging bright field and dark field device, a bright field imaging device, a dark field imaging device, a bright field and dark field imaging device, or any combination thereof. In this manner, the measurement device may be configured to function as a single measurement device or as multiple measurement devices. Because multiple measurement devices may be integrated into a single measurement device of the system, optical elements of a first measurement device, for example, may also be optical elements of a second measurement device.

In an embodiment, the processor may include a local processor coupled to the measurement device and a remote controller computer coupled to the local processor. The local processor may be configured to at least partially process the one or more output signals. The remote controller computer may be configured to receive the at least partially processed one or more output signals from the processor. In addition, the remote controller computer may be configured to determine at least the first property and the second property of the specimen from the at least partially processed one or more output signals. Furthermore, the remote controller computer may be configured to determine additional properties of the specimen from the at least partially processed one or more output signals. In an additional embodiment, the remote controller computer may be coupled to a process tool such as a semiconductor fabrication process tool. In this manner, the remote controller computer may be further configured to alter a parameter of one or more instruments coupled to the process tool in response to at least the determined first or second property of the specimen using an in situ control technique, a feedback control technique, and/or a feedforward control technique.

An additional embodiment relates to a method for determining at least two properties of a specimen. The method may include disposing a specimen upon a stage. The stage may be coupled to a measurement device. The measurement device may include an illumination system and a detection system. In addition, the method may include directing energy toward a surface of the specimen using the illumination system. The method may also include detecting energy propagating from the surface of the specimen using the detection system. The method may further include generating one or more output signals in response to the detected energy. Furthermore, the method may include processing the one or more output signals to determine at least a first property and a second property of the specimen.

In an embodiment, the first property may include a characteristic of an implanted region of the specimen. The second property may include a presence of defects on the specimen. In addition, the processor may be configured to determine other properties of the specimen from the one or more output signals. In an additional embodiment, a semiconductor device may be fabricated by the method. For example, the method may include forming a portion of a semiconductor device upon a specimen such as a semiconductor substrate.

In an embodiment, processing the one or more output signals to determine at least a first property and a second property of the specimen may include at least partially processing the one or more output signals using a local processor. The local processor may be coupled to the measurement device. Processing the one or more output signals may also include sending the partially processed one or more output signals from the local processor to a remote controller computer. In addition, processing the one or more output signals may include further processing the partially processed one or more output signals using the remote controller computer. In an additional embodiment, the remote controller computer may be coupled to a process tool such as a semiconductor fabrication process tool. In this manner, the method may include altering a parameter of one or more instruments coupled to the semiconductor fabrication process tool using the remote controller computer in response to at least the determined first or second property of the specimen. Altering the parameter of the measurements may include using an in situ control technique, a feedback control technique, and/or a feedforward control technique.

Additional embodiments relate to a computer-implemented method for controlling a system configured to determine at least two properties of a specimen. The system may include a measurement device. In this manner, controlling the system may include controlling the measurement device. In addition, the measurement device may include an illumination system and a detection system. The measurement device may also be coupled to a stage. Controlling the measurement device may include controlling the illumination system to direct energy toward a surface of the specimen. Additionally, controlling the measurement device may include controlling the detection system to detect energy propagating from the surface of the specimen. The method may also include generating one or more output signals in response to the detected energy. The computer-implemented method may further include processing the one or more output signals to determine at least a first property and a second property of the specimen. For example, the first property may include a characteristic of an implanted region of the specimen. The second property may include a presence of defects on the specimen. In addition, the processor may be configured to determine other properties of the specimen from the one or more output signals.

An embodiment relates to a system configured to determine at least two properties of a specimen. The system may include a stage configured to support the specimen. The system may also include a measurement device coupled to the stage. The measurement device may include an illumination system configured to direct energy toward a surface of the specimen. The measurement device may also include a detection system coupled to the illumination system. The detection system may be configured to detect energy propagating from the surface of the specimen. The measurement device may be configured to generate one or more output signals in response to the detected light. The system may also include a processor coupled to the measurement device. The processor may be configured to determine at least a first property and a second property of the specimen from the one or more output signals.

In an embodiment, the first property may include an adhesion characteristic of the specimen. The second property may include a thickness of the specimen. In addition, the processor may be configured to determine other properties of the specimen from the one or more output signals. In an embodiment, the measurement device may include an eddy current device, a photoacoustic device, a spectroscopic ellipsometer, an ellipsometer, an X-ray reflectometer, a grazing X-ray reflectometer, an X-ray diffractometer, or any combination thereof. In this manner, the measurement device may be configured to function as a single measurement device or as multiple measurement devices. Because multiple measurement devices may be integrated into a single measurement device of the system, optical elements of a first measurement device, for example, may also be optical elements of a second measurement device.

In an embodiment, the processor may include a local processor coupled to the measurement device and a remote controller computer coupled to the local processor. The local processor may be configured to at least partially process the one or more output signals. The remote controller computer may be configured to receive the at least partially processed one or more output signals from the local processor. In addition, the remote controller computer may be configured to determine at least the first property and the second property of the specimen from the at least partially processed one or more output signals. Furthermore, the remote controller computer may be configured to determine additional properties of the specimen from the at least partially processed one or more output signals. In an additional embodiment, the remote controller computer may be coupled to a process tool such as a semiconductor fabrication process tool. In this manner, the remote controller computer may be ether configured to alter a parameter of one or more instruments coupled to the semiconductor fabrication process tool in response to at least the determined first or second property of the specimen using an in situ control technique, a feedback control technique, and/or a feedforward control technique.

An additional embodiment relates to a method for determining at least two properties of a specimen. The method may include disposing a specimen upon a stage. The stage may be coupled to a measurement device. The measurement device may include an illumination system and a detection system. In addition, the method may include directing energy toward a surface of the specimen using the illumination system. The method may also include detecting energy propagating from the surface of the specimen using the detection system. The method may further include generating one or more output signals in response to the detected energy. Furthermore, the method may include processing the one or more output signals to determine at least a first property and a second property of the specimen.

In an embodiment, the first property may include an adhesion characteristic of the specimen. The second property may include a thickness of the specimen. In addition, the processor may be configured to determine other properties of the specimen from the one or more output signals. In an additional embodiment, a semiconductor device may be fabricated by the method. For example, the method may include forming a portion of a semiconductor device upon a specimen such as a semiconductor substrate.

In an embodiment, processing the one or more output signals to determine at least a first property and a second property of the specimen may include at least partially processing the one or more output signals using a local processor. The local processor may be coupled to the measurement device. Processing the one or more output signals may also include sending the partially processed one or more output signals from the local processor to a remote controller computer. In addition, processing the one or more output signals may include further processing the partially processed one or more output signals using the remote controller computer. In an additional embodiment, the remote controller computer may be coupled to a process tool such as a semiconductor fabrication process tool. In this manner, the method may include altering a parameter of one or more instruments coupled to the process tool using the remote controller computer in response to at least the determined first or second property of the specimen. Altering the parameter of the instruments may include using an in situ control technique, a feedback control technique, and/or a feedforward control technique.

Additional embodiments relate to a computer-implemented method for controlling a system configured to determine at least two properties of a specimen. The system may include a measurement device. In this manner, controlling the system may include controlling the measurement device. In addition, the measurement device may include an illumination system and a detection system. The measurement device may also be coupled to a stage. Controlling the measurement device may include controlling the illumination system to direct energy toward a surface of the specimen. Additionally, controlling the measurement device may include controlling the detection system to detect energy propagating from the surface of the specimen. The method may also include generating one or more output signals in response to the detected energy. The computer-implemented method may further include processing the one or more output signals to determine at least a first property and a second property of the specimen. For example, the first property may include an adhesion characteristic of the specimen. The second property may include a thickness of the specimen. In addition, the processor may be configured to determine other properties of the specimen from the one or more output signals.

An embodiment relates to a system configured to determine at least two properties of a specimen. The system may include a stage configured to support the specimen. The system may also include a measurement device coupled to the stage. The measurement device may include an illumination system configured to direct energy toward a surface of the specimen. The measurement device may also include a detection system coupled to the illumination system. The detection system may be configured to detect energy propagating from the surface of the specimen. The measurement device may be configured to generate one or more output signals in response to the detected energy. The system may also include a processor coupled to the measurement device. The process may be configured to determine at least a first property and a second property of the specimen from the one or more output signals.

In an embodiment, the first property may include a concentration of an element in the specimen. The second property may include a thickness of the specimens. In addition, the processor may be configured to determine other properties of the specimen from the one or more output signals. In an embodiment, the measurement device may include a photo-acoustic device, an X-ray reflectometer, a grazing X-ray reflectometer, an X-ray diffractometer, an eddy current device, a spectroscopic ellipsometer, an ellipsometer, or any combination thereof. In this manner, the measurement device may be configured to function as a single measurement device or as multiple measurement devices. Because multiple measurement devices may be integrated into a single measurement device of the system optical elements of a first measurement device, for example, may also be optical elements of a second measurement device.

In an embodiment, the processor may include a local processor coupled to the measurement device and a remote controller computer coupled to the local processor. The local processor may be configured to at least partially process the one or more output signals. The remote controller computer may be configured to receive the at least partially processed one or more output signals from the processor. In addition, the remote controller computer may be configured to determine at least the first property and the second property of the specimen from the at least partially processed one or more output signals. Furthermore, the remote controller computer may be configured to determine additional properties of the specimen from the at least partially processed one or more output signals. In an additional embodiment, the remote controller computer may be coupled to a process tool such as a semiconductor fabrication process tool. In this manner, the remote controller computer may be further configured to alter a parameter of one or more instruments coupled to the process tool in response to at least the determined first or second property of the specimen using an in situ control technique, a feedback control technique, and/or a feedforward control technique.

An additional embodiment relates to a method for determining at least two properties of a specimen. The method may include disposing a specimen upon a stage. The stage may be coupled to a measurement device. The measurement device may include an illumination system and a detection system. In addition, the method may include directing energy toward a surface of the specimen using the illumination system. The method may also include detecting energy propagating from the surface of the specimen using the detection system. The method may further include generating one or more output signals in response to the detected energy. Furthermore, the method may include processing the one or more output signals to determine at least a first property and a second property of the specimen.

In an embodiment, the first property may include a concentration of an element in the specimen. The second property may include a thickness of the specimen. In addition, the processor may be configured to determine other properties of the specimen from the one or more output signals. In an additional embodiment, a semiconductor device may be fabricated by the method. For example, the method may include forming a portion of a semiconductor device upon a specimen such as a semiconductor substrate.

In an embodiment, processing the one or more output signals to determine at least a first property and a second property of the specimen may include at least partially processing the one or more output signals using a local processor. The local processor may be coupled to the measurement device. Processing the one or more output signals may also include sending the partially processed one or more output signals from the local processor to a remote controller computer. In addition, processing the one or more output signals may include further processing the partially processed one or more output signals using the remote controller computer. In an additional embodiment, the remote controller computer may be coupled to a process tool such as a semiconductor fabrication process tool. In this manner, the method may include altering a parameter of one or more instruments coupled to the process tool using the remote controller computer in response to at least the determined first or second property of the specimen. Altering the parameter of the instruments may include using an in situ control technique, a feedback control technique, and/or a feedforward control technique.

Additional embodiments relate to a computer-implemented method for controlling a system configured to determine at least two properties of a specimen. The system may include a measurement device. In this manner, controlling the system may include controlling the measurement device. In addition, the measurement device may include an illumination system and a detection system. The measurement device may also be coupled to a stage. Controlling the measurement device may include controlling the illumination system to direct energy toward a surface of the specimen. Additionally, controlling the measurement device may include controlling the detection system to detect energy propagating from the surface of the specimen. The method may also include generating one or more output signals in response to the detected energy. The computer-implemented method may further include processing the one or more output signals to determine at least a first property and a second property of the specimen. For example, the first property may include a concentration of an element in the specimen. The second property may include a thickness of the specimen. In addition, the processor may be configured to determine other properties of the specimen from the one or more output signals.

An embodiment relates to a system coupled to a deposition tool. The deposition tool may be configured to form a layer of material on a specimen. The layer of material may be formed on the specimen by the deposition tool. The measurement device may be configured to determine a characteristic of a layer of material prior to, during, or after formation of the layer. The system may include a stage configured to support the specimen. The measurement device may include an illumination system configured to direct energy toward a surface of the specimen prior to, during ,or after formation of the layer. The measurement device may also include a detection system coupled to the illumination system. The detection system may be configured to detect energy propagating from the surface of the specimen prior to, during, or after formation of the layer. The measurement device may be configured to generate one or more output signals in response to the detected energy. The system may also include a processor coupled to the measurement device. The processor may be configured to determine a characteristic of the layer from the one or more output signals. The processor may also be coupled to the deposition tool. The processor may be configured to alter a parameter of one or more instruments coupled to the deposition tool. Additionally, the processor may be configured to alter a parameter of the instruments coupled to the deposition tool in response to the determined characteristic of the formed layer.

In an embodiment, the measurement device may include a non-imaging scatterometer, a scatterometer, a spectroscopic scatterometer, a reflectometer, a spectroscopic reflectometer, an ellipsometer, a spectroscopic ellipsometer, a bright field imaging device, a dark field imaging device, a bright field and dark field imaging device, a coherence probe microscope, an interference microscope, an optical profilometer, or any combination thereof. In this manner, the measurement device may be configured to function as a single measurement device or as multiple measurement devices. Because multiple measurement devices may be integrated into a single measurement device of the system, optical elements of a first measurement device, for example, may also be optical elements of a second measurement device. The deposition tool may include any tool configured to form a layer upon a semiconductor substrate. Deposition tools may include chemical vapor deposition tools, physical vapor deposition tool, atomic layer deposition tools, and electroplating tools.

In an embodiment, the processor may include a local processor coupled to the measurement device and/or the deposition tool and a remote controller computer coupled to the local processor. The local processor may be configured to at least partially process the one or more output signals. The remote controller computer may be configured to receive the at least partially processed one or more output signals from the processor. In addition, the remote controller computer may be configured to determine a characteristic of the formed layer on the specimen from the at least partially processed one or more output signals. Furthermore, the remote controller computer may be configured to determine additional properties of the specimen from the at least partially processed one or more output signals. The remote controller computer may also be coupled to a deposition tool. In this manner, the remote controller computer may be further configured to alter a parameter of one or more instruments coupled to the deposition tool in response to at least the determined characteristic of a layer formed upon the specimen using an in situ control technique, a feedback control technique, and/or a feedforward control technique.

An additional embodiment relates to a method of evaluating a characteristic of a layer formed upon a specimen. The method may include depositing a layer upon a specimen using a deposition tool. The measurement device may include an illumination system and a detection system. In addition, the method may include directing energy toward a surface of the specimen using the illumination system. The method may also include detecting energy propagating from the surface of the specimen using the detection system. The method may further include generating one or more output signals in response to the detected light. Furthermore, the method may include processing the one or more output signals to determine a characteristic of the formed layer.

In an embodiment, the processor may be configured to determine a characteristic of the formed layer. In addition, the processor may be configured to determine other properties of the specimen from the one or more output signals. In an additional embodiment, a semiconductor device may be fabricated by the method. For example, the method may include forming a portion of a semiconductor device upon a specimen such as a semiconductor substrate.

In an embodiment, processing the one or more output signals to determine a characteristic of a formed layer may include at least partially processing the one or more output signals using a local processor. The local processor may be coupled to the measurement device. Processing the one or more output signals may also include sending the partially processed one or more output signals from the local processor to a remote controller computer. In addition, processing the one or more output signals may include further processing the partially processed one or more output signals using the remote controller computer. In an additional embodiment, the remote controller computer may be coupled to the deposition tool. In this manner, the method may include altering a parameter of one or more instruments coupled to the deposition tool using the remote controller computer in response to at least the determined characteristic of the formed layer on the specimen. Altering the parameter of the deposition tool may include using an in situ control technique, a feedback control technique, and/or a feedforward control technique.

Additional embodiments relate to a computer-implemented method for controlling a system that includes a deposition tool and a measurement device. Controlling the system may include controlling the measurement device, the deposition tool, or both. In addition, the measurement device may include an illumination system and a detection system. The measurement device may also be coupled to a stage. Controlling the measurement device may include controlling the illumination system to direct energy toward a surface of the specimen. Additionally, controlling the measurement device may include controlling the detection system to detect energy propagating from the surface of the specimen. The method may also include generating one or more output signals in response to the detected energy. The computer-implemented method may further include processing the one or more output signals to determine at least a characteristic of the layer as it is formed or after it is formed. In addition, the processor may be configured to determine other properties of the specimen from the one or more output signals.

An embodiment relates to a system that includes an etch tool coupled to a beam profile ellipsometer. The etch tool may be configured to direct chemically reactive and/or ionic species toward a specimen. The beam profile ellipsometer may be configured to determine a property of an etched region of the specimen during or after the etching process. The beam profile ellipsometer may include an illumination system configured to direct an incident beam of light having a known polarization state toward a surface of the specimen during or after etching of the specimen. The measurement device may also include a detection system coupled to the illumination system. The detection system may be configured to generate one or more output signals representative of light returned from the specimen during or after etching of the specimen. The system may also include a processor coupled to the measurement device. The processor may be configured to determine a property of the etched region of a specimen from the one or more output signals. The processor may also be coupled to the etch tool. The processor may alter a parameter of one or more instruments coupled to the etch tool. Additionally, the processor may be configured to alter a parameter of the instruments coupled to the etch tool in response to the properties of the etched layer.

In an embodiment, the system may also include a non-imaging scatterometer, a scatterometer, a spectroscopic scatterometer, a reflectometer, a spectroscopic reflectometer, an ellipsometer, a spectroscopic ellipsometer, a bright field and/or dark field imaging device, a bright field and/or dark field non-imaging device, a coherence probe microscope, an interference microscope, or any combination thereof. In this manner, the system may be configured to function as a single measurement device or as multiple measurement devices. Because multiple measurement devices may be integrated into a single measurement device of the system, optical elements of a first measurement device, for example, may also be optical elements of a second measurement device.

In an embodiment, the processor may include a local processor coupled to the beam profile ellipsometer and/or the etch tool and a remote controller computer coupled to the local processor. The local processor may be configured to at least partially process the one or more output signals. The remote controller computer may be configured to receive the at least partially processed one or more output signals from the processor. In addition, the remote controller computer may be configured to determine a property of an etched region on the specimen from the at least partially processed one or more output signals. Furthermore, the remote controller computer may be configured to determine additional properties of the specimen from the at least partially processed one or more output signals. The remote controller computer may also be coupled to a etch tool. In this manner, the remote controller computer may be further configured to alter a parameter of one or more instruments coupled to the etch tool in response to at least the determined property of the etched region of the specimen using an in situ control technique, a feedback control technique, and/or a feedforward control technique.

An additional embodiment relates to a method of evaluating an etched region of a specimen with a beam profile ellipsometer. The method may include etching a layer upon a specimen using an etch tool. The beam profile ellipsometer may include an illumination system and a detection system. In addition, the method may include directing light toward a surface of the specimen using the illumination system. The method may also include detecting light propagating from the surface of the specimen using the detection system. The method may further include generating one or more output signals in response to the detected light. Furthermore, the method may include processing the one or more output signals to a property of the etched region of the specimen.

In addition, the method may include processing the one or more output signals to determine other properties of the specimen from the one or more output signals. In an additional embodiment, a semiconductor device may be fabricated by the method. For example, the method may include forming a portion of a semiconductor device upon a specimen such as a semiconductor substrate.

In an embodiment, processing the one or more output signals to determine a property of an etched region of a specimen may include at least partially processing the one or more output signals using a local processor. The local processor may be coupled to the beam profile ellipsometer. Processing the one or more output signals may also include sending the partially processed one or more output signals from the local processor to a remote controller computer. In addition, processing the one or more output signals may include further processing the partially processed one or more output signals using the remote controller computer. In an additional embodiment, the remote controller computer may be coupled to the etch tool. In this manner, the method may include altering a parameter of one or more instruments coupled to the etch tool using the remote controller computer in response to at least the determined characteristic of the formed layer on the specimen. Altering the parameter of the etch tool may include using an in situ control technique, a feedback control technique, and/or a feedforward control technique.

Additional embodiments relate to a computer-implemented method for controlling a system that includes an etch tool and a beam profile ellipsometer. Controlling the system may include controlling the beam profile ellipsometer, the etch tool, or both. In addition, the beam profile ellipsometer may include an illumination system and a detection system. The beam profile ellipsometer may also be coupled to a stage. Controlling the beam profile ellipsometer may include controlling the illumination system to direct light toward a surface of the specimen. Additionally, controlling the beam profile ellipsometer may include controlling the detection system to detect light propagating from the surface of the specimen. The method may also include generating one or more output signals in response to the detected light. The computer-implemented method may further include processing the one or more output signals to determine at least a property of an etched region of a specimen during etching, after the region is etched, or both. In addition, the processor may be configured to determine other properties of the specimen from the one or more output signals.

An embodiment relates to a system that includes an ion implanter coupled to a measurement device. The measurement device may be configured to determine at least a characteristic of an implanted region of a specimen. The measurement device may be configured to determine a characteristic of an implanted region of a specimen during or after implantation of the specimen. The system may include a stage configured to support the specimen. The measurement device may include an illumination system configured to periodically direct two or more beams of light toward a surface of the specimen during or after implantation. In one embodiment, the measurement device may direct an incident beam of light to a specimen to periodically excite a region of the specimen during implantation. Additionally, the measurement device may direct a sample beam of light to the excited region of the specimen. The measurement device may also include a detection system coupled to the illumination system. The detection system may be configured to measure an intensity of the sample beam reflected from the excited region of the specimen. The measurement device may also be configured to generate one or more output signals in response to the measured intensity.

The system may also include a processor coupled to the measurement device. The processor may be configured to determine a characteristic of an implanted region from the one or more output signals. The processor may also be coupled to the ion implanter. The processor may be configured to alter a parameter coupled to one or more instruments coupled to the ion implanter. Additionally, the processor may be configured to alter a parameter of one or more instruments coupled to the ion implanter in response to the determined characteristic of the implanted region.

In an embodiment, the measurement device may include a non-imaging scatterometer, a scatterometer, a spectroscopic scatterometer, a reflectometer, a spectroscopic reflectometer, a bright field and/or dark field imaging device, a bright field and/or dark field non-imaging device, a coherence probe microscope, an interference microscope, an optical profilometer, a modulated optical reflectance device, or any combination thereof. In this manner, the measurement device may be configured to function as a single measurement device or as multiple measurement devices. Because multiple measurement devices may be integrated into a single measurement device of the system, optical elements of a first measurement device, for example, may also be optical elements of a second measurement device.

In an embodiment, the processor may include a local processor coupled to the measurement device and/or the ion implanter and a remote controller computer coupled to the local processor. The local processor may be configured to at least partially process the one or more output signals. The remote controller computer may be configured to receive the at least partially processed one or more output signals from the processor. In addition, the remote controller computer may be configured to determine a characteristic of the implanted region of the specimen from the at least partially processed one or more output signals. Furthermore, the remote controller computer may be configured to determine additional properties of the specimen from the at least partially processed one or more output signals. The remote controller computer may also be coupled to an ion implanter. In this manner, the remote controller computer may be further configured to alter a parameter of one or more instruments coupled to the ion implanter in response to at least the determined property of the ion implantation region of the specimen using an in situ control technique, a feedback control technique, and/or a feedforward control technique.

An additional embodiment relates to a method of evaluating an implanted region of a specimen. The method may include implanting ions into a region of a specimen using an ion implanter. The measurement device may include an illumination system and a detection system. In addition, the method may include directing an incident beam of light toward a region of the specimen to periodically excite the region of the specimen during implantation or after implantation. A sample beam may also be directed to the excited region of the specimen. The method may also include measuring an intensity of light propagating from the excited region of the specimen using the detection system. The method may further include generating one or more output signals in response to the measured intensity. Furthermore, the method may include processing the one or more output signals to determine a characteristic of the implanted region. In addition, the method may include processing the one or more output signals to determine other properties of the specimen from the one or more output signals. In an additional embodiment, a semiconductor device may be fabricated by the method. For example, the method may include forming a portion of a semiconductor device upon a specimen such as a semiconductor substrate.

In an embodiment, processing the one or more output signals to determine a property of an ion implantation region may include at least partially processing the one or more output signals using a local processor. The local processor may be coupled to the measurement device. Processing the one or more output signals may also include sending the partially processed one or more output signals from the local processor to a remote controller computer. In addition, processing the one or more output signals may include further processing the partially processed one or more output signals using the remote controller computer. In an additional embodiment, the remote controller computer may be coupled to the ion implanter. In this manner, the method may include altering a parameter of one or more instruments coupled to the ion implanter using the remote controller computer in response to at least the determined property of the ion implanted region of the specimen. Altering the parameter of the ion implanter may include using an in situ control technique, a feedback control technique, and/or a feedforward control technique.

Additional embodiments relate to a computer-implemented method for controlling a system that includes an ion implanter and a measurement device. Controlling the system may include controlling the measurement device, the ion implanter, or both. In addition, the measurement device may include an illumination system and a detection system. The measurement device may also be coupled to a stage. Controlling the measurement device may include controlling the illumination system to direct light toward a surface of the specimen. Additionally, controlling the measurement device may include controlling the detection system to detect light propagating from the surface of the specimen. The method may also include generating one or more output signals in response to the detected light. The computer-implemented method may further include processing the one or more output signals to determine at least a characteristic an implanted region of the specimen. In addition, the method may include determining other properties of the specimen from the one or more output signals.

An embodiment relates to a system that includes a process chamber coupled to a measurement device. The process chamber may be configured to fabricate a portion of a semiconductor device on a specimen. The measurement device may be configured to determine a presence of defects on a specimen. The measurement device may be configured to determine a presence of defects on a specimen prior to, during, or after fabrication of a portion of the semiconductor device on the specimen. In one embodiment, the measurement device may be configured to detect micro defects. The system may include a stage configured to support the specimen. The stage may be configured to rotate.

The measurement device may include an illumination system configured to direct energy toward a surface of the specimen prior to, during, or after fabrication. Additionally, the measurement device may be configured to direct energy toward a surface of the specimen while the stage is stationary or while the stage is rotating. The measurement device may also include a detection system coupled to the illumination system. The detection system may be configured to detect energy propagating from the surface of the specimen. The detection system may detect energy prior to, during, or after fabrication. The detection system may also be configured to detect energy while the stage is stationary or rotating. The measurement device may also be configured to generate one or more output signals in response to the detected energy.

The system may also include a processor coupled to the measurement device. The processor may be configured to a presence of defects on a surface of the specimen from the one or more output signals. The processor may also be coupled to the process chamber. The processor may control a parameter of one or more instruments coupled to the process chamber. Additionally, the processor may be configured to alter a parameter of one or more instruments coupled to the process chamber in response to the detection of micro defects on the surface of the specimen.

In an embodiment, the measurement device may include a non-imaging scatterometer, a scatterometer, a spectroscopic scatterometer, a reflectometer, a spectroscopic reflectometer, an ellipsometer, a spectroscopic ellipsometer, a bright field and/or dark field imaging device, a bright field and/or dark field non-imaging device, a coherence probe microscope, an interference microscope, an optical profilometer, or any combination thereof. In this manner, the measurement device may be configured to function as a single measurement device or as multiple measurement devices. Because multiple measurement devices may be integrated into a single measurement device of the system, optical elements of a first measurement device, for example, may also be optical elements of a second measurement device.

In an embodiment, the processor may include a local processor coupled to the measurement device and/or the process chamber and a remote controller computer coupled to the local processor. The local processor may be configured to at least partially on process the one or more output signals. The remote controller computer may be configured to receive the at least partially processed one or more output signals from the local processor. In addition, the remote controller computer may be configured to determine a presence of defects on the specimen from the at least partially processed one or more output signals. Furthermore, the remote controller computer may be configured to determine additional properties of the specimen from the at least partially processed one or more output signals. The remote controller computer may also be coupled the process chamber. In this manner, the remote controller computer may be further configured to alter a parameter of one or more instruments coupled to the process chamber in response to a determined presence of defects on the specimen using an in situ control technique, a feedback control technique, and/or a feedforward control technique.

An additional embodiment relates to a method of evaluating a presence of defects on a surface of a specimen using a system that includes a process tool and a measurement device. The method may be used to detect a presence of micro defects on a specimen. The method may include fabricating a portion of a semiconductor device on a specimen using a process tool. The measurement device may include an illumination system and a detection system. In addition, the method may include directing energy toward a surface of the specimen. The method may also include detecting energy propagating from the specimen using the detection system. The method may further include generating one or more output signals in response to the detected energy. Furthermore, the method may include processing the one or more output signals to determine a presence of defects on the specimen. The measurement device may be configured to determine the presence of defects prior to, during, or after a process. The specimen may also be placed on a stage. The method may include determining a presence of defects on the specimen while the stage is stationary or a while the stage is rotating.

In addition, the method may include determining other properties of the specimen from the one or more output signals. In an additional embodiment, a semiconductor device may be fabricated by the method. For example, the method may include forming a portion of a semiconductor device upon a specimen such as a semiconductor substrate.

In an embodiment, processing the one or more output signals to determine a presence of defects on a specimen may include at least partially processing the one or more output signals using a local processor. The local processor may be coupled to the measurement device. Processing the one or more output signals may also include sending the partially processed one or more output signals from the local processor to a remote controller computer. In addition, processing the one or more output signals may include further processing the partially processed one or more output signals using the remote controller computer. In an additional embodiment, the remote controller computer may be coupled to the process tool. In this manner, the method may include altering a parameter of one or more instruments coupled to the process tool using the remote controller computer in response to the one or more output signals. Altering the parameter of the process tool may include using an in situ control technique, a feedback control technique, and/or a feedforward control technique.

Additional embodiments relate to a computer-implemented method for controlling a system that includes a process tool and a measurement device. Controlling the system may include controlling the measurement device, the process tool, or both. In addition, the measurement device may include an illumination system and a detection system. The measurement device may also be coupled to a stage. Controlling the measurement device may include controlling the illumination system to direct energy toward a surface of the specimen. Additionally, controlling the measurement device may include controlling the detection system to detect energy propagating from the surface of the specimen. The method may also include generating one or more output signals in response to the detected energy. The computer-implemented method may further include processing the one or more output signals to determine a presence of defects on the specimen prior to, during, or subsequent to processing. In addition, the processor may be configured to determine other properties of the specimen from the one or more output signals.

An embodiment relates to a system that may be configured to determine a presence of defects on multiple surfaces of a specimen. The system may include a stage configured to support the specimen. The system may also include a measurement device coupled to the stage. The stage may be configured to move. The measurement device may include an illumination system configured to direct energy toward a front side and a back side of the specimen. The illumination system may be used while the stage is stationary or moving. The measurement device may also include a detection system coupled to the illumination system. The detection system may be configured to detect energy propagating along multiple paths from the front and back sides of the specimen. The system may also include a processor coupled to the measurement device. The measurement device may be configured to generate one or more output signals in response to the detected light. The processor may be configured to determine a presence of defects on the front and back sides of the specimen from the one or more output signals.

In addition, the processor may be configured to determine other properties of the specimen from the one or more output signals. In an embodiment, the measurement device may include a non-imaging scatterometer, a scatterometer, a spectroscopic scatterometer, a reflectometer, a spectroscopic reflectometer, an ellipsometer, a spectroscopic ellipsometer, a bright field and/or dark field imaging device, a bright field and/or dark field non-imaging device, a coherence probe microscope, an interference microscope, an optical profilometer, or any combination thereof. In this manner, the measurement device may be configured to function as a single measurement device or as multiple measurement devices. Because multiple measurement devices may be integrated into a single measurement device of the system, optical elements of a first measurement device, for example, may also be optical elements of a second measurement device.

In an embodiment, the processor may include a local processor coupled to the measurement device and a remote controller computer coupled to the local processor. The local processor may be configured to at least partially process the one or more output a signals. The remote controller computer may be configured to receive the at least partially processed one or more output signals from the processor. In addition, the remote controller computer may be configured to determine a presence of defects on the front and back sides of the specimen from the at least partially processed one or more output signals. Furthermore, the remote controller computer may be configured to determine additional properties of the specimen from the at least partially processed one or more output signals. In an additional embodiment, the remote controller computer may be coupled to a process tool such as a semiconductor fabrication process tool. In this manner, the remote controller computer may be further configured to alter a parameter of one or more instruments coupled to the process tool in response to at least the determined first or second property of the specimen using an in situ control technique, a feedback control technique, and/or a feedforward control technique.

An additional embodiment relates to a method for determining defects on multiple surfaces of a specimen. The method may include disposing a specimen upon a stage. The stage may be coupled to a measurement device. The measurement device may include an illumination system and a detection system. In addition, the method may include directing energy toward a front side and a back side of the specimen using the illumination system. The method may also include detecting energy propagating along multiple paths from the front and back sides of the specimen using the detection system. The method may further include generating one or more output signals in response to the detected energy. Furthermore, the method may include processing the one or more output signals to determine the presence of defects on the front and back sides of the specimen.

In addition, the processor may be configured to determine other properties of the specimen from the one or more output signals. In an additional embodiment, a semiconductor device may be fabricated by the method. For example, the method may include forming a portion of a semiconductor device upon a specimen such as a semiconductor substrate.

In an embodiment, processing the one or more output signals to determine the presence of defects on multiple surfaces of the specimen may include at least partially processing the one or more output signals using a local processor. The local processor may be coupled to the measurement device. Processing the one or more output signals may also include sending the partially processed one or more output signals from the local processor to a remote controller computer. In addition, processing the one or more output signals may include further processing the partially processed one or more output signals using the remote controller computer. In an additional embodiment, the remote controller computer may be coupled to a process tool such as a semiconductor fabrication process tool. In this manner, the method may include altering a parameter of one or more instruments coupled to the process tool using the remote controller computer in response to a determined presence of defects on multiple surfaces of the specimen. Altering the parameter of the instruments may include using an in situ control technique, a feedback control technique, and/or a feedforward control technique.

Additional embodiments relate to a computer-implemented method for controlling a system configured to determine defects on multiple surfaces of a specimen. The system may include a measurement device. In this manner, controlling the system may include controlling the measurement device. In addition, the measurement device may include an illumination system and a detection system. The measurement device may also be coupled to a stage. Controlling the measurement device may include controlling the illumination system to direct energy toward a surface of the specimen. Additionally, controlling the measurement device may include controlling the detection system to detect energy propagating from the surface of the specimen. The stage may be configured to move. The method may also include controlling the stage such that the specimen is moved during analysis. The method may further include generating one or more output signals in response to the detected energy. The computer-implemented method may further include processing the one or more output signals to determine a presence of defects on multiple surfaces of the specimen.

In an embodiment, any of the systems, as described herein, may be used during the production of a semiconductor device. A semiconductor device may be formed using one or more semiconductor processing steps. Each processing step may cause a change to a specimen. After a processing step, a portion of the semiconductor device may be formed upon a specimen. Prior to, during, or subsequent to a processing step, the specimen may be placed on a stage of a system configured to determine at least two properties of the specimen. The system may be configured according to any of the above embodiments.

After the first and second properties are determined, these properties may be used to determine further processing steps for formation of the semiconductor device. For example, the system may be used to evaluate if a semiconductor process is performing adequately. If a semiconductor process is not performing adequately, data obtained from the system may be used to determine further processing the specimen. In another embodiment, detection of an incorrectly processed specimen may indicate that the specimen should be removed from the semiconductor process. By using a multiple analysis system such as described above, processing of semiconductor devices may be enhanced. The time required for testing may be reduced. Also, the use of multiple tests may ensure that only apparently properly processed specimens are advanced to the next processing steps. In this manner, yield of semiconductor devices may increase.

BRIEF DESCRIPTION OF THE DRAWINGS

Other objects and advantages of the invention will become apparent upon reading the following detailed description and upon reference to the accompanying drawings in which:

FIG. 10 depicts a schematic side view of an embodiment of a system configured to determine a critical dimension of a specimen;

FIG. 22 depicts a schematic side view of an embodiment of a system coupled to a chemical-mechanical polishing tool;

Figure 1:
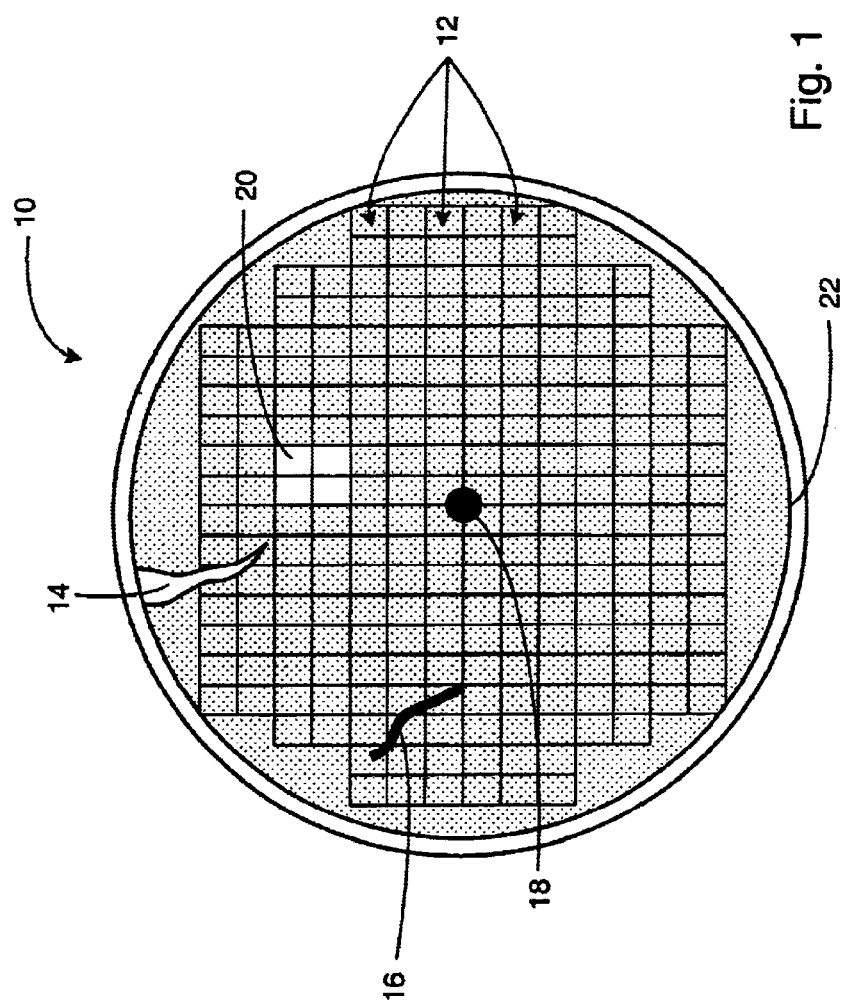
FIG. 1 depicts a schematic top view of an embodiment of a specimen having a plurality of dies and a plurality of defects on a surface of a specimen.

While the invention is susceptible to various modifications and alternative forms, specific embodiments thereof are shown by way of example in the drawings and will herein be described in detail. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

DETAILED DESCRIPTION OF THE PREFERRED EMBODIMENTS

Turning now to the drawings, FIG. 1 illustrates a schematic top view of an embodiment of a surface of specimen 10. Specimen 10 may include a substrate such as a monocrystalline silicon substrate, a silicon germanium substrate, or a gallium arsenide substrate. In addition, specimen 10 may include any substrate suitable for fabrication of semiconductor devices. Specimen 10 may include plurality of dies 12 having repeatable pattern features. Alternatively, specimen 10 may be unpatterned such as a virgin semiconductor wafer or an unprocessed wafer. In addition, specimen 10 may include a glass substrate or any substrate formed from a substantially transparent material, which may be suitable for fabrication of a reticle. Furthermore, specimen 10 may include any specimen known in the art.

In addition, specimen 10 may include one or more layers arranged upon a substrate. For example, layers which may be formed on a substrate may include, but are not limited to, a resist, a dielectric material, and/or a conductive material. The resist may include photoresist materials that may be patterned by an optical lithography technique. The resist may include other resists, however, such as e-beam resists or X-ray resists that may be patterned by an e-beam or an X-ray lithography technique, respectively. Examples of an appropriate dielectric material may include, but are not limited to, silicon dioxide, silicon nitride, silicon oxynitride, and titanium nitride. In addition, examples of an appropriate conductive material may include aluminum, polysilicon, and copper. Furthermore, a specimen may also include semiconductor devices such as transistors formed on a substrate such as a wafer.

Figure 2A:
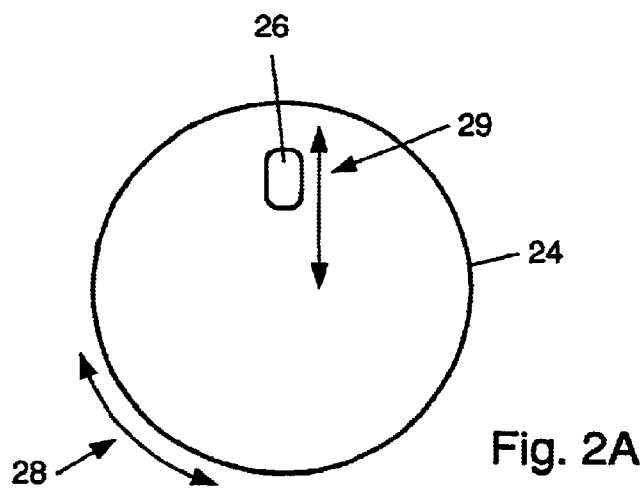
FIG. 2a depicts a schematic top view of an embodiment of a stage configured to move rotatably during use and a measurement device configured to move linearly during use.
Figure 2B:
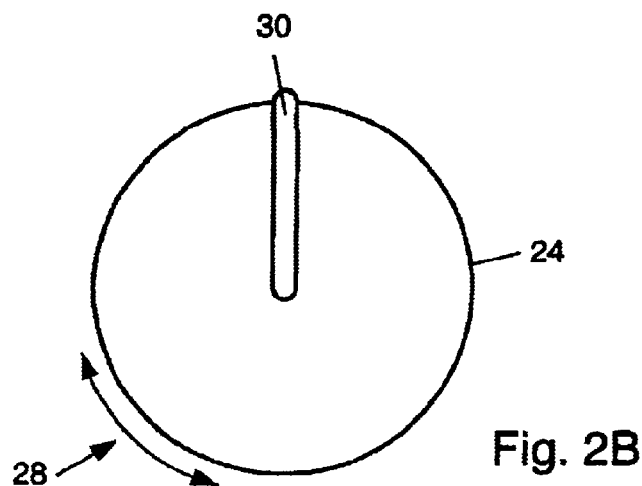
FIG. 2b depicts a schematic top view of an embodiment of a stage configured to move rotatably during use and a stationary measurement device.

FIGS. 2a and 2b illustrate a schematic top view of an embodiment of stage 24 configured to support a specimen. The stage may be a vacuum chuck or an electostatic chuck in this manner, a specimen may be held securely in place on the stage. In addition, the stage may be a motorized translation stage, a robotic wafer handler, or any other suitable mechanical device known in the art. In an embodiment, the system may include measurement device 26 coupled to the stage. As such, the stage may be configured to impart relative motion to the specimen with respect to the measurement device. In an example, the stage may be configured to move the specimen relative to the measurement device in a linear direction. The relative motion of the stage may cause an incident beam of energy from an energy source of a measurement device to traverse the surface of the specimen while leaving the angle of incidence at which light strikes the surface of the specimen substantially unchanged. As used herein, the term "measurement device" is generally used to refer to a metrology device, an inspection device, or a combination metrology and inspection device.

As shown in FIGS. 2a and 2b, stage 24 may be configured to rotate in clockwise and counterclockwise directions as indicated by vector 28 such that a specimen may be oriented with respected to measurement device 26 in a pluarlity of directions. As such, the stage may also be used to correct an orientation of a specimen such that a specimen may be substantially aligned with respect to a measurement device during measurement or inspection. In addition, stage 24 may be further configured to rotate and to move lineraly simultaneously. Examples of methods for aligning a specimen to a measurement device are illustrated in U.S. Pat. No. 5,682,242 to Eylon, U.S. Pat. No. 5,867,590 to Eylon, and U.S. Pat. No. 6,038,029 to Finarov, and are incorporated by reference as if fully set forth herein.

In an embodiment, stage, 24 may be further configured to move along a z-axis to alter a distance between a specimen and measurement device 26. For example, altering a distance between a specimen and a measurement device may substantially focus a beam of energy from an energy source of the measurement device on the surface of the specimen. Examples of focusing systems are illustrated in U.S. Pat. No. 5,604,344 to Finarov, and U.S. Pat. No. 6,124,924 to Feldman et al., which are incorporated by reference as if fully set forth herein. An example for focusing a charged particle beam on a specimen is illustrated in European Patent Application No. EP 1 081 741 A2 to Pearl et al., and is incorporated by reference as if fully set forth herein.

As shown in FIG. 2a, stage 24 may be configured to move with respect to measurement device 26, and the measurement device may be configured to move with respect to the stage. For example, measurement device 26 may be configured to move linearly along a direction indicated by vector 29 while stage 24 may be configured to move rotatably. As such, an incident beam of energy from an energy source of the measurement device may traverse a radius of the stage as the stage is rotating.

As shown in FIG. 2b, measurement device 30 may be configured to be relatively stationary in a position relative to stage 24. Devices (not shown) including, but not limited to, a deflector such as an acousto-optical deflector ("AOD") within measurement device 30 may be configured to linearly alter a position of an incident beam with respect to the stage. An example of an AOD is illustrated in PCT Application No. WO 01/14925 A1 to Allen et al., and is incorporated by reference as if fully set forth herein. In this manner, the incident beam may traverse a radius of the stage as the stage is rotating. In addition, by altering a position of an incident beam with respect to the stage using such devices, registry of the measurement device with a pattern formed on a surface of a specimen may be maintained. The device may be configured to cause an incident beam of energy from an energy source of the measurement device to traverse the surface of the specimen while leaving the angle of incidence at which the beam of energy strikes the surface of the specimen substantially unchanged.

In a further embodiment, measurement device 30 may include a plurality of energy sources such as illumination systems and a plurality of detection systems. The plurality of illumination systems and the plurality of detection systems may be arranged in two linear arrays. The illumination systems and the detection systems may be arranged such that each illumination system may be coupled to one of the detection systems. As such, measurement device 30 may be configured as a linear imaging device. In this manner, the measurement device may be configured to measure or inspect any location on a surface of specimen substantially simultaneously or sequentially. In addition, the measurement device may be configured such that measurements may be made at multiple locations on a specimen substantially simultaneously while the stage may be rotating. Furthermore, the stage and the measurement device may be configured to move substantially continuously or intermittently. For example, the stage and the measurement device may be moved intermittently such that the system may be configured as a move-acquire-measure system.

A measurement device and stage configured, as described above, to control and alter the measurement or inspection location of the specimen may provide several advantages in comparison to currently used systems. For example, currently used systems configured to inspect multiple locations on a specimen may include a stationary measurement device and a stage configured to move laterally in two independent directions. Alternatively, currently used systems may include a stationary stage and a measurement device configured to alter a position of e-beam of energy incident on a specimen by altering a position of two mirrors in a fist direction and a position of two mirrors in a second direction An example of such a system is illustrated in U.S. Pat. No. 5,517,312 to Finarov and U.S. Pat. No. 5,764,365 to Finarov, and are incorporated by reference as if fully set forth herein. An additional system may include a stage configured to rotate and a laser light source configured to move radially. Such a system may be unsuitable for measurement or inspecting a patterned specimen. Additional examples of currently used systems are illustrated in U.S. Pat. No. 5,943,122 to Holmes, and is incorporated by reference as if fully set forth herein.

As the lateral dimension of specimens such as wafers increases to 300 mm, moving a specimen linearly during inspection or measurement may become impractical due to space requirements of a typical semiconductor fabrication facility. In addition, moving such a specimen may become extremely expensive due to the cost of maintaining a relatively larger clean space for such tools. As such, a system configured as described in above embodiments may be configured to inspect or measure an entire surface of a specimen without linearly moving the specimen.

Figure 3:
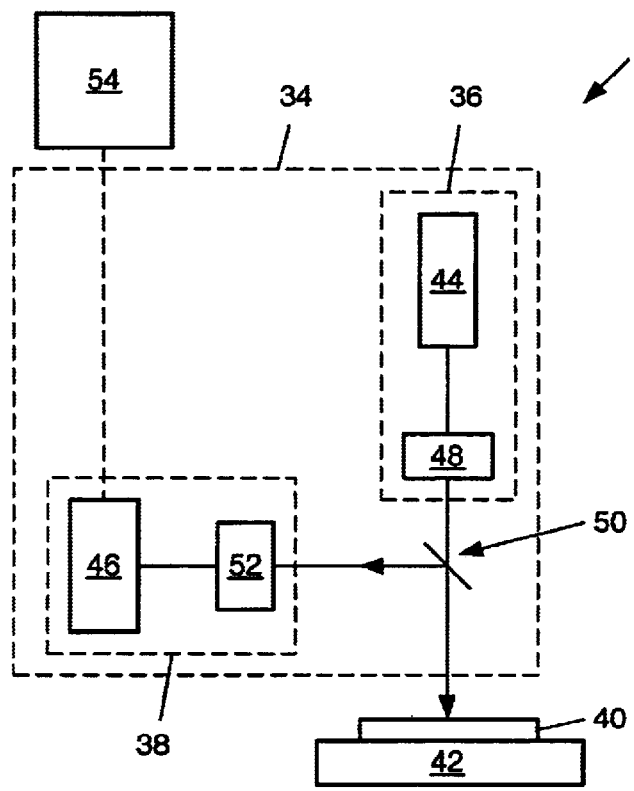
FIG. 3 depicts a schematic side view of an embodiment of a system having one illumination system and one detection system.

FIG. 3 illustrates a schematic side view of an embodiment of system 32 configured to determine at least two properties of a specimen. System 32 may include measurement a device 34 having illumination system 36 and detection system 38. Illumination system 36 may be configured to direct light toward a surface of specimen 40 disposed upon stage 42. Stage 42 may be configured as described in above embodiments. Detection system 38 may be coupled to illumination system 36 and may be configured to detect light propagating from the surface of the specimen. For example, detection system 38, illumination system 36, and additional optical components may be arranged such that spectrally reflected light or scattered light propagating from the surface of specimen 40 may be detected by the detection system.

Illumination system 36 may include energy source 44. Energy source 44 may be configured to emit monochromatic light. For example, a suitable monochromatic light source may be a gas laser or a solid state laser diode. Alternatively, the energy source may be configured to emit electromagnetic radiation of multiple wavelengths, which may include ultraviolet light, visible light, infrared light, X-rays, gamma rays, microwaves, or radio-frequencies. In addition, the energy source may be configured to emit another source of energy source such as an beam of electrons, protons, neutrons, ion, or molecules For example, a thermal field emission source is typically used as an electron source.

Detection system 38 may include detector 46. Detector 46 may include light sensitive sensor devices including, but not limited to, a photodetector, a multi-cell photodetector, an interferometer, an array of photodiodes such as a linear sensor array, a conventional spectrophotometer, a position sensitive detector, photomultiplier tubes, avalanche photodiodes, a charge-coupled device ("CCD") camera, a time delay integration ("TDI") camera, a video camera, a pattern recognition device, and an imaging system. In addition, the detector may include solid state detectors such as Schottky solid state barrier detectors.

In addition, measurement device 34 may include any number of additional optical components (not shown). Appropriate optical components may include, but are not limited to, beam splitters or dichroic mirrors, quarter wave plates, polarizers such as linear and circular polarizers, rotating polarizers, rotating analyzers, collimators, focusing lenses, additional lenses, folding mirrors, partially transmissive mirrors, filters such as spectral or polarizing filter, spatial filters, reflectors, deflectors, and modulators. Each of the additional optical components may be coupled to or disposed within the illumination system or the detection system. Furthermore, the measurement device may include a number of additional electromagnetic devices (not shown) that may include magnetic condenser lenses, magnetic objective lenses, electrostatic deflection systems, beam limiting apertures, and Wien filters.

An arrangement of the illumination system, the detection system, and additional optical and electromagnetic components may vary depending on, for example, the technique or techniques used to determine at least the two properties of the specimen. The arrangement of the illumination system, the detection system, and additional optical and electromagnetic components may also depend on the properties of the specimen, which are being determined. For example, as shown in FIG. 3, measurement device 34 may include optical component 48 disposed within or coupled to illumination system 36. Optical component 48 may include, but is not limited to, a polarizer, a spectral or polarizing filter, and a quarter wave plate. In addition, measurement device 34 may include beam splitter 50 and optical component 52. Optical component 52 may be disposed within or coupled to detection system 38. Optical component 52 may include, but is not limited to, a quarter wave plate, a collimator, and a focusing lens.

Figure 4:
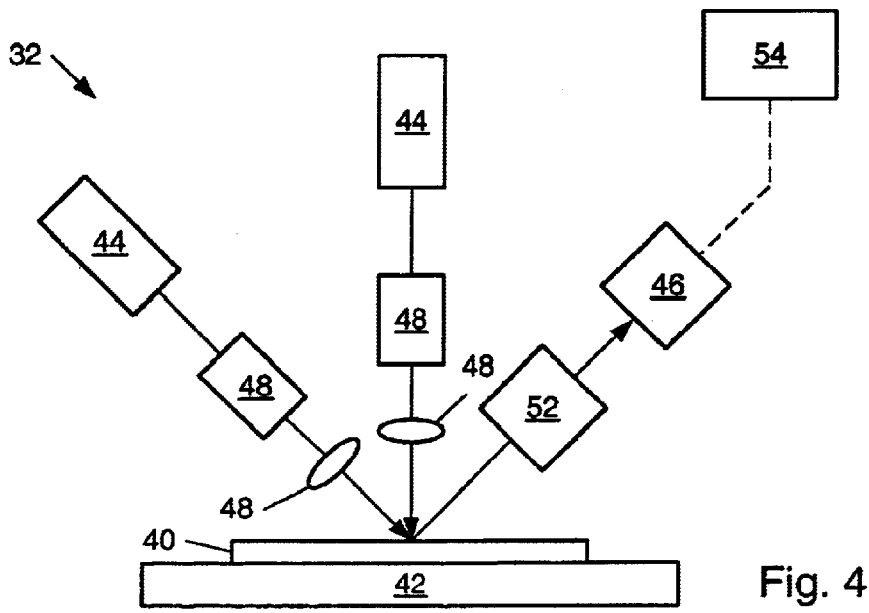
FIG. 4 depicts a schematic side view of an embodiment of a system having multiple illumination systems and one detection system.
Figure 5:
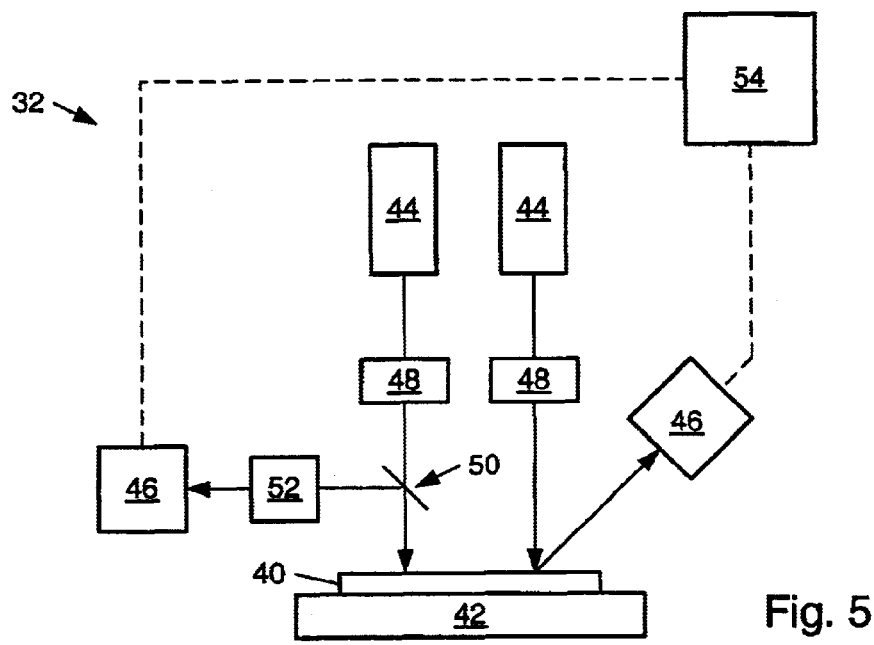
FIG. 5 depicts a schematic side view of an embodiment of a system having multiple illumination systems and multiple detection system.

FIGS. 4–7 illustrate alternate embodiments of measurement device 34 of system 32. As will be further described herein, elements of system 32, which may be similarly configured in each of the embodiments illustrated in FIGS. 3–7 have been indicated by the same reference characters. For example, energy source 44 may be similarly configured in each of the embodiments illustrated in FIGS. 3–7. As shown in FIG. 4, measurement device 34 may include a plurality of energy sources 44. Each of energy sources may be configured to emit substantially similar types of energy or different types of energy. For example, the plurality of energy sources 44 may include any of the light sources described herein. The light sources may be configured to emit broadband light. Alternatively, the light sources may include two emit different types of light. For example, one of the light sources may be configured to emit light of a single wavelength, and the other light source may be configured to emit broadband light. In addition, the energy sources may be configured to direct a beam of energy to substantially the same location on the surface of specimen 40, as shown in FIG. 4. Alternatively, the plurality of energy sources 44 may be configured to direct a beam of energy to substantially different locations on the surface of specimen 40, as shown in FIG. 5. For example, as shown in FIG. 5, the plurality of energy sources may be configured to direct energy to laterally spaced locations on the surface of specimen 40. The plurality of energy sources shown in FIG. 5 may also be configured as described above.

As shown in FIG. 4, measurement device may include detector 46 coupled to the plurality of energy sources 44. In this manner, detector 46 may be positioned with respect to the plurality of energy sources such that the detector may be configured to detect different types of energy propagating from the surface of specimen 40 such as specularly reflected light and scattered light. The detector may also be configured to detect different types of energy propagating from the surface of the specimen substantially simultaneously. For example, the detector may include an array of photodiodes. A first portion of the array of photodiodes may be configured to detect only incident light from one of the plurality of light sources propagating from the surface of the specimen. A second portion of the array of photodiodes may be configured to detect only incident light from the other of the plurality of light source propagating from the surface of the specimen. As such, the detector may be configured to detect incident light from each of a plurality of light sources propagating from the surface of the specimen substantially simultaneously. Alternatively, the plurality of energy sources may be configured to intermittently direct energy to the surface of the specimen. As such, the detector may be configured to detect incident energy from each of the plurality of energy sources propagating from the surface of the specimen intermittently.

As shown in FIG. 5, measurement device 34 may include a plurality of detectors 46. Each of the plurality of detectors may be coupled to one of the plurality of energy sources 44. In this manner, each detector 46 may be positioned with respect to one of the energy sources such that the detector may be configured to detect incident energy from one of the energy sources propagating from the surface of specimen 40. For example, one of the detectors may be positioned with respect to a first light source to detect light scattered from the surface of the specimen. In an example, scattered light may include dark field light propagating along a dark field path. A second of the plurality of detectors may be positioned with respect to a second light source to detect light specularly reflected from the surface of the specimen such as bright field light propagating along a bright field path. The plurality of detectors may be configured as described in above embodiments. For example, the plurality of detectors may include two different detectors or two of the same type of detectors. For example, a first detector may be configured as a conventional spectrophotometer, and a second detector may be configured as a quad-cell detector. Alternatively, both detectors may be configured as an array of photodiodes.

As shown in FIG. 4, measurement device 34 may also include multiple optical components 48. For example, optical components 48 may be coupled to each of the plurality of energy sources 44. In an example, a first of the optical components may be configured as a polarizer, and a second of the optical components may be configured as a focusing lens. Alternatively, as shown in FIG. 5, measurement device 34 may include one optical component 48 coupled to each of the plurality of energy sources 44. Each of the optical components 48 may be configured as described herein. In addition, as shown in FIG. 5, measurement device 34 may include an optical component such as beam splitter 50 coupled to one of the plurality of energy Sources. For example, beam splitter 50 may be positioned along a path of light directed from a light source. Beam splitter 50 may be configured to transmit light from the light source and to reflect light propagating from the surface of the specimen. The beam splitter may be configured to reflect light propagating from the surface of the specimen such that the reflected light may be directed to detector 46. In addition, beam splitters may be positioned along a path of the light directed from each of the plurality of light sources. Optical component 52 may also be coupled to detector 46, as shown in FIG. 4, and may be configured as, for example, a quarter wave plate, a collimator, and a focusing lens. Optical component 52 may be further configured as described herein. Multiple optical components 52 may also be coupled to each of the detectors. The position and the configuration of each of the optical components may vary, however, depending on the properties of the specimen to be determined by the system as will be described in more detail below.

Figure 6:
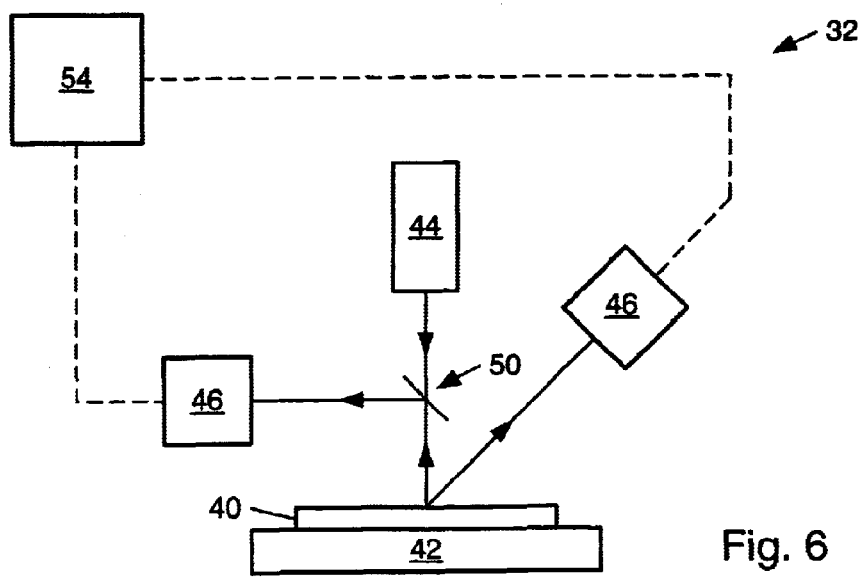
FIG. 6 depicts a schematic side view of an embodiment of a system having one illumination system and multiple detection systems.
Figure 7:
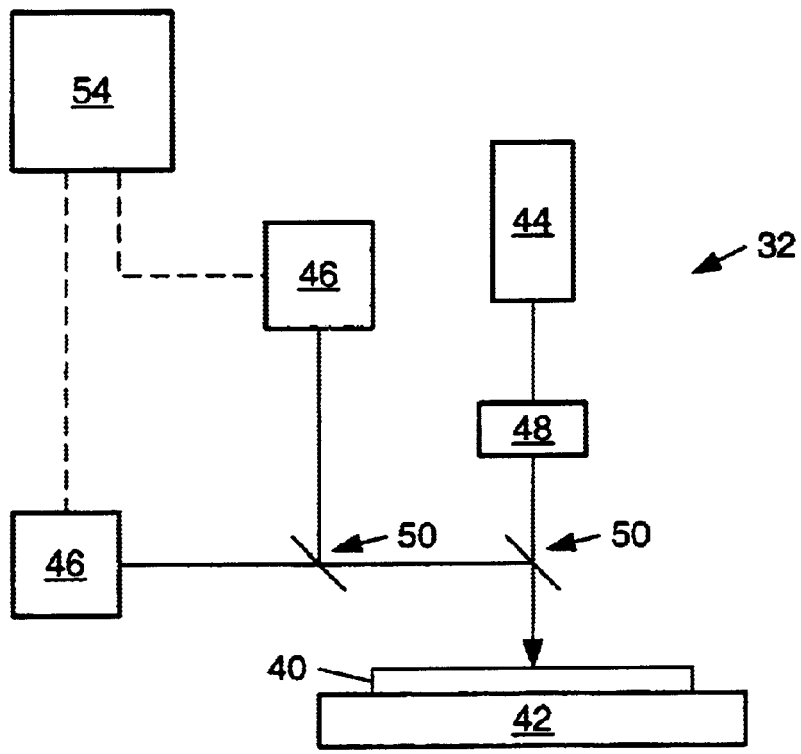
FIG. 7 depicts a schematic side view of an embodiment of a system having one illumination system and multiple detection systems.

FIGS. 6 and 7 illustrate schematic side views of additional embodiments of system 32. As shown in these figures, measurement device 34 may include a single energy source 44. In addition, measurement device 34 may include a plurality of detectors 46. The detectors may include any of devices as described herein. Each of the plurality of detectors 46 may be positioned at a different angle with respect to energy source 44. For example, as shown in FIG. 6, one of the detectors may be configured to detect dark field light propagating along a dark field path. The second detector may be configured to detect bright field light propagating along a bright field path. Alternatively, as shown in FIG. 7, each of the plurality of detectors may be configured to detect specularly reflected light. The plurality of detectors may be similarly configured, for example, as photodiode arrays. Alternatively, the plurality of detectors maybe configured as different detectors such as a conventional spectrophotometer and a quad cell detector.

In addition, the illumination system may be configured to direct different types of energy to the surface of the specimen at varying intervals. For example, the energy source may be configured to emit one type of light. As shown in FIG. 7, optical component 48 may be coupled to energy source 44. Optical component 48 may also be configured to alter the light emitted by energy source 44 at varying intervals. For example, optical component 48 may be configured as a plurality of spectral and/or polarizing filters that may be rotated in a path of the light emitted by energy source 44 at varying intervals or a liquid crystal display ("LCD") filter that may be controlled by a controller coupled to the filter. The controller may be configured to alter the transmissive, reflective, and/or polarization properties of the LCD filter at varying intervals. The properties of the LCD filter may be altered to change a spectral property or a polarization state of the light emitted from the energy source. In addition, each of the plurality of detectors may be suitable to detect a different type of light propagating from the surface of the specimen. As such, the measurement device may be configured to measure substantially different optical characteristics of the specimen at varying intervals. In this manner, measurement device 34 may be configured such that energy directed to the surface of the specimen and the energy returned from the surface of the specimen may vary depending on, for example, the properties of the specimen to be measured using the system.

In an embodiment, system 32, as shown in FIGS. 3–7, may include processor 54 coupled to measurement device 34. The processor may be configured to receive one or more output signals generated by a detector of the measurement device. The one or more output signals may be representative of the detected energy returned from the specimen. The one or more output signals,may be an analog signal or a digital signal. The processor may be configured to determine at least a first property and a second property of the specimen from the one or more output signals generated by the detector. The first property may include a critical dimension of specimen 40, and the second property may include overlay misregistration of specimen 40. For example, the measurement device may include, but is not limited to, a scatterometer, a non-imaging scatterometer, a spectroscopic scatterometer, a reflectometer, a spectroscopic reflectometer, an ellipsometer, a spectroscopic ellipsometer, a beam profile ellipsometer, a bright field imaging device, a dark field imaging device, a bright field and dark field imaging device, a bright field non-imaging device, a dark field non-imaging device, a bright field and dark field non-imaging device, a coherence probe microscope, an interference microscope, an optical profilometer, or any combination thereof. In this manner, the system may be configured as a single measurement device or as multiple measurement devices.

Because multiple measurement devices may be integrated into a single system, optical elements of a first measurement device, for example, may also be used as optical elements of a second measurement device. In addition, multiple measurement devices may be coupled to a common stage, a common handler, and a common processor. The handler may include a mechanical device configured to dispose a specimen on the common stage and to remove a specimen from the common stage or any other handler as described herein. In addition, the system may be configured to determine a critical dimension and an overlay misregistration of a specimen sequentially or substantially simultaneously. In this manner, such a system may be more cost, time, and space efficient than systems currently used in the semiconductor industry.

Figure 8:
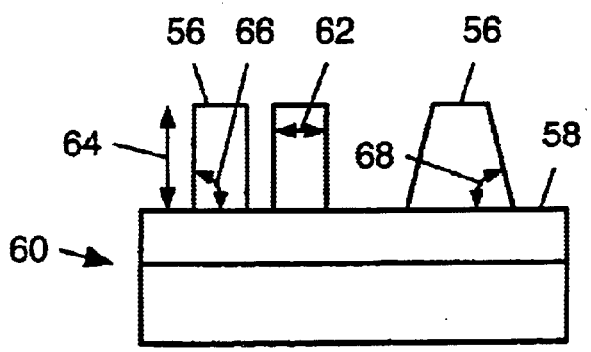
FIG. 8 depicts a schematic side view of an embodiment of a specimen.

FIG. 8 illustrates a schematic side view of an embodiment of a specimen. As shown in FIG. 8, a plurality of features 56 may be formed upon upper surface 58 of specimen 60. For example, features formed on an upper surface of the specimen may include local interconnects, gate structures such as gate electrodes and dielectric sidewall spacers, contact holes, and vias. The plurality of features, however, may also be formed within the specimen. Features formed within the specimen may include, for example, isolation structures such as field oxide regions within a semiconductor substrate and trenches. A critical dimension may include a lateral dimension of a feature defined in a direction substantially parallel to an upper surface of the specimen such as width 62 of feature 56 on specimen 60. Therefore, a critical dimension may be generally defined as the lateral dimension of a feature when viewed in cross section such as a width of a gate or interconnect or a diameter of a hole or via. A critical dimension of a feature may also include a lateral dimension of a feature defined in a direction substantially perpendicular to an upper surface of the specimen such as height 64 of feature 56 on specimen 60.

In addition, a critical dimension may also include a sidewall angle of a feature. A "sidewall angle" may be generally defined as an angle of a side (or lateral) surface of a feature with respect to an upper surface of the specimen. In this manner, a feature having a substantially uniform width across a height of the feature may have sidewall angle 66 of approximately 90°. Features of a specimen such as a semiconductor device that have a substantially uniform width across a height of the features may be formed relatively closely together thereby increasing device density of the semiconductor device. In addition, such a device may have relatively predictable and substantially uniform electrical properties. A feature having a tapered profile or non-uniform width across a height of the feature may have sidewall angle 68 of less than approximately 90°. A tapered profile may be desired if a layer may be formed upon the feature. For example, a tapered profile may reduce the formation of voids within the layer formed upon the feature.

Overlay misregistration may be generally defined as a measure of the displacement of a lateral position of a feature on a first level of a specimen with respect to a lateral position of a feature on a second level of a specimen. The first level may be formed above the second level. For example, overlay misregistration may be representative of the alignment of features on multiple levels of a semiconductor device. Ideally, overlay misregistration is approximately zero such that features on a first level of a specimen may be perfectly aligned to features on a second level of a specimen. For example, a significant overlay misregistration may cause undesirable contact of electrical features on first and second levels of a specimen. In this manner, a semiconductor device formed on such a significantly misaligned specimen may have a number of open or short circuits thereby causing device failure.

An extent of overlay misregistration of a specimen may vary depending on, for example, performance characteristics of a lithography process. During lithography, a reticle, or a mask, may be disposed above a resist arranged on a first level of the specimen. The reticle may have substantially transparent regions and substantially opaque regions that may be configured in a pattern, which may be transferred to the resist. The reticle may be positioned above a specimen by an exposure tool configured to detect a position of an alignment mark on the specimen. In this manner, overlay misregistration may be caused by performance limitations of an exposure tool to detect an alignment mark and to alter a position of the reticle with respect to the specimen.

Figure 9:
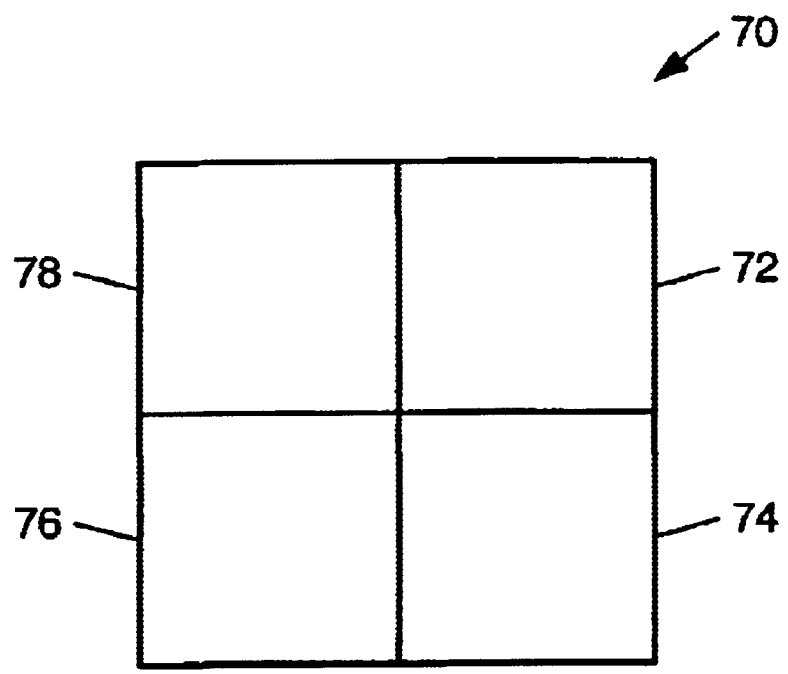
FIG. 9 depicts a schematic top view of an embodiment of a system having a plurality of measurement devices.

FIG. 9 illustrates a schematic top view of an embodiment of system 70 having a plurality of measurement devices. Each of the measurement devices may be configured as described herein. For example, each of the measurement devices may be configured to determine at least one property of a specimen. In addition, each of the measurement devices may be configured to determine a different property of a specimen. As such, system 70 may be configured to determine at least four properties of a specimen. For example, measurement device 72 may be configured to determine a critical dimension of a specimen. In addition, measurement device 74 may be configured to determine overlay misregistration of the specimen in a first lateral direction. Measurement device 76 may be configured to determine overlay misregistration of the specimen in a second lateral direction.

The first lateral direction may be substantially orthogonal to the second lateral direction. Furthermore, measurement device 78 may be configured as a pattern recognition device. As such, system 70 may be configured to determine at least four properties of the specimen simultaneously or sequentially. In addition, each of the measurement devices may be configured to determine any property of a specimen as described herein.

FIG. 10 illustrates a schematic side view of an embodiment of system 80 configured to determine at least two properties of a specimen. For example, system 80 may be configured to determine at least a critical dimension of a specimen. As such, system 80 may be included in system 70 as described in above embodiments. System 80 may include broadband light source 82. The term "broadband light" is generally used to refer to radiation having a frequency-amplitude spectrum that includes two or more different frequency components. A broadband frequency-amplitude spectrum may include a broad range of wavelengths such as from approximately 190 nm to approximately 1700 nm. The range of wavelengths, however, may be larger or smaller depending on, for example, the light source capability, the sample being illuminated, and the property being determined. For example, a xenon arc lamp may be used as a broadband light source and may be configured to emit a light beam including visible and ultraviolet light.

System 80 may also include beam splitter 84 configured to direct light emitted from light source 82 to a surface of a specimen 85. The beam splitter may be configured as a beam spotter mirror that may be configured to produce a continuous broadband spectrum of light. System 80 may also include lens 86 configured to focus light propagating from beam splitter 84 onto a surface of specimen 85. Light returned from the surface of specimen 85 may pass through beam splitter 84 to diffraction grating 88. The diffraction grating may be configured to disperse light returned from the surface of the specimen. The dispersed light may be directed to a spectrometer such as detector array 90. The detector array may include a linear photodiode array. The light may be dispersed by a diffraction grating as it enters the spectrometer such that the resulting first order diffraction beam of the sample beam may be collected by the linear photodiode array. Examples of spectroscopic reflectometers are illustrated in U.S. Pat. No. 4,999,014 to Gold et al., and U.S. Pat. No. 5,747,813 to Norton et al. and are incorporated by reference as if fully set forth herein.

The photodiode array, therefore, may measure the reflectance spectrum 92 of the light returned from the surface of the specimen. A relative reflectance spectrum may be obtained by dividing the intensity of the returned light of the reflectance spectrum at each wavelength by a relative reference intensity at each wavelength. A relative reflectance spectrum may be used to determine the thickness of various films on the wafer. In addition, the reflectance at a single wavelength and the refractive index of the film may also be determined from the relative reflectance spectrum. Furthermore, a model method by modal expansion ("MMME") model 94 may be used to generate library 96 of various reflectance spectrums. The MMME model is a rigorous diffraction model that may be used to calculate the theoretical diffracted light "fingerprint" from each grating in the parameter space. Alternative models may also be used to calculate the theoretical diffracted light, however, including, but not limited to, a rigorous coupling waveguide analysis ("RCWA") model. The measured reflectance spectrum 92 may be fitted to the various reflectance spectrums in library 96. The fitted data 97 may be used to determine critical dimension 95 such as a lateral dimension, a height, and a sidewall angle of a feature on the surface of a specimen as described herein. Examples of modeling techniques are illustrated in PCT Application No. WO 99/45340 to Xu et al., and is incorporated by reference as if fully set form herein.

Figure 11A:
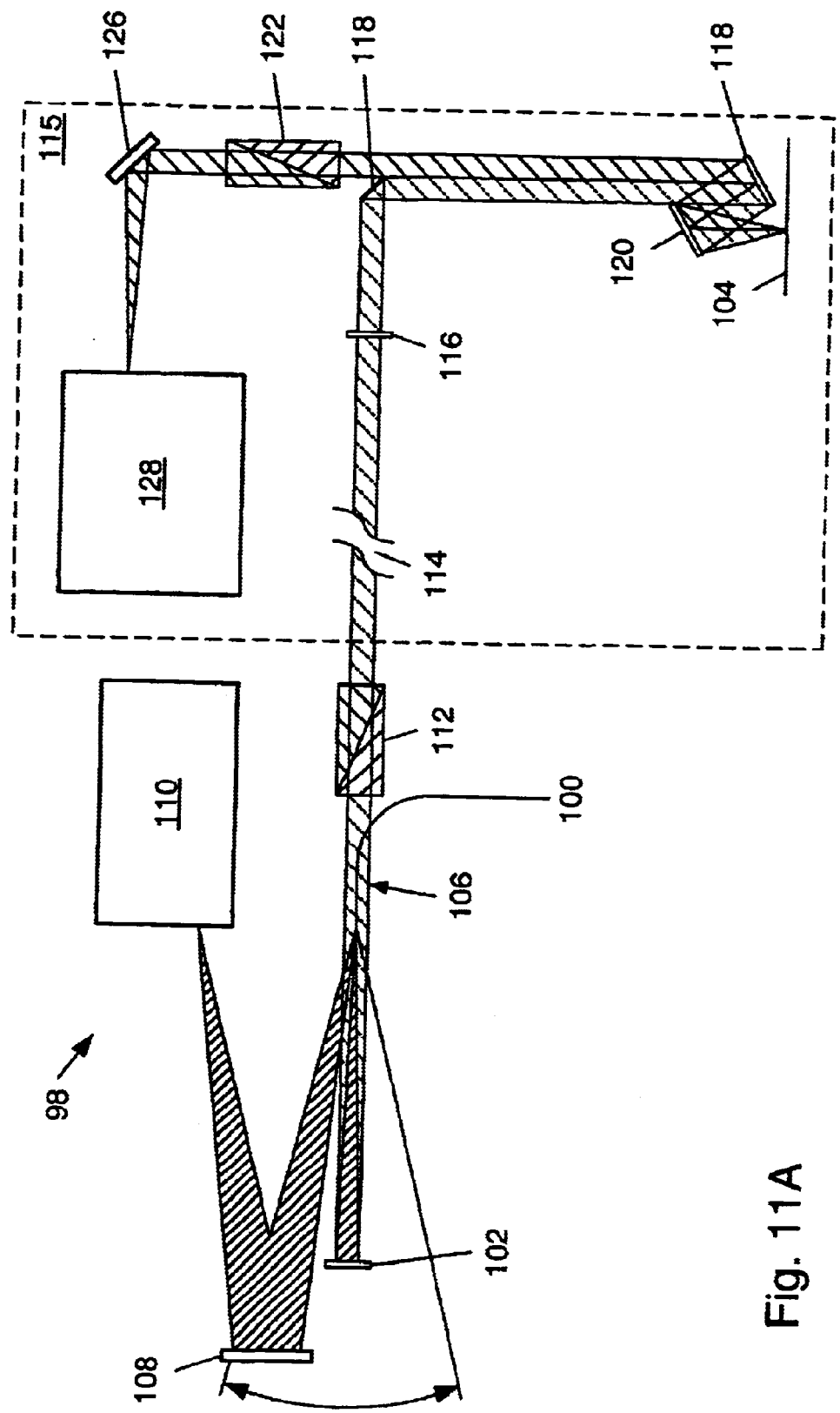
FIG. 11a depicts a schematic side view of an embodiment of a measurement device configured to determine a critical dimension of a specimen.
Figure 11B:
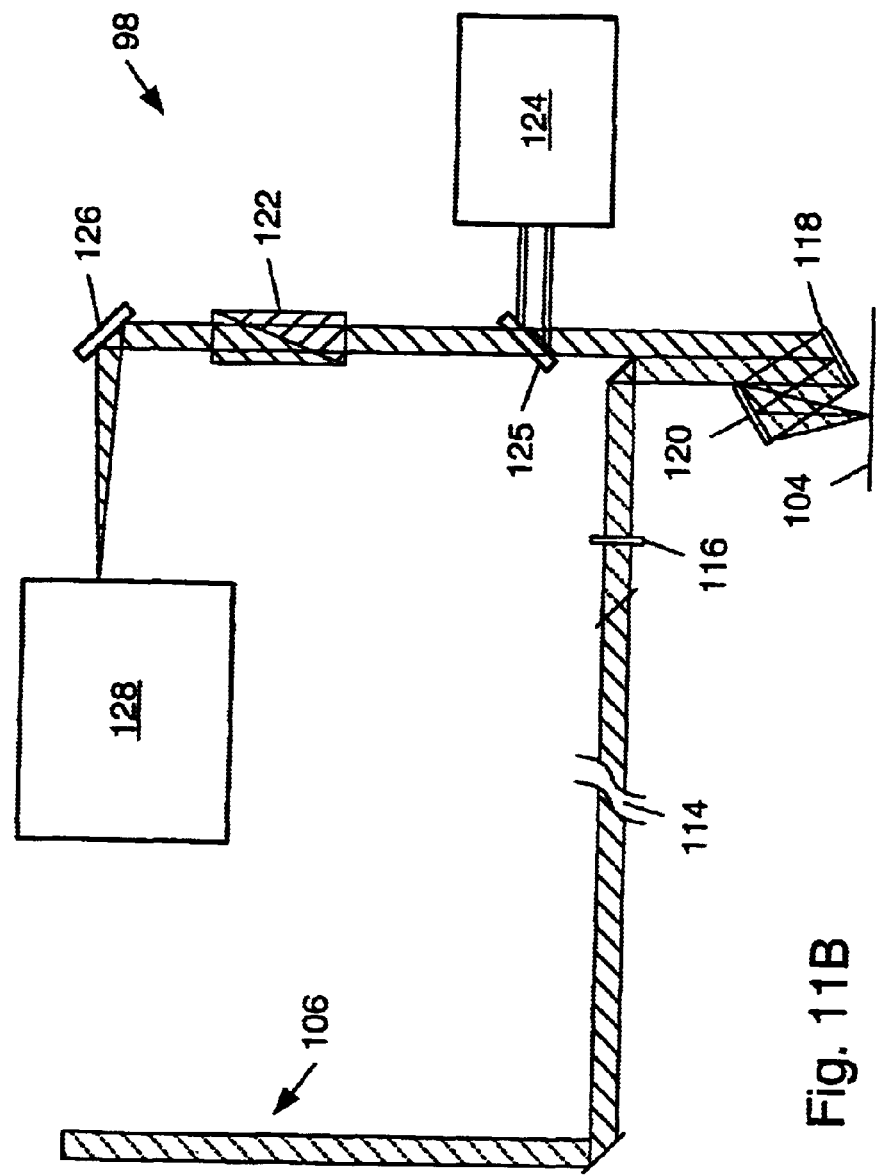
FIG. 11b depicts a schematic side view of an embodiment of a portion of a measurement device configured to determine a critical dimension of a specimen.

FIG. 11a and 11b illustrate additional schematic side views of an embodiment of measurement device 98 configured to determine a property such as a critical dimension of a specimen. The measurement device may be coupled to system 80 described above. Measurement device 98 may include fiber optic light source 100. The fiber optic light source may be configured to emit and direct light to collimating mirror 102. Collimating mirror 102 may be configured to alter a path of the light emitted by the fiber optic light source such that it propagates toward a surface of specimen 104 in substantially one direction along path 106. Light emitted by fiber optic light source 100 may also be directed to reflective mirror 108. Reflective mirror 108 may be configured to direct the light emitted by the fiber optic light source to reference spectrometer 110. Reference spectrometer 110 may be configured to measure an intensity of tight emitted by the fiber optic light source. In addition, reference spectrometer 110 may be configured to generate one or more output signals in response to the measured intensity of light. As such, the signal generated by reference spectrometer 110 may be used to monitor variations in the intensity of light emitted by the fiber optic light source.

Measurement device 98 may also include polarizer 112. Polarizer 112 may be oriented at a 45° angle with respect to path 106 of the light. Polarizer 112 may be configured to alter a polarization state of the light such that light propagating toward a surface of the specimen may be linearly or circularly polarized. Measurement device 98 may also include light piston 114 positioned along path 106 of the light. The light piston may be configured to alter a direction of the path of the light propagating toward the surface of the specimen. For example, portion 115 of the measurement device may be configured to move with respect to the specimen to measure multiple locations on the specimen. In this manner, the light position may be configured to cause light propagating along path 106 to traverse the surface of the specimen while leaving the angle of incidence at which light strikes the surface of the specimen substantially unchanged.

The measurement device may also include apodizer 116. Apodizer 116 may have a two dimensional pattern of alternating relatively high transmittance areas and substantially opaque areas. The alternating pattern may have a locally averaged transmittance function such as an apodizing function. As such, an apodizer may be configured to reduce a lateral area of an illuminated region of a specimen to improve a focusing resolution of the measurement device. The measurement device may also include a plurality of mirrors 118 configured to direct light propagating along path 106 to a surface of a specimen. In addition, the measurement device may also include reflecting objective lens 20 configured to direct the light to the surface of the specimen. For example, a suitable reflecting objective may have a numerical aperture ("NA") of approximately 0.1 such that light may be may be directed at a surface of the specimen at high angles of incidence.

Light returned from the surface of the specimen may be reflected by objective lens 120 and one of the mirrors to analyzer 122. Analyzer 122 may be configured to split the light returned from the surface of the specimen into two reflected light beams based on the polarization state of the light. For example, analyzer 112 may be configured to generate two separate beams of light having substantially different polarization states. As shown in FIG. 11b, measurement device may also include autofocus sensor 124. Autofocus sensor 124 may include a split photodiode detector configured to receive a substantially focused image of the illuminated spot on the specimen. The focused image of the spot may be provided by beam splitter 125 positioned along an optical path between analyzer 122 and mirror 118. For example, the beam splitter may be configured to direct a portion of the light returned from specimen 104 to the autofocus sensor. Autofocus sensor 124 may include two photodiodes configured to measure an intensity of the image and to send a signal representative of the measured intensity to a processor. The output of autofocus sensor may be called a focus signal. The focus signal may be a function of sample position. The processor may be configured to determine a focus position of the specimen with respect to the measurement device using a position of an extremum in the focus signal.

The measurement device may also include mirror 126 configured to direct light returned from the surface of the specimen to spectrometer 128. Spectrometer 128 may be configured to measure an intensity of the s and p components of reflectance across a spectrum of wavelengths. The term "s component" is generally used to describe the component of polarized radiation having an electrical field that is substantially perpendicular to the plane of incidence of the reflected beam. The term "p component" is generally used to describe the component of polarized radiation having an electrical field in the plane of incidence of the reflected beam. The measured reflectance spectrum may be used to determine a critical dimension, a height, and a sidewall angle of a feature on the surface of the specimen as described herein. For example, a relative reflectance spectrum may be obtained by dividing the intensity of the returned light at each wavelength measured by spectrometer 128 by a relative reference intensity at each wavelength measured by reference spectrometer 110 of the measurement device. The relative reflectance spectrum may be fitted to a theoretical model of the data such that a critical dimension, a height, and a sidewall angle may be determined.

In an embodiment, a measurement device configured as an interference microscope may include a an energy source such as a xenon lamp configured to emit an incident beam of light. An appropriate energy source may also include a light source configured to emit coherent light such as light that may be produced by a laser. The measurement device may further include additional optical components configured to direct the incident beam of light to a surface of the specimen. Appropriate additional optical components may include condenser lenses, filters, diffusers, aperture stops, and field stops. Additional optical components may also include beam splitters, microscopic objectives, and partially transmissive mirrors.

In an embodiment, a measurement device configured as an interference microscope may include a energy source such as a xenon lamp configured to emit an incident beam of light. An appropriate energy source may also include a light source configured to emit coherent light such as light that may be produced by a laser. The measurement device may further include additional optical components configured to direct the incident beam of light to a surface of the specimen. Appropriate additional optical components may include condenser lenses, filters, diffusers, aperture stops, and field stops. Additional optical components may also include beam splitters, microscopic objectives, and partially transmissive mirrors.

The optical components may be arranged within the measurement device such that a first portion of the incident beam of light may be directed to a surface of a specimen. The optical components may be further arranged within the measurement device such that a second portion of the incident beam of light may be directed to a reference mirror. For example, the second portion of the incident beam of light may be generated by passing the incident beam of light through a partially transmissive mirror prior to directing the sample beam to a surface of the specimen. Light reflected from the surface of the specimen may then be combined with light reflected from the reference mirror. In an embodiment, the detection system may include a conventional interferometer. The reflected incident beam of light may be combined with the reference beam prior to striking the interferometer. Since the incident beam of light reflected from the surface of the specimen and the reference beam reflected from the reference mirror are not in phase, interference patterns may develop in the combined beam. Intensity variations of the interference patterns in the combined beam may be detected by the interferometer.

The interferometer may be configured to generate a signal responsive to the detected intensity variations of the interference patterns of the combined beam. The generated signal may be processed to provide surface information about the measured surface. The measurement device may also include a spotter microscope to aid in control of the incident beam of light. The spotter microscope may be electronically coupled to the measurement device to provide some control of the incident beam of light. Examples of interference microscopes and methods of use are illustrated in U.S. Pat. No. 5,112,129 to Davidson et al., U.S. Pat. No. 5,438,313 to Mazor et al., U.S. Pat. No. 5,712,707 to Ausschnitt et al., U.S. Pat. No. 5,757,507 to Ausschnitt et al., U.S. Pat. No. 5,805,290 to Ausschnitt et al., U.S. Pat. No. 5,914,784 to Ausschnitt et al., U.S. Pat. No. 6,023,338 to Bareket, all of which are incorporated by reference as if fully set forth herein.

In an additional embodiment, a measurement device configured as an optical profilometer may be used to determine a height of a surface of a specimen. Optical profilometers may be configured to use light scattering techniques, light sectioning, and various interferometric optical profiling techniques as described herein. An optical profilometer may be configured to measure interference between light on two beam paths. As a height of a surface of a specimen changes, one of the beam path lengths may change thereby causing a change in the interference patterns. Therefore, the measured interference patterns may be used to determine a height of a surface of a specimen. A Nomarski polarization interferometer may be suitable for use as an optical profilometer.

In an embodiment, an optical profilometer may include a light source such as a tungsten halogen bulb configured to emit an incident beam. The light source may be configured to emit light of various wavelengths such as infrared light, ultraviolet light, and/or visible light. The light source may also be configured to emit coherent light such as light produced from a laser. The optical profilometer may also include optical components configured to direct the light to a surface of a specimen. Such optical components may include any of the optical components as described herein. The optical profilometer may further include a rotating analyzer configured to phase shift the electromagnetic radiation, a charge coupled device ("CCD") camera, a frame grabber, and electronic processing circuits. A frame grabber is a device that may be configured to receive a signal from a detector such as a CCD camera and to convert the signal (i.e., to digitize an image). A quarter wavelength plate and spectral filter may also be included in the optical profilometer. A polarizer and Nomarski prism may be configured to illuminate the specimen with two substantially orthogonally polarized beams laterally offset on the specimen surface by a distance smaller than the resolution limit of the objectives. After returned from the specimen, the light beams may be recombined by the Nomarski prism.

In an embodiment, the optical profilometer may include a conventional interferometer. Interference patterns of the recombined light beams may be detected by the interferometer. The detected interference patterns may be used to determine a surface profile of the specimen. An example of an optical profilometer is illustrated in U.S. Pat. No. 5,955,661 to Samsavar et al., which is incorporated by reference as if fully set forth herein. An example of a measurement device configured to determine overlay misregistration is illustrated in U.S. patent application Ser. No. 09/639,495, "Metrology System Using Optical Phase," to Nikoonahad et al., filed Aug. 14, 2000, and is incorporated by reference as if fully set forth herein.

In an embodiment, measurement device 78 may be configured as a pattern recognition device. Measurement device 78 may include a light source such as a lamp configured to emit broadband light, which may include visible and ultraviolet radiation. The measurement device may also include a beam splitting mirror configured to direct a portion of the light emitted by the light source to an objective thereby forming a sample bean of light. The objective may include reflective objectives having several magnifications. For example, the objective may include a 15× Schwartchild design all-reflective objective, a 4× Nikon CFN Plan Apochromat, and a 1× UV transmissive objective. The three objectives may be mounted on a turret configured to rotate such that one of the three objectives may be placed in a path of the sample beam of light. The objective may be configured to direct the sample beam of light to a surface of a specimen.

Light returned from the surface of the specimen may pass back through the objective and the beam splitting mirror to a sample plate of the measurement device. The sample plate may be a reflective fused silica plate with an aperture formed through the plate. The light returned from the surface of the specimen may be partially reflected off of the sample plate and through a relatively short focal length achromat. The returned light may be reflected from a folding mirror to a beam splitter cube. The beam splitter cube may be configured to direct a portion of the returned light to a pentaprism. The pentaprism may be configured to reflect the portion of the returned light. The reflected portion of the returned light may also pass through additional optical components of measurement device 78 such as a relatively long focal length achromat and a filter. The reflected portion of the returned light may pass to a folding mirror configured to direct the returned light to a video camera. In addition, the video camera may be configured to generate a non-inverted image of the surface of the specimen. An example of a pattern recognition device is illustrated in U.S. Pat. No. 5,910,842 to Piwonka-Corle et al., and is incorporated by reference as if fully set forth herein.

In an additional embodiment, the measurement device may be configured as a non-imaging scatterometer, a scatterometer, or a spectroscopic scatterometer. Scatterometry is a technique involving the angle-resolved measurement and characterization of light scattered from a structure. For example, structures arranged in a periodic pattern on a specimen such as repeatable pattern features may scatter or diffract incident light into different orders. A diffracted light pattern from a structure may be used as a "fingerprint" or "signature" for identifying a property of the repeatable pattern features. For example, a diffracted light pattern may be analyzed to determine a property of repeatable pattern features on a surface of a specimen such as a period, a width, a step height, a sidewall angle, a thickness of underlying layers, and a profile of feature on a specimen.

A scatterometer may include a light source configured to direct light of a single wavelength toward a surface of the specimen. For example, the light source may include a gas laser or a solid state laser diode. Alternatively, the light source may be configured to direct light of multiple wavelengths toward a surface of the specimen. As such, the scatterometer may be configured as a spectroscopic scatterometer. In an example, the light source may be configured to emit broadband radiation. An appropriate broadband light source may include a white light source coupled to a fiber optic cable configured to randomize a polarization state of the emitted light and may create a substantially uniform incident beam of light. Light emitted from the fiber optic cable may pass through a plurality of optical components arranged within the measurement device. For example, light emitted from the fiber optic cable may pass through a slit aperture configured to limit a spot size of the incident beam of light. A spot size may be generally defined as a surface area of a specimen that may be illuminated by an incident beam of light. Light emitted from the fiber optic cable may also pass through a focusing lens. Furthermore, light emitted from the fiber optic cable may be further passed through a polarizer configured to produce an incident beam of light having a known polarization state. The incident beam of light having a known polarization state may be directed to a surface of the specimen.

The scatterometer may also include a detection system that may include a spectrometer. The spectrometer may be configured to measure an intensity of different wavelengths of light scattered from a surface of a specimen. In an embodiment, the zeroth diffraction order intensity may be measured. Although for some repeatable pattern features, measurement of higher diffraction order intensities may also be possible. A signal responsive to the zeroth and/or higher diffraction order intensities at different wavelengths generated by the spectrometer may be sent to a processor coupled to the spectrometer. The processor may be configured to determine a signature of a structure on a surface of the specimen. In addition, the processor may be configured to determine a property of repeatable pattern features on the surface of the specimen. For example, the processor may be further configured to compare the determined signature to signatures of a database. Signatures of the database may include signatures determined experimentally with specimens having brown characteristics and/or signatures determined by modeling. A property of a repeatable pattern feature may include a period, a width, a step height, a sidewall angle, a thickness of underlying layers, and a profile of the features on a specimen.

As described above, the scatterometer may include a polarizer coupled to the illumination system. The polarizer may be fiber configured to transmit light emitted by a light source of the illumination system of a first polarization state and to reflect light emitted by a light source of a second polarization state. In addition, the scatterometer may also include an analyzer coupled to the detection system. The analyzer may be configured to transmit light of substantially the same polarization state as the polarizer. For example, the analyzer may be configured to transmit light scattered from the surface of the specimen having the first polarization state. In an additional embodiment, the spectrometer may include a stage coupled to the illumination system and the detection system. The stage may be configured as described herein. In this manner, characteristics of repeatable pattern features having substantially different characteristics formed on a surface of a specimen may be determined sequentially or simultaneously. Examples of measurement devices are illustrated in PCT Application No. WO 99/45340 to Xu et al., and is incorporated by reference as if fully set forth herein. Additional examples of measurement devices configured to measure light scattered from a specimen are illustrated in U.S. Pat. No. 6,081,325 to Leslie et al., U.S. Pat. No. 6,201,601 to Vaez-Iravani et al., and U.S. Pat. No. 6,215,551 to Nikoonahad et al., and are incorporated by reference as if fully set forth herein.

A measurement device such as a scatterometer may be either an imaging device or a non-imaging device. In imaging devices, a lens may capture light scattered from a surface of a specimen. The lens may also preserve spatial information encoded in the reflected light (e.g., a spatial distribution of light intensity). In addition, the scatterometer may include a detector configured as an array of light sensitive devices such as a charge-coupled device ("CCD") camera, a CMOS photodiode, or a photogate camera Alternatively, in non-imaging devices, light from a light source may be directed to a relatively small area on a surface of a specimen. A detector such as a photomultiplier tube, a photodiode, or an avalanche photodiode may detect scattered or diffracted light and may produce a signal proportional to the integrated light intensity of the detected light.

In an additional embodiment, the measurement device may be configured as a bright field imaging device, a dark field imaging device, or a bright field and dark field imaging device. "Bright field" generally refers to a collection geometry configured to collect specularly reflected light from a specimen. A bright field collection geometry may have any angle of incidence although typically it may have an angle of incidence normal to the specimen plane. A bright field imaging device may include a light source configured to direct light to a surface of a specimen. The light source may also be configured to provide substantially continuous illumination of a surface of a specimen. The light source may be, for example, a fluorescent lamp tube. Continuous illumination may also be achieved by a string of point light sources coupled to a light diffusing element. The light source may also include any of the light sources as described herein.

A bright field imaging device may also include a bright field imaging system configured to collect bright field light propagating along a bright field path from the surface of a specimen. The bright field light may include light specularly reflected from the surface of the specimen. The bright field imaging system may include optical components such as slit mirrors and an imaging lens. The slit mirrors may be configured to direct bright field light propagating along a bright field path from the surface of a specimen to the imaging lens. The imaging lens may be configured to receive bright field light reflected from the slit mirrors. The imaging lens may be, for example, a fixed lens configured to reduce optical aberrations in the bright field light and to reduce effects of intensity reduction at an edge of the imaging field. The imaging lens may also be configured to concentrate light passing through the lens onto light sensitive devices positioned behind the imaging lens. The light sensitive devices may include, but are not limited to, an 8000 PN diode element line scan sensor array, a CCD camera, a TDI camera, or other suitable device type.

One or more output signals of the light sensitive devices may be transmitted to an image computer for processing. An image computer may be a parallel processing system that may be commonly used by the machine vision industry. The image computer may also be coupled to a host computer configured to control the bright field imaging device and to perform data processing functions. For example, data processing functions may include determining a presence of defects on a surface of a specimen by comparing multiple output signals of the light sensitive devices generated by illuminating multiple locations on the specimen. Multiple locations on the specimen may include, for example, two dies of a specimen, as illustrated in FIG. 1.

"Dark field" generally refers to a collection geometry configured to collect only scattered light from a specimen. "Double dark field" generally refers to an inspection geometry using a steep angle oblique illumination, and a collection angle outside of the plane of incidence. Such an arrangement may include a near-grazing illumination angle and a near-grazing collection angle to suppress surface scattering. This suppression occurs because of the dark fringe (also known as the Weiner fringe) near the surface that may occur due to interfering incident and reflected waves. A dark field imaging device may include any of the light sources as described herein. A double dark field device may be either an imaging device or a non-imaging device.

A dark field imaging device may also-include a dark field imaging system configured to collect dark field light propagating along a dark field path from the surface of a specimen. The dark field imaging system may include optical components, an image computer, and a host computer as described herein. In this manner, a presence of defects on a surface of a specimen may be determined from a dark field image of the specimen as described herein. An example of an inspection system configured for dark field imaging is illustrated in PCT Application No. WO 99/31490 to Almogy, and is incorporated by reference as if fully set forth herein.

In addition, a measurement device may include bright field and dark field light sources, which may include one or more light sources. Each of the light sources may be arranged at different angles of incidence with respect to the surface of the specimen. Alternatively, each of the light sources may be arranged at the same angle of incidence with respect to the surface of the specimen. The measurement device may also include bright field and dark field imaging systems as described above. For example, the measurement device may include one or more imaging systems. Each of the imaging systems may be arranged at different angles of incidence with respect to the surface of the specimen. Alternatively, each of the imaging systems may be arranged at the same angle of incidence with respect to the surface of the specimen. As such, the measurement device may be configured to operate as a bright field and dark field imaging device. Each of the imaging systems may be coupled to the same image computer, which may be configured as described above. In addition, the image computer may be coupled to a host computer, which may be configured as described above. The host computer may also be configured to control both the bright field components and the dark field components of the measurement device.

The bright field, dark field, and bright field and dark field devices, however, may also be configured as non-imaging devices. For example, the detectors described above may be replaced with a photomultiplier tube, a photodiode, or an avalanche photodiode. Such detectors may be configured to produce a signal proportional to the integrated light intensity of the bright field light and/or the dark field light.

Figure 12:
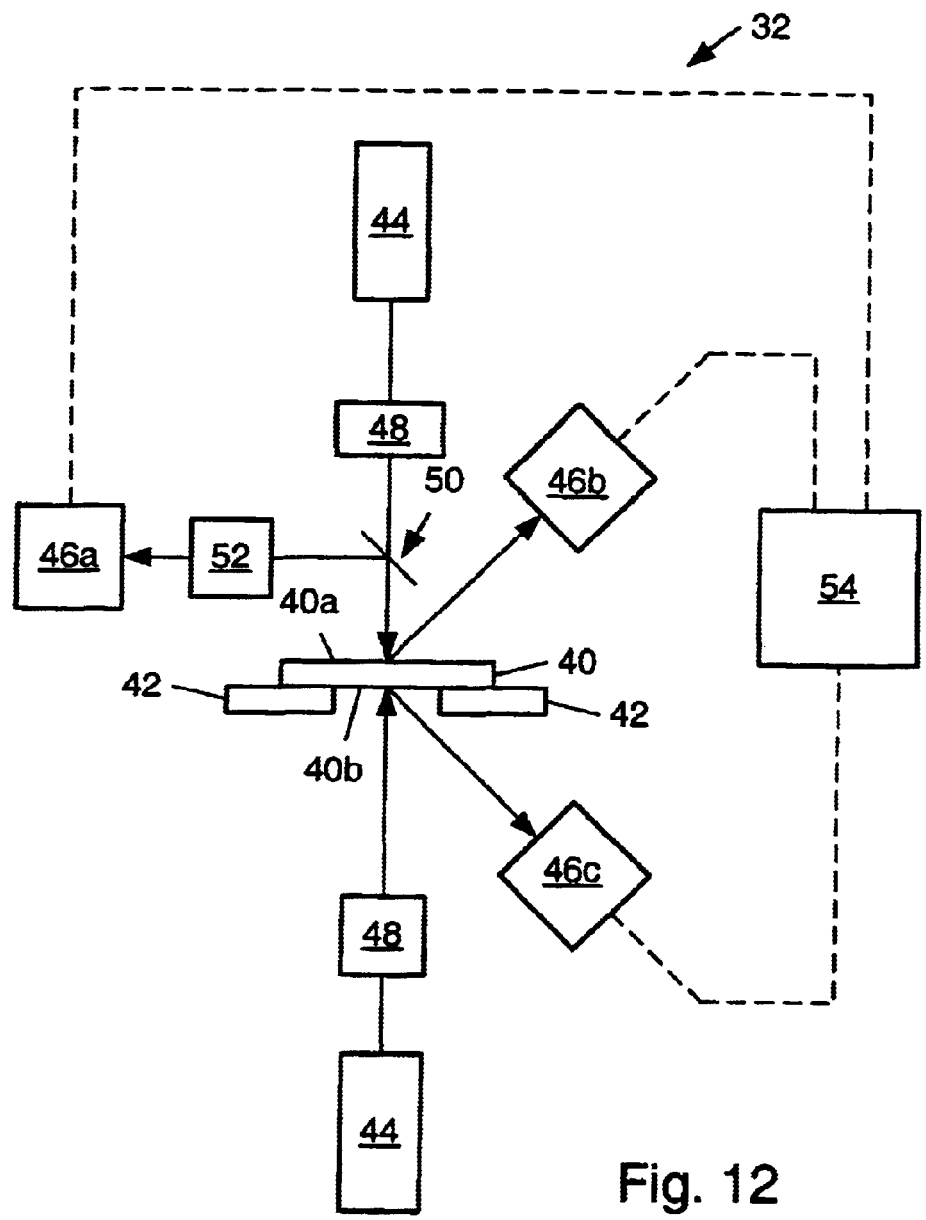
FIG. 12 depicts a schematic side view of an embodiment of a system configured to determine multiple properties of multiple surfaces of a specimen.

FIG. 12 illustrates a schematic side view of an alternate embodiment of system 32 configured to determine at least two properties of a specimen during use. As will be fiber described herein, elements of system 32 which may be similarly configured in each of the embodiments illustrated in FIGS. 3–7 and 12 have been indicated by the same reference characters. For example, stage 42 may be similarly configured in each of the embodiments illustrated in FIGS. 3–7 and 12.

As used herein, the terms "front side" and "back side" generally refer to opposite sides of a specimen. For example, the term, a "front side", or "upper surface," of a specimen such as a wafer may be used to refer to a surface of the wafer upon which semiconductor devices may be formed. Likewise, the term, a "back side", or a "bottom surface," of a specimen such as a wafer may be used to refer to a surface of the wafer which is substantially free of semiconductor devices.

System 32 may include stage 42 configured to support specimen 40. As shown in FIG. 12, stage 42 may contact a back side of the specimen proximate to an outer lateral edge of the specimen to support the specimen. For example, the stage may include a robotic wafer handler configured to support a spectrum. In alternative embodiments, an upper surface of the stage may be configured to have a surface area less than a surface area of the back side of the specimen. In this manner, stage 42 may contact a back side of the specimen proximate to a center, or an inner surface area, of the specimen to support the specimen. In an example, the stage may include a vacuum chuck or an electrostatic chuck. Such a stage may be disposed within a process chamber of a process tool such as a semiconductor fabrication process tool and may be configured to support the specimen during a process step such as a semiconductor fabrication process step. Such a stage may also be included in any of the other measurement devices as described herein.

System 32 may include a measurement device coupled to the stage. The measurement device may include a plurality of energy sources 44. A first of the plurality of energy sources 44 may be configured to direct energy toward front side 40a of specimen 40. As shown in FIG. 12, two detectors 46a and 46b may be coupled to the first of the plurality of energy sources. The two detectors may be positioned at different angles with respect to the first energy source. In this manner, each of the detectors may be configured to detect different types of energy propagating from front side 40a of specimen 40. For example, detectors 46b may be configured to detect dark field light propagating from the front side of specimen 40. In addition, detector 46a may be configured to detect bright field light propagating from the front side of specimen 40. In an alternative embodiment, however, a single detector, either detector 46a or detector 46b, may be included in the measurement device and may be coupled to the first energy source. Additional components such as component 48 may also be coupled to the energy source. For example, component 48 may include any of the optical components as described herein.

The measurement device may also include component 50. Component 50 may include, for example, a beam splitter configured to transmit light from the light source toward specimen 40 and to reflect light propagating firm specimen 40 toward detector 46a. The measurement device may also include additional component 52 coupled to detector 46a. Component 52 may be configured as described in above embodiments. In addition, such a component may also be coupled to detector 46b. The position and the configuration of each of the components may vary, however, depending on, for example, the properties of the specimen to be measured with the system.

In an embodiment, a second of the plurality of energy sources 44 may be configured to direct energy toward back side 40b of specimen 40. The measurement device may also include detector 46c coupled to the second energy source. In addition, multiple detectors may be coupled to the second energy source. Detector 46c may be positioned with respect to the second energy source such that a particular type of energy propagating from back side 40b of specimen 40 may be detected. For example, detector 46c may be positioned with respect to the second energy source such that dark field light propagating along a dark field path from the back side 40b of specimen 40 may be detected. Additional component 48 may also be coupled to the second energy source. Component 48 may include any of the optical components as described herein. Furthermore, system 32 may include processor 54. Processor 54 may be coupled to each of the detectors 46a, 46b, and 46c, as shown in FIG. 12. The processor may be configured as described herein.

According to the above embodiment, therefore, system 32 may be configured to determine at least two properties on at least two surfaces of a specimen. For example, system 32 may be configured to determine a presence of defects on a front side of the specimen. In addition, system 32 may be configured to determine a presence of defects on a back side of the specimen. Furthermore, the system may be configured to determine a presence of defects on an additional surface of the specimen. For example, the system may be configured to determine a presence of defects on a front side, a back side, and an edge of the specimen. As used herein, the term "an edge" of a specimen generally refers to an outer lateral surface of the specimen substantially normal to the front and back sides of the specimen. Furthermore, the system may also be configured to determine a presence of defects on more than one surface of the specimen simultaneously.

In an additional embodiment, the system may also be configured to determine a number of defects on one or more surfaces of a specimen, a location of defects on one or more surfaces of a specimen, and/or a we of defects on one or more surfaces of a specimen sequentially or substantially simultaneously. For example, the processor may be configured to determine a number, location, and/or type of defects on one or more surfaces of a specimen from the energy detected by the measurement device. Examples of methods for determining the type of defect present on a surface of a specimen are illustrated in U.S. Pat. No. 5,831,865 to Berezin et al., and is incorporated by reference as if fully set forth herein. Additional examples of methods for determining the type of defects present on a surface of a specimen are illustrated in WO 99/67626 to Ravid et al., WO 00/03234 to Ben-Porath et al., and WO 00/26646 to Hansen, and are incorporated by reference as if fully set forth herein.

Furthermore, processor 54 may be further configured to determine at least three properties of the specimen. The three properties may include a critical dimension of the specimen, an overlay misregistration of the specimen, and a presence, a number, a location, and/or a type of defects on one or more surfaces of the specimen. In this manner, the system may be configured to determine a critical dimension of the specimen, an overlay misregistration of the specimen, and a presence, a number, a location, and/or a type of defects on one or more surfaces of the specimen sequentially or substantially simultaneously.

The system may be configured to determine micro and/or macro defects on one or more surfaces of a specimen sequentially or substantially simultaneously. An example of a system configured to determine macro and micro defects sequentially is illustrated in U.S. Pat. No. 4,644,172 to Sandland et al., which is incorporated by reference as if fully set forth herein. Macromicro optics, as described by Sandland, may be incorporated into a measurement device, as described herein, which may be coupled to one stage. The stage may be configured as described herein. In this manner, the macromicro optics of Sandland may be configured to determine micro and/or macro defects on one or more surfaces of a specimen substantially simultaneously. In addition, the macro micro optics of Sandland may be configured to determine micro and macro defects on one or more surfaces of a specimen sequentially while the specimen is disposed on a single stage. Alternatively, the measurement device may include optical components configured as illustrated in U.S. Pat. No. 5,917,588 to Addiego, which is incorporated by reference as if fully set forth herein. For example, a measurement device, as described herein, may include micro optics, as described by Sandland, coupled to macro optics of the after develop inspection ("ADI") Macro inspection system, as described by Addiego.

Micro defects may typically have a lateral dimension of less than approximately 25 µm. Macro defects may include yield limiting large scale defects having a lateral dimension of greater than about 25 µm. Such large scale defects may include resist or developer problems such as lifting resist, thin resist, extra photoresist coverage, incomplete or missing resist, which may be caused by clogged dispense nozzles or an incorrect process sequence, and developer or water spots. Additional examples of macro defects may include regions of defocus ("hot spots"), reticle errors such as tilted reticles or incorrectly selected reticles, scratches, pattern integrity problems such as over or under developing of the resist, contamination such as particles or fibers, and non-uniform or incomplete edge bead removal ("EBR"). The term "hot spots" generally refers to a photoresist exposure defect that may be caused, for example, by a depth of focus limitation of an exposure tool, an exposure tool malfunction, a non-planar surface of a specimen at the time of exposure, foreign material on a back side of a specimen or on a surface of a supporting device, or a design constraint. For example, foreign material on the back side of the specimen or on the surface of a supporting device may effectively deform the specimen. Such deformation of the specimen may cause a non-uniform focal surface during an exposure process. In addition, such a non-uniform focal surface may be manifested on the specimen as an unwanted or missing pattern feature change.

Each of the above described defects may have a characteristic signature under either dark field or bright field illumination. For example, scratches may appear as a bright line on a dark background under dark field illumination. Extra photoresist and incomplete photoresist coverage, however, may produce thin film interference effects under bright field illumination. In addition, large defocus defects may appear as a dim or bright pattern in comparison to a pattern produced by a laterally proximate die under dark field illumination. Other defects such as defects caused by underexposure or overexposure of the resist, large line width variations, large particles, comets, striations, missing photoresist, underdeveloped or overdeveloped resist, and developer spots may have characteristic signatures under bright field and dark field illumination.

As shown in FIG. 1, a surface of specimen 10 may have a plurality of defects. Defect 14 on the surface of specimen 10 may be incomplete resist coverage. For example, incomplete resist coverage may be caused by a malfunctioning coating tool or a malfunctioning resist dispense system. Defect 16 on the surface of specimen 10 may be a surface scratch. Defect 18 on the surface of specimen 10 may be a non-uniform region of a layer of resist. For example, such a non-uniform region of the resist may be caused by a malfunctioning coating tool or a malfunctioning post apply bake tool. Defect 20 on the surface of specimen 10 may be a hot spot. In addition, defect 22 on the surface of specimen 10 may be non-uniform edge bead removal ("EBR"). Each of the defects described above may be present in any location on a surface of specimen 10. In addition, any number of each of the defects may also be present on the surface of the specimen.

Additional examples of methods and systems for determining a presence of defects on a surface of a specimen are illustrated in U.S. Pat. No. 4,247,203 to Levy et al., U.S. Pat. No. 4,347,001 to Levy et al., U.S. Pat. No. 4,378,159 to Galbraith, U.S. Pat. No. 4,448,532 to Joseph et al., U.S. Pat. No. 4,532,650 to Wihl et al., U.S. Pat. No. 4,555,798 to Broadbent, Jr. et al., U.S. Pat. No. 4,556,317 to Sandland et al., U.S. Pat. No. 4,579,455 to Levy et al., U.S. Pat. No. 4,601,576 to Galbraith, U.S. Pat. No. 4,618,938 to Sandland et al., U.S. Pat. No. 4,633,504 to Wihl, U.S. Pat. No. 4,641,967 to Pecen, U.S. Pat. No. 4,644,172 to Sandland et al., U.S. Pat. No. 4,766,324 to Saadat et al., U.S. Pat. No. 4,805,123 to Specht et al., U.S. Pat. No. 4,818,110 to Davidson, U.S. Pat. No. 4,845,558 to Tsai et al., U.S. Pat. No. 4,877,326 to Chadwick et al., U.S. Pat. No. 4,898,471 to Vaught et al., U.S. Pat. No. 4,926,489 to Danielson et al., U.S. Pat. No. 5,076,692 to Neukermans et al., U.S. Pat. No. 5,189,481 to Jann et al., U.S. Pat. No. 5,264,912 to Vaught et al., U.S. Pat. No. 5,355,212 to Wells et al., U.S. Pat. No. 5,537,669 to Evans et al., U.S. Pat. No. 5,563,702 to Emery et al., U.S. Pat. No. 5,565,979 to Gross, U.S. Pat. No. 5,572,598 to Wihl et al., U.S. Pat. No. 5,604,585 to Johnson et al., U.S. Pat. No. 5,737,072 to Emery et al., U.S. Pat. No. 5,798,829 to Vaezlravani, U.S. Pat. No. 5,633,747 to Nikoonahad, U.S. Pat. No. 5,822,055 to Tsai et al., U.S. Pat. No. 5,825,482 to Nikoonahad et al., U.S. Pat. No. 5,864,394 to Jordan, et al., U.S. Pat. No. 5,883,710 to Nikoonahad et al., U.S. Pat. No. 5,917,588 to Addiego, U.S. Pat. No. 6,020,214 to Rosengaus et al., U.S. Pat. No. 6,052,478 to Wihl et al., U.S. Pat. No. 6,064,517 to Chuang et al., U.S. Pat. No. 6,078,386 to Tsai et al., U.S. Pat. No. 6,081,325 to Leslie et al., U.S. Pat. No. 6,175,645 to Elyasaf et al., U.S. Pat. No. 6,178,257 to Alumot et al., U.S. Pat. No. 6,122,046 to Almogy, and U.S. Pat. No. 6,215,551 to Nikoonahad et al., all of which are incorporated by reference as if fully set forth herein. Additional examples of defect inspection methods and apparatuses are illustrated in PCT Application Nos. WO 99/38002 to Elyasaf et al., WO 00/68673 to Reinhron et al., WO 00/70332 to Lehan, WO 01/03145 to Feuerbaum et al., and WO 01/13098 to Almogy et al., and are incorporated by reference as if fully set forth herein. Further examples of defect inspection methods and apparatuses are illustrated in European Patent Application Nos. EP 0 993 019 A2 to Dotan, EP 1 061 358 A2 to Dotan, EP 1 061 571 A2 to Ben-Porath, EP 1 069 609 A2 to Harvey et al., EP 1 081 489 A2 to Karpol et al., EP 1 081 742 A2 to Pearl et al., and EP 1 093 017 A2 to Kenan et al., which are incorporated by reference as if fully set forth herein. As such, the embodiments described above may also include features of any of the systems and methods illustrated in all of the patents which have been incorporated by reference herein.

In a further embodiment, the systems as described herein may also be configured to determine a flatness measurement of the specimen. "Flatness" may be generally defined as an average of the topographic characteristics of an upper surface of the specimen across a surface area of the specimen. For example, the topographic characteristics may include, but are not limited to, a roughness of an upper surface of a specimen and a planar uniformity of an upper surface of a layer arranged on the specimen. Roughness and planar uniformity of the upper surface of a layer may vary depending on, for example, processes performed on the specimen prior to measurement, which may include, in an example of semiconductor fabrication, etch, deposition, plating, chemical-mechanical polishing, or coating.

As described herein, a processor may be configured to determine at least three properties of the specimen from the detected energy. The three properties may include a critical dimension of the specimen, an overlay misregistration of the specimen, and a flatness of the specimen. In addition, the process may be configured to determine four properties of the specimen from the detected energy. The four properties may include critical dimension, overlay misregistration, flatness, and a presence, a number, a location, and/or a type of defects on the specimen. As such, the system may be configured to determine a critical dimension of the specimen, an overlay misregistration of the specimen, a flatness measurement, and/or a presence, a number, a location, and/or a type of defects on a surface of the specimen sequentially or substantially simultaneously.

Figure 13:
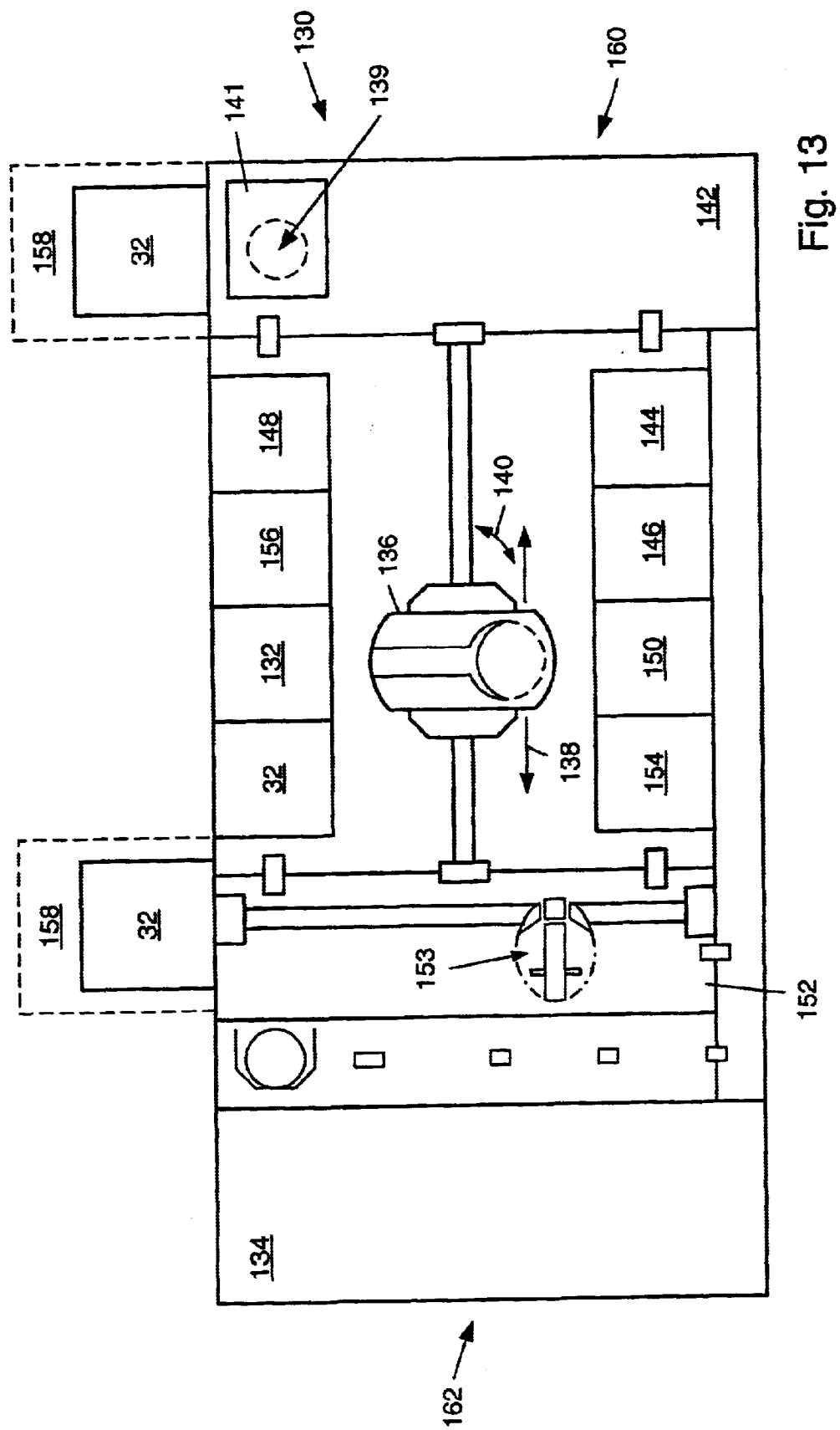
FIG. 13 depicts a schematic top view of an embodiment of a system coupled to a semiconductor fabrication process tool.

FIG. 13 illustrates a schematic top view of an embodiment of system 32 coupled to a semiconductor fabrication process tool. For example, the system may he coupled to lithography tool 130. A lithography tool, which may be commonly referred to a lithography track or cluster tool, may include a plurality of process chambers 132, 144, 146, 148, 150, 154, and 156. The number and configuration of the process chambers may vary depending on, for example, the type of wafers processed in the lithography tool. Examples of lithography tools and processes are illustrated in U.S. Pat. No. 5,393,624 to Ushijima, U.S. Pat. No. 5,401,316 to Shiraishi et al., U.S. Pat. No. 5,516,608 to Hobbs et al., U.S. Pat. No. 5,968,691 to Yoshioka et al., and U.S. Pat. No. 5,985,497 to Phan et al., and are incorporated by reference as if fully set forth herein. Lithography tool 130 may be coupled to an exposure tool, which may include exposure chamber 134. A first portion of the process chambers may be configured to perform a step of a lithography process prior to exposure of a resist. A second portion of the process chambers may be configured to perform a step of the lithography process subsequent to exposure of the resist.

In an embodiment, lithography tool 130 may also include at least one robotic wafer handler 136. Robotic wafer handler 136 may be configured to move a specimen from a first process chamber to a second process chamber. For example, the robotic wafer handler may be configured to move along a direction generally indicated by vector 138. In addition, the robotic wafer handler may also be configured to rotate in a direction indicated by vector 140 such that a specimen may be moved from a first process chamber located on first side of the lithography tool to a second process chamber located on a second side of the lithography tool. The first side and the second side may be located on substantially opposite sides of the lithography tool. The robotic wafer handler may also be configured to move a specimen from lithography tool 130 to exposure chamber 134 of the exposure tool. In this manner, the robotic wafer handler may move a specimen sequentially through a series of process chambers such that a lithography process may be performed on the specimen.

The robotic wafer handler may be also configured to move specimen 139 from cassette 141 disposed within load chamber 142 of the lithography tool to a process chamber of the lithography tool. The cassette may be configured to hold a number of specimens which may be processed during the lithography process. For example, the cassette may be a front opening unified pod ("FOUP"). The robotic wafer handler may be configured to dispose the specimen in a process chamber such as surface preparation chamber 144. The surface preparation chamber may be configured to form an adhesion promoting chemical such as hexamethyldisilazane ("HMDS") on the surface of the specimen. HMDS may be deposited at a temperature of approximately 80° C. to approximately 180° C. Subsequent to the surface preparation process, the robotic wafer handier may be configured to remove the specimen from surface preparation chamber 144 and place the specimen into chill chamber 146. As such, chill chamber 146 may be configured to reduce a temperature of the specimen to a temperature suitable for subsequent processing (e.g., approximately 20° C. to approximately 25° C.).

In an additional embodiment, an anti-reflective coating may be formed on the surface of the specimen. The anti-reflective coating may be formed on the specimen by spin coating followed by a post apply bake process. Since tie post apply bake process for an anti-reflective coating generally may involve heating a coated specimen from approximately 170° C. to approximately 230° C., a chill process may also be performed subsequent to this post apply bake process.

A resist may be also formed upon the specimen. The robotic wafer handler may be configured to place the specimen into resist apply process chamber 148. A resist may be automatically dispensed onto an upper surface of the specimen. The resist may be distributed across the specimen by spinning the specimen at a high rate of speed. The spinning process may dry the resist such that the specimen may be removed from the resist apply process chamber without adversely affecting the coated resist. The robotic wafer handler may be configured to move the specimen from resist apply process chamber 148 to post apply bake process chamber 150. The post apply bake process chamber may be configured to heat the resist-coated specimen at a temperature of approximately 90° C. to approximately 140° C. The post apply bake process may be used to drive solvent out of the resist and to alter a property of the resist such as surface tension. Subsequent to the post apply bake process, the robotic wafer handler may be configured to move the specimen from the post apply bake process chamber 150 to chill process chamber 146. In this manner, a temperature of the specimen may be reduced to approximately 20° C. to approximately 25° C.

The robotic wafer handler may also be configured to move the specimen from chill process chamber 146 to exposure chamber 134. The exposure chamber may include interface system 152 coupled to lithography tool 130. Interface system 152 may include mechanical device 153 configured to move specimens between the lithography tool and the exposure chamber. The exposure tool may be configured to align a specimen in the exposure chamber and to expose the resist to energy such as deep-ultraviolet light. In addition, the exposure tool may be configured to expose the resist to a particular intensity of energy, or dose, and a particular focus condition. Many exposure tools may be configured to alter dose and focus conditions across a specimen, for example, from die to die. The exposure system may also be configured to expose an outer lateral edge of the specimen. In this manner, resist disposed proximal an outer lateral edge of the specimen may be removed. Removing the resist at the outer lateral edge of a specimen may reduce contamination in subsequent processes.

The robotic wafer handler may be further configured to move the specimen from exposure chamber 134 to post exposure bake process chamber 154. The specimen may then be subjected to a post exposure bake process step. For example, the post exposure bake process chamber may be configured to heat the specimen to a temperature of approximately 90° C. to approximately 150° C. A post exposure bake process may drive a chemical reaction in a resist, which may enable portions of the resist to be removed in subsequent processing. As such, the performance of the post exposure, process may be critical to the overall performance of the lithography process.

Subsequent to the post exposure process, the robotic wafer handler may be configured to move the specimen from post expose bake process chamber 154 to chill process chamber 146. After the specimen has been chilled, the robotic wafer handler may be configured to move the specimen to develop process chamber 156. The develop process chamber may be configured to sequentially dispense a developer chemical and water on the specimen such that a portion of the resist may be removed. As such, resist remaining on the specimen may be patterned. Subsequent to the develop process step, the robotic wafer handler may be configured to move the specimen from the develop process chamber to a hard bake process chamber or a post develop bake process chamber. A hard bake process may be configured to heat a specimen to a temperature of approximately 90° C. to approximately 130° C. A hard bake process may drive contaminants and any excess water from the resist and the specimen. The temperature of the specimen may be reduced by chill process as described herein.

In an embodiment, system 32 may be arranged laterally proximate to lithography tool 130 or another semiconductor fabrication process tool. As shown in FIG. 13, system 32 may be located proximate cassette end 160 of lithography tool 130 or proximate exposure tool end 162 of lithography tool 130. In addition, a location of system 32 with respect to lithography tool 130 may vary depending on, for example, a configuration of the process chambers within lithography tool 130 and clean room constraints for space surrounding lithography tool 130. In an alternative embodiment, system 32 may be disposed within lithography tool 130. A position of system 32 within lithography tool 130 may vary depending on, for example, a configuration of the process chambers within lithography tool 130. In addition, a plurality of systems 32 may be arranged laterally proximate and/or disposed within lithography tool 130. Each system may be configured to measure at least two different properties of a specimen. Alternatively, each system may be similarly configured.

In either of these embodiments, robotic wafer handler 136 may be configured to move a specimen from lithography tool 130 to a stage within system 32. For example, robotic wafer handler 136 may be configured to move a specimen to a stage within system 32 prior to or subsequent to a lithography process or between steps of a lithography process. Alternatively, a stage within system 32 may be configured to move a specimen from system 32 to lithography tool 130. In an example, the stage may include a wafer handler configured to move a specimen from system 32 to a process chamber of the lithography tool 130. Furthermore, the stage of system 32 may be configured to move the specimen from a first process chamber to a second process chamber within lithography tool 130. System 32 may also be coupled to the stage such that system 32 may move with the stage from a first process chamber to a second process chamber within lithography tool 130. In this manner, the system may be configured to determine at least two properties of a specimen as the specimen is being moved from a first process chamber to a second process chamber of lithography tool 130. An example of an apparatus and a method for scanning a substrate in a processing system is illustrated in European Patent Application No. EP 1 083 424 A2 to Hunter et al., and is incorporated by reference as if fully set forth herein.

Figure 14:
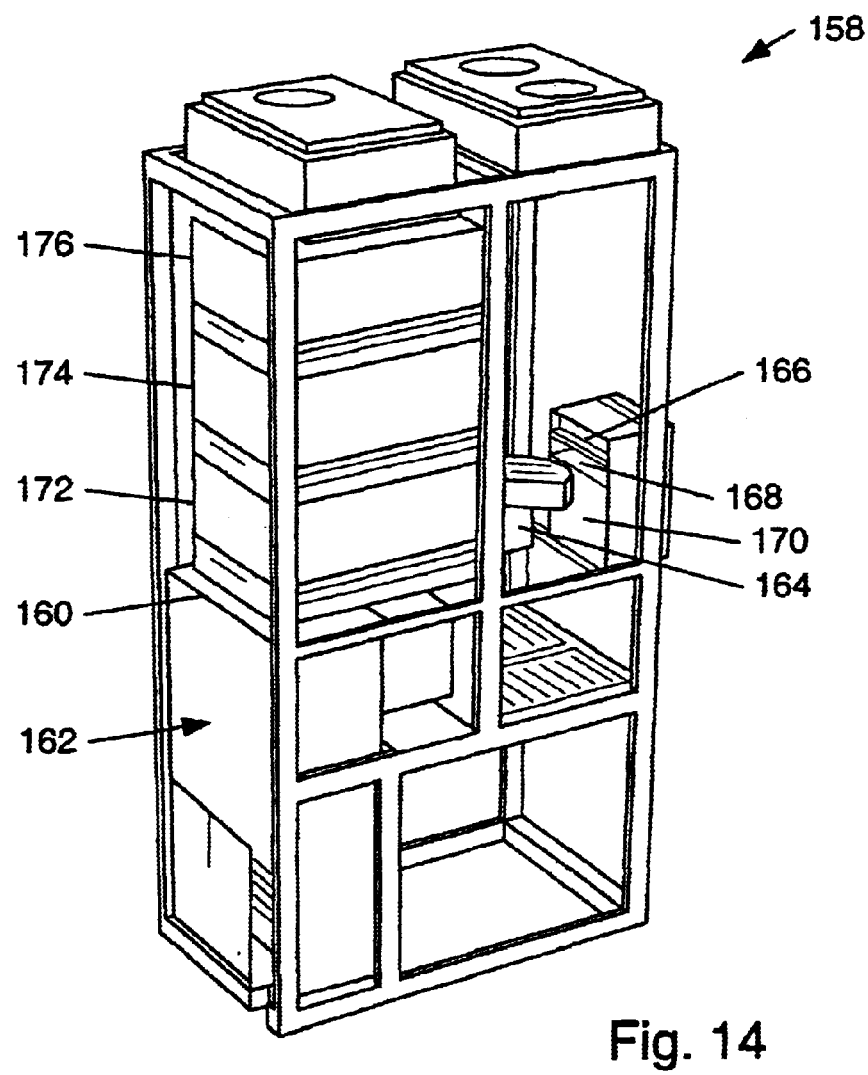
FIG. 14 depicts a perspective view of an embodiment of a system configured to be coupled to a semiconductor fabrication process tool.
Figure 15:
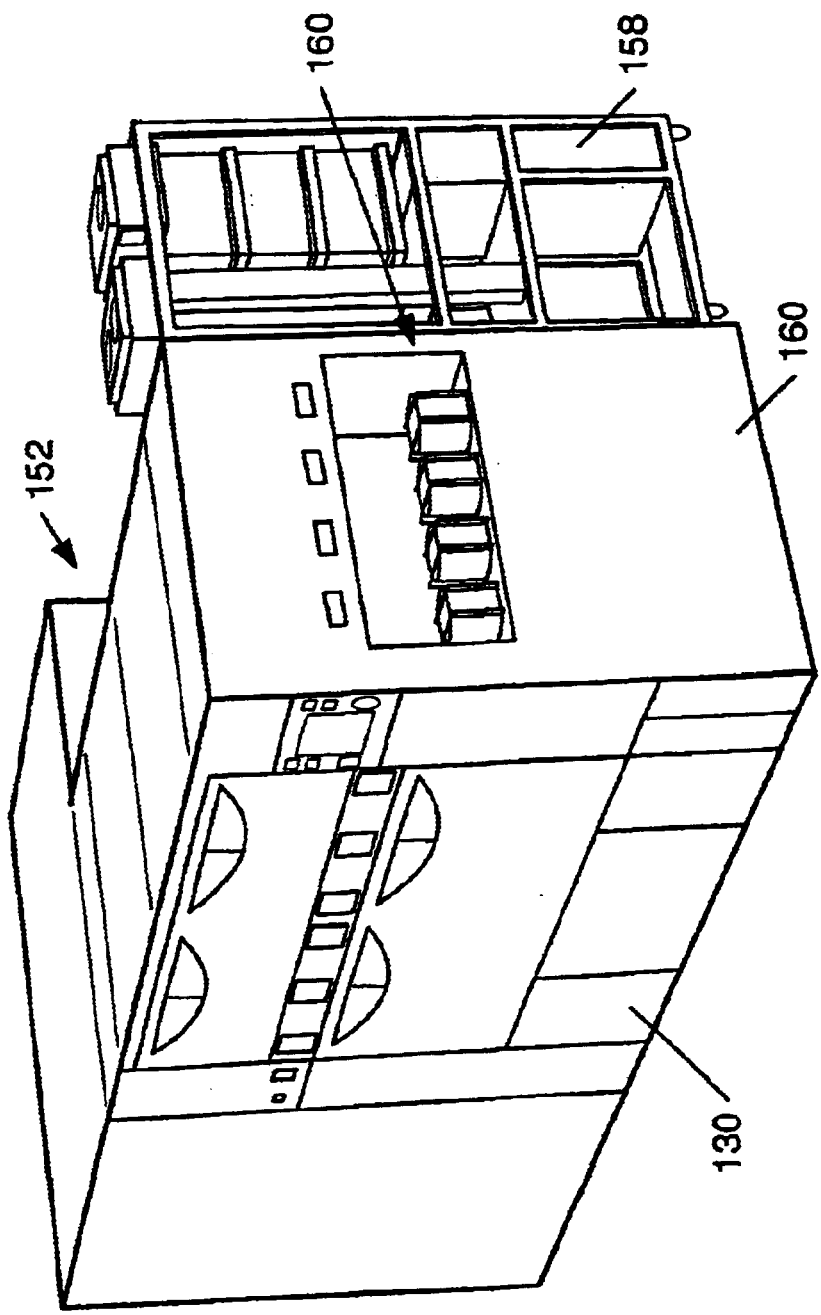
FIG. 15 depicts a perspective view of an embodiment of a system coupled to a semiconductor fabrication process tool.

In an embodiment, system 32 may be configured as an integrated station platform ("ISP") system. A system may be configured as a stand-alone cluster tool. Alternatively, the ISP system may be coupled to a process tool. FIG. 14 illustrates a perspective view of an embodiment of ISP system 158 that may be arranged laterally proximate and coupled to a semiconductor fabrication process tool such as lithography tool 130. In this manner, ISP system 158 may be configured as a cluster tool coupled to lithography tool 130. For example, as shown in phantom in FIG. 13, ISP system 158 may be coupled to cassette end 160 of lithography tool 130. FIG. 15 further illustrates a perspective view of an embodiment of ISP system 158 coupled to cassette end 160 of lithography tool 130. As further shown in phantom in FIG. 13, ISP system 158 may be also coupled to interface system 152 at exposure tool end 162 of lithography tool 130. ISP system 158 may be further configured as illustrated in U.S. Pat. No. 6,208,751 to Almogy, which is incorporated by reference as if fully set forth herein.

ISP system 158 may also be coupled to multiple process tools. For example, ISP system may be configured as a wafer buffer station between a lithography tool and an etch tool. In this manner, the ISP system may be configured to receive a specimen from the lithography tool subsequent to a lithography process and to send the specimen to an etch tool for an etch process. In addition, the ISP system may be configured to determine one or more properties of the specimen between the lithography and etch process. An example of a wafer buffer station is illustrated in PCT Application No. WO 99/60614 to Lapidot, and is incorporated by reference as if fully set forth herein. ISP system 158 may be farther configured as described by Lapidot.

ISP system 158 may include one or more measurement chambers. For example, the ISP system may have three measurement chambers 172, 174, 176. A measurement device may be disposed within each measurement chamber. Each measurement device may be configured as described herein. The measurement chambers may be arranged in unit 160. Environmental conditions within unit 160 may be controlled substantially independently from environmental conditions of the space surrounding ISP system 158. For example, environmental conditions within unit 160 such as relative humidity, particulate count, and temperature may be controlled by controller computer 162 coupled to the ISP system. Such a unit may be commonly referred to as a "mini-environment."

In addition, the one or more measurement chambers may be arranged such that first measurement chamber 172 may be located below second measurement chamber 174 and such that second measurement 174 may be located below third measurement chamber 176. In this manner, a lateral area or "footprint" of the ISP system may be reduced. Furthermore, because ISP system 158 may be coupled to a semiconductor fabrication process tool, one front interface mechanical standard ("FIMS") drop may be coupled to both the semiconductor fabrication process tool and the ISP system. As such, less FIMS drops may be required in a fabrication facility ("fab"), and in particular a 300 mm wafer fab. A FIMS drop may be a mechanical device configured to lower a FOUP from an overhead transportation system to a semiconductor fabrication process tool or a standalone inspection or metrology tool. An example of a specimen transportation system is illustrated in U.S. Pat. No. 3,946,484 to Aronstein et al., and is incorporated by reference as if fully set forth herein.

In an embodiment, ISP system 158 may also include wafer handler 164, receiving station 166, sending station 168, and buffer cassette station 170. Receiving station 166 and sending station 168 may be configured such that a wafer handler of a semiconductor fabrication process tool may move a specimen to the receiving station and from the sending station. Buffer cassette station 170 may be configured to hold a number of specimens depending on, for example, the relative input and output rates of a semiconductor fabrication process tool and ISP system 158. Receiving station 166 may also be configured to alter a position of a specimen such that the specimen may be substantially aligned to a measurement device coupled to one of the measurement chambers. For example, the receiving station may be configured to detect a positioning mark such as a notch or a flat on the specimen and to move the specimen linearly and/or rotatably. Buffer cassette station 170 and receiving station 166 may be further configured a buffer station as illustrated in U.S. Pat. No. 6,212,691 to Dvir, which is incorporated by reference as if fully described herein.

The ISP wafer handler may be configured to remove a specimen from the receiving station. In addition, the ISP wafer handler may be further configured to move the specimen into one of the measurement chambers. Furthermore, the ISP wafer handler may be configured to move the specimen into each measurement chambers in a sequence. In this manner, the ISP system may be configured to determine at least one property of the specimen in each of the plurality of measurement chambers in a parallel pipeline fashion.

In addition, the measurement device coupled to each measurement chamber may each be configured to determine a different property of a specimen. For example, a measurement device coupled to first measurement chamber 172 may be configured to determine overlay misregistration of a specimen. A measurement device coupled to second measurement chamber 174 may be configured to determine a critical dimension of the specimen. A measurement device coupled to third measurement chamber 176 may be configured to determine a presence of macro defects on a surface of the specimen. In alternative embodiments, a measurement device coupled to one of the measurement chambers may be configured to determine a presence of micro defects on a surface of the specimen or a thin film characteristic of the specimen. A thin film characteristic may include a thickness, an index of refraction, or an extinction coefficient as described herein. Additionally, wafer handler 164 may be configured to move the specimen from each measurement chamber to sending station 168.

Because ISP system 158 may be coupled to a semiconductor fabrication,process tool such as lithography tool 130, properties of a specimen may be determined faster than stand alone metrology and inspection tools. Therefore, a system, as described herein, may reduce the turn-around-time for determining properties of a specimen. A reduced turn-around-time may provide significant advantages for process control. For example, a reduced turn-around-time may provide tighter process control of a semiconductor fabrication process than stand alone metrology and inspection tools. Tighter process control may provide, for instance, a reduced variance in critical dimension distributions of features on a specimen.

In addition, a system as described herein may be configured to adjust a drifting process mean to a target value and to reduce variance in critical dimension distribution of features on a specimen by accounting for autocorrelation in the critical dimension data For example, the critical dimension distribution of features on a specimen after a develop process step may be reduced by altering a parameter of an instrument coupled to an exposure tool or a develop process chamber. Such an altered parameter may include, but is not limited to, an exposure dose of an exposure process or a develop time of a develop process. In addition, a linear model of control may be used and only the offset terms may be updated or adapted. A linear model of control may include a control function such as: y=Ax+c, where A and c are experimentally or theoretically determined control parameters, x is a critical dimension of the specimen or another such determined property of the specimen, and y is a parameter of an instrument coupled to the semiconductor fabrication process tool. Alternatively, a parameter of an instrument coupled to a semiconductor fabrication tool such as the exposure tool may be altered by using an exponentially weighted moving average of the offset terms. A proportional and integral model of control may include a control function such as: $c_1 = \alpha E_{t-del} + (1-\alpha) c_{t-1}$, wherein $\alpha$ is an experimentally or theoretically determined control parameter, $E_{t-del}$ is a determined property of the specimen, and $c_t$ is a parameter of an instrument coupled to the semiconductor fabrication process tool.

Variance in critical dimension distribution after develop may be dramatically reduced by a system as described herein. For example, adjusting a critical dimension mean to a target value of a lot (i.e., 25) of wafers using lot-to-lot feedback control may reduce critical dimension variance by approximately 65%. In addition, lot-to-lot feedback control may be effective if critical dimension within lot critical dimensions are correlated. For example, low autocorrelation may result in no reduction of critical dimension variance using lot-to-lot feedback control. High autocorrelation, however, may result in a 15% reduction of critical dimension variance using lot-to-lot feedback control. Controlling critical dimension variance using wafer-to-wafer feedback control, however, may be effective even if lot critical dimensions are non correlated. For example, low autocorrelation may result in a 25% reduction in critical dimension variance using wafer-to-wafer feedback control Successful feedback control may depend on a proven APC frame work, robust process modeling, high throughput metrology, efficient production methodology to reduce metrology delay, and enabling of process tool wafer based control. In addition, the effect of turn-around-time on control of production wafers may also be examined by using multiple lot averaged control to adjust drift in the mean critical dimension. A target critical dimension may be set to be approximately equal to the mean of the critical dimension data. As such, lot-to-lot control may result in an 8% improvement in critical dimension variance. In addition, wafer-to-wafer control may results in an 18% improvement in critical dimension variance.

Figure 16:
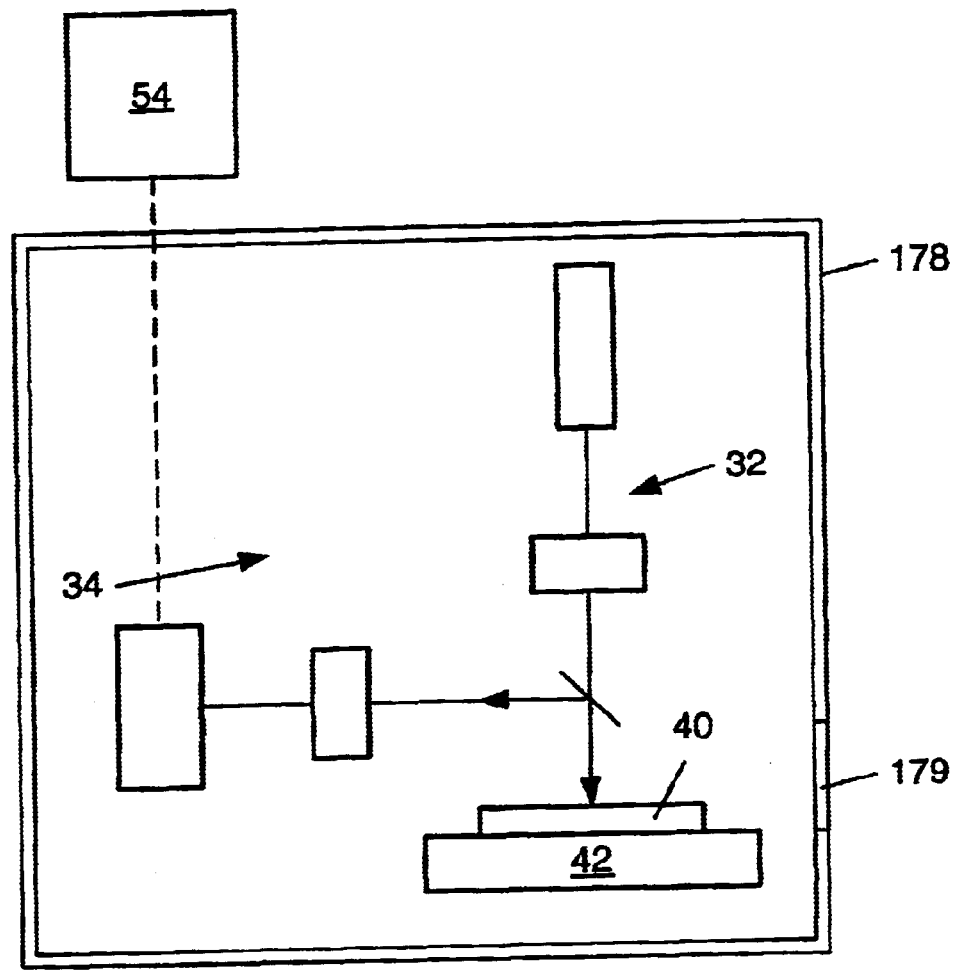
FIG. 16 depicts a schematic side view of an embodiment of a system disposed within a measurement chamber.

FIG. 16 illustrates a schematic side view of an embodiment of system 32 disposed within measurement chamber 178. For example, system 32 may include stage 42 disposed within measurement chamber 178. In addition, system 32 may include measurement device 34 disposed within measurement chamber 178. Measurement chamber 178 may also include opening 179 and a mechanical device (not shown) coupled to opening 179. In addition, measurement chamber 178 may include a plurality of such openings and a mechanical device coupled to each of the openings. The mechanical device may be configured to place an object such as a thin sheet of metal in front of opening 179 and to remove the object from the opening. In this manner, the mechanical device may be configured to provide access to the measurement chamber, for example, when specimen 40 is being disposed upon stage 42 through opening 179. Specimen 40 may be disposed upon stage 42 by any of the methods or devices as described herein. Subsequent to disposing specimen 40 on stage 42, the object may be placed in front of opening 179 by the mechanical device such that environment conditions such as relative humidity, temperature, and particulate count within the measurement chamber may be maintained and/or controlled. In this manner, system 32 may be configured to determine a property of specimen 40 under maintained and/or controlled environmental conditions, which may increase the reliability of the system. In addition, exposure of components of system 32 including, but not limited to, measurement device 34 to environmental conditions external to the measurement chamber may be reduced. As such, contamination and/or degradation of the components of system 32 may be reduced thereby reducing the probability of system failure, associated maintenance and repair costs, and increasing a lifetime of the system.

The system may also include processor 54 disposed outside of measurement chamber 178. In this manner, the processor, which may be configured as a controller computer, may be accessed outside of the measurement chamber, for example, by an operator. In addition, arranging processor 54 external to measurement chamber 178 may reduce the dimensions of measurement chamber 178. By reducing the dimensions of measurement chamber 178, system 32 may be coupled to or disposed within a larger number of process tools than a conventional metrology and/or inspection system. For example, measurement chamber 178 may be configured to have approximately the same dimensions as a process chamber of a semiconductor fabrication process tool. In this manner, system 32 may be disposed within an existing semiconductor fabrication process tool, as shown in FIG. 13, without altering an arrangement of the process chambers of the semiconductor fabrication process tool. For example, measurement chamber 178 may disposed within the tool by replacing one of the process chambers with measurement chamber 178. System 32 may be further configured as described herein.

Figure 17:
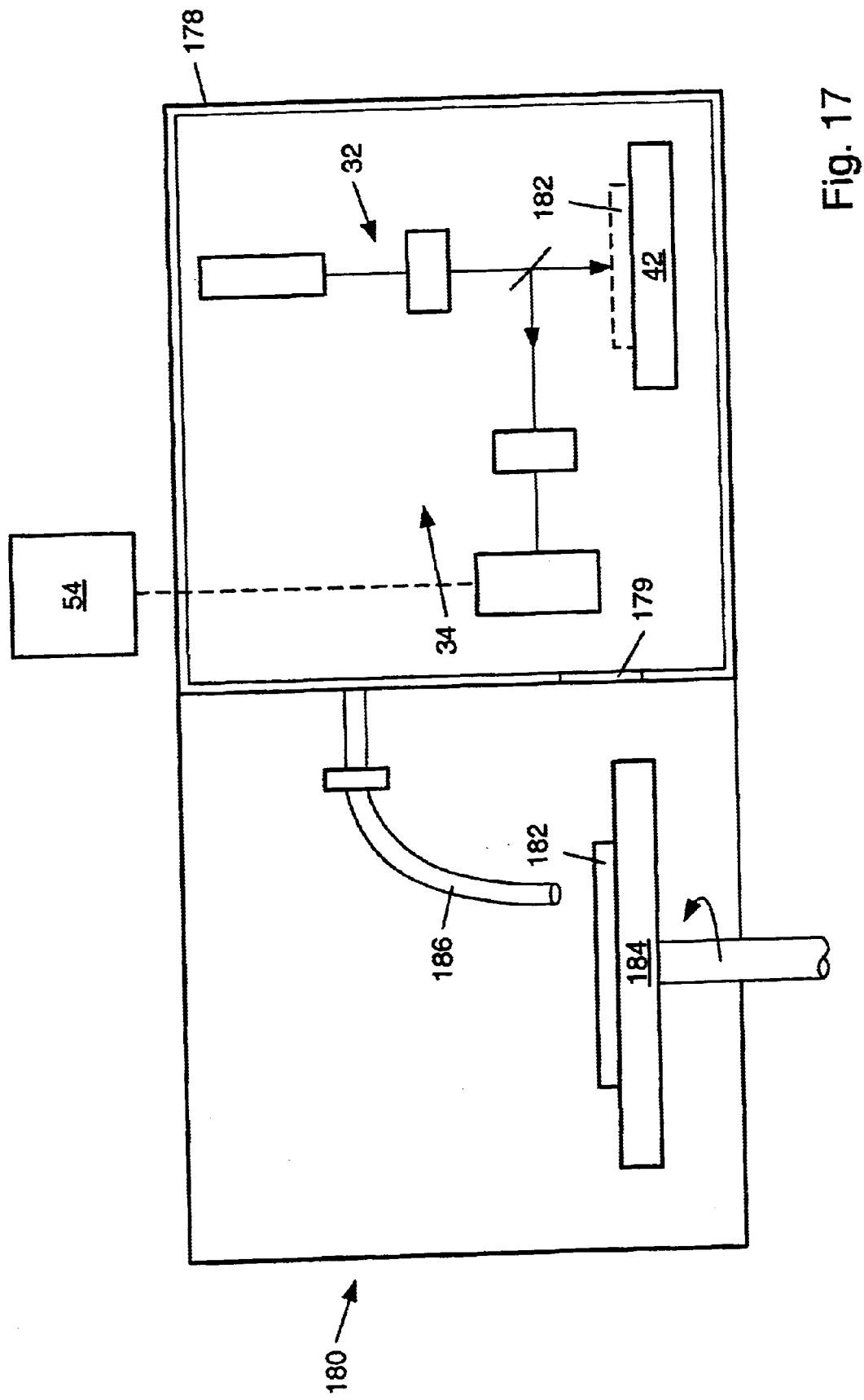
FIG. 17 depicts a schematic side view of an embodiment of a measurement chamber arranged laterally proximate to a process chamber of a semiconductor fabrication process tool.

FIG. 17 illustrates a schematic side view of an embodiment of measurement chamber 178 coupled to a process tool such as a semiconductor fabrication process tool. As shown in FIG. 17, measurement chamber 178 may be arranged laterally proximate to process chamber 180 of a process tool. Alternatively, the measurement chamber may be arranged vertically proximate to process chamber 180. For example, the measurement chamber may be arranged above or below process chamber 180. As shown in FIG. 17, process chamber 180 may be a resist apply chamber as described herein. For example, specimen 182 may be disposed upon stage 184. Stage 184 may be configured as a motorized rotating chuck or any other device known in the art. A resist may be dispensed onto specimen 182 from dispense system 186. Dispense system 186 may be coupled to a resist supply and may include a number of pipes and/or hoses and controls such as valves such that resist may be transferred from the resist supply to specimen 182. The dispense system may also be coupled to a controller computer, which may be configured to control the dispense system. For example, the controller computer may include processor 54 as described herein. Stage 184 may be configured to rotate such that the dispensed resist may spread over specimen 182 and such that solvent may evaporate from the dispensed resist. Process chamber 180, however, may include any of the process chambers as described herein. In addition, measurement chamber 178, process chamber 180, and processor 54 may be arranged in a modular architecture as illustrated in PCT Application No. WO 99/03133 to Mooring et al., which is incorporated by reference as if fully set forth herein.

In an embodiment, therefore, specimen 182 may be easily and quickly be moved from process chamber 180 to measurement chamber 178 (or from measurement chamber 178 to process chamber 180) by a robotic wafer handler of a process tool by a wafer handler of an ISP system, or by stage 42 as described herein. In this manner, system 32 may be configured to determine at least a first property and a second property of the specimen between process steps of a process. For example, in a lithography process, first and second properties of a specimen may be determined subsequent to resist apply and prior to exposure. In an additional example, first and second properties of a specimen may be determined subsequent to exposure and prior to post exposure bake. In a further example, first and second properties of a specimen may be determined subsequent to post exposure bake and prior to develop. First and second properties of a specimen may also be determined subsequent to develop. Furthermore, such a system may be configured to determine at least a first property and a second property of the specimen prior to substantially an entire process or subsequent to substantially an entire process. A system configured as described above may also have a relatively short turnaround-time. As described above, therefore, such a system may provide several advantages over currently used metrology and inspection systems.

A process tool such as a semiconductor fabrication process tool may include a number of support devices such as stage 184, as shown in FIG. 17, which may be configured to support the specimen during a process step. For example, a support device may be disposed within each process chamber coupled to a process tool. Appropriate support devices may include, but are not limited to, a spin coater, a bake plate, a chill plate, an exposure stage, and an electrostatic chuck in an etch or deposition chamber. Each support device may have an upper surface upon which a specimen may be disposed. An upper surface of each support device may be substantially parallel to an upper surface of other support devices arranged within the process tool, i.e., orientations of each support device within each process chamber, respectively, may be substantially parallel. In an embodiment, a stage of a system, as described herein, may also have an upper surface which may be substantially parallel to an upper surface of a support device of the process tool, as shown in FIG. 17, i.e., an orientation of the stage within a measurement chamber such as measurement chamber 178 may be substantially parallel to orientations of each support device within each process chamber, respectively.

In an alternate embodiment, a stage of a system, as described herein, may have an upper surface that may be arranged at an angle with respect to an upper surface of a support device, i.e., an orientation of the stage within a measurement chamber may be at an angle to orientations of each support device within each process chamber, respectively. For example, an upper surface of the stage may be arranged at a 90° angle with respect to an upper surface of a support device of a process tool. Alternatively, an upper surface of the stage may also be arranged at an angle of less than 90° with respect to an upper surface of the support device. At such angles, a vacuum may be pulled on a surface of a specimen to maintain a position of the specimen on the stage.

An orientation of a measurement device disposed within a measurement chamber with such a stage may also be altered. For example, the measurement device may be arranged at an angle such that a spatial relationship (i.e., any of the spatial arrangements shown in FIGS. 3–7, 11a–12, and 16–17) between the measurement device and the stage may be maintained Such a stage may also be arranged at an angle with respect to an illumination system and a detection system of the measurement device. In this mariner, a specimen may be tilted with respect to the measurement device during inspection or metrology processes which may be performed by a system as described herein.

An angled orientation of the stage within a measurement chamber as described above may allow a lateral dimension of the measurement chamber to be reduced. For example, the illumination system, the detection system, and the stage may be arranged in a more compact geometry than conventional inspection and metrology systems. In particular, a lateral dimension of a measurement chamber may be greatly reduced for relatively large diameter specimen such as 200 mm wafers and 300 mm wafers. As such, disposing such a measurement device within a semiconductor fabrication process tool may be less likely to require retrofitting of the semiconductor fabrication process tool. Therefore, existing configurations of semiconductor fabrication process tools may be less likely to prohibit disposing the system within the semiconductor fabrication process tool.

Figure 18:
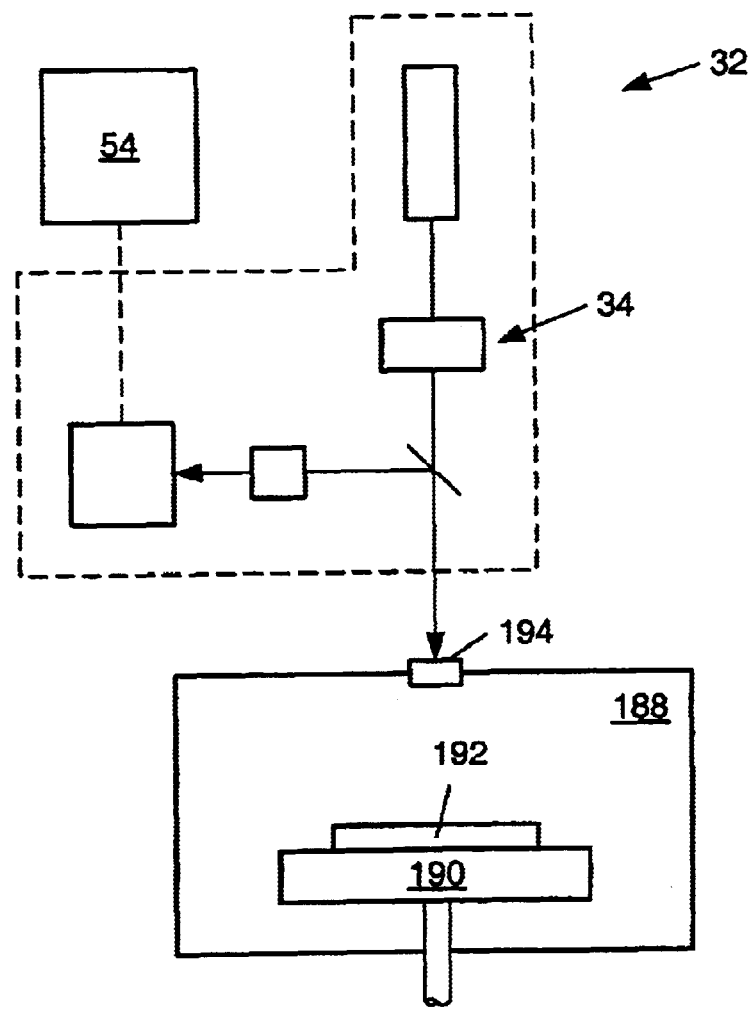
FIG. 18 depicts a schematic side view of an embodiment of a system coupled to a process chamber of a semiconductor fabrication process tool.

FIG. 18 illustrates a schematic side view of an embodiment of system 32 coupled to process chamber 188. The process chamber may be a process chamber coupled to a semiconductor fabrication process tool. Stage 190 may be disposed within process chamber 188. Stage 190 may be configured to support specimen 192, for example, during a semiconductor fabrication process step. System 32 may be coupled to process chamber 188 such that measurement device 34 may be external to process chamber 188 but may be coupled to stage 190 disposed within the process chamber. For example, process chamber 188 includes one or more relatively small sections 194 of a substantially transparent material disposed within one or more walls of the process chamber. Sections 194 may be configured to transmit a beam of energy from an energy source of the measurement device outside the process chamber to a surface of a specimen within the process chamber. Sections 194 may also be configured to transmit a beam of energy returned from the surface of the specimen to a detector of measurement device 34 outside process chamber 188. The substantially transparent material may have optical or material properties such that the beam of energy from the energy source and the returned beam of energy may pass through sections 194 of the process chamber without undesirably altering the properties of the directed and returned energy beams. For example, undesirably altering the properties of the energy beams may include, but is not limited to, altering a polarization or a wavelength of the energy beams and increasing chromatic aberration of the energy beams. In addition, sections 194 may be configured such that deposition of process residue from a chemical using during processing of a specimen may be reduced as described in PCT Application No. 99/65056 to Grimbergen et al., which is incorporated by reference as if fully set forth herein.

An appropriate system and method for coupling a measurement device external to a process chamber and a stage disposed within the process chamber may vary, however, depending on, for example, a configuration of the process chamber and/or a configuration of the measurement device. For example, the placement and dimensions of relatively small section 194 disposed within the walls of process chamber 188 may vary depending on the configuration of the components within the process chamber. As such, exposure of measurement device 34 to chemicals and environmental conditions within process chamber 188 may, be reduced, and even substantially eliminated. Furthermore, measurement device 34 may be externally coupled to process chamber 188 such that the measurement device may not alter operation, performance, or control of a process step carried out in process chamber 188.

A measurement device, as shown in FIG. 18, may be configured to direct energy toward a surface of a specimen during a step of a process such as, in an example of a lithography process as described above, during a chill process subsequent to a post apply bake process, a post exposure bake process, a develop process, or any of the process steps as described herein. In addition, the measurement device may be configured to detect energy returned from the surface of the specimen during the step of the process. The measurement device may be configured to detect energy returned from a specimen substantially continuously or at various time intervals during a process step.

The system may include a processor configured to determine at least a first and a second property of a specimen during a process step. For example, the processor may be configured to determine at least two properties of a specimen such as critical dimension and overlay misregistration from the energy detected during a process step. In an additional embodiment, the processor may also be configured to detect variations in the energy detected by a measurement device during the process step. For example, the processor may be configured to obtain a signature characterizing the process step. The signature may include at least one singularity representative of an end of the process step.

In an additional embodiment, the processor may also be coupled to a process tool such as a lithography tool and may be configured to alter a parameter of an instrument coupled to the process tool. For example, the processor may alter a parameter of an instrument coupled to a process tool in response to the detected singularity as described above. The parameter of the instrument may be altered such that the process step may be terminated subsequent to detection of the singularity. In addition, the processor may be configured to alter a parameter of an instrument of a process tool in response to at least one determined property of the specimen using an in situ control technique.

In an additional embodiment, the processor may be configured to monitor a parameter of an instrument coupled to a process tool such as a semiconductor fabrication process tool. For example, the processor may be coupled to a resist apply process chamber of a lithography tool and may be configured to monitor a parameter of an instrument coupled to the resist apply chamber. In this manner, the processor may be configured to monitor a spin speed of a motorized chuck of the resist apply chamber, a dispense time of a dispense system of the resist apply chamber, and/or a temperature and a humidity of the resist apply chamber. The processor may be further configured as described in an example of a method and apparatus for providing real-time information identifying tools visited by a wafer under inspection and the process parameters used at those tools illustrated in European Patent Application No. EP 1 071 128 A2 to Somekh, which is incorporated by reference as if fully set forth herein. In addition, the processor may be configured to determine a relationship between at least one determined property of a specimen and a monitored parameters of an instrument coupled to a process tool. For example, the processor may be configured to determine a relationship between a presence of defects on the surface of a resist layer formed on a specimen and a monitored temperature and/or humidity of the resist apply chamber. Furthermore, the processor may be configured to alter the monitored parameter of the instrument in response to the determined relationship. For example, the processor may be configured to use a determined relationship to alter a parameter of an instrument coupled to the resist apply chamber such that the temperature and humidity of the resist apply chamber may be altered in response to a determined presence of defects on the surface of the specimen.

The processor may also be configured to alter a parameter of an instrument coupled to a process tool in response to at least one determined property using a feedback control technique. Furthermore, the processor may also be configured to alter a parameter of an instrument coupled to a process tool in response to at least one determined property using a feedforward control technique. For example, the system may be configured to determine at least two properties of a specimen during a develop process. The processor may be configured to alter a parameter of an instrument coupled to the develop process chamber in response to at least one of the determined properties during developing of the specimen or prior to developing additional specimens. In addition, the processor may be configured to alter a parameter of an instrument coupled to a process chamber such as a hard bake process chamber in response to at least one of the determined properties prior to further processing of the specimen in the process chamber. In addition examples, the processor may be configured to alter a parameter of an instrument coupled to an exposure tool, a post exposure bake chamber, a resist apply chamber, and any other tools or chamber included in the cluster tool.

In a further embodiment, the processor may be configured to compare at least one determined property of the specimen and properties of a plurality of specimens. For example, the plurality of specimens may include product wafers processed prior to the processing of the specimen. At least two properties of the plurality of specimens may be determined prior to processing of the specimen with a system as described herein. The plurality of specimens may also include specimens within the same lot as the specimen or specimens within a different lot than the specimen. As such, the processor may be configured to monitor a process such as a semiconductor fabrication process using a wafer-to-wafer comparison technique or a lot-to-lot comparison technique. In this manner, the processor may be configured to monitor the performance of the process and to determine if the performance of the process or a process tool is drifting. A method and apparatus for reducing lot to lot CD variation in semiconductor wafer processing is illustrated in European Patent Application No. EP 1 065 567 A2 to Su, and is incorporated by reference as if fully set forth herein.

Alternatively, the processor may be configured to compare at least one determined property of the specimen to a predetermined range for at least the one property. The predetermined range may be determined, for example, from design constraints for the specimen. In addition, the predetermined range may be determined by using a statistical process control method to determine an average of at least the one property and additional statistical parameters such as a variance of at least the one property for a process. In addition, the processor may be configured to generate an output signal if at least the one determined property is outside of a predetermined range. The output signal may be a visual signal such as a signal displayed on a monitor coupled to the processor. The monitor may be disposed in a semiconductor fabrication facility such that the displayed signal may be viewed by an operator. Alternatively, the output signal may be any signal known in the art such as an audible signal or a plurality of signals.

In addition, subsequent to determining the property of the specimen, the processor may be configured to determine if additional processing of the specimen may be performed. Additional processing of the specimen may be altered or performed to alter the determined property. Such additional processing may be commonly referred to as "reworking." In this manner, the processor may be configured to make automated rework decisions. For example, such additional processing may include reprocessing the specimen such that one or more process steps, which may have already been performed on the specimen, may be repeater. In addition, a parameter of one or more instruments coupled to one or more process chambers configured to perform the repeated process steps may be altered in response to the determined property using a feedforward control technique. In this manner, such additional processing of the specimen may be configured to alter the determined property by altering a parameter of the instrument in response to the determined property. As such, such additional processing may alter the determined property such that the determined property may be substantially equal to an expected value for the property or may be within a predetermined range for the property.

In an additional embodiment, the processor may be configured to alter a sampling frequency of a measurement device in response to at least one determined property of a specimen. For example, if a determined property is substantially different than an expected value for the property, or if a determined property is outside of a predetermined range for the property, then the processor may increase the sampling frequency of the measurement device. The sampling frequency may be altered, for example, such that the measurement device is configured to direct and detect energy from an increased number of locations on the specimen. In this manner, the sampling frequency may be altered using an in situ control technique. In addition, the sampling frequency of the measurement device may be altered to determine statistical data of the determined proper across the specimen such as an average. As such, the determined property may be classified as a random defect, a repeating defect, or as another such defect.

In an additional example, the sampling frequency of a measurement device may be altered such that subsequent measurement or inspection of the specimen may be increased. In this manner, the sampling frequency may be altered using a feedforward control technique. Subsequent measurement or inspection may include transferring the specimen to an additional system, which may be configured as described herein, to further examine the determined property of the specimen. An appropriate additional system for such further examination of the determined property of the specimen may include a system having a higher sensitivity, a higher magnification, and/or an increased resolution capability than the system used to initially determine the property.

Alternatively, the sampling frequency may be altered such that the measurement device is configured to direct and detect energy from an increased number of locations on additional specimens that may be in the same lot as the specimen. Furthermore, the sampling frequency may be altered such that the measurement device is configured to direct and detect energy from an increased number of specimens in the same lot as the specimen or from a number of specimens in an increased number of lots. In this manner, the sampling frequency may be altered using a feedback control technique. As such, the sampling frequency may be altered using an in situ control technique, a feedforward control technique, or a feedback control technique. In addition, each of these control techniques may be used to alter the sampling frequency of a measurement device on a to within-wafer basis, a within-lot basis, and/or a lot-to-lot basis.

In a further embodiment, the processor may be configured to generate a database. The database may include a set of data that may include at least first and second properties of a specimen. The processor may be also be configured to calibrate the measurement device using the database. For example, the set of data may include at least a first and second property of a reference specimen. The measurement device may be configured to determine the first and second properties of the reference specimen. In this manner, the processor may be configured to calibrate the measurement device by comparing the first and second properties of the reference specimen in the database and the determined first and second properties of the reference specimen. For example, the processor may be configured to determine a correction factor from the comparison of the first and second properties in the database and the determined first and second properties of the reference specimen. In addition, the processor may be configured to use the correction factor to determine first and second properties of additional specimens.

In an additional embodiment, the processor may be configured to monitor the measurement device using the database. For example, the database may include at least two properties of a specimen. The system may be configured to determine at least the two properties of the specimen at predetermined intervals of time. The processor may be configured to compare at least the two properties of the specimen determined at different times. As such, the processor may be configured to determine if the performance of the measurement device is changing over time. In an additional example, the processor may be configured to generate a set of data that may include at least a first property and a second determined property of a plurality of specimens at predetermined time intervals. As such, the processor may also be configured to compare at least the first and second properties of a plurality of specimens using the database. The first and second properties of a specimen or a plurality of specimens may be determined using the measurement device or using a plurality of measurement devices. The processor may be further coupled to the plurality of measurement devices. Therefore, the processor may also be configured to calibrate the plurality of measurement devices using the database as described above. In addition, the processor may also be configured to monitor the plurality of measurement devices using the database as described above.

As described above, the processor may be coupled to a plurality of measurement devices. In an additional embodiment, the processor may be configured to alter a parameter of an instrument coupled to at least one of the plurality of measurement devices. Each of the measurement devices may be configured as a stand-alone metrology or inspection device. Alternatively, each of the measurement devices may be coupled to at least one of a plurality of process tools as described herein. Furthermore, the processor may be coupled to at least one process tool. In this manner, the processor may be configured to alter a parameter of an instrument coupled to at least one of the plurality of process tools. In addition, the processor may be configured to alter a parameter of a plurality of instruments. Each of the instruments may be coupled to one of the plurality of process tools. The processor, however, may also be configured to alter a parameter of a plurality of instruments coupled to at least one of the plurality of process tools. For example, the processor may be configured to alter a parameter of the instrument in response to at least one of the determined properties using an in-situ control technique, a feedback control technique, and a feedforward control technique.

In an embodiment, the processor may include a local processor coupled to the measurement device. The processor, however, may also include a remote controller computer or a remote controller computer coupled to a local processor. The local processor may be configured to at least partially process a signal generated by the measurement device. The signal may be generated by the detection system and may be an analog signal or a digital signal. For example, the system may also include an analog-to-digital converter. The analog-to-digital converter may be configured to convert a signal generated by the detection system such that a digital signal may be sent to the local processor or the remote controller computer. In addition, the remote controller computer may be configured to farther process the at least partially processed signal. For example, the local processor may be configured to determine at least a first property and a second property of a specimen. In this manner, the remote controller computer may be configured to further process at least the two determined properties. For example, fiber processing the determined properties may include comparing the determined properties to a predetermined range for each property. In addition, the remote controller computer may be configured to generate an output signal if the determined properties are outside of the predetermined range.

The processor may also take various forms, including, for example, a personal computer system, mainframe computer system, workstation, network appliance, Internet appliance, personal digital assistant ("PDA"), television system, or other device. In general, the term "processor" may be broadly defined to encompass any device having a processor, which executes instructions from a memory medium. Examples of processors and control methods are illustrated in U.S. Pat. No. 4,571,685 to Kamoshida, U.S. Pat. No. 5,859,964 to Wang et al., U.S. Pat. No. 5,866,437 to Chen et al., U.S. Pat. No. 5,883,374 to Mathews, U.S. Pat. No. 5,896,294 to Chow et al., U.S. Pat. No. 5,930,138 to Lin et al., U.S. Pat. No. 5,966,312 to Chen, U.S. Pat. No. 6,020,957 to Rosengaus et al., and are incorporated by reference as if fully set forth herein. Additional examples of processors and control methods are illustrated in PCT Application Nos. WO 99/59200 to Lamey et al and WO 00/15870 to Putnam-Pite et al., and are incorporated by reference as if fully set forth herein.

Figure 19:
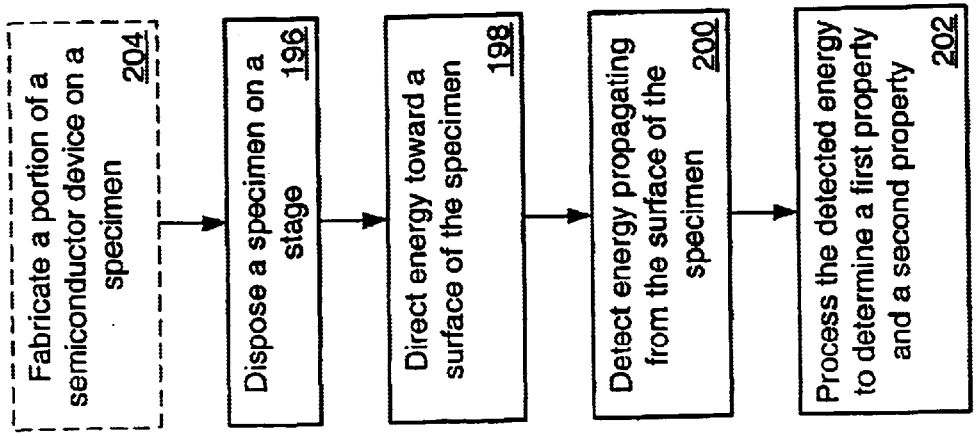
FIG. 19 depicts a flow chart illustrating an embodiment of a method for determining at least two properties of a specimen.

FIG. 19 illustrates an embodiment of a method for determining at least two properties of a specimen. As shown in step 196, the method may include disposing a specimen upon a stage. The stage may be coupled to a measurement device. The measurement device may be configured as described herein. For example, the measurement device may include an illumination system and a detection system. As shown in step 198, the method may include directing energy toward a surface of a specimen using the illumination system. In addition, the method may include detecting energy propagating from the surface of the specimen, as shown in step 200. Furthermore, the method may include processing the detected energy to determine at least a first property and a second property of a specimen, as shown in step 202. The first property may include a critical dimension of the specimen. A critical dimension may include, but is not limited to, a lateral dimension of a feature of the specimen. A feature may be formed on an upper surface of the specimen or in the specimen as described herein. The second property may include an overlay misregistration of the specimen. Overlay misregistration may include a lateral displacement of a first feature on a first level of a specimen with respect to a second feature on a second level of a specimen. The first level may be formed above the second level.

The stage may be configured as described herein. For example, the stage may be configured to move laterally and rotatably. In this manner, the method may include laterally or rotatably moving the stage. Laterally or rotatably moving the stage may include arranging the specimen such that energy from the measurement device may be directed to and may propagate from the specimen. The method may also include laterally and/or rotatably moving the stage while energy is being directed toward a surface of the specimen and while energy is being detected from the surface of the specimen. As such, the method may include moving the stage laterally and/or rotatably during measurement or inspection of a surface of a specimen. In this manner, light may be directed to and may propagate from a plurality of locations on a surface of the specimen during measurement or inspection of a surface of the specimen. As such, the system may be configured to determine at least two properties of a specimen at multiple locations on the specimen. In a further embodiment, the method may include rotating the stage while moving the measurement device linearly along a lateral dimension of a specimen as described herein.

An illumination system of the measurement device may be configured as described herein. In addition, a detection system of the measurement device may be configured as described herein. For example, the measurement device may include, but is not limited to, a non-imaging scatterometer, a scatterometer, a spectroscopic scatterometer, a reflectometer, a spectroscopic reflectometer, a spectroscopic ellipsometer, bright field imaging device, a dark field imaging device, a bright field and dark field imaging device, a coherence probe microscope, an interference microscope, and an optical profilometer. In addition, the measurement device may include any combination of the above devices. As such, the measurement device may be configured to function as a single measurement device or as multiple measurement devices. Because multiple measurement devices may be integrated into a single measurement device of a system, optical elements of a first measurement device, for example, may also be optical elements of a second measurement device.

In an embodiment, the method may include processing the detected energy to determine a third property of the specimen. A third property of the specimen may include, but is not limited to, a presence, a number, a location, and/or a type of defects on the surface of the specimen and a flatness measurement of the specimen. The defects may include macro defects and/or micro defects as described herein. In addition, the method may include processing the detected energy to determine a third property and a fourth property of a specimen. For example, the third property may include a presence, a number, a location, and/or a type of defects on the surface of the specimen, and the fourth property may include a flatness measurement of the specimen. As such, the method may be used to determine a critical dimension, an overlay misregistration, a presence, a number, a location, and/or a type of defects on the specimen, and a flatness measurement of the specimen. The method may include determining such properties of a specimen sequentially or substantially simultaneously. In an additional embodiment, the method in may include directing energy toward a front side and/or a back side of a specimen. As such, the method may also include detecting energy propagating from the front side and/or the back side of the specimen, respectively. In this manner, the method may also include determining a presence, a number, a location, and/or a type of defects on a back side of the specimen. The defects may include macro defects.

In an embodiment, the stage and measurement device may be coupled to a process tool such as a semiconductor fabrication process tool. The semiconductor fabrication process tool may include a lithography tool as described herein. The stage and measurement device may be arranged laterally proximate to the process tool as described herein. For example, the stage and measurement device may be disposed within an ISP system as described above. Alternatively, the stage and the measurement device may be disposed within the process tool. For example, the stage and measurement device may be disposed within a measurement chamber. The measurement chamber may be coupled to the process tool. For example, the measurement chamber may be arranged laterally proximate to a process chamber of the process tool. Alternatively, the measurement chamber may be arranged vertically proximate to a process chamber of the process tool. The measurement chamber may be configured to isolate the measurement device and the stage from environmental conditions within the process tool.

In an embodiment, a support device may be disposed within a process chamber of the process tool. The support device may be configured to support the specimen during a process step. For example, a support device disposed within a resist apply chamber of a lithography tool may include a chuck coupled to a motorized rotation device. As such, the support device may be configured to support the specimen during a resist apply process step of a lithography process. A support device may also include, for example, a bake plate disposed within a post apply bake chamber. The bake plate may be configured to support the specimen during a post apply bake process step of the lithography process. An upper surface of the support device may be substantially parallel to an upper surface of the stage of the system. Alternatively, an upper surface of the stage may be angled with respect to an upper surface of the support device. The stage may also be configured to hold a specimen in place at such an angle by drawing a vacuum through an upper surface of the stage or by an appropriate mechanical device. In this manner, a stage and measurement device may be substantially perpendicular to a support device disposed within a process chamber. As such, the system may be arranged essentially on its "side." The term "side," as used herein, generally refers to a lateral sidewall of a conventional metrology or inspection system. The orientation of the stage with respect to a support device of a process chamber may vary depending on, for example, the dimensions of a process tool and an arrangement of process chambers within the process tool. For example, the stage may be arranged at a perpendicular angle with respect to the support device such that the measurement device and stage may be disposed within an existing process tool. In this manner, the system may be disposed within a process tool without reconfiguration of the process chambers.

In an additional embodiment, the process tool may include a wafer handler configured as described herein. For example, the wafer handler may be configured to remove a specimen from a process chamber subsequent to a step of a process. The wafer handler may also be configured to place a specimen into a process chamber prior to a step of a process. In this manner, the wafer handler may be configured to move the specimen from a first process chamber to a second process chamber between steps of a process. Disposing the specimen upon the stage, as shown in step 196, may include moving the specimen from the process tool to the stage using the wafer handler. In addition, the method may include moving the specimen to the process tool subsequent to directing energy toward a surface of the specimen and detecting energy propagating from a surface of the specimen. In this manner, the method may include determining at least two properties of the specimen between process steps of a process.

In an alternative embodiment, the stage of the system may be disposed within a process chamber of the process tool. As such, the stage may be configured to function as a support device as described herein and may support the specimen during a process step. In this manner, disposing the specimen upon a stage, as shown in step 196, may include disposing the specimen upon a support device within a process chamber of a process tool. The method may also include directing energy toward a surface of the specimen and detecting energy propagating from the surface of the specimen during a process step. In this manner, the system may be configured to determine at least two properties of a specimen at predetermined time intervals during a process step. In an embodiment, the method may also include obtaining a signature characterizing a process step. The signature may include at least one singularity that may be representative of an end of the process step as described herein. Furthermore, the method may include altering a parameter of an instrument coupled to a process tool in response to at least one of the determined properties using an in situ control technique.

In an embodiment, the stage and the measurement device may be coupled to a wafer handler of a process tool. The wafer handler may be configured to support and move a specimen as described herein. In this manner, the method may include directing energy toward a surface of the specimen and detecting energy propagating from the surface of the specimen during movement of the specimen. As such, the method may also include determining at least two properties of a specimen while moving a specimen from a first process chamber to a second process chamber. In is manner, the method may include determining at least two properties of a specimen between any two process steps of a process. For example, the method may include chilling the specimen in a first process chamber. In addition, the method may include applying resist to the specimen in the second process chamber.

In additional examples, the method may include chilling the specimen in a first process chamber subsequent to a post apply bake process step. The method may also include exposing the specimen in the second process chamber. In a further example, the method may include chilling the specimen in a first process chamber subsequent to a post exposure bake process and developing the specimen in a second process chamber. Additionally, the method may include developing the specimen in a first process chamber and baking the specimen in a second process chamber.

Furthermore, the method may include developing the specimen in a first process chamber and receiving the specimen in a wafer cassette in the second process chamber. In this manner, the method may include determining at least two properties of a specimen between any two process steps of a semiconductor fabrication process.

In an alternative embodiment, the measurement device may be coupled to a process chamber such that moving the specimen to or from the process chamber may include moving the specimen under the measurement device. In this manner, the stage may include the wafer handler.

In an embodiment, the method may include comparing the determined properties of a specimen and determined properties of a plurality of specimens. For example, the method may include monitoring and evaluating a semiconductor fabrication process using a wafer-to-wafer control technique. In addition, the method may include comparing properties of a specimen determined at a first location on the specimen to properties of the specimen determined at a second location on the specimen. As such, the method may include monitoring and evaluating a semiconductor fabrication process using a within-wafer control technique. Alternatively, the method may also include comparing the determined properties of a specimen to a predetermined range for each property. The predetermined range may vary depending on, for example, design constraints for each property such as an acceptable range of lateral dimensions for a feature on the specimen or an acceptable presence of defects on the surface of the specimen. The method may also include generating an output signal if the determined properties of the specimen are outside of the predetermined range for the property. The output signal may take various forms such as a visual signal and/or an audible signal. In addition, the output signal may be configured to indicate which of the determined properties is outside of the predetermined range and the extent to which the determined property is outside of the predetermined range.

In an additional embodiment, the method may include altering a sampling frequency of the measurement device in response to at least the determined first or second property of the specimen. For example, the method may include increasing a sampling frequency of the measurement device in response to the determined properties. The sampling frequency may be increased such that at least two properties may be determined at an increased number of locations on a single specimen. Alternatively, the sampling frequency may be increased such that at least two properties may be determined for an increased number of specimens such as within a lot of wafers. In addition, the sampling frequency may be increased such that at least two properties may be determined for an increased number of lots.

In an embodiment, the method may also include altering a parameter of an instrument coupled to a measurement device in response to at least one of the determined properties of the specimen using a feedback control technique. For example, if a property of the specimen is determined to be outside of a predetermined range, the method may include increasing a sampling frequency of a measurement device prior to determining at least two properties of additional specimens with the measurement device. The additional specimens may have been subjected to substantially the same process step or process as the specimen having at least one property outside of the predetermined range in this manner, the method may include sampling an increased number of specimens such that data may be generated, which may be used to determine if the property of the specimen outside of the predetermined range is occurring systematically or randomly.

In an additional embodiment, the method may include altering a parameter of an instrument coupled to a measurement device in response to at least one of the determined properties of a specimen using a feedforward control technique. For example, the method may include determining at least two properties of a specimen subsequent to a first process step of a process using a measurement device. The method may also include determining at least two properties of a specimen subsequent to a second process step of the process using the measurement device. If one of the properties of the specimen determined after the first process step is outside of the predetermined range, a sampling frequency of the measurement device may be increased prior to determining at least two properties after the second process step. For example, the second process step may include reprocessing the specimen or performing a process step of a process which has been altered in response to at least one of the properties determined after the first process step. For example, the second process step may be configured to alter the property of the specimen such that the property may be within the predetermined range subsequent to the second process step. In this manner, the method may be used to determine if the second process step has altered the property of the specimen.

In an additional embodiment, the method may include generating a database. The database may include at least two determined properties of a specimen. The method may also include calibrating the measurement device using the database. For example, the database may include at least a first and second property of a reference specimen. In addition, the method may include determining the first and second properties of the reference specimen with the measurement device. In this manner, the method may include calibrating the measurement device by comparing at least one of the properties of the reference specimen in the database and at least one of the properties of the reference specimen determined with the measurement device. For example, the method may include determining a correction factor from the comparison of at least one property of the reference specimen and using the correction factor to determine at least the first and second properties of additional specimens.

In an additional embodiment, the method may include monitoring the determined properties generated by the measurement device using the database. For example, the database may include at least two properties of a specimen. The method may also include determining at least the two properties of the specimen at predetermined intervals of time. In this manner, the method may be include comparing at least the two properties of the specimen in the database to at least the two properties of the specimen determined at various times. As such, the method may include determining if the performance of the measurement device is changing over time. In an additional example, the method may include generating a database that may include at least two properties of a plurality of specimens. At least the two properties of the plurality of specimens may be determined using the measurement device. As such, the method may include comparing at least one of the determined properties of a plurality of specimens using the database. Alternatively, the first and second properties of the plurality of specimens may be determined using a plurality of measurement devices; Therefore, the method may also include calibrating the plurality of measurement devices using the database as described above. In addition, the method may also include monitoring the determined properties generated by the plurality of measurement devices as described above. In an embodiment, the method may also include altering a parameter of an instrument coupled to each of the plurality of measurement devices in response to at least one of the determined properties of a specimen. Altering a parameter of an instrument coupled to each of a plurality of measurement devices may include any of the embodiments described herein.

In a further embodiment, the method may include altering a parameter of an instrument coupled to a process tool such as a semiconductor fabrication process tool in response to at least one of the determined properties of the specimen using a feedback control technique. For example, the method may include altering a parameter of an instrument coupled to a lithography tool in response to a determined property as described above. In addition, the method may include altering a parameter of an instrument in response to at least one of the determined properties of the specimen using an in situ control technique. For example, the method may include terminating a process step at approximately a time that a singularity is detected by a measurement device.

Additionally, the method may also include altering a parameter of an instrument coupled to a process tool in response to at least one of the determined properties using a feedforward control technique. For example, the method may include determining at least two properties of a specimen during a develop process in a develop process chamber. In addition, the method may include altering a parameter of an instrument coupled to a process chamber in response to at least one of the determined properties prior to further processing of the specimen in the process chamber. In addition, the method may include altering a parameter of an instrument coupled to each of a plurality of process tools in response to at least one of the determined properties of the specimen. Altering the parameter of an instrument coupled to each of a plurality of process tools may include any of the embodiments described herein.

In an additional embodiment, the method may include monitoring a parameter of an instrument coupled to a process tool. For example, the method may include monitoring a parameter of an instrument coupled to a resist apply chamber of a lithography tool. In this manner, the method may include monitoring a spin speed of a motorized chuck of the resist apply chamber, a dispense time of a dispense system of the resist apply chamber, and/or a temperature and a humidity of the resist apply chamber. In addition, the method may include determining a relationship between a determined property of a specimen and the monitored parameter of an instrument. For example, the method may include determining a relationship between a presence of defects on the surface of a resist formed on a specimen and the temperature and/or humidity of the resist apply chamber. Furthermore, the method may include altering the monitored parameter of the instrument in response to the relationship. For example, the method may include using a determined relationship to alter a parameter of an instrument coupled to the resist apply chamber such that the temperature and humidity of the resist apply chamber may be altered in response to a determined presence of defects on the surface of the specimen. In an additional embodiment, the method may include altering a parameter of an instrument coupled to each of a plurality of process tools in response to at least one determined property of the specimen. Altering a parameter of an instrument coupled to each of a plurality of process tools may include any of the embodiments as described herein.

Figure 20:
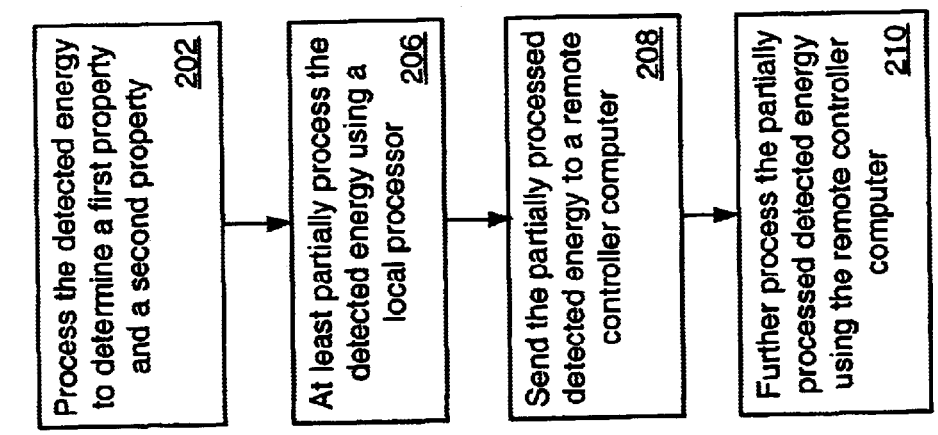
FIG. 20 depicts a flow chart illustrating an embodiment of a method for processing detected light returned from a surface of the specimen.

In an additional embodiment, processing the detected energy may include using a processor to determine the first and second properties of a specimen. The processor may be coupled to the measurement device. The method may, therefore, include sending a signal representative of the detected energy to the processor. The processor may also be configured as described in above embodiments. For example, the processor may include a local processor coupled to a remote controller computer. The local processor may be coupled to a measurement device as described in above embodiments. FIG. 20 illustrates an embodiment of a method for determining at least two properties of a specimen. For example, as shown in step 202, the method may include processing the detected energy to determine a first property and a second property of the specimen using a processor. As shown in step 206, processing the detected light may also include at least partially processing the detected energy using a local processor. The method may also include sending the partially processed detected energy from the local processor to a remote controller computer, as shown in step 208. In addition, the method may further include further processing the at least partially processed detected light using the remote controller computer, as shown in step 210.

In an embodiment, at least partially processing the detected energy may include determining at least two properties of a specimen. As such, further processing the detected energy may include processing the determined properties of the specimen. For example, processing the determined properties may include generating a database as described in above embodiments. In addition, processing the determined properties may include using at least one of the determined properties and a relationship between at least one property of the specimen and a parameter of an instrument coupled to a process tool to determine an altered parameter of the instrument. At least partially processing the detected light and further processing the detected light may also include additional steps as described herein.

An embodiment also relates to a semiconductor device that may be fabricated by a method, which may include any of the steps as described herein. For example, an embodiment of a method for fabricating a semiconductor device is illustrated in FIG. 19. As shown in step 204, the method may include fabricating a portion of the semiconductor device on a specimen such as a wafer. Fabricating a portion of a semiconductor device may include using a semiconductor fabrication process to process the specimen. Appropriate semiconductor fabrication processes may include, but are not limited to, lithography, etch, ion implantation, chemical vapor deposition, physical vapor deposition, chemical-mechanical polishing, and plating. In addition, fabricating a portion of the semiconductor device may include using a step of a semiconductor fabrication process to process the specimen.

In an embodiment, a method for fabricating a semiconductor device may also include disposing a specimen upon a stage, as shown in step 196. In addition, a method for fabricating a semiconductor device may further include directing energy toward a surface of the portion of the semiconductor device formed on the specimen, as shown in step 198. The method may also include detecting energy propagating from a surface of the portion of the semiconductor device formed on the specimen, as shown in step 200. As further shown in step 202, the method may further include processing the detected light to determine at least two properties of the portion of the semiconductor device formed on the specimen. Furthermore, a method for fabricating a semiconductor device may include any of the steps as described herein.

Figure 21:
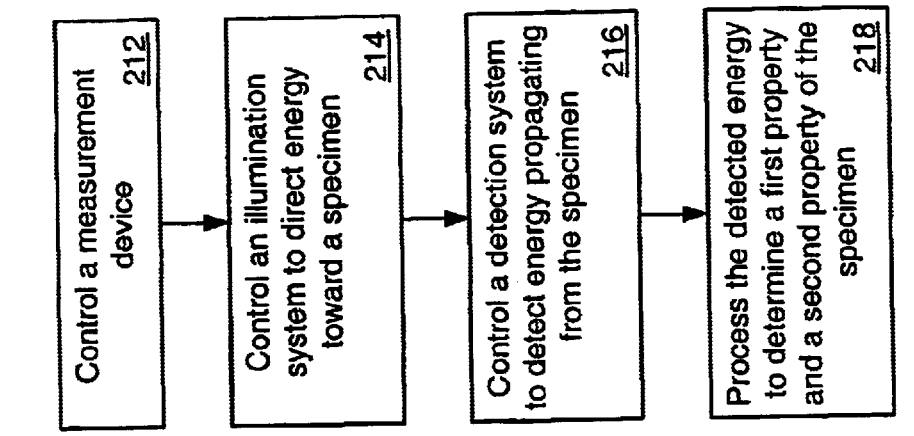
FIG. 21 depicts a flow chart illustrating an embodiment of a method for controlling a system configured to determine at least two properties of a specimen.

FIG. 21 illustrates an embodiment of a computer-implemented method for controlling a system to determine at least two properties of a specimen. In an embodiment, the system may include a measurement device. As shown in step 212, the method may include controlling the measurement device, which may include an illumination system and a detection system The measurement device may be coupled to a stage. The measurement device may further be configured as described herein. In addition, the method may include controlling the illumination system to direct energy toward a surface of a specimen, as shown in step 214. The method may further include controlling the detection system to detect energy propagating from the surface of the specimen, as shown in step 216. Furthermore, the method may include processing the detected energy to determine at least a first property and a second property of the specimen, as shown in step 218. The first property may include a critical dimension of the specimen. The critical dimension may include, but is not limited to, a lateral dimension, a height, and/or a sidewall angle of a feature formed on a surface of the specimen. Alternatively, the critical dimension may include a lateral dimension, a height, and/or a sidewall angle of a feature formed within a specimen. The second property may include an overlay misregistration of the specimen.

In an embodiment, the method may also include controlling the stage, which may be configured to support the specimen. For example, the method may include controlling the stage to move the stage laterally, rotatably, or laterally and rotatably. The stage may be controlled to move while the illumination system is directing energy toward the surface of the specimen and while the detection system is detecting energy propagating from the surface of the specimen.

In an additional embodiment, the method may also include processing the detected energy to determine a third property of the specimen. For example, the third property may include a presence of defects on a surface of the specimen. The third property may also include a number, a location, and/or a type of defects on a surface of the specimen. The defects may include micro defects, macro defects, or micro and macro defects. In an embodiment, the method may also include controlling the illumination system to direct energy toward a back side of the specimen. The method may further include controlling the detection system to detect energy propagating from the back side of the specimen. As such, the third property of the specimen may also include a presence of defects on the back side of the specimen. Such defects may include macro defects. In addition, a third property may also include a flatness measurement of the specimen. In an additional embodiment, the method may also include processing the detected light to determine a third and a fourth property of the specimen. In this manner, the third and fourth properties may include, but are not limited to, a presence, a number, a location, and/or a type of defects on a surface of the specimen and a flatness measurement of the specimen. In addition, the method may include determining at least two of the properties substantially simultaneously. The method, however, may also include determining all four of the properties described above sequentially or substantially simultaneously.

In an embodiment, the stage and the measurement device may be coupled to a process tool as described herein. For example, the stage and measurement device may be coupled to a lithography tool. The method may also include controlling a wafer handler of the process tool to move the specimen from the process tool to the stage. The wafer handler may be configured as described herein. Alternatively, the method may include controlling the stage to move the specimen from the system to the process tool.

In a further embodiment, the method may also include controlling the stage to move the specimen from a first process chamber to a second process chamber. The first and second process chambers may be configured as described herein. In this manner, the method may also include controlling the illumination system to direct energy toward a surface of the specimen while the stage is moving the specimen from the first process chamber to the second process chamber. In addition, the method may also include controlling the detection system to detect energy propagating from the surface of the specimen while the stage is moving the specimen from the first process chamber to the second process chamber. As such, the method may include determining at least two properties of the specimen between any two process steps of a process.

In an additional embodiment, the method may include controlling the illumination system to direct energy toward a surface of the specimen during a process step. In addition, the method may also include controlling the detection system to detect energy propagating from the surface of the specimen during the process step. As such, the method may also include processing the detected energy to determine at least two properties of the specimen at predetermined time intervals during the process step. In this manner, the method may also include controlling the system to obtain a signature characterizing the process step. The signature may include at least one singularity, which may be representative of an end of the process step. In addition, the method may also include controlling the system to alter a parameter of an instrument coupled to the process tool in response to the determined properties using an in situ control technique. Furthermore, the computer-implemented method may also include any of the steps as described herein.

In an embodiment, a controller may be coupled to the system. The controller may be a computer system configured to operate software to control the system according to the above embodiments. The computer system may include a memory medium on which computer programs may be stored for controlling the system and processing the detected energy. The term "memory medium" is intended to include an installation medium, e.g., a CD-ROM, or floppy disks, a computer system memory such as DRAM, SRAM, EDO RAM, Rambus RAM, etc., or a non-volatile memory such as a magnetic media, e.g., a hard drive, or optical storage. The memory medium may include other types of memory as well, or combinations thereof. In addition, the memory medium may be located in a first computer in which the programs are executed, or may be located in a second different computer that connects to the first computer over a network In the latter instance, the second computer provides the program instructions to the first computer for execution. Also, the computer system may take various forms, including a personal computer system, mainframe computer system, workstation, network appliance, Internet appliance, personal digital assistant ("PDA"), television system or other device. In general, the term "computer system" may be broadly defined to encompass any device having a processor, which executes instructions from a memory medium.

The memory medium may be configured to store a software program for the operation of the system to determine at least two properties of a specimen. The software program may be implemented in any of vanous ways, including procedure-based techniques, component-based techniques, and/or object-oriented techniques, among others. For example, the software program may be implemented using ActiveX controls, C++ objects, JavaBeans, Microsoft Foundation Classes ("MFC"), or other technologies or methodologies, as desired. A CPU, such as the host CPU, executing code and data from the memory medium may include a means for creating and executing the software program according to the methods described above.

Various embodiments further include receiving or storing instructions and/or data implemented in accordance with the foregoing description upon a carrier medium. Suitable carrier media include memory media or storage media such as magnetic or optical media, e.g., disk or CD-ROM, as well as signals such as electrical, electromagnetic, or digital signals, conveyed via a communication medium such as networks and/or a wireless link.

An embodiment relates to a system which may be configured to determine at least two properties of a specimen, which may include a presence of defects on the specimen and a thin film characteristic of the specimen. For example, a presence of defects may be determined on a front side or a back side of a specimen as described herein. The defects may also include subsurface defects and/or a presence of macro defects on a backside of a specimen, which may include copper contamination and/or resist contamination. In addition, the thin film characteristic may include a thickness of a film such as copper. The system may be configured as described herein. In addition, the processor of such a system may be configured to determine additional properties of the specimen from energy detected by a measurement device. In an embodiment, the measurement device may be configured as a non-imaging scatterometer, a scatterometer, a spectroscopic scatterometer, a reflectometer, a spectroscopic reflectometer, an ellipsometer, a spectroscopic ellipsometer, a bright field imaging device, a dark field imaging device, a bright field and dark field imaging device, a bright field non-imaging device, a dark field non-imaging device, a bright field and dark field non-imaging device, a double dark field device, a coherence probe microscope, an interference microscope, an optical profilometer, a dual beam spectrophotometer, a beam profile ellipsometer, or any combination thereof. In this manner, the measurement device may be configured to function as a single measurement device or as multiple measurement devices. Because multiple measurement devices may be integrated into a single measurement device of the system, optical elements of a first measurement device, for example, may also be optical elements of a second measurement device. Such a system may be coupled to a chemical-mechanical polishing tool, a deposition tool, an etch tool, a cleaning tool such as a wet or dry stripping tool, or a thermal tool such as a furnace configured to perform rapid thermal processing ("RTP") of a specimen as described herein. Examples of cleaning tools are illustrated in PCT Application No. WO 00/17907 and "Chemically Assisted Laser Removal of Photoresist and Particles from Semiconductor Wafers," by Genut et al. of Oramir Semiconductor Equipment Ltd., Israel, presented at the $28^{th}$ Annual Meeting of the Fine Particle Society, Apr. 1–3, 1998, which are incorporated by reference as if fully set forth herein.

Spectroscopic ellipsometry may include focusing an incidence beam of polarized light on a specimen and monitoring a change in polarization of at least a portion of the beam propagating from the specimen across a broad spectrum of wavelengths. Examples of spectroscopic ellipsometers are illustrate in U.S. Pat. No. 5,042,951 to Gold et al., U.S. Pat. No. 5,412,473 to Rosencwaig et al., U.S. Pat. No. 5,581,350 to Chen et al., U.S. Pat. No. 5,596,406 to Rosencwaig et al., U.S. Pat. No. 5,596,411 to Fanton et al., U.S. Pat. No. 5,771,094 to Carter et al., U.S. Pat. No. 5,798,837 to Aspnes et al., U.S. Pat. No. 5,877,859 to Aspnes et al., U.S. Pat. No. 5,889,593 to Bareket et al., U.S. Pat. No. 5,900,939 to Aspnes et al., U.S. Pat. No. 5,917,594 to Norton, U.S. Pat. No. 5,973,787 to Aspnes et al., U.S. Pat. No. 6,184,984 to Lee et al., and are incorporated by reference as if fully set forth herein. Additional examples of spectroscopic ellipsometers are illustrated in PCT Application No. WO 99/02970 to Rosencwaig et al. and is incorporated by reference as if fully set forth herein.

A measurement device configured as a spectroscopic ellipsometer may include a polarizer, which may be coupled to the detection system. A beam propagating from the specimen pass through the polarizer. Prior to passing through the polarizer, the returned beam may have elliptical polarization. After passing through the polarizer, the beam may be linearly polarized. The reflected light then pass through an analyzer coupled to the detection system and into a dispersion element, or a spectrometer. The dispersion element may be configured to separate beam components having different wavelengths. The separated components of the beam may be detected by individual elements of a detector array. The polarizer is usually rotating such that a time varying intensity may be detected by the elements of the detector array.

A processor of the system may receive a signal responsive to the detected light from each element of the detector array and may process the signal as described herein For example, an intensity of light at each element of the detector array may be converted to ellipsometric parameters, $\psi$ and $\Delta$, by mathematical equations known in the art. The ellipsometric parameters may be typically shown as tan $\psi$ and cos $\Delta$. Tan $\psi$ is the amplitude of the complex ratio of the s and p components of the reflectivity of the sample, and $\Delta$ is the phase of the complex ratio of the s and p components of the reflectivity of the sample. The term "s component" is used to describe the component for the polaized radiation having an electrical field perpendicular to the plane of incidence of the reflected beam. The term "p component" is used to describe the component for the polarized radiation having an electrical field in the plane of incidence of the reflected beam. For very tin films, tan $\psi$ may be independent of thickness, and $\Delta$ may be linearly proportional to the thickness.

Software integrated into the processor of the system may be configured to convert the ellipsometric parameters, $\psi$ and $\Delta$, to an optical property of a specimen using a mathematical, or optical, model. Typically, a personal computer having a software package operable to rapidly performing data-fitting calculations such as a least-squares fitting technique may be appropriate for this use. Because ellipsometric parameters including $\psi$ and $\Delta$ may be determined at small increments across a broad spectrum of wavelengths and at several angles, several hundred data points may be included in the calculations. Several software packages configured for use with spectroscopic ellipsometers that are capable of handling such a large amount of data are commercially available. The processor that may be used to receive a signal responsive to the detected light from each element of the detector array may be also used to perform the iterative data-fitting calculations. Examples of such software packages may be incorporated into operating systems of spectroscopic ellipsometers, which have been included by reference above, and are typically commercially available.

There are several optical models that may be used to analyze ellipsometric data. Examples, of such models include, but are not limited to, a cauchy model, a harmonic oscillator model, and a polynomial series expansion model. An appropriate model, however, may be chosen based on specimen characteristics, desired optical properties of the specimen, and the computational difficulty associated with the model. For example, the cauchy model is a relatively straightforward mathematical model. The cauchy model, however, may not be valid for wavelengths at which a specimen exhibits absorption. Additionally, optical properties of several layers of a specimen may also be determined simultaneously by using an appropriate optical model or a combination of optical models. Therefore, when using spectroscopic ellipsometry to analyze a specimen, one or more optical models may be more appropriate for analysis than others.

Thicknesses, indexes of refraction, and extinction coefficients for a layer of a specimen, a portion of a layer of a specimen, or several layers of a specimen may be determined from ellipsometric parameters using an optical model. The index of refraction, "n," is related to the speed of light as it moves through a medium and is dependent upon the wavelength of the light. The extinction coefficient, "k," is also dependent upon wavelength and relates to absorption of light by a medium. The extinction coefficient may also be used to determine the absorption coefficient for a given a wavelength. Further discussion of the ellipsometric parameters and the optical properties of materials is illustrated in U.S. Pat. No. 4,905,170 to Forouhi, et al. and is incorporated by reference as if fully set forth herein.

FIG. 22 illustrates an embodiment of a system configured to determine at least two properties of a specimen coupled to chemical-mechanical polishing tool 222. Chemical-mechanical polishing ("CMP") may typically be used in the semiconductor industry to partially remove or planarize a layer on a specimen. Chemical-mechanical polishing may include holding and/or rotating a specimen against a rotating polishing platen under controlled pressure. Chemical-mechanical polishing tool 222 may include polishing head 224 configured to hold specimen 226 against polishing platen 228. Polishing head 224 may include a number of springs 230 or another suitable mechanical device, which may be configured to apply an adjustable pressure to a back side of specimen 226. Polishing head 224 may also be configured to rotate around a central axis of the polishing head. In addition, polishing head 224 may also be configured to move linearly with respect to the polishing platen.

Polishing platen 228 may also include a polishing pad 232. The polishing pad may have a back layer, which may be configured such that polishing pad 232 may be securely coupled to polishing platen 228. Polishing pad 232 may also have an upper layer which may be configured to contact and polish specimen 226. The upper layer of polishing pad 232 may include, for example, an open cell foamed polyurethane material or a polyurethane layer having a grooved surface. The upper layer may also include additional abrasive materials or particles configured to partially remove or polish specimen 226. Polishing platen 228 may also be configured to rotate around a central axis of the polishing platen. For example, polishing platen 228 may be configured to rotate in a first direction, and polishing head 224 may be configured to rotate in a second direction. The first direction may be substantially opposite to the second direction.

Chemical-mechanical polishing tool 222 may also include dispense system 234. The dispense system may be configured to automatically dispense a polishing chemical such as a chemical polishing slurry onto polishing pad 232. A chemical polishing slurry may include abrasive particles and at least one chemical. For example, abrasive particles may include fused-silica particles, and a chemical may include potassium hydroxide. Alternatively, polishing pad 232 may be sufficiently abrasive such that the chemical polishing solution may be substantially free of particles. Suitable combinations of a polishing chemical and a polishing pad may vary depending on, for example, a composition and a topography of an upper layer on specimen 226 which is being partially removed or planarized and/or a composition and a topography of an underlying layer.

A system configured to determine at least two properties of a specimen may include measurement device 220 coupled to chemical-mechanical polishing tool 222. The measurement device may be configured according to any of the embodiments described herein. For example, measurement device 220 may be a non-imaging dark field device, a non-imaging bright field device, a non-imaging dark field and bright field device, a double dark field device, a dark field imaging device, a bright field imaging device, a dark field and bright field imaging device, a spectroscopic ellipsometer, a spectroscopic reflectometer, a dual beam spectrophotometer, and a beam profile ellipsometer. In addition, the measurement device may include any combination of the above devices. As such, the measurement device may be configured to function as a single measurement device or as multiple measurement devices. Because multiple measurement devices may be integrated into a single measurement device of the system, optical elements of a first measurement device, for example, may also be optical elements of a second measurement device.

The measurement device may be coupled to the chemical-mechanical polishing tool such that the measurement device may be external to polishing platen 228. In this manner, the measurement device may be coupled to chemical-mechanical polishing tool 222 such that the measurement device may not interfere with the operation, performance, or control of the chemical-mechanical polishing process. For example, polishing platen 228 and polishing pad 232 may be retrofitted such that a small section of a substantially optically transparent material 236 may be disposed within the polishing platen and the polishing pad. The configuration of the chemical-mechanical polishing tool, however, may determine the placement and dimensions of the transparent material section 236.

The small section of transparent material 236 may transmit an incident beam of light from a light source of measurement device 220 outside the polishing platen to a surface of specimen 226 held in place by polishing head 224 and light propagating from a surface of specimen 226 to a detector of measurement device 220 external to the polishing platen. The optically transparent material 236 may have optical or material properties such that light from a light source of measurement device 220 and light propagating from a surface of specimen 226 may pass through the transparent sections of the polishing platen and the polishing pad without undesirably altering the properties of the incident and returned light beams.

Polishing chemicals such as chemical-polishing slurries, however, may include abrasive particles, chemicals, and material removed from the specimen, which may interfere with light from the light source and light propagating from a surface of the specimen. In an embodiment, therefore, the section of transparent material 236 may be configured to function as a self-clearing objective. The self-clearing objective may include an optical component configured to transmit light from a light source toward a surface of specimen 226. A self-clearing objective may also be configured to flow a substantially transparent fluid between the self-clearing objective and the specimen. The flowing fluid may be configured to remove abrasive particles, chemicals, and material removed from the specimen such that light may be transmitted from the measurement device to the specimen and from the specimen to a detector of the measurement device without undesirable alterations in the optical properties of the light. Examples of self clearing objectives are illustrated in U.S. patent application Ser. No. 09/396,143, "Apparatus and Methods for Performing Self-Clearing Optical Measurements," to Nikoonahad et al., and Ser. No. 09/556,238, "Apparatus and Methods for Detecting Killer Particles During Chemical Mechanical Polishing," to Nikoonahad et al., and are incorporated by reference as if fully set forth herein. In this manner, the measurement device may be coupled to a stage (i.e., polishing platen 228) disposed within the process chamber and configured to support the specimen.

Examples of chemical-mechanical polishing systems and methods are illustrated in U.S. Pat. No. 5,730,642 to Sandhu et al., U.S. Pat. No. 5,872,633 to Holzapfel et al., U.S. Pat. No. 5,964,643 to Birang et al., U.S. Pat. No. 6,012,966 to Ban et al., U.S. Pat. No. 6,045,433 to Dvir et al., U.S. Pat. No. 6,159,073 to Wiswesser et al., and U.S. Pat. No. 6,179,709 to Redeker et al., and are incorporated by reference as if fully set forth herein. Additional examples of chemical-mechanical polishing systems and methods are illustrated in PCT Application Nos. WO 99/23449 to Wiswesser, WO 00/00873 to Campbell et al., WO 00/00874 to Campbell et al., WO 00/18543 to Fishkin et al., WO 00/26609 to Wiswesser et al., and WO 00/26613 to Wiswesser et al., and European Patent Application Nos. EP 1 022 093 A2 to Birang et al. and EP 1 066 925 A2 to Zuniga et al., and are incorporated by reference as if fully set forth herein. An additional example of an integrated manufacturing tool including electroplating, chemical-mechanical polishing, clean and dry stations is illustrated PCT Application No. WO 99/25004 to Sasson et al., and is incorporated by reference as if fully set forth herein.

An embodiment relates to a system that may be configured to determine at least two properties of a specimen including a presence of defects on a specimen and a critical dimension of the specimen. The system may be configured as described herein. For example, the system may include a processor coupled to a measurement device and configured to determine at least a presence of defects and a critical dimension of the specimen from one or more output signals of the measurement device. In addition, the processor may be configured to determine other properties of the specimen from the one or more output signals. In an embodiment, the measurement device may include a non imaging scatterometer, a scatterometer, a spectroscopic scatterometer, a reflectometer, a spectroscopic reflectometer, an ellipsometer, a spectroscopic ellipsometer, a bright field imaging device, a dark field imaging device, a bright field and dark field imaging device, a bright field non-imaging device, a dark field non-imaging device, a bright field and dark field non-imaging device, a coherence probe microscope, an interference microscope, an optical profilometer, or any combination thereof. Such a system may be coupled to a process tool such as a lithography tool, an etch tool, a deposition tool, or a plating tool as described herein.

In an embodiment, a system configured to determine at least a presence of defects on a specimen and a critical dimension of the specimen may be coupled to an etch tool as described herein. The presence of defects may include a presence of defects on a back side of the specimen. In addition, the system may be further configured to determine a number, a location, and/or a type of defects on the specimen. The system may be coupled to the etch tool such that at least a presence of defects on the specimen and a critical dimension of the specimen may be determined prior to and subsequent to an etch process or a step of an etch process. As described herein, at least one of the determined properties may be used to alter a parameter of one or more instruments coupled to a process tool. For example, a determined critical dimension of the specimen may be used to alter a parameter of one or more instruments coupled to a lithography tool using a feedforward control technique or a feedback control technique. In addition, a determined presence of defects on the specimen may be used to alter a parameter of one or more instruments coupled to the lithography tool using a feedforward control technique or a feedback control technique.

In an embodiment, a system may be configured to determine at least two properties of a specimen including a critical dimension of the specimen and a thin film characteristic of the specimen. The system may be configured as described herein. For example, the system may include a processor coupled to a measurement device. The processor may be configured to determine at least a critical dimension and a thin film characteristic of the specimen from one or more output signals generated by the measurement device. In addition, the processor may be configured to determine other properties of the specimen from the one or more output signals. In an embodiment, the measurement device may include a non-imaging scatterometer, a scatterometer, a spectroscopic scatterometer, a reflectometer, a spectroscopic reflectometer, an ellipsometer, a spectroscopic ellipsometer, a photo-acoustic device, a grazing X-ray reflectometer, a bright field imaging device, a dark field imaging device, a bright field and dark field imaging device, a coherence probe microscope, an interference microscope, an optical profilometer, a dual beam spectrophotometer, a beam profile ellipsometer, or any combination thereof. Such a system may be coupled to a process tool such as a lithography tool, an etch tool, a deposition tool, or a plating tool as described herein.

In addition, a system configured to determine at least a critical dimension and a thin film characteristic of a specimen may be coupled to a chemical-polishing tool. For example, the processor may be configured to determine a critical dimension of a feature on the specimen from one or more output signals from a non-imaging scatterometer, a scatterometer, or a spectroscopic scatterometer. In addition, the processor may be configured to determine a thickness of a layer on the specimen from one or more output signals from a reflectometer, a spectroscopic reflectometer, an ellipsometer, a spectroscopic ellipsometer, a photo-acoustic device, and/or a grazing X-ray reflectometer. For example, an ellipsometer or a spectroscopic ellipsometer may be configured to generate one or more output signals responsive to a thickness of metal and semi-metallic layers having relatively thin thicknesses and relatively thick transient layers. A photo-acoustic device may be configured to generate one or more output signals responsive to a thickness of relatively thin metal layers, and a grazing X-ray reflectometer may be confirm to generate one or more output signals responsive to relatively thick and relatively thin layers. In this manner, a system, as described herein, may be configured to determine a thickness of layers having a broad range of thicknesses and materials.

The system may be coupled to a chemical-mechanical polishing tool according to any of the embodiments described herein. For example, the measurement device may be coupled to a polishing pad of a chemical-mechanical polishing tool such that the system may determine at least two properties of a specimen disposed upon the polishing pad. Alternatively, the measurement device may be coupled to a chemical-mechanical polishing tool such that the system may determine at least two properties of a specimen being disposed upon or removed from the polishing pad. For example, the measurement device may be coupled to a chemical-mechanical polishing tool such that a robot wafer handler may move below or above the measurement device. In an alternative embodiment, the measurement device may be coupled to a robotic wafer handler of a chemical-mechanical polishing tool. In this manner, the system may be configured to determine at least two properties of the specimen as the robotic wafer handler is moving the specimen.

In a further embodiment, the measurement chamber may be coupled to and disposed laterally or vertically proximate an exit chamber of a chemical-mechanical polishing tool. An exit chamber of a chemical-mechanical polishing tool may include a water bath configured to receive a specimen subsequent to a chemical-mechanical polishing process. The water bath may be used to remove chemicals, slurry particles, and/or specimen particles remaining on the specimen subsequent to a chemical-mechanical polishing process. In this manner, the system may be configured to determine at least two properties of the specimen, as the specimen is disposed within or moving through the exit chamber.

In an additional embodiment, the measurement device may be disposed in a measurement chamber, as described with rest to and shown in FIG. 16. The measurement chamber may be coupled to a chemical-mechanical polishing tool, as shown in FIG. 17. For example, the measurement chamber may be disposed laterally or vertically proximate one or more polishing chambers of a chemical-mechanical polishing tool. In addition, the measurement chamber may be disposed laterally or vertically proximate a load chamber of a chemical-mechanical polishing tool. A load chamber of a chemical-mechanical polishing tool may be configured to support multiple specimens such as a cassette of wafers that are to be processed in the chemical-mechanical polishing tool. A robotic wafer handler may be configured to remove a specimen from the load chamber prior to processing and to dispose a processed specimen into the load chamber.

Furthermore, the measurement chamber may be disposed in other locations proximate a chemical-mechanical polishing tool such as anywhere proximate the chemical-mechanical polishing tool where there is sufficient space for the system and anywhere a robotic wafer handler may fit such that a specimen may be moved between a polishing pad and the system.

In an additional embodiment, a system may be configured to determine at least three properties of a specimen including a critical dimension of the specimen, a presence of defects on the specimen, and a thin film characteristic of the specimen. The defects may also include subsurface defects and/or a presence of macro defects on a backside of a specimen, which may include, but are not limited to, copper contamination and/or resist contamination. In addition, the thin film characteristic may include a thickness of a film such as copper. The system may be configured as described herein. For example, the system may also include a processor coupled to a measurement device and configured to determine at least a critical dimension, a presence of defects, and a thin film characteristic of the specimen from one or more output signals generated by the measurement device.

In addition, the processor may be configured to determine other properties of the specimen from the one or more output signals. In an embodiment, the measurement device may include a non-imaging scatterometer, a scatterometer, a spectroscopic scatterometer, a reflectometer, a spectroscopic reflectometer, an ellipsometer, a spectroscopic ellipsometer, a bright field imaging device, a dark field imaging device, a bright field and dark field imaging device, a bright field non-imaging device, a dark field nor-imaging device, a bright field and dark field non-imaging device, a coherence probe microscope, an interference microscope, an optical profilometer, a dual beam spectrophotometer, a beam profile ellipsometer, or any combination thereof. Such a system may be coupled to a process tool such as a lithography tool, an etch tool, a deposition tool, or a plating tool as described herein.

In an embodiment, a system may be configured to determine at least two properties of a specimen including a presence of macro defects on the specimen and a presence of micro defects on the specimen. The system may be configured as described herein. For example, the system may include a processor coupled to a measurement device. The processor may be configured to determine at least a presence of macro defects and a presence of micro defects on the specimen from one or more output signals generated by the measurement device. In addition, the processor may be configured to determine other properties of the specimen from the one or more output signals. For example, the processor may be configured to determine a presence of subsurface defects such as voids from one or more output signals generated by a measurement device such as an e-beam device, an X-ray reflectometer, or an X-ray fluorescence device. Such voids may be problematic, in particular for copper structures, if the voids fill with chemicals such as plating solutions, which may corrode the metal. In addition, the processor may be configured to determine a thickness of a metal layer such as copper on the specimen from one or more output signals generated by a measurement device such as an X-ray reflectometer and/or an X-ray fluorescence device.

Furthermore, the processor may be configured to determine a presence of macro defects on a backside of a specimen from one or more output signals generated by a measurement device such as an optical fluorescence device. The macro defects may include copper contamination and/or resist contamination. An optical fluorescence device may be configured to direct a beam of light to a surface of a specimen to induce fluorescence of the specimen. The directed beam of light may have a wavelength of approximately 364 nm. The wavelength of the directed beam of light may vary, however, depending upon, for example, a material that may be a defect. The optical fluorescence device may be further configured to detect fluorescence of the specimen and to generate one or more output signals in response to the detected fluorescence. A processor may be configured to determine a presence of macro defects, for example, by comparing detected fluorescence at multiple points on the specimen.

In an embodiment, the measurement device may include a non-imaging scatterometer, a scatterometer, a spectroscopic scatterometer, a reflectometer, a spectroscopic reflectometer, an ellipsometer, a spectroscopic ellipsometer, a bright field imaging device, a dark field imaging device, a bright field and dark field imaging device, a bright field non-imaging device, a dark field non-imaging device, a bright field and dark field non-imaging device, a double dark field device, a coherence probe microscope, an interference microscope, an optical profilometer, an e-beam device such as a scanning electron microscope or a tunneling electron microscope, an X-ray reflectometer, an X-ray fluorescence device, an optical fluorescence device, an eddy current imaging device, and a relatively large pot e-beam device, or any combination thereof. For example, an appropriate combination may include an eddy current imaging device and a relatively large-spot e-beam device. An eddy current imaging device may generate one or more output signals that may be used as a qualitative excursion monitor for a presence of macro defects on a surface of the specimen. The eddy current imaging device may be configured as described herein. A large-spot e-beam device such as a scanning electron microscope may have relatively low resolution and a relatively low data rate. One or more output signals generated by such an e-beam device may include a voltage contrast that may vary depending upon a presence of defects such as macro defects on the surface of the specimen. An example of an e-beam device is illustrated in U.S. Patent Application entitled "Sectored Magnetic Les," by John A. Notte IV, filed on Jun. 15, 2001, which is incorporated by reference as if fully set forth herein.

Such a system may be coupled to any of the process tools as described herein. For example, the system may be coupled to a lithography tool or an etch tool as described herein.

In an embodiment, a system may be configured to determine at least two properties of a specimen including a presence of macro defects on at least one surface of the specimen and overlay misregistration of the specimen. The determined properties may also include a number, a location, and a type of macro defects present on at least one surface of the specimen. At least one surface of the specimen may include a back side and/or a front side of the specimen. The system may be configured as described herein For example, the system may include a processor coupled to a measurement device. The processor may be configured to determine at least a presence of macro defects and overlay misregistration of the specimen from one or more output signals generated by the measurement device. In addition, the processor may be configured to determine other properties such as a critical dimension of a feature on the specimen from the one or more output signals. In an embodiment, the measurement device may include a scatterometer, a non-imaging scatterometer, a spectroscopic scatterometer, a reflectometer, a spectroscopic reflectometer, an ellipsometer, a spectroscopic ellipsometer, a beam profile ellipsometer, a bright field imaging device, a dark field imaging device, a bright field and dark field imaging device, a bright field non-imaging device, a dark field non-imaging device, a bright field and dark field non-imaging device, a coherence probe microscope, an interference microscope, an optical profilometer, or any combination thereof.

Such a system may be coupled to any of the process tools as described herein. For example, the system may be coupled to a process tool such as a lithography tool, an etch tool, and a deposition tool. The system may be coupled to the process tool according to any of the embodiments as described herein. For example, the measurement device may be coupled to a process chamber of the process tool such that the system may determine at least two properties of a specimen disposed within the process chamber. Alternatively, the measurement device may be coupled to a process chamber of the process tool such that the system may determine at least two properties of a specimen being disposed within or removed from the process chamber. For example, the measurement device may be coupled to the process chamber such that a robot wafer handler may move below or above the measurement device. In an alternative embodiment, the measurement device may be coupled to a robotic wafer handler of the process tool. In this manner, the system may be configured to determine at least two properties of the specimen as the robotic wafer handler is moving the specimen.

In an additional embodiment, the measurement device may be disposed in a measurement chamber, as described with respect to and shown in FIG. 16. The measurement chamber may be coupled to the process tool, as shown in FIG. 17. For example, the measurement chamber may be disposed laterally or vertically proximate one or more process chambers of the process tool. For example, the deposition tool may include a cluster of process chambers that may each be configured to perform substantially similar processes or different processes. In addition, the measurement chamber may be disposed laterally or vertically proximate a load chamber of the process tool. A load chamber of a deposition tool may be configured to support multiple specimens such as a cassette of wafers that are to be processed in the process tool. A robotic wafer handler may be configured to remove a specimen from the load chamber prior to processing and to dispose a processed specimen into the load chamber. Furthermore, the measurement chamber may be disposed in other locations proximate a process tool such as anywhere proximate the process tool where there is sufficient space for the system and anywhere a robotic wafer handler may fit such that a specimen may be moved between a process chamber and the system.

In addition, a parameter of one or more instruments coupled to a process tool may be altered in response to the properties determined by the system using a feedback control technique, an in situ control technique, and/or a feedforward control technique. For example, a presence of macro defects on the surface such as a presence of macro defects on a back side of a specimen determined by the system prior to, during, and/or subsequent to an etch process, a deposition process, and/or a chemical-mechanical process may be used to alter a parameter of one or more instruments coupled to a lithography tool using a feedforward control technique. In this example, the determined presence of macro defects on the back side of the specimen may be used to alter a dose and focus condition of an exposure tool during exposure of the specimen during a lithography process. In an additional example, overlay misregistration of a specimen determined by the system prior to, during, and/or subsequent to an etch process and/or a deposition process may be used to alter a parameter of one or more instruments coupled to a lithography tool using a feedforward control technique. In this example, the determined overlay misregistration may be used to alter a lateral alignment of a reticle in an exposure tool during exposure of the specimen during a lithography process.

A deposition tool may be configured for chemical vapor deposition, as described below, or for physical vapor deposition. Physical vapor deposition may commonly be used in the semiconductor industry to form a layer of a conductive material upon a specimen such as a wafer. A physical vapor deposition tool may include a vacuum process chamber in which argon ions may be generated. In addition, a support device may be disposed within the process chamber. The support device may be configured to support a specimen during a physical vapor deposition process. In addition, a circular-shaped metal target may be disposed above the support device. The physical vapor deposition tool may also include an annular metal coil interposed between the support device and the metal target. The annular metal coil may be made of the same material as the metal target. A physical vapor deposition tool may also include a voltage controller configured to supply a voltage to the metal target, the metal coil, and the support device. The voltage controller may be further configured to generate voltage biases between the metal target and the support device and between the support device and the metal coil. The voltage biases may cause argon ions to bombard the metal target and the metal coil to release metal atoms, which may then sputter onto a surface of a specimen on the support device. Examples of physical vapor deposition systems and methods are illustrated in U.S. Pat. No. 5,754,297 to Nulman, U.S. Pat. No. 5,935,397 to Masterson, U.S. Pat. No. 6,039,848 to Moslehi et al., U.S. Pat. No. 6,080,287 to Drewery et al., and U.S. Pat. No. 6,099,705 to Chen et al., and are incorporated by reference as if fully set forth herein.

A system, as described herein, may be coupled to a physical vapor deposition tool. For example, the system may be disposed within a measurement chamber. The measurement chamber may be configured as described herein. The measurement chamber may be located proximate a process chamber of the physical vapor deposition tool. Alternatively, the system may be coupled to a process chamber of the physical vapor deposition tool. In this manner, the system may be integrated into a physical vapor deposition tool. As such, the system may be configured to determine at least two properties of a specimen prior to, during, or subsequent to a physical vapor deposition process. Such arrangements of a system and a process chamber are described with reference to and illustrated in, for example, FIGS. 17 and 18. Process chambers 180 and 188, as illustrated in FIGS. 17 and 18, may be configured differently than shown such that the process chamber may be configured for a physical vapor deposition process. For example, process chamber 180 may not include dispense system 186 and, instead, may include various devices and components as described above. Furthermore, a system may be coupled to a wafer handler of a physical vapor deposition tool. Therefore, the system may be configured to determine at least two properties of a specimen while the specimen is being moved into a process chamber or out of a process chamber of a physical vapor deposition tool.

Plating may commonly be used in the semiconductor industry to form a layer of metal upon a specimen such as a wafer. A plating tool may include a process chamber such as a plating bath. A plurality of support devices may be disposed within the plating bath. Each of the support devices may be configured to support a specimen during a plating process. The plating tool may also include a cathode electrode arranged above and in contact with an upper surface of a specimen. In addition, the plating tool may include an anode electrode located beneath the specimen. A plating solution may flow into the plating bath from an inlet port and may be ejected upwardly onto a surface of a specimen. Furthermore, the plating tool may include a heater configured to heat the plating solution during a plating process. Controlling the temperature of the plating solution may be critical to forming a metal layer without defects such as structural changes, hardening, and/or plating bum of the layer. In addition, characteristics of a metal layer formed on a specimen may vary depending on additional characteristics of the plating solution. For example, the characteristics of a layer of plated metal may depend on a metal ion concentration in the plating solution, the pH level of the plating solution, and the specific gravity of the plating solution. An example of a system and a method for plating specimens is illustrated in U.S. Pat. No. 5,344,491 to Katou, and is incorporated by reference as if fully set forth herein.

As described herein, a system may be coupled to a plating tool. For example, the system may be disposed within a measurement chamber. The measurement chamber may be configured as described herein. The measurement chamber may be located proximate a process chamber of the plating tool. Alternatively, the system may be coupled to a process chamber of the plating tool. Therefore, the system may be configured to determined at least two properties of a specimen prior to, during, or subsequent to a plating process. Such arrangements of a system and a process chamber are described with reference to and illustrated in, for example, FIGS. 17 and 18. Process chambers 180 and 188, as illustrated in FIGS. 17 and 18, may be configured differently than shown such that the process chamber may be configured for a plating process. For example, process chamber 180 may not include dispense system 186 and, instead, may include various devices and components as described above. In addition, a system may be coupled to a wafer handler of a plating tool as described herein. As such, a system may be configured to determine at least two properties of a specimen while a specimen is being disposed within or removed from a process chamber of a plating tool.

An embodiment relates to a system which may be configured to determine at least a flatness measurement of the specimen, a presence of defects on the specimen, and a thin film characteristic of a specimen. The defects may include subsurface defects and/or a presence of macro defects on a backside of a specimen, which may include, but are not limited to, copper contamination and/or resist contamination. In addition, the thin film characteristic may include a thickness of a film such as copper. The system may be configured as described herein. For example, the system may include a processor coupled to a measurement device. The processor may be configured to determine at least a flatness measurement of the specimen, a presence of defects on the specimen, and a thin film characteristic of a specimen from one or more output signals generated by the measurement device. In addition, the processor may be configured to determine other properties of the specimen from the one or more output signals. In an embodiment, the measurement device may include a non-imaging scatterometer, a scatterometer, a spectroscopic scatterometer, a reflectometer, a spectroscopic reflectometer, an ellipsometer, a spectroscopic ellipsometer, a bright field imaging device, a dark field imaging device, a bright field and dark field imaging device, a bright field non-imaging device, a dark field non-imaging device, a bright field and dark field non-imaging device, a double dark field device, a coherence probe microscope, an interference microscope, an interferometer, an optical profilometer, a dual beam spectrophotometer, a beam profile ellipsometer, or any combination thereof. In this manner, the measurement device may be configured to function as a single measurement device or as multiple measurement devices.

Such a system may be coupled to a chemical-mechanical polishing tool as described above. In this manner, the system may be configured to determine at least the three properties of a specimen prior to, during, or subsequent to a chemical-mechanical polishing process. Alternatively, such a system may be disposed within a measurement chamber, which may be configured as described herein. The measurement chamber may be located proximate the chemical-mechanical polishing tool. Therefore, such a system may be configured to determine at least the three properties of the specimen prior to or subsequent to a chemical-mechanical polishing process. Therefore, the flatness measurement of a specimen may include a measure of stress-induced curvature of a specimen due to a chemical-mechanical polishing process. In addition, the processor may be configured to alter a parameter of an instrument coupled to a chemical-mechanical polishing tool in response to the flatness measurement using a feedforward control technique. For example, the processor may be configured to alter a pressure of the polishing head coupled to the chemical-mechanical polishing tool in response to the flatness measurement using a feedforward control technique. In addition, the polishing head may be configured such that pressure across the polishing head may vary from zone to zone. Therefore, altering a pressure of the polishing head may include altering a pressure of one or more zones of the polishing head. In this manner, a system as described herein may be used to increase a planarity of an upper surface of the specimen subsequent to chemical-mechanical polishing.

Alternatively, such a system may be coupled to a thermal tool such as a furnace or a rapid thermal annealing furnace. As such, the flatness measurement of a specimen may include a measure of stress-induced curvature of a specimen due to thermal processing. In addition, such a system may also be coupled to an etch tool, a lithography tool, or a wafer manufacturing tool as described herein.

In an embodiment, a system may be configured to determine at least an overlay misregistration of a specimen and a flatness measurement of the specimen. The system may be configured as described herein. For example, the system may include a processor coupled to a measurement device. The processor may be configured to determine at least an overlay misregistration of a specimen and a flatness measurement of the specimen from one or more output signals generated by the measurement device. In addition, the processor may be configured to determine other properties of the specimen from the one or more output signals. In an embodiment, the measurement device may include a non-imaging scatterometer, a scatterometer, a spectroscopic scatterometer, a reflectometer, a spectroscopic reflectometer, a spectroscopic ellipsometer, a bright field imaging device, a dark field imaging device,a bright field and dark field imaging device, a coherence probe microscope, an interference microscope, an interferometer, an optical profilometer, a dual beam spectrophotometer, a beam profile ellipsometer, or any combination thereof. The system may be further configured to determine at least an overlay misregistration of a specimen and a flatness measurement of the specimen sequentially or substantially simultaneously. For example, the system may be coupled to a lithography tool as described herein. In addition, the system may be configured to determine at least a flatness measurement of the specimen prior to an exposure step of a lithography process. The system may also be configured to determine an overlay misregistration of a specimen prior to the exposure step.

As described herein, a system may be configured to determine at least a characteristic of an implanted region of the specimen and a presence of defects on the specimen. The system may be configured as described herein. For example, the system may include a processor configured to determine at least a characteristic of an implanted region of the specimen and a presence of defects on the specimen from one or more output signals generated by a measurement device. In addition, the processor may be configured to determine other properties of the specimen from the one or more output signals. In an embodiment, the measurement device may include a modulated optical reflectometer, an X-ray reflectance device, an eddy current device, a photoacoustic device, a spectroscopic ellipsometer, a non-imaging scatterometer, a scatterometer, a spectroscopic scatterometer, a reflectometer, a spectroscopic reflectometer, an ellipsometer, a bright field non-imaging device, a dark field non-imaging device, a bright field and dark field non-imaging device, a bright field imaging device, a dark field imaging device, a bright field and dark field imaging device, a coherence probe microscope, an interference microscope, an optical profilometer, a dual beam spectrophoto meter, or any combination thereof.

An ion implantation process typically involves producing a beam of ions and driving at least some of the ions into a semiconductor substrate. The implantation of ions into a semiconductor substrate may alter electrical properties of the semiconductor substrate. The electrical properties of the implanted semiconductor substrate may vary depending on a concentration of ions implanted into the semiconductor substrate. The electrical properties of the implanted semiconductor substrate may also vary depending on the depth of the implanted portion of the semiconductor substrate and the distribution of the implanted ions as a function of thickness. Such characteristics of the implanted region of the semiconductor substrate may vary depending on a number of factors including, but not limited to, a type of the ions, implantation energy, implantation dose, and masking materials formed on the semiconductor substrate.

In some embodiments, an optical property of an upper, middle, or lower portion of the masking material may be used to determine a characteristic of implanted ions in the masking material such as depth of the implanted ions or a characteristic of the implantation process such as implantation energy. For example, during an ion implantation process, ions will be driven into the masking material. The implantation of ions into the masking material may cause physical damage to an upper surface of the masking material, and ions driven into the masking material may reside in the middle portion of the masking material. The depth to which implantation of ions causes damage to the upper portion of the masking material may be a function of the energy of the ions. The depth to which the ions are driven into the masking material may also be a function of the energy of the ions. For example, higher energy implantation processes may cause more damage to an upper portion of the masking material and may drive the ions farther into the masking material than lower energy ion implantation process. Therefore, the depth of the upper and middle portions of the masking material may be related to the implant energy of the ion implantation process. The depth of the upper and middle portions of the masking material may also be related to other process conditions of the ion implantation such as the species of ions being implanted or the implant dose. In addition, the measured thickness of the lower portion of the masking material may also vary depending upon ion implantation energy. The thickness of the upper, middle, and lower portions may be determined by measuring an optical property of the masking material. The implantation of ions into the masking material or the implanted masking material resulting from the ion implantation process may, therefore, be determined as a function of the measured optical property of the masking material.

In additional embodiments, an implanted masking material may be analyzed as a single, substantially homogenous, layer. Therefore, an optical property of substantially an entire implanted masking material may also be measured. The entire implanted masking material may include the upper, middle, and lower portions of the implanted masking material as described above. The individual optical properties of the upper, middle, and lower portions may, therefore, be effectively included in the measurement of the optical property of the entire implanted masking material. For example, an optical property of the entire implanted masking layer may include added or averaged optical properties of individual layers. An optical property of a masking material measured as a single layer may be used to determine the ion implantation conditions. In one example, an optical property of substantially the entire thickness of the masking material may be compared to an optical property of substantially the entire thickness of the masking material prior to ion implantation. Therefore, the comparison of the optical properties may indicate a change in the optical property of the masking material subsequent to the ion implantation. A change in the optical property of the masking material may be attributed to implanted ions present in the masking material subsequent to an implantation process. In addition, an optical property of substantially the entire implanted masking material may also be compared to an optical property of substantially an entire masking material implanted using known conditions. In this manner, comparing the optical properties of the two implanted masking materials may indicate if the ion implantation process is drifting over time or across several semiconductor substrates.

In one embodiment, the optical property of the masking material may be a thickness, an index of refraction (or refractive index), or an extinction coefficient of the masking material or a portion of the masking material. The optical property of the masking material may be measured using a broadband radiation technique such as spectroscopic ellipsometry or spectroscopic reflectometry. The thickness of the masking material may also be measured separately using an additional optical technique such as dual-beam spectrophotometry. Examples of dual-beam spectrophotometry methods and systems are illustrated in U.S. Pat. No. 5,652,654 to Asimopoulos, U.S. Pat. No. 5,699,156 to Carver, and U.S. Pat. No. 5,959,812 to Carver, and are incorporated by reference as if fully set forth herein. Additionally, several optical properties of the masking material may be measured simultaneously. For example, a thickness of the upper, middle, and lower portions of the implanted masking material may be measured simultaneously. In addition, an index of refraction and an extinction coefficient may be measured simultaneously for an implanted masking material or a portion of an implanted masking material. Depending on the number of optical properties measured, several characteristics of the ion implantation process and/or the implanted masking material may also be determined simultaneously. Characteristics of the ion implantation process may include, but are not limited to, implant dose, implant energy, and implant species. Characteristics of the implanted masking material may include, but are not limited to, concentration of the implanted ions in the masking material and the presence of implanted ions in the masking material.

In an embodiment, the measured optical property of the implanted masking material may also be used to determine a characteristic of an implanted portion of the semiconductor substrate. The implanted portion of the semiconductor substrate may be formed during the implantation of ions into the masking material or during subsequent ion implantation processes. Characteristics of an implanted portion of a semiconductor substrate may include a depth of the implanted portion, a concentration of ions in the implanted portion, and a distribution of implanted ions as a function of the thickness of the implanted portion. Such characteristics may be a function of a measured optical property of the masking material. The function may describe a relationship between the optical property of the implanted masking material and the implantation of ions into the semiconductor substrate. The function may be determined experimentally by implanting a masking material and a portion of a semiconductor substrate simultaneously. The optical property of the implanted masking layer and the electrical properties of the implanted portion of the semiconductor substrate may then be measured. The electrical properties of the implanted portion of the semiconductor substrate may be related to characteristics of the implantation of ions into the semiconductor substrate such as depth of the implanted portion or distribution of the implanted ions as a function of thickness of the semiconductor substrate. A number of wafers may be processed and measured in this manner in order to generate a set of data that may be used to determine a functional relationship between an optical property of an implanted masking material and a characteristic of implanted ions in a semiconductor substrate.

Alternatively, the functional relationship may include a mathematical or theoretical model that describes a relationship between implantation in a masking material and implantation into a semiconductor substrate. For example, a mathematical or theoretical model may be used to determine the depth of an implanted portion of a semiconductor substrate using implant energy, implant dose, or depth of the implanted region of the masking material as determined from an optical property of the implanted masking material. An example of a method for using spectroscopic ellipsometry and spectroscopic reflectometry to monitor ion implantation is illustrated in U.S. patent application Ser. No. 09/570,135, "Method of Monitoring Ion Implants by Examination of an Overlying Masking Material" to Strocchia-Rivera, filed on May 12, 2000, and is incorporated by reference as if fully set forth herein.

Optical evaluation of an ion implantation process may provide several advantages over current methods to evaluate an ion implantation process. For example, an optical method may provide non-destructive testing and may not interfere with processing of a semiconductor substrate or the performance of a fabricated semiconductor device. Furthermore, optical evaluation of the masking material may not require additional processing such as annealing of the semiconductor substrate on which the masking material is formed. Therefore, evaluation of an ion implantation process using an optical method such as a broadband radiation technique may be performed during the ion implantation process.

In an employment, a system configured to evaluate an ion implantation process as described herein may be coupled to an ion implanter. The system may include a measurement device as described herein. The measurement device may be coupled to a process chamber of the ion implanter as shown, for example, in FIG. 17. The measurement device may be coupled to the ion implanter such that the measurement device may be external to the ion implanter. In this manner, exposure of the components of the measurement device to chemical and physical conditions within the ion implanter may be reduced, and even eliminated. Furthermore, the device may be externally coupled to the ion implanter such that the measurement device does not interfere with the operation, performance, or control of the ion implantation process.

The measurement device, however, may be configured to focus an incident beam of broadband radiation onto a specimen in the ion implanter. The measurement device may also be configured to detect at least a portion of a beam of broadband radiation returned from the specimen. For example, a process chamber of an ion implanter may include small sections of a substantially optically transparent material disposed within walls of the process chamber. The small sections of transparent material may be configured to transmit the incident and returned beams of broadband radiation from an illumination system outside the process chamber to a specimen within the process chamber and from the specimen to a detection system outside the process chamber. The optically transparent material may be further configured to transmit incident and returned beams of light without undesirably altering the optical properties of the incident and reflected beams. An appropriate method for coupling a measurement device to an ion implanter may vary, however, depending upon, for example, a configuration of the ion implanter. For example, placement and dimensions of the transparent material sections disposed within the walls of the process chamber may depend on the configuration of the components within the process chamber. Therefore, a measurement device coupled to an ion implanter may be configured to measure optical properties of the masking material, optical properties of a portion of the masking material, optical properties of a multi-layer masking stack, or optical properties of the specimen during the implantation process.

In an additional embodiment, the system may also include a processor coupled to the measurement device and the ion implanter. The processor may be configured to interface with the measurement device and the ion implanter. For example, the processor may receive signals and/or data from the ion implanter representative of parameters of an instrument coupled to the ion implanter. The processor may also be configured to receive signals and/or data from the measurement device representative of light returned from the specimen or at least one property of the implanted region of a specimen. Additionally, the processor may be further configured to control the measurement device and the ion implanter. For example, the processor may alter a characteristic of the implanted region of the specimen by altering a parameter of an instrument coupled to the ion implanter. Therefore, the system may monitor and control the implantation of ions during a process.

In an additional embodiment, the system may be configured to monitor or measure variations in at least one optical property of the implanted masking material. For example, the measurement device may be configured to measure an optical property of the implanted masking material substantially continuously or at predetermined time intervals during an ion implantation process. The processor may, therefore, receive one or more output signals from the measurement device that may be representative of light returned from the specimen. The processor may also monitor variations in the one or more output signals over the duration of the ion implantation process. By analyzing variations in the one or more output signals during implantation, the processor may also generate a signature representative of the implantation of the ions into the masking material. The signature may include at least one singularity that may be characteristic of an endpoint of the ion implantation process. An appropriate endpoint for an ion implantation process may he a predetermined concentration of ions in a masking material or in a specimen. In addition, the predetermined concentration of ions may vary depending upon the semiconductor device feature being fabricated by the ion implantation process. After the processor has detected the singularity of the signature, the processor may stop the implantation of ions by altering a level of a parameter of an instrument coupled to the ion implanter.

In an embodiment, a method for fabricating a semiconductor device may include implanting ions into a masking material and a semiconductor substrate. The masking material may be arranged on the semiconductor substrate such that predetermined regions of the semiconductor substrate may be implanted with ions. For example, portions of the masking material may be removed by a lithography process and/or etch process to expose regions of the semiconductor substrate to an implantation process. During an ion implantation process, typically, an entire semiconductor substrate may be scanned with a beam of dopant ions. Therefore, the remaining portions of masking material may inhibit the passage of dopant ions into underlying regions of the semiconductor substrate during an ion implantation process. As such, patterning the masking material may provide selective implantation of ions into exposed regions of the specimen.

The exposed regions may be regions of a specimen in which features of a semiconductor device are to be formed. For example, a dielectric material overlying a channel region of a gate during an ion implantation process may prevent implantation of ions into the gate conductor or the channel region beneath the gate conductor. The exposed regions of the specimen may, therefore, correspond to a particular feature of the semiconductor device being fabricated such as a junction region. Alternatively, ions may be implanted through a masking material and into underlying regions of the semiconductor substrate. In this manner, the masking material may include a thin gate dielectric material arranged over junction regions of a transistor. Implantation of ions through a masking material may enhance the electrical properties of the implanted region of the semiconductor substrate, for example, by randomizing the directional paths of the ions which are being driven into the specimen. The masking material may also be formed over a substantially planar specimen or over a non-planar specimen.

Fabricating a semiconductor device may also include monitoring implantation of ions into the semiconductor substrate by measuring at least one optical property of the masking material during the ion implantation process. The optical property of the masking material may be altered by the implantation of ions into the masking material. As such, the method for fabricating a semiconductor device may also include determining at least one characteristic of the implanted ions in the semiconductor substrate. The characteristic may be determined, for example, using a function that describes a relationship between the optical property of the implanted masking material and the implantation of ions into the semiconductor substrate.

In an embodiment, any material that may be substantially transparent to at least a portion of the light produced by a measurement device, as described above, may be used as a masking material for evaluation of an ion implantation process involving measurement of optical properties of a masking material. In one embodiment, the masking material may be a resist. An appropriate resist may include photoresist materials that may be patterned by an optical lithography technique. Other resists, however, may also be used such as e-beam resists or X-ray resists, which may be patterned by an e-beam or an X-ray lithography technique, respectively. In another embodiment, the masking material may include an inorganic material. Inorganic masking materials that may be used to inhibit ion implantation include, but are not limited to, silicon dioxide, silicon nitride, titanium nitride, polycrystalline silicon, cobalt silicide, and titanium silicide. The inorganic masking material may be formed by deposition techniques, such as chemical vapor deposition, or thermal growth techniques. The inorganic masking materials may be patterned using an etch technique.

In another embodiment, the masking material may include two or more layers of different masking materials arranged in a stack. For example, the masking material may include a resist formed upon an inorganic material. The inorganic material may include any material that inhibits the implantation of ions through the masking material. When used as part of a masking material, the inorganic material may not be transparent or may not exhibit any substantial changes in optical properties when exposed to ions. The subsequent optical analysis may be done on the overlying resist material rather than on the underlying organic masking material. The inorganic material may be formed on a specimen prior to coating the specimen with a resist. This additional inorganic material, in combination with an overlying resist, may serve as the masking stack. An appropriate masking material may vary depending on, for example, an ion implantation process or an ion implanter configuration.

During ion implantation processes, and especially in processes using relatively high dosage levels, a semiconductor substrate may be significantly damaged due to the implantation of dopant ions into regions of the semiconductor substrate. For example, an implanted region of such a damaged semiconductor substrate may include of an upper crystalline damaged layer and an intermediate layer of amorphous silicon. The damage in the upper crystalline layer may be caused, for example, by electronic collisions between atoms of the semiconductor substrate and the implanted ions. Displacement damage, however, may not be produced if ions entering the semiconductor substrate do not have enough energy per nuclear collision to displace silicon atoms from their lattice sites. Increasing the dose of ions, and in particular relatively heavy ions, may produce an amorphous region in which the displaced atoms per unit volume may approach the atomic density of the semiconductor substrate. As the implant dose of the ion implantation process increases, the thickness of the amorphous layer may also increase. The presence of an amorphous layer of silicon may act as a boundary that may reflect optical radiation. Reflection of light by the amorphous layer may also effect the reflectance and ellipsometric measurements. Therefore, measurement of an optical property of the amorphous silicon layer may also be used to monitor the processing conditions of an ion implantation process.

In an embodiment, an optical property of an implanted portion of a semiconductor substrate may be measured. The optical property may be a thickness, an index of refraction, or an extinction coefficient of the implanted portion. In addition, several optical properties of the implanted portion of the semiconductor substrate may be measured substantially simultaneously. The optical property of the implanted portion of the semiconductor substrate and the optical property of the implanted masking material may also be measured substantially simultaneously. A characteristic of the implanted ions in the semiconductor substrate may be determined from the measured optical property of the implanted portion of the semiconductor substrate. This characteristic may, therefore, be related to the implantation of ions into a portion of the semiconductor substrate or a characteristic of the resulting implanted semiconductor substrate. For example, the characteristic may be an implant energy, an implant dose, or an implant species of the ion implantation process. In addition, the characteristic may be a concentration of ions, a depth, a distribution of the implanted ions as a function of thickness, or a presence of the implanted ions in the implanted portion of the semiconductor substrate. In addition, optical properties of the implanted portion of the semiconductor substrate may be used to determine several characteristics substantially simultaneously, which may include, but are not limited to, any of the characteristics as described above. A characteristic of the semiconductor substrate and a characteristic of the implanted ions in the masking material may also be determined substantially simultaneously.

In an additional embodiment, optical properties of the implanted portion of the semiconductor substrate may be measured using a broadband wavelength technique as described herein. For example, a measurement device, as described herein, may be configured to use a broadband wavelength technique to measure optical properties of an implanted portion of a semiconductor substrate. Additionally, the measurement device may be coupled to an ion implanter as described above such that measuring an optical property of the implanted portion of the semiconductor substrate may be performed during an ion implantation process. Therefore, variations in an optical property of the implanted portion of the semiconductor substrate may also be measured during an ion implantation process. In this manner, a signature characterizing the implantation of ions into the semiconductor substrate may be obtained. This signature may include a singularity characteristic of an end of the implantation process. As described above, an appropriate endpoint may be, for example, a predetermined concentration of ions in the semiconductor substrate. An appropriate processor, as described herein, may then reduce or substantially stop processing of the semiconductor substrate by controlling the ion implanter.

In an embodiment, the measured optical properties of the implanted masking material may be used to determine processing conditions for subsequent ion implantation processes of additional specimens such as additional semiconductor substrates or semiconductor device product wafers. For example, the implant energy of the implantation of ions into the masking material may be determined using the measured optical property of the implanted masking material. The determined implant energy may be used to determine depth of an implanted portion of a semiconductor substrate during an ion implantation process. The depth of the implanted portion of the semiconductor substrate may also be determined from a measured optical property of the implanted portion of the semiconductor substrate.

The determined depth of the implanted portion of the semiconductor substrate may be less than a predetermined depth. The predetermined depth may vary depending on, for example, a feature fabricated during the ion implantation process. Therefore, before processing additional semiconductor substrates, or product wafers, the implant energy or another process condition of the ion implantation process may be altered such that a depth of an implanted portion of the additional semiconductor substrates may be approximately equal to the predetermined depth. For example, an implant energy of the ion implantation process may be increased to drive the ions deeper into the semiconductor substrate. In this manner, measured optical properties of a masking material may be used to determine and alter process conditions of an ion implantation process using a feedback control technique. In an additional embodiment, measured optical properties of an implanted portion of a semiconductor substrate may be used to determine and alter process conditions of an ion implantation process using a feedback control technique.

In an additional embodiment, measured optical properties of an implanted masking material may be used to determine process conditions of additional semiconductor fabrication processes that may be performed subsequent to an ion implantation process. Additional semiconductor fabrication processes may include, but are not limited to, a process to anneal the implanted regions of a semiconductor substrate and a process to remove the masking material. For example, an implant energy of an ion implantation process may be determined using a measured optical property of an implanted masking material. The determined implant energy may be used to determine a depth that ions may be implanted into a semiconductor substrate using the ion implantation process. Alternatively, a depth of the implanted portion of a semiconductor substrate may also be determined using a measured optical property of the implanted semiconductor substrate.

The determined depth of the implanted portion of the semiconductor substrate may be greater than a predetermined depth. Process conditions of an annealing process performed subsequent to the ion implantation process, however, may be optimized for the predetermined depth. Therefore, before annealing an implanted semiconductor substrates having the determined depth, a process condition of the annealing process such as anneal time or anneal temperature may be altered. In this example, the anneal time of the annealing process may be increased to ensure substantially complete recrystal ion of the amorphous layer formed in the semiconductor substrate by the ion implantation process. In this manner, measured optical properties of a masking material may be used to determine process conditions of a semiconductor fabrication process performed subsequent to an ion implantation process using a feedforward control technique. Measured optical properties of an implanted portion of a semiconductor substrate may also be used to determine process conditions of a semiconductor fabrication process performed subsequent to an ion implantation process using a feedforward control technique.

A set of data that may include measured optical properties of a masking material may be collected and analyzed. The set of data may be used to determine processing conditions of an ion implantation process or to monitor the processing conditions over time. Process control methods as described herein may also be used in conjunction with electrical testing of an implanted region of a semiconductor substrate. The combination of optical and electrical analysis may provide a larger amount of characterization data for an ion implantation process. The characterization data may be used to assess the mechanisms of ion implantation, to determine the cause of defects, and to alter process conditions. In addition, this process control strategy may b used to qualify, or characterize the performance of, a new ion implanter. Furthermore, this process control strategy may be used to determine an appropriate masking material and masking material thickness in development of an ion implantation process. The process control method may also be used to compare the performance of two or more ion implanters. Such a process control method may be used in a manufacturing facility in which several ion implanters may be used in parallel to manufacture one type of device or product.

In an embodiment, a system may be configured to determine at least an adhesion characteristic of a specimen and a thickness of the specimen. The system may be configured as described herein. For example, the system may also include a processor coupled to a measurement device. In addition, the processor may be configured to determine other properties of the specimen from the detected light. In an embodiment, the measurement device may include a photo-acoustic device, a spectroscopic ellipsometer, an ellipsometer, an X-ray reflectometer, a grazing X-ray reflectometer, an X-ray diffractometer, a non-imaging scatterometer, a scatterometer, a spectroscopic scatterometer, a reflectometer, a spectroscopic reflectometer, a bright field imaging device, a dark field imaging device, a bright field and dark field imaging device, a coherence probe microscope, an interference microscope, an optical profilometer, an eddy current device, an acoustic pulse device, or any combination thereof. The processor may be configured to determine at least an adhesion characteristic and a thickness of the specimen from one or more output signals from the measurement device.

In an embodiment, an acoustic pulse device or a photo-acoustic device may be configured to use acoustic pulses to characterize a layer formed upon a specimen. For example, acoustic pulses may be used to determine a thickness of a layer such as a metal disposed on a specimen. An advantage of an acoustic pulse device is that measuring a property of a layer formed on a specimen with the device is substantially nondestructive. An acoustic pulse device may be configured to apply a laser pulse to a specimen. The laser pulse may be absorbed within one absorption length from an upper surface of the layer thereby causing a rise in local surface temperature. Depending on temperature coefficient of expansion (expansivity) of a layer, the layer may undergo thermal stresses, which may generate an elastic pulse in the layer. The elastic pulse may propagate across the layer at approximately the velocity of sound. The time of flight for the elastic pulse across the layer may be measured and may be used to determine a thickness of the layer. Measuring the time of flight for the elastic pulse may include steps of the methods described below.

In one embodiment, a laser pulse of radiation may be applied to a first surface area of a specimen to non-destructively generate an elastic pulse in the specimen. The elastic pulse may cause the first surface area to move. The acoustic pulse device may include an interferometer configured to detect an acoustic echo of the pulse traversing the specimen. The interferometer may also be configured to provide a pair of pulses including a probe pulse and a reference pulse of radiation. The interferometer may be further configured to direct the probe pulse to the first surface area when it is moved by the elastic pulse and a reference pulse to a second surface area. The second surface area may be laterally spaced from the first surface area. The interferometer may also be configured to monitor the reflection of the pulses off of the surface of the specimen. The reflection of the pair of pulses may be used to determine a thickness of a layer on the specimen. For example, a processor of the system may be configured to determine a thickness of the layer using one or more output signals from the interferometer.

In an embodiment, a method for non-destructively measuring properties of a specimen may include directing a pump pulse of radiation to a first surface area of the specimen to non-destructively generate an elastic pulse in the specimen. The generated elastic pulse may cause the first surface area to move. The method may also include directing a probe pulse and a reference pulse of radiation to the specimen using an interferometer. Directing the probe and reference pulses may include directing the probe pulse to the first surface area when it is moved by the elastic pulse and directing the reference pulse to a second surface area. The second surface area may be laterally spaced from the first surface area. In addition, the method may include monitoring reflections of the probe and reference pulses. The method may also include determining a thickness of a layer on the specimen. Both of the above described acoustic-pulse method are described in further detail in U.S. Pat. No. 6,108,087 to Nikoonahad et al. and U.S. patent application Ser. No. 09/310,017, both of which are incorporated by reference as if fully set forth herein. Other methods for measuring films using acoustic waves are also described in U.S. Pat. No. 6,108,087.

In another embodiment, an acoustic pulse device may be configured to determine a thickness of a layer by using a probe pulse and a reference pulse that are substantially in phase with each other. The in-phase pulses may be used to measure an acoustic echo created by a pump pulse applied to an area of the layer. The applied pump pulse may create an elastic pulse that may propagate through the layer. The probe pulse may be directed to the area of the specimen through which the elastic pulse propagates. The reference pulse may be directed to substantially the same surface area or a different surface area of the sample such that the pair of pulses may be modified by the specimen. The modified pulses may interfere at a detector. For example, at least one of the pulses may be modulated in phase or frequency before or after modification by the sample and prior to detection by the detector. By processing one or more output signals from the detector, a thickness of a layer on the specimen may be determined.

In one embodiment, an optical delay may be used to alter a time relationship between the pump pulse and the probe pulse. In this manner, the probe pulse may be directed to the specimen surface when it is influenced by the elastic pulse created by the pump pulse. The reference and probe pulses may be directed along substantially the same optical path between an optical source and a detector. Such a configuration may reduce, and even minimize, random noise in one or more output signals of the detector, which may be caused, for example, by environmental factors. Such a configuration is further described in U.S. patent application Ser. No. 09/375,664, which is incorporated by reference as if fully set forth herein.

Acoustic pulse devices, as described above, may be incorporated into any of the systems and/or process tools as described herein.

In an embodiment, a system may be configured to determine at least a concentration of an element in a specimen and a thickness of a layer on the specimen. The system may be configured as described herein. For example, the system may also include a processor coupled to a measurement device. The processor may be configured to determine at least a concentration of an element in a specimen and a thickness of a layer formed on the specimen from one or more output signals generated by the measurement device. In addition, the processor may be configured to determine other properties of the specimen from the detected light. In an embodiment, the measurement device may include a photo-acoustic device, an X-ray reflectometer, a grazing X-ray reflectometer, an X-ray diffractometer, an eddy current device, a spectroscopic ellipsometer, an ellipsometer, a non-imaging scatterometer, a scatterometer, a spectroscopic scatterometer, a reflectometer, a spectroscopic reflectometer, a bright field imaging device, a dark field imaging device, a bright field and dark field imaging device, a coherence probe microscope, an interference microscope, an optical profilometer, an eddy current device, or any combination thereof.

An X-ray reflectance ("XRR") technique may be used to measure a property of a specimen such as a concentration of an element in a thickness of a layer or at an interface between layers on a specimen. X-ray reflectance may also be used to determine a thickness of a layer or an interface between layers on a specimen. Layers which may be measured by X-ray reflectance may include layers substantially transparent to light such as dielectric materials and layers substantially opaque to light such as metals. X-ray reflectance may include irradiating a surface of a specimen with X-rays and detecting X-rays reflected from the surface of the specimen. A thickness of a layer may be determined based on interference of X-rays reflected from the surface of the specimen. In addition, reflection of X-rays from the surface of the specimen may vary depending on refractive index changes at a surface of a layer on the specimen and at an interface between layers on the specimen and the density of the layer or of the interface. Therefore, a complex refractive index in an X-ray regime may be directly proportional to a density of a layer. In this manner, a concentration of an element in a layer or at an interface between layers may be determined based on the density and thickness of the layer.

X-ray reflectance may be performed at different angles of incidence depending upon, for example, characteristics of a specimen. An X-ray reflectance curve may be generated by a processor using one or more output signals responsive to the detected X-rays reflected from the surface of the specimen. The X-ray reflectance curve may include an average reflectance component, which may be caused by bulk properties of the specimen. The average reflectance component may be subtracted from the one or more output signals such that an interference oscillation component curve may be generated. Parameters of the interference oscillation component curve may be converted, and a Fourier transform may be performed. A thickness of a layer may be determined by a position of a peak of a Fourier coefficient, F(d). In addition, a peak intensity of the Fourier coefficient, F(d), may be used to determine a layer density or an interface density. For example, a relationship between a peak intensity of a Fourier coefficient and a layer density may be simulated and may be used to determine a layer density. Alternatively, a layer density may be determined based on the X-ray reflectance curve by fitting the curve to model data using a mathematical method such as a nonlinear least squares curve-fitting method. In such a method, several of the fitted parameters may be inter-related. Therefore, parameters that may be substantially constant across specimens may be fixed at average values in order to prevent multiple solutions.

A concentration of an element on a surface of a layer or at an interface between layers may be determined by using data that may describe a relationship between interface layer density and concentration. The data may be generated by another analytical technique such as secondary ion mass spectroscopy ("SIMS"). SIMS may involve removing material from a sample by sputtering ions from the surface of the sample and analyzing the sputtered ions by mass spectrometery. Examples of SIMS techniques are illustrated in U.S. Pat. No. 4,645,929 Criegern et al., U.S. Pat. No. 4,912,326 to Naito, U.S. Pat. No. 6,078,0445 to Maul et al., and U.S. Pat. No. 6,107,629 to Benninghoven et al., and are incorporated by reference as if fully set forth herein. In this manner, a plurality of samples having various elemental concentrations may be prepared. The samples may be analyzed by XRR to determine density of the layer or interface of interest and may also be analyzed by SIMS to determine a concentration of the layer or interface of interest. A relationship between density and concentration may then be determined. The determined relationship may be used to determine concentration of an element on a surface of a layer or at an interface between layers in additional specimen.

A device configured to measure X-ray reflectance of a layer or an interface between layers of a specimen may include a measurement chamber. A specimen may be supported within the measurement chamber by a stage or another mechanical device. An appropriate stage or mechanical device may be configured to maintain a position of the specimen during measurement and for moving the specimen before, during, and/or after X-ray reflectance measurements. The stage or mechanical device may also be further configured as described herein. The measurement chamber may also be configured as a process chamber of a process tool, which may be used for semiconductor fabrication. For example, the process chamber may include a deposition chamber in which a metal film a may be formed on a specimen or an ion implantation chamber in which ions may be driven into a specimen. In this manner, X-ray reflectance measurements may be performed prior to, during, or subsequent to a process performed in the process chamber. The measurement chamber may also be disposed within or proximate a process tool such that a specimen may be moved from a process chamber of the process tool to the measurement chamber. In one example, the measurement chamber may be coupled to a chemical-mechanical polishing tool such that X-ray reflectance measurements may be performed prior to or subsequent to a process step of a chemical-mechanical polishing process.

The device configured to measure X-ray reflectance of a layer or an interface between layers of a specimen may also include an X-ray source such as a rotor X-ray source. X-rays generated by the X-ray source may be passed through a germanium monochromator. The measurement chamber may also include a beryllium window in a wall of the measurement chamber through which the X-rays may enter the measurement chamber. In this manner, X-rays may be directed to a surface of a specimen supported within the measurement chamber. In addition, the device may include an X-ray detector arranged on a side of the measurement chamber opposite to the X-ray source. As such, X-rays reflected from the surface of the specimen may be detected. The system may also include a controller computer configured to control the device and/or individual components of the device. The controller computer may also be configured to process a signal generated by the detector in response to the detected X-rays and to determine a concentration of an element in a layer or an interface between layers of a specimen. The controller computer may be further configured as a processor as described herein. Additional examples of X-ray reflectance methods and systems are illustrated in U.S. Pat. No. 5,740,226 to Komiya et al. and U.S. Pat. No. 6,040,198 to Komiya et al., which are incorporated by reference as if fully set forth herein.

In an embodiment, an eddy current device may be configured to measure a thickness of a layer formed upon a specimen. Eddy current devices may also be configured to measure junction leakage in a specimen. An eddy current device may include a sensor configured to apply an alternating current to a specimen. The applied alternating current may cause an eddy current in the specimen. The resistance or conductance of the specimen may be analyzed using the eddy current. A thickness of a layer on the specimen may be determined by a change in resistance or conductivity. Methods for using eddy currents to determine a thickness of a layer on a specimen are illustrated in U.S. Pat. No. 6,086,737 to Harada, and U.S. Patent Application entitled "In-Situ Metallization Monitoring Using Eddy Current Measurements, by K. Kehman, S. M. Lee, W. Johnson, and J. Fielden, which are incorporated by reference as if fully set forth herein.

A sensor or an eddy current device may include a capacitor and an inductor. During use, the sensor may be positioned proximate to the specimen When a layer formed on the specimen is conductive or magnetic, the inductor may be configured to couple an alternating ("ac") electromagnetic field to the layer. The alternating electromagnetic field may induce eddy (i.e., Foucault) currents in the layer, and two effects may be present. First, the layer may act as a lossy resistor, and the effect will be a resistive loading on a sensor circuit, which will lower the amplitude of the resonant signal and lower the resonant frequency. Second, a decrease in the layer thickness may produce an effect as though a metal rod were being withdrawn from the coil of the inductor thereby causing a change in inductance as well as a frequency shift. As the thickness of the layer changes, either by addition or removal, the eddy currents may change, and thus their resistive loading effect and magnitude of frequency shift may change as well. When a layer is not present, there will be no effect on the sensor circuit (i.e., no resistive loading, no inductance change, no frequency shift). Thus, a change in thickness of a layer may be monitored substantially continuously or intermittently by monitoring changes in any of these parameters.

Note that any conductive film may be monitored using an eddy current device, not just a layer such as a thin film on a semiconductor substrate. For example, in an electroplating process, metal ions in a plating solution dissolved from a metal block electrode acting as an anode may be deposited on a target at the cathode to form a film. Eddy current measurements may be used to monitor formation of the film on the target during the electroplating process, both in-situ and real time.

Eddy current devices and measurements may be used in a variety of applications. In one embodiment, an eddy current device may be coupled to a chemical mechanical polishing tool. In this application, the eddy current device may be used to determine one or more endpoints of the polishing process and/or a thickness of one or more polished layers prior to, during, or subsequent to the polishing process. In another embodiment, an eddy current device may be coupled to a deposition tool. In this case, the eddy current device may be utilized to detect a thickness of a deposited layer, either after the layer is deposited or while the layer is being deposited. The eddy current device may also be used to determine one or more endpoints of the deposition process.

In another method, monitoring eddy current characteristics and surface photovoltage may be used in combination to determine a junction leakage in a specimen. Generally, a specimen such as a semiconductor substrate may include a first type junction and a second type junction. Junction leakage may be monitored by applying varying light to the semiconductor substrate, measuring a surface photovoltage created on the surface of the semiconductor substrate, and measuring the eddy current characteristic for the semiconductor substrate in response to the light. A junction leakage characteristic of at least one of the junction types may be determined from the combination of surface photovoltage and the eddy current characteristics. The use of eddy current monitoring to measure junction leakage is described in further detail in U.S. Pat. No. 6,072,320 to Verkuil, which is incorporated herein by reference.

Eddy current measurement devices may be included in any of the systems, as described herein. For example, a system may include an eddy current measurement device coupled to a measurement device configured as a spectroscopic ellipsometer. In this manner, a processor of the system may be configured to determine at least two characteristics of a specimen, which may include a thickness of a layer on a specimen and a critical dimension of a feature on the specimen. The layer may include a barrier layer, and the feature may include a "seat."

A system including an eddy current measurement device and a spectroscopic ellipsometer may be coupled to a process tool such as an atomic layer deposition ("ALD") tool. ALD may be used to form a barrier layer and/or a seat. ALD may typically be a technique for depositing thin films that may involve separating individual reactants and taking advantage of the phenomenon of surface adsorption. For example, when a specimen is exposed to a gas, the specimen may be coated with a layer of the gas. Upon removing the gas, for example, by pumping the gas out of the process chamber with a vacuum pump, under certain circumstances a monolayer of the gas may remain on a surface of the specimen. At relatively moderate temperatures (i.e. room temperature), the monolayer may be held relatively weakly on the surface of the specimen by physical adsorption forces. At higher temperatures, a surface chemical reaction may occur, and the gas may be held relatively strongly on the surface of the specimen by chemisorption forces. A second reactant may be introduced to the process chamber such that the second reactant may react with the adsorbed monolayer to form a layer of solid film. In this manner, relatively thin solid films such as barrier layers may be grown one monolayer at a time. In addition, such thin solid films may be amorphous, polycrystalline, or epitaxial depending on, for example, the specific process.

Figure 23:
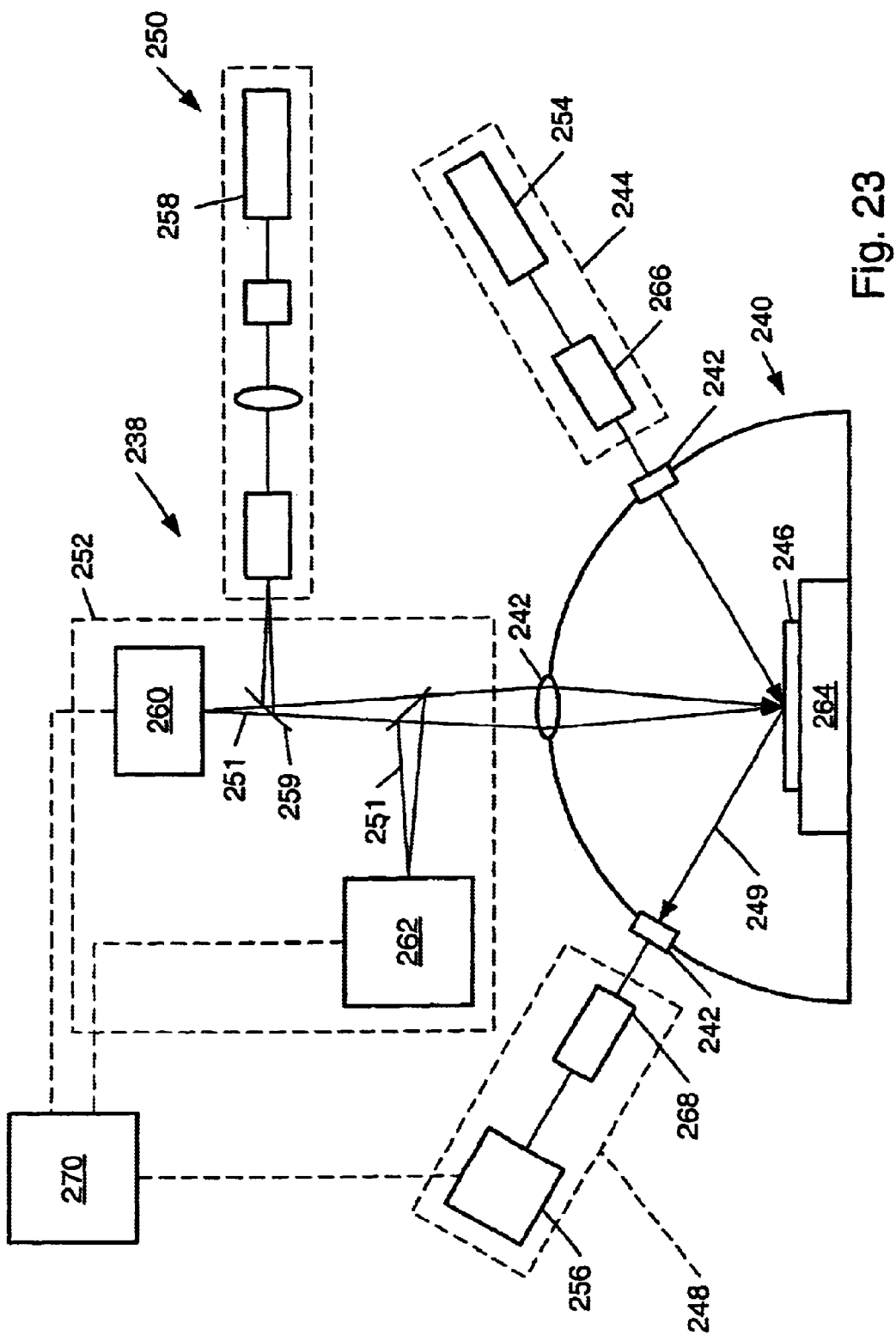
FIG. 23 depicts a schematic side view of an embodiment of a system coupled to a chemical vapor deposition tool.

FIG. 23 illustrates an embodiment of a system configured to evaluate a deposition process. In an embodiment, a system may include measurement device 238 coupled to deposition tool 240. Measurement device 238 may be coupled to deposition tool 240 such that the measurement device may be external to a process chamber of the deposition tool. As such, exposure of the measurement device to chemical and physical conditions within the process chamber may be reduced, and even eliminated. Furthermore, the measurement device may be externally coupled to the process chamber such that the measurement device may not alter operation, performance, or control of the deposition process. For example, a process chamber may include relatively small sections of a substantially optically transparent material 242 disposed within walls of the process chamber. The configuration of a deposition tool, however, may determine an appropriate method to couple the measurement device to the deposition tool. For example, placement and dimensions of substantially optically transparent material sections 242 disposed within the walls of the process chamber may vary depending on, for example, the arrangement of the components within the process chamber. In addition, measurement device 238 may be coupled external to the process chamber such that the measurement device may direct energy to a surface of the specimen and may detect energy returned from a surface of the specimen as a specimen is being placed within and/or being removed from the process chamber. A surface of the specimen may include a front side of the specimen or a back side of the specimen.

The deposition tool may be a chemical vapor deposition tool or a physical vapor deposition tool configured to deposit dielectric materials or conductive materials Examples of deposition tools are illustrated in U.S. Pat. No. 4,232,063 to Rosler et al., U.S. Pat. No. 5,695,568 to Sinha et al., U.S. Pat. No. 5,882,165 to Maydan et al., U.S. Pat. No. 5,935,338 to Lei et al., U.S. Pat. No. 5,963,783 to Lowell et al., U.S. Pat. No. 6,103,014 to Lei et al., U.S. Pat. No. 6,112,697 to Sharan et al., and U.S. Pat. No. 6,114,216 to Yieh et al., and PCT Application Nos. WO 99/39183 to Gupta et al., WO 00/07226 to Redinbo et al., and are incorporated by referee as if fully set forth herein.

In an alternative embodiment, measurement device 238 may be disposed in a measurement chamber, as described with respect to and shown in FIG. 16. The measurement chamber may be coupled to deposition tool 240, as shown in FIG. 17. For example, the measurement chamber may be disposed laterally or vertically proximate one or more process chambers of deposition tool 240. For example, the deposition tool may include a cluster of process chambers that may each be configured to perform substantially similar processes or different processes. In addition, the measurement chamber may be disposed laterally or vertically proximate a load chamber of deposition tool 240. A load chamber of a deposition tool may be configured to support multiple specimens such as a cassette of wafers that are to be processed in the deposition tool. A robotic wafer handler may be configured to remove a specimen from the load chamber prior to processing and to dispose a processed specimen into the load chamber. Furthermore, the measurement chamber may be disposed in other locations proximate a deposition tool such as anywhere proximate the deposition tool where there is sufficient space for the system and anywhere a robotic wafer handler may fit such that a specimen may be moved between a process chamber and the system.

In this manner, a robotic wafer handler of deposition tool 240, stage 264, or another suitable mechanical device may be configured to move specimen 246 to and from the measurement chamber and process chambers of the deposition tool. In addition, the robotic wafer handler, the stage, or another suitable mechanical device may be configured to move specimen 246 between process chambers of the deposition tool and the measurement chamber. Measurement device 238 may be further coupled to deposition tool 240 as further described with respect to FIG. 17.

Measurement device 238 may include first illumination system 244 configured to direct light having a known polarization state to specimen 246 such that a region of the specimen may be illuminated prior to, during, or subsequent to a deposition process. A portion 249 of the light directed to specimen 246 by first illumination system 244 may propagate from the illuminated region of the specimen. In addition, the measurement device may include detection system 248 configured to analyze a polarization state of light 249 propagating from the surface of specimen 246 prior to, during, or subsequent to a deposition process. In this manner, the measurement device may be configured to operate as a spectroscopic ellipsometer.

In addition, measurement device 238 may include second illumination system 250 configured to direct light having a known polarization state to specimen 246 such that a region of the specimen may be illuminated during a deposition process. A portion 251 of the light directed to specimen 246 by second illumination system 250 may propagate from the illuminated region of the specimen along a path of the directed light. In addition, the measurement device may include detection system 252 configured to measure an intensity of the light propagating from the surface of specimen 246 prior to, during, or subsequent to a deposition process. In this manner, the measurement device may also be configured to operate as a spectroscopic reflectometer. The measurement device, however, may also be configured to operate as a beam profile ellipsometer and a null ellipsometer.

The relatively small sections of substantially optically transparent material 242 may be configured to transmit light from light source 254 of first illumination system 244 outside the process chamber to a surface of specimen 246 within the process chamber and to transmit light propagating from the surface of the specimen to detector 256 outside the process chamber. In addition, relatively small sections of substantially optically to transparent material 242 may be configured to transmit light from light source 258 of second illumination system 250 outside the process chamber to a surface of specimen 246 within the process chamber and to transmit light propagating from the surface of the specimen to detectors 260 and 262 outside the process chamber. The substantially optically transparent material may have optical or material properties such that the light from light sources 254 and 258 and the light propagating from a surface of specimen 246 may pass through relatively small sections 242 disposed within process chamber without undesirably altering the optical properties of the directed and returned light. In addition, the substantially optically transparent material may be configured to focus light from light sources 254 and 258 onto the surface of specimen 246. In this manner, measurement device 238 may be coupled to stage 264 disposed within the process chamber. Stage 264 may be configured as described herein.

Spectroscopic ellipsometry may include focusing an incidence beam of polarized light on a specimen and monitoring a change in polarization for at least a portion of the incidence beam reflected from the specimen across a broad spectrum of wavelengths. Examples of spectroscopic ellipsometers are illustrated in U.S. Pat. No. 5,042,951 to Gold et al., U.S. Pat. No. 5,412,473 to Rosencwaig et al., U.S. Pat. No. 5,581,350 to Chen et al., U.S. Pat. No. 5,596,406 to Rosencwaig et al., U.S. Pat. No. 5,596,411 to Fanton et al., U.S. Pat. No. 5,771,094 to Carter et al., U.S. Pat. No. 5,798,837 to Aspnes et al., U.S. Pat. No. 5,877,859 to Aspnes et al., U.S. Pat. No. 5,889,593 to Bareket et al., U.S. Pat. No. 5,900,939 to Aspnes et al., U.S. Pat. No. 5,910,842 to Piwonka-Corle et al., U.S. Pat. No. 5,917,594 to Norton, U.S. Pat. No. 5,973,787 to Aspnes et al., and U.S. Pat. No. 6,256,097 to Wagner and are incorporated by reference as if fully set forth herein. Additional examples of spectroscopic devices are illustrated in PCT Application No. WO 99/02970 to Rosencwaig et al. and is incorporated by reference as if fully set forth herein.

Light source 254 may include any of the light sources as described herein, which may be configured to emit broadband light. Illumination system 244 may include optical component 266 positioned along a path of the emitted light. Optical component 266 may be configured to alter a polarization state of the emitted light such that light having a known polarization state such as linearly or circularly polarized light may be directed to a surface of specimen 246. In addition, illumination system 244 may also include an additional optical component (not shown) configured to focus and direct light emitted from light source 254 to the surface of specimen 246. Detection system 248 may also include optical component 268 positioned along a path of the light propagating from the surface of the specimen. Optical component 268 may be configured to function as an analyzer of a spectroscopic ellipsometer. Detection system 248 may also include a dispersion element such as a spectrometer (not shown). The dispersion element may be configured to separate light propagating from the surface of the specimen having different wavelengths. The separated components of the beam may be detected by individual elements of detector 256, which may be configured to function as a detector array. The polarizer may be configured to rotate such that a time varying intensity may be detected by the elements of the detector array. Processor 270 may be configured to receive one or more output signals from detector 256 and may be configured to process the data.

Output signals from detector 256 may be responsive to an intensity of light at elements of the detector array. Processor 270 may be configured to convert the output signals to ellipsometric parameters, ψ and δ, by mathematical equations known in the art as described above. Processor 270 may be configured to convert the ellipsometric parameters, ψ and δ, to a property of a layer being formed upon a surface of specimen 246 using a mathematical, or optical, model as described herein. For example, processor 270 may be configured to determine a thickness, an index of refraction, and an extinction coefficient of a layer, a portion of a layer, or, several layers on specimen 246 from the ellipsometric parameters by using an optical model. A thickness, an index of refraction, and an extinction coefficient may be commonly referred to as "thin film" characteristics of a layer.

Alternatively, processor 270 may be configured to determine a critical dimension of a feature on specimen 246 from one or more output signals from measurement device 238. For example, a critical dimension of a feature may include, but is not limited to, a lateral dimension such as a width, a vertical dimension such as a height, and a sidewall profile as described herein. In addition, processor 270 may be further configured to determine a thickness, an index or refraction, and/or an extinction coefficient of a layer of the specimen, and a critical dimension of a feature on the specimen from one or more output signals from measurement device 238. For example, processor 270 may be configured to compare one or more output signals from the measurement device with one or more predetermined tables that may include expected output signals versus wavelength for different characteristics such as width, height, and sidewall profile. Expected output signals versus wavelength for different characteristics of a predetermined table may be determined, for example, experimentally with specimens of known characteristics and/or theoretically through mathematical modeling.

In addition, processor 270 may be configured to compare one or more output signals from measurement device 238 with one or more predetermined tables that may include expected output signals versus wavelength for different characteristics and interpolated data between the expected output signals versus wavelength. Alternatively, processor 270 may be configured to perform an iteration using one or more starting guesses through (possibly approximate) equations to converge to a good fit for one or more output signals from the measurement device. Suitable equations may include, but are not limited to, any non-linear regression algorithm known in the art.

In an additional embodiment, the system may further include a calibration ellipsometer (not shown). The calibration ellipsometer may be configured to determine a thickness of a reference layer on a specimen. The thickness of the reference layer may then be measured using the spectroscopic ellipsometer of the measurement device as described herein. A phase offset of the thickness measurements of the reference layer generated by the calibration ellipsometer and the measurement device may be determined by processor 270. The processor may be configured to use the phase offset to determine additional layer thicknesses from measurements made by the measurement device. The calibration ellipsometer may also be coupled to the process chamber of the deposition tool. As such, the calibration ellipsometer may be used to reduce, and even eliminate, variations in measured ellipsometer parameters. For example, measurements of the ellipsometric parameter, δ, may vary due to changing environmental conditions along one or more optical paths of the measurement device. Such a variation in the ellipsometric parameter, δ, may alter thickness measurements of a layer on a specimen. Therefore, a calibration ellipsometer may be used to reduce, and even eliminate, a drift in thickness measurements of a layer on a specimen.

Spectroscopic reflectometry may include focusing a broadband radiation bean on a specimen and measuring a reflectance spectrum and index of refraction of the specimen from which a thickness of a layer may be determined. Example of spectroscopic reflectometers are illustrated in U.S. Pat. No. 4,999,014 to Gold et al., and U.S. Pat. No. 5,747,813 to Norton et al. and are incorporated by reference as if fully set forth herein. Second illumination system 250 may include light source 258 such as xenon arc lamp. Light source 258 may also include any light source configured to emit broadband light, which may include visible and ultraviolet light. Second illumination system 250 may also be coupled to beam splitter 259. Beam splitter 259 may be configured to direct light emitted by light source 258 to a surface of specimen 246 such that a substantially continuous broadband spectrum of light may be directed to the surface of specimen 246.

The sample beam may be focused onto a region of specimen 246, and at least a portion of the sample beam reflected from the illuminated region may be passed through a spectrometer (not shown) of detection system 252. In addition, detection system 252 may include a diffraction grating (not shown) configured to disperse light passing therethrough as it enters the spectrometer. In this manner, a resulting first order diffraction beam may be collected by detector 260 or detector 262, which may include a linear photodiode array. The photodiode, array, therefore, may measure a sample reflectance spectrum. A relative reflectance may be obtained by dividing the sample light intensity at each wavelength by a relative reference intensity at each wavelength. A relative reflectance spectrum may be used to determine the thickness of one or more layers on the specimen. In addition, reflectance at a single wavelength and a refractive index of one or more layers may also be determined from the relative reflectance spectrum.

Furthermore, a model method by modal expansion ("MMME") model may be used to generate a library of various reflectance spectrums. As described herein, the MMME model is a rigorous diffraction model that may be used to determine the theoretical diffracted light "fingerprint" from each grating in the parameter space. Alternative models may also be used to calculate the theoretical diffracted light such as a rigorous coupling waveguide analysis ("RCWA!") model. The measured reflectance spectrum may be fitted to the library of various reflectance spectrums.

The polarization state and the intensity of light propagating from a surface of specimen 246 may be altered during formation of a layer on specimen 246. For example, during a deposition process, such as chemical vapor deposition ("CVD") and low pressure chemical vapor deposition ("LPCVD") processes, a layer may be formed on specimen 246 by introducing reactant gases such as silane, chlorosilane, nitrogen and/or ammonia in the process chamber. The reactant gases may decompose and react at a heated surface of a specimen to form a deposited layer of material. In this manner, a thickness of the layer being formed on a surface of specimen 246 may increase during the deposition process.

As the thickness of the layer increases during the deposition process, the reflectivity of the surface of the layer may vary approximately sinusoidally with variations in the thickness of the layer. Therefore, the intensity of the returned light may vary depending on a thickness of the deposited layer. In addition, the intensity of the returned light may be approximately equal to the square of the field magnitude according to the equation: $I_r=|E_R|^2$. $I_R$ can also be expressed in terms of the ellipsometric parameters, $\psi$ and $\delta$. For very thin layers, tan $\psi$ may be independent of thickness, and $\delta$ is linearly proportional to the thickness of the layer. In this manner, one or more output signals responsive to the intensity of the light returned from the specimen generated by the measurement device may be used to determine a thickness of the layer.

In addition, thickness variations of a layer on a specimen may vary depending on, for example, parameters of an instrument coupled to the deposition tool. Parameters of an instrument coupled to the deposition tool may determine the process conditions of a deposition process. For example, a deposition rate may be defined as a thickness of a layer formed on a surface of a specimen in a period of time. The deposition rate, therefore, may affect variations in the thickness of a layer on a specimen during a deposition process. A deposition rate may be substantially constant throughout a deposition process. Alternatively, a deposition rate may vary throughout a deposition process. The deposition rate may vary depending on a number of parameters of one or more instruments coupled to the deposition tool that may include, but are not limited to, temperature within the process chamber, temperature gradients in the process chamber, pressure within the process chamber, total flow rates of the reactant gases, reactant gas ratios, and a flow rate of one or more dopant gases. In this manner, intensity variations of light propagating from a surface of the specimen may vary depending upon parameters of an instrument coupled to the deposition tool. Therefore, a processor coupled to a measurement device may be configured to determine a parameter of an instrument coupled to a deposition tool from the measured intensity variations of the light propagating from a surface of the specimen during a deposition process.

In an embodiment, a processor coupled to a measurement device, as shown in FIG. 23, may be configured to determine a property of a layer formed on a specimen from detected light. The measurement device may be configured as described in above embodiments. The property of the formed layer may include, but is not limited to, a thickness, an index of refraction, an extinction coefficient, a critical dimension, or any combination thereof. Subsequent to a deposition process, the specimen may be polished such that an upper surface of the deposited material may be substantially planar. Subsequent to polishing, a layer of resist may be formed on the deposited layer and the layer of resist may be exposed to pattern the resist during a lithography process. In this manner, selected regions of the deposited layer may be exposed, and at least a portion of the selected regions may be removed in an etch process. A conductive material such as aluminum or copper may be deposited in the etched portions of the deposited layer and on an upper surface of the deposited layer, for example, by a physical vapor deposition process. The specimen may be polished such that an upper surface of the specimen may be substantially planar. In this manner, a number of semiconductor features such as inter-level contact structures may be formed on the specimen.

The properties of the semiconductor features formed on the specimen may vary depending upon, for example, properties of the deposited layer and the conductive material and process conditions of the deposition, polishing, lithography, etch, and physical vapor deposition processes. As such, properties of semiconductor features on a specimen may be determined using the determined properties of the deposited layer. In addition, a processor coupled to the measurement device may also be configured to determine a presence of defects such as foreign material on the deposited layer prior to, during, or subsequent to the deposition process from the detected light.

In an additional embodiment, processor 270, as shown in FIG. 23, may be coupled to measurement device 238 and deposition tool 240. The processor may be configured to interface with the measurement device and the deposition tool. For example, the processor may receive one or more signals from the deposition tool during a deposition process. The signals may be representative of a parameter of one or more instruments coupled to the deposition tool. The processor may also be configured to receive one or more signals from the measurement device. Signals from the measurement device may be representative of the detected light from detector 256, 260, and 262 as described herein. In an additional embodiment, measurement device 238 may be configured, as described herein, to measure variations in the intensity of light propagating from the specimen during a deposition process. For example, measurement device 238 may be configured to measure the intensity of light propagating from the specimen substantially continuously or at predetermined time intervals during a deposition process. The processor may, therefore, be configured to monitor variations in output signals from the measurement device during a deposition process. In this manner, the processor may be configured to determine a relationship between the monitored variations and/or the output signals from the measurement device and output signals from the deposition tool responsive to a parameter of one or more instruments coupled to the deposition tool. As such, the processor may be configured to alter a parameter of one or more instruments coupled to the deposition tool using the determined relationship. In addition, the processor may be configured to determine a parameter of one or more instruments using the determined relationship and one or more output signals from the measurement device.

Additionally, the processor may be further configured to control the measurement device and the deposition tool. For example, the processor may be configured to alter a parameter of an instrument coupled to the deposition tool in response to the detected light. In this manner, the processor may be configured to alter a parameter of an instrument coupled to the deposition tool using an in situ control technique. In addition, the processor may be configured to alter a parameter of an instrument coupled to the measurement device in response to the detected light. For example, the processing device may be configured to alter a sampling frequency of the measurement device in response to the detected light.

By analyzing variations in output signals from the measurement device during a deposition process, processor 270 may also generate a signature, which may be representative of the formation of a layer on specimen 246. The signature may include at least one singularity that may be characteristic of an endpoint of the deposition process. For example, an appropriate endpoint for a deposition process may be a predetermined thickness of a layer on the specimen. A predetermined thickness of a layer on the specimen may be larger or smaller depending upon, for example, the semiconductor device fabricated by the deposition process. After the processor has detected the singularity of the signature, the processor may be configured to reduce, and even terminate, deposition of the layer on the specimen by altering a parameter of an instrument coupled to the deposition tool.

In an embodiment, processor 270 may be configured to use one or more output signals from measurement device 238 to determine a parameter of one or more instruments coupled to deposition tool 240 for deposition of layers on additional specimens. For example, a thickness of a layer on a specimen may be determined using one or more output signals from measurement device 238. The thickness of the layer on the specimen may be greater than a predetermined thickness. Therefore, before processing additional specimens, a flow rate of a reactant gas or another parameter of one or more instruments coupled to the deposition tool may be altered. In this manner, a thickness of layers formed on the additional specimens may be closer to the predetermined thickness than the measured layer. For example, the flow rate of the reactant gas used in the deposition process may be decreased to deposit a thinner layer on the additional specimens. In this manner, the processor may be used to alter a parameter of one or more instants coupled to a deposition tool in response to one or more output signals of the measurement device using a feedback control technique.

In an additional embodiment, processor 270 may be configured to determine a parameter of one or more instruments coupled to a process tool, configured to perform additional semiconductor fabrication processes, using one or more output signals from measurement device 238. The additional semiconductor fabrication processes may be performed subsequent to a deposition process. Additional semiconductor fabrication processes performed subsequent to a deposition process may include, but are not limited to, a chemical-mechanical polishing process configured to planarize a deposited layer on the specimen. For example, a thickness of a layer deposited on a specimen during a deposition process may be determined using one or more output signals from the measurement device. The determined thickness of the deposited layer may be greater than a predetermined thickness for the layer.

Process conditions of a subsequent polishing process, however, may be optimized for the predetermined thickness of the deposited layer on the specimen. Therefore, before polishing the deposited layer, a parameter of one or more instruments coupled to a polishing tool such as process time or pressure applied to a back side of the specimen may be altered such that an upper surface of the deposited layer may be planarized. For example, a process time may be increased to ensure substantially complete planarization of the deposited layer. In this manner, the processor may be configured to alter a parameter of an instrument coupled to a chemical mechanical polishing tool in response to one or more output signals from the measurement device using a feedforward control technique. In addition, the processor, and the measurement device may be further configured according to any of the embodiments described herein. For example, a processor coupled to the measurement device may also be configured to detect defects on the specimen, a thickness of a deposited material, a sheet resistivity of a deposited material, a thermal diffusivity of a deposited material, or any combination thereof during the deposition process using one or more output signals from the measurement device.

In an embodiment, a method for determining a characteristic of a specimen during a deposition process may include disposing the specimen upon a stage. The stage may be disposed within a process chamber of a deposition tool, as shown in FIG. 23. The stage may also be configured to support the specimen during a deposition process. The measurement device may be coupled to the deposition tool, as shown in FIG. 23. As such, the stage may be coupled to a measurement device. In addition, the measurement device may be configured as described in above embodiments. The method may include directing light to a surface of the specimen. The directed light may have a known polarization state. The directed light may strike the surface of the specimen. A layer may be formed on the surface of the specimen during the deposition process.

In addition, the method may include detecting light propagating from the surface of the specimen during the deposition process. The method may also include generating one or more output signals responsive to an intensity and/or a polarization state of the detected light. The intensity and/or polarization state of the detected light may vary depending on, for example; one or more characteristics of a layer formed on the specimen. Therefore, such one or more output signals may be used to determine one or more characteristics of the formed layer. In this manner, the method may include determining one or more characteristics of a layer being formed on a specimen. Furthermore, the method may include determining one or more characteristics of more than one layer being formed on the specimen. The one or more characteristics may include, but are not limited to, a thickness, an index of refraction, an extinction coefficient of one or more layers on the specimen, a critical dimension of a feature on the specimen, a presence of defects on the specimen, or any combination thereof.

In additional embodiments, the method for determining a characteristic of a layer on a specimen during a deposition process may include steps of any methods as described herein. For example, the method may include altering a parameter of an instrument coupled to the deposition tool in response to one or more output signals responsive to an intensity and/or a polarization state of the detected light. In this manner, the method may include altering a parameter of an instrument coupled to the deposition tool using a feedback control technique, an in situ control technique, or a feedforward control technique. In addition, the method may include altering a parameter of an instrument coupled to the measurement device in response to the one or more output signals. For example, the method may include altering a sampling frequency of the measurement device in response to the one or more output signals. Furthermore, the method may include obtaining a signature characterizing deposition of a layer on the specimen. The signature may include at least one singularity representative of an endpoint of the deposition process. For example, an appropriate endpoint for a deposition process may be a predetermined thickness of a layer formed on the specimen. In addition, the predetermined thickness may be larger or smaller depending upon, for example, the semiconductor device feature fabricated by the deposition process. Subsequent to obtaining the singularity representative of the endpoint, the method may include altering a parameter of an instrument coupled to the deposition tool to reduce, and even terminate, the deposition process.

In an embodiment, a computer-implemented method may be used to control a system configured to determine a characteristic of a layer during a deposition process. The system may include a measurement device coupled to a deposition tool, as described herein. The method may include controlling the measurement device. Controlling the measurement device may include controlling a light source to direct light to a surface of the specimen such that the directed light may strike the surface of the specimen. The directed light may have a known polarization state. In addition, controlling the measurement device may include controlling a detector to detect light propagating from the surface of the specimen during the deposition process. Furthermore, the method may include processing the detected light to determine an intensity or a polarization state of the detected light. For example, the method may include processing the detected light and generating one or more output signals responsive to the detected light. The method may further include determining one or more characteristics of a layer being formed on the specimen using the one or more output signals. The one or more characteristics may include a thickness, an index of refraction, and an extinction coefficient of the layer on the specimen, a critical dimension of a feature on the specimen, a presence of defects on the specimen, or any combination thereof.

In additional embodiments, the computer-implemented method for controlling a system to determine a characteristic of a layer being formed on a specimen during a deposition process may include steps of any of the methods as described herein. For example, the method may include controlling an instrument coupled to the deposition tool to alter a parameter of the instrument in response to the one or more output signals. Controlling an instrument coupled to the deposition tool may include using a feedback control technique, an in situ control technique, and/or a feedforward control technique. In addition, the method may include controlling an instrument coupled to the measurement device to alter a parameter of the instrument in response to the one or more output signals. For example, the method may include controlling an instrument coupled to the measurement device to alter a sampling frequency of the measurement device in response to the one or more output signals.

In an additional example, the computer-implemented method may include controlling the measurement device to obtain a signature characterizing deposition of a layer on the specimen. The signature may include at least one singularity representative of an endpoint of the deposition process. For example, an appropriate endpoint for a deposition process may be a predetermined thickness of a layer deposited on the specimen. Subsequent to obtaining the singularity representative of the endpoint, the method may include controlling a parameter of an instrument coupled to the deposition tool to alter the parameter of the instrument to reduce, and even terminate, deposition of the layer on the specimen.

An additional embodiment relates to a method for fabricating a semiconductor device. The method may include disposing a specimen such as a wafer upon a stage. The stage may be disposed within a process chamber of a deposition tool. The stage may be configured to support the specimen during a deposition process. A measurement device may also be coupled to the process chamber of the deposition tool. In this manner, the stage may be coupled to the measurement device. The method may further include forming a portion of a semiconductor device upon the specimen. For example, forming a portion of a semiconductor device may include depositing a layer of material on the specimen. Depositing the layer on the specimen may include forming a layer of a dielectric material over a specimen having a plurality of dies. The plurality of dies may include repeatable pattern features. For example, the deposited layer may be used to electrically isolate proximate or adjacent features of a semiconductor device that may be formed on the specimen.

The method for fabricating a semiconductor device may also include directing light toward a surface of the specimen. The directed light may have a known polarization state. The method may also include detecting light propagating from the surface of the specimen during the deposition process. In addition, the method may include determining an intensity and/or a polarization state of the detected light. The intensity and/or the polarization state of the detected light may vary depending upon, for example, one or more characteristics of a layer formed on the specimen. The method may also include generating one or more output signals responsive to an intensity and/or a polarization state of the detected light. In this manner, the method may include determining a characteristic of a layer deposited on the specimen using the one or more output signals. The characteristic may include a thickness, an index of refraction, and an extinction coefficient of the layer on the specimen, a critical dimension of a feature on the specimen, or any combination thereof.

In additional embodiments, the method for fabricating a semiconductor device may include steps of any of the methods as described herein. For example, the method may include altering a parameter of an instrument coupled to the deposition tool in response to the one or more output signals. Altering a parameter of an instrument coupled to the deposition tool may include using a feedback control technique, an in situ control technique, and/or a feedforward control technique. In addition, the method may include altering a parameter of an instrument coupled to the measurement device in response to the one or more output signals. For example, the method may include altering a sampling frequency of the measurement device in response to the one or more output signals. Furthermore, the method may include obtaining a signature characterizing deposition of a layer on the specimen. The signature may include at least one singularity representative of an endpoint of the deposition process. For example, an appropriate endpoint for a deposition process may be a predetermined thickness of a layer deposited on the specimen. Subsequent to obtaining the singularity representative of the endpoint, the method may include altering a parameter of an instrument coupled to the deposition tool to reduce, and even terminate, the deposition process.

Figure 24:
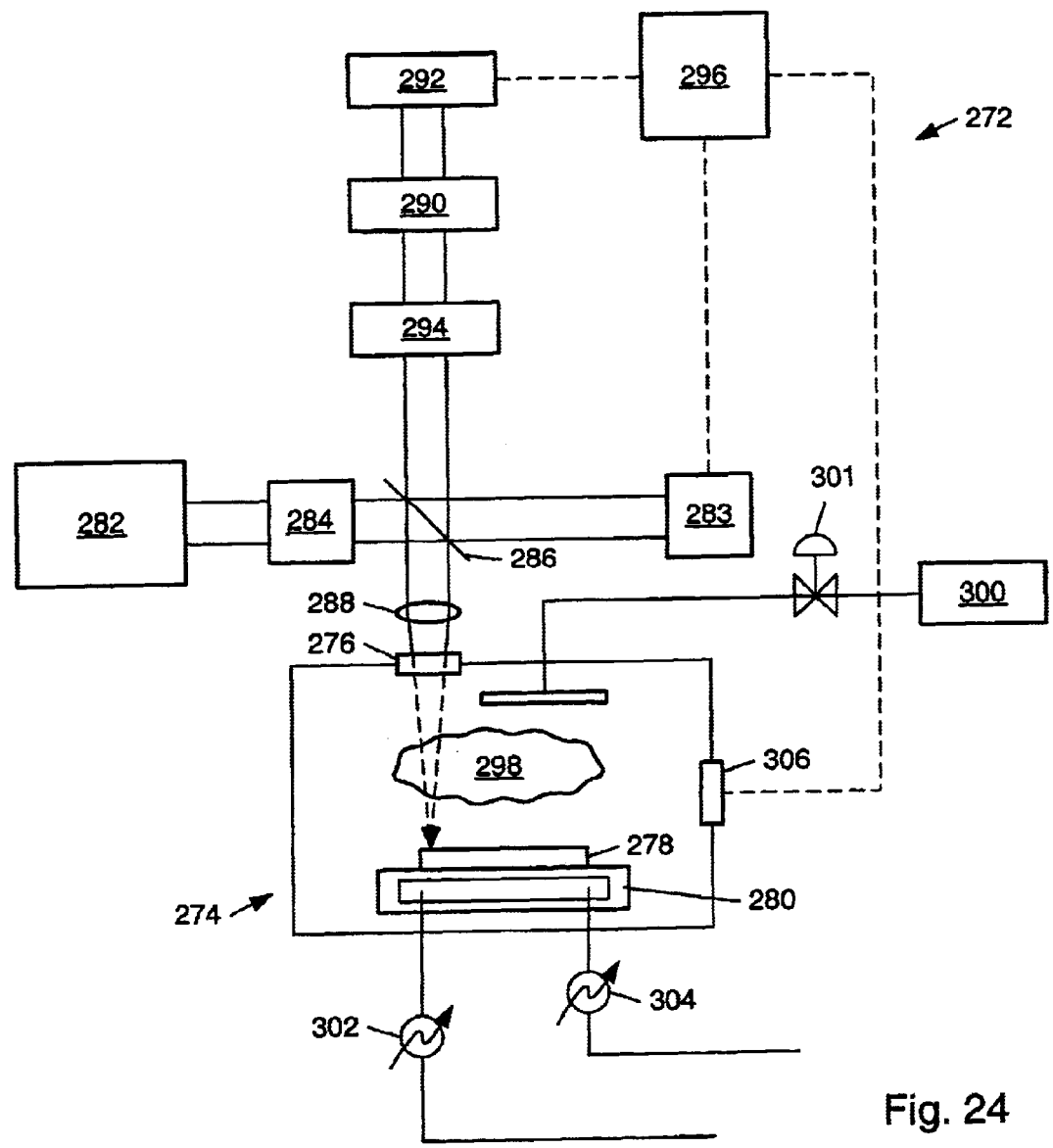
FIG. 24 depicts a schematic side view of an embodiment of a system coupled to an etch tool.

FIG. 24 illustrates an embodiment of a system configured to evaluate an etch process. In an embodiment, a system configured to evaluate an etch process may include measurement device 272 coupled to process chamber 274 of an etch tool. Measurement device 272 may be coupled to process chamber 274 such that the measurement device may be external to the process chamber. As such, exposure of the measurement device to chemical and physical conditions within the process chamber may be reduced, and even eliminated. Furthermore, the measurement device may be externally coupled to the process chamber such that the measurement device may not alter the operation, performance, or control of the etch process. For example, a process chamber may include one or more relatively small sections of a substantially optically transparent material 276 disposed within walls of process chamber 274. The configuration of process chamber 274, however, may determine an appropriate method to couple measurement device 272 to the process chamber. For example, the placement and dimensions of substantially optically transparent material sections 276 within walls of the process chamber may vary depending on, for example, the configuration of the components within the process chamber.

In an alternative embodiment, measurement device 272 may be disposed in a measurement chamber, as described with respect to and shown in FIG. 16. The measurement chamber may be coupled to process chamber 274 of an etch tool, as shown in FIG. 17. For example, the measurement chamber may be disposed laterally or vertically proximate one or more process chambers of an etch tool. In this manner, a robotic wafer handler of an etch tool, stage 280, or another suitable mechanical device may be configured to move specimen 278 to and from the measurement chamber and process chambers of the etch tool. In addition, the robotic wafer,handler, the stage, or another suitable mechanical device may be configured to move specimen 278 between process chambers of the etch tool and the measurement chamber. Measurement device 272 may be further coupled to process chamber 272 as further described with respect to FIG. 17.

Examples of etch tools are illustrated in U.S. Pat. No. 4,842,683 to Cheng et al., U.S. Pat. No. 5,215,619 to Cheng et al., U.S. Pat. No. 5,614,060 to Hanawa, U.S. Pat. No. 5,770,099 to Rice et al., U.S. Pat. No. 5,882,165 to Maydan et al., U.S. Pat. No. 5,849,136 to Mintz et al., U.S. Pat. No. 5,910,011 to Cruse, U.S. Pat. No. 5,926,690 to Toprac et al., U.S. Pat. No. 5,976,310 to Levy, U.S. Pat. No. 6,072,147 to Koshiishi et al., U.S. Pat. No. 6,074,518 to Imafuku et al., U.S. Pat. No. 6,083,363 to Ashtiani et al., and U.S. Pat. No. 6,089,181 to Suemasa et al., U.S. Pat. No. 6,110,287 to Arai et al., and are incorporated by reference as if fully set forth herein. An additional example of a measurement device coupled to an etch tool is illustrated in PCT Application No. WO 99/54926 to Grimbergen et al., and is incorporated by reference as if fully set forth herein. In WO 99/54926, a measurement device coupled to an etch tool is described as a "reflectance thickness measuring machine," which is substantially different than a measurement device as described herein. An example of an apparatus for estimating voltage on a wafer located in a process chamber is illustrated in European Patent Application No. EP 1 072 894 A2 to Loewenhardt et al., and is incorporated by reference as if fully set forth herein.

Measurement device 272 may be configured to direct an incident beam of light having a known polarization state to specimen 278 such that a region of the specimen may be illuminated prior to, during, or subsequent to an etch process. In addition, the measurement device may be configured to analyze a polarization state of the light returned from the illuminated region of the specimen prior to, during, or subsequent to an etch process. For example, the measurement device may include a beam profile ellipsometer. Additionally, however, measurement device 272 may include a spectroscopic beam profile ellipsometer, a null ellipsometer, and/or a spectroscopic ellipsometer. Furthermore, measurement device 272 may be configured as a scatterometer as described herein.

The relatively small sections of transparent material 276 may transmit an incident beam of light from a light source outside the process chamber to a specimen within the process chamber and a returned light beam from specimen 278 to a detector outside the process chamber. The optically transparent material may have optical or material properties such that the incident beam of light and the returned light beam may pass through the relatively small sections of transparent material without substantially undesirably altering the optical properties of the incident and returned light beams. In this manner, measurement device 272 may be coupled to stage 280 disposed within the process chamber and configured to support the specimen 278.

Measurement device 272 may include light source 282 configured to generate an incident beam of light. Light source 282 may include, for example, a laser configured to emit light having a known polarization state such as a gas laser or a solid state laser diode. Such lasers typically may emit light having a single wavelength of 633 nm and 670 nm, respectively. Measurement device 272 may also include polarization section 284 which may include, but is not limited to, a linear or circular polarizer or a birefringent quarter wave plate compensator. The polarization section may be configured to convert linear polarized light into circularly polarized light. In this manner, an incident beam of light having a known polarization state may be directed toward the specimen. In addition, measurement device 272 may include beam splitter 286 configured to direct at least a portion of the incident beam of light to an upper surface of specimen 278. Beam splitter 286 may also be configured to direct the incident beam through high numerical aperture ("NA") lens 288. In this manner, measurement device 272 may be configured to direct the incident beam of light to specimen 278 at a number of angles of incidence. For example, high NA lens 288 may have a numerical aperture of approximately 0.9. The numerical aperture of the lens may be larger or smaller, however, depending on, for example, the number of angles of incidence required. In addition, high NA lens 288 may be configured to focus the incident beam to a very small spot size on the upper surface of specimen 278. In this manner, the incident beam may be directed at a number of angles of incidence to a single feature or region on the specimen. Beam splitter 286 may also be configured to transmit a portion of the incident beam light such that the transmitted portion of the incident beam of light may be configured to strike detector 283. Detector 283 may be configured to monitor fluctuations in the output power of light source 282.

Light returned from the surface of specimen 278 may pass back through high NA lens 288 and beam splitter 286 to polarizer 290. Polarizer 290 may include, for example, a rotating polarizing filter. The measurement device may also include detector 292 configured to measure an intensity of the returned light at a number of angles of incidence. For example, detector 292 may include a diode array that may be radially positioned in a two-dimensional array such that the intensity of returned light may be measured at a number of angles of incidence.

In an alternative embodiment, light returned from the specimen may pass through quarter-wave plate 294. The quarter-wave plate may be configured to retard the phase of one of the polarization states of the returned light by about 90 degrees. In such a measurement device, polarizer 290 may be configured to cause the two polarization states to interfere. Detector 292 for such a measurement device may include a quad-cell detector having four quadrants. Each quadrant of the detector may be configured to generate one or more output signals approximately proportional to the magnitude of the power of the returned light striking the quadrant of the detector. Each signal may represent an integration of the intensities of the returned light at different angles of incidence. Such a quad-cell detector may also be configured to operate as a full power detector if the one or more output signals from all of the quadrants are summed.

In each of the embodiments described above, processor 296 may be configured to determine a thickness, an index of refraction, an extinction coefficient of the specimen and/or a critical dimension of a feature on the specimen from one or more output signals of detector 292. For example, processor 296 may determine a thickness of a layer or a feature on specimen 278 or a thickness of a feature such as an isolation structure formed in specimen 278 from one or more output signals of detector 292.

In an additional alternative embodiment, light source 282 may be configured to generate broadband light having a known polarization state. An appropriate light source may include a polychromatic light source such as a tungsten halogen lamp. For such a configuration of the measurement device, light returned from the specimen may be passed through a filter (not shown). The filter may be configured to pass light through two quadrants of the filter and to block light through two other quadrants of the filter. As such, light passed through the filter may have an ellipsometric signal, $\delta$, of only one sign, for example, positive. After passing through the filter, the returned light may pass through a spatial filter (not shown) having a small aperture. The spatial filter may be configured to limit the wavelength of light that may be directed to detector 292. As such, the width of the aperture of the spatial filter may be larger or smaller depending on, for example, the desired wavelength resolution.

The measurement device may also include a grating (not shown) configured to focus the returned light such that light from all angles of incidence may be combined and to angularly disperse the returned light as a function of wavelength. The grating may include a curved grating and a curved mirror, a lens and a separate planar grating, or a prism. Detector 292 may include an array of a plurality of individual detector elements. In this manner, the detector may be configured to measure an intensity of returned light over a narrow wavelength regime and a number of angles of incidence. As such, the spatial filter, the grating, and the detector may have a configuration substantially similar to a conventional spectophotometer.

The measurement device may be further configured to perform a second measurement of light returned from the surface of the specimen. In this measurement, light passed through the filter may have an ellipsometric signal, $\delta$, opposite to the sign of the light passed through the filter for the first measurement (i.e., negative). In the additional embodiments described above, processor 296 may also be configured to determine a thickness, an index of refraction, an extinction coefficient of the specimen, and/or a critical dimension of a feature on the specimen from one or more output signals of the detector. For example, the processor may be configured to determine a thickness of a layer on specimen 278 or a feature such as an isolation structure formed in specimen 278 from the one or more output signals of the detector. Examples of beam profile ellipsometers are illustrated in U.S. Pat. No. 5,042,951 to Gold et al., U.S. Pat. No. 5,181,080 to Fanton et al., U.S. Pat. No. 5,596,411 to Fanton et al., U.S. Pat. No. 5,798,837 to Aspnes et al., and U.S. Pat. No. 5,900,939 to Aspnes et al., and are incorporated by reference as if fully set forth herein.

In an additional embodiment, the system may further include a calibration ellipsometer (not shown). The calibration ellipsometer may be configured to determine a thickness of a reference layer on a specimen. The thickness of the reference layer may be measured using the measurement device as described herein. A phase offset of the thickness measurements of the reference layer generated by the calibration ellipsometer and the measurement device may be determined by processor 296. The processor may be configured to use the phase offset to determine additional layer thicknesses from measurements made by the measurement device. The calibration ellipsometer may also be coupled to process chamber 274 of the etch tool. As such, the calibration ellipsometer may be used to reduce, and even eliminate, variations in measured ellipsometer parameters. For example, measurements of the ellipsometric parameter, $\delta$, may vary due to changing environmental conditions along one or more optical paths of the measurement device. Such a variation in the ellipsometric parameter, $\delta$, may alter thickness measurements of a layer on a specimen. Therefore, a calibration ellipsometer may be used to reduce, and even eliminate, a drift in thickness measurements of a layer on a specimen.

The polarization state of light returned from a specimen may be altered during etching of the specimen. For example, during an etch process such as a reactive ion etch ("RIE") or a plasma etch process, a selectively exposed layer on the specimen may be removed by chemical reactions involving chemical reactive species of plasma 298 and a surface of specimen 278 and ionic species of plasma 298 striking the surface of specimen 278. In this manner, a thickness of the selectively exposed layer may be removed during the etch process. As the thickness of the layer is reduced during the etch process, the reflectivity of the layer may vary approximately sinusoidally with variations in the thickness of the layer. Therefore, the intensity of the returned light may vary depending on a thickness of the selectively exposed layer. In addition, the intensity of the returned light may be approximately equal to the square of the field magnitude according to the equation: $I_r = [E<]infR[<s]up2$. $I_r$ can also be expressed in terms of the ellipsometric parameters, $\psi$ and $\delta$. For very thin layers, tan $\psi$ may be independent of thickness, and $\delta$ may be approximately linearly proportional to the thickness of the layer. In this manner, output signals from the measurement device responsive to the intensity of the light returned from the specimen may be used to determine a thickness of the layer.

An etch rate may be defined as a thickness of a layer on a specimen that may be removed in a period of time. The etch rate, therefore, may determine the variations in the thickness of a layer on a specimen during an etch process. An etch rate may be substantially constant throughout an etch process. Alternatively, an etch rate may vary throughout an etch process. For example, an etch rate may decrease exponentially throughout an etch process. The etch rate may be determined by a number of parameters of one or more instruments coupled to the etch tool. For example, one parameter may include a flow rate of etchant gases from gas source 300 to process chamber 274 of the etch tool. The flow rate may vary depending upon, for example, a parameter such as a position or a setting of an instrument such as valve 301. In addition, such parameters may also include radio frequency power values, which may be determined by instruments such as power supplies 302 and 304 coupled to process chamber 274. An additional parameter may include a pressure within the process chamber and may be determined by instrument 306, which may be configured as a pressure gauge.

Such parameters may affect thickness variations of a layer on a specimen during an etch process. For example, as pressure decreases in a process chamber, a thickness of a layer on a specimen may be removed at an increased rate during the etch process. In this manner, an intensity of a returned sample beam may vary depending upon a parameter of one or more instruments coupled to the process chamber of the etch tool. Therefore, processor 296 coupled to measurement device 272 may be configured to determine a parameter of an instrument coupled to process chamber 274 of the etch tool from the measured intensity of the returned sample beam during an etch process.

In an embodiment, processor 296 coupled to measurement device 272 may be configured to receive one or more output signals from detector 292. In addition, the processor may be configured to determine a property of an etched region of specimen 278 from the one or more output signals. Measurement device 272 may be configured as described herein. For example, measurement device 272 may be configured as a beam profile ellipsometer, a spectroscopic beam profile ellipsometer, a null ellipsometer, a spectroscopic ellipsometer and/or a scatterometer as described herein. Therefore, property of the etched region may include, but is not limited to, a thickness, an index of refraction, an extinction coefficient, a critical dimension of a feature on the specimen, or any combination thereof. Thickness, index of refraction, and/or extinction coefficient may be commonly referred to as "thin film" characteristics.

Subsequent to an etch process, a specimen may be stripped to remove residual masking material from the specimen. In addition, a material such as a conductive material may be deposited upon the specimen. The specimen may also be polished such that an upper surface of the specimen may be substantially planar. In this manner, a number of semiconductor features such as interlevel contact structures may be formed on the specimen. The properties of the semiconductor features formed on the specimen may vary depending on, for example, one or more properties of the etched region and process conditions of the stripping, deposition, and polishing processes. As such, properties of a semiconductor feature on specimen 278 may be determined using the determined properties of the etched region. In addition, processor 296 coupled to measurement device 272 may also be configured to determine a presence of defects such as foreign material on the specimen, prior to, during, or subsequent to the etch process from one or more output signals from detector 292.

In an additional embodiment, processor 296 may be coupled to measurement device 272 and process chamber 274 of an etch tool. Processor 296 may be configured to interface with measurement device 272 and process chamber 274. For example, processor 296 may receive one or more output signals from a device coupled to process chamber 274 during an etch process. Such one or more output signals may be responsive to a parameter of an instrument coupled to the process chamber such as pressure gauge 306. Processor 296 may also be configured to receive one or more output signals from detector 292 as described herein.

In an additional embodiment, the measurement device may be configured, as described above, to measure variations in the intensity of light returned from the specimen during an etch process. For example, the measurement device may be configured to measure the intensity of light returned from the specimen substantially continuously or at predetermined time intervals during an etch process. The processor may, therefore, receive output signals responsive to the intensity of light returned from the specimen from the measurement device and may monitor variations in the output signals during an etch process. In addition, processor 296 may be configured to determine a relationship between the output signals from measurement device 272 and a parameter of one or more instruments coupled to process chamber 274. As such, processor 296 may be configured to alter a parameter of one or more instants coupled to process chamber 274 in response to the determined relationship. In addition, the processor may be configured to determine a parameter of the instrument using the relationship and one or more output signals from the measurement device.

Additionally, processor 296 may be further configured to control measurement device 272 and etch tool 274. For example, the processor may be configured to alter a parameter of an instrument coupled to the etch tool in response to one or more output signals from the measurement device. The processor may be configured to alter a parameter of an instrument coupled to the etch tool using a feedback control technique, an in situ control technique, and/or a feedforward control technique. In addition, the processor may be configured to alter a parameter of an instrument coupled to the measurement device in response to one or more output signals from the measurement device. For example, the processor may be configured to alter a sampling frequency of the measurement device in response to the output signals from the measurement device, as described herein.

By analyzing variations in output signals from the measurement device during an etch process, the processor may also generate a signature that may be responsive to the etch process. The signature may include at least one singularity that may be characteristic of an endpoint of the etch process. For example, an endpoint for an etch process may be a predetermined thickness of a layer on the specimen. A predetermined thickness of a layer on the specimen may be larger or smaller depending upon, for example, a semiconductor device being fabricated on the specimen. In addition, an endpoint for an etch process may be approximately complete removal of a layer on a specimen. Such an endpoint may correspond to etching through substantially an entire thickness of a layer such that an underlying layer of material may be exposed for subsequent processing. After the processor has detected the singularity of the signature, the processor may reduce, and even terminate, etching of the specimen by altering a parameter of an instrument coupled to the etch tool. A method for detecting an endpoint of an etch process is illustrated in PCT Application Nos. WO 00/03421 to Sui et al. and WO 00/60657 to Grimbergen et al., and is incorporated by reference as if fully set forth herein.

In an embodiment, the processor may be configured to determine a parameter of one or more instruments coupled to the etch tool for subsequent etch processes of additional specimens using one or more output signals from the measurement device. For example, a thickness of a layer on the specimen may be determined using one or more output signals from the measurement device. The thickness of the layer on the specimen may be, for example, greater than a predetermined thickness. The predetermined thickness may vary depending on, for example, a feature of a semiconductor device, which may be fabricated during the etch process. Before processing additional specimens, a radio frequency power or another parameter of one or more instruments coupled to the etch tool may be altered. For example, the radio frequency power of the etch process may be increased to etch a greater thickness of a layer on additional specimens. In this manner, a thickness of a layer on additional specimens etched by the etch process may be closer to the predetermined thickness than the layer measured on the specimen. In this manner, the processor may be configured to alter a parameter of one or more instruments coupled to an etch tool in response to output signals from the measurement device using a feedback control technique.

In an additional embodiment, the processor may be configured to determine process conditions of additional semiconductor fabrication processes using one or more output signals from the measurement device. The additional semiconductor fabrication processes may be performed subsequent to an etch process. Additional semiconductor fabrication processes performed subsequent to the etch process may include, but are not limited to, a process to strip a masking material on the specimen. Typically, a masking material may be patterned on a specimen using a lithography process such that regions of the specimen may be exposed during subsequent processing. At least a portion of the exposed regions of the specimen may be removed during a subsequent etch process.

Masking material remaining on the specimen after the etch process may be removed by a stripping process. A thickness of a masking material on a specimen during or subsequent to an etch process may be determined using one or more output signals from the measurement device. The determined thickness of the masking material on the specimen subsequent to an etch process may be, for example, greater than a predetermined thickness. Current process conditions of a stripping process, however, may be optimized for the predetermined thickness of the masking material on the specimen. Therefore, before stripping the masking material, a process condition of the stripping process such as process time or process temperature may be altered such that substantially the entire masking material may be removed by the stripping process. For example, a process time of the stripping process may be increased such that approximately an entire thickness of the masking material may be removed from the specimen. In this manner, the processor may be configured to alter a parameter of an instrument coupled to a stripping tool in response to one or more output signals from the measurement device using a feedforward control technique. In addition, the processor may be further configured according to any of the embodiments described herein.

In an embodiment, a method for determining a characteristic of a specimen during an etch process may include disposing specimen 278 upon stage 280. Stage 280 may be disposed within process chamber 274 of an etch tool. The stage may be configured to support the specimen during an etch process. Measurement device 272 may be coupled to process chamber 274 of the etch tool as described herein. As such, stage 280 may be coupled to measurement device 272. In addition, measurement device 272 may be configured as described herein. The method may include directing an incident beam of light to a region of the specimen. The incident beam of light may have a known polarization state. The directed incident beam of light may illuminate the region of the specimen at multiple angles of incidence during the etch process. The illuminated region of the specimen may be an exposed region of the specimen being removed during the etch process.

In addition, the method may include detecting light returned from the illuminated region of the specimen during the etch process. The method may also include generating one or more output signals in response to the detected light. The one or more output signals may be responsive to a polarization state of the light returned from the illuminated region of the specimen. Therefore, the method may include determining a change in a polarization state of the incident beam of light returned from the specimen. The change in the polarization state of the incident beam of light returned from the specimen may vary depending upon, for example, one or more characteristics of the specimen such as a thickness of a layer on the specimen. In this manner, the method may include determining one or more characteristics of a layer on the specimen using the one or more output signals. Furthermore, the method may include determining one or more characteristics of more than one layer on the specimen using the one or more output signals. Such characteristics may include a thickness, an index of refraction, and an extinction coefficient of the layer on the specimen, a critical dimension of a feature on the specimen, or any combination thereof.

In additional embodiments, the method for determining a characteristic of a layer on a specimen during an etch process may include any steps of the embodiments as described herein. For example, the method may include altering a parameter of one or more instruments coupled to the etch tool in response to one or more output signals from the measurement device. In this manner, the method may include altering a parameter of one or more instruments coupled to the etch tool using a feedback control technique, an in situ control technique, and/or a feedforward control technique. In addition, the method may include altering a parameter of one or more instruments coupled to the measurement device in response to one or more output signals from the measurement device. For example, the method may include altering a sampling frequency of the measurement device in response to one or more output signals from the measurement device.

Furthermore, the method may include obtaining a signature characterizing an etch process. The signature may include at least one singularity representative of an endpoint the etch process. For example, an endpoint of an etch process may be a predetermined thickness of a layer on the specimen. In addition, the predetermined thickness may be larger or smaller depending upon, for example, a semiconductor device being fabricated on the specimen. Subsequent to obtaining the singularity representative of the endpoint, the method may include altering a parameter of one or more instruments coupled to the etch tool to reduce, and even terminate, the etch process.

An additional embodiment relates to a computer-implemented method for controlling a system configured to determine a characteristic of a specimen during an etch process. The system may include a measurement device coupled to an etch tool as described herein. The method may include controlling the measurement device to detect light returned from a region of the specimen during an etch process. For example, controlling the measurement device may include controlling a light source to direct an incident beam of light to a region of the specimen during an etch process. The light source may be controlled such that the incident beam of light may illuminate the region of the specimen at multiple angles of incidence during the etch process. The incident beam of light may have a known polarization state. The illuminated region of the specimen may include a region of the specimen being removed during the etch process. In addition, controlling the measurement device may include controlling a detector to detect at least a portion of light returned from the illuminated region of the specimen during the etch process. The method may also include generating one or more output signals responsive to the detected light. Furthermore, the method may include processing the one or more output signals to determine a change in a polarization state of the incidence beam of light returned from the illuminated region of the specimen. The method may further include determining one or more characteristics of a layer on the specimen using the one or more output signals. The characteristics may include, but are not limited to, a thickness, an index of refraction, an extinction coefficient of the layer on the specimen, and/or a critical dimension of a feature on the specimen, or any combination thereof.

In additional embodiments, the computer-implemented method for controlling a system configured to determine a characteristic of a specimen during an etch process may include steps of any of the embodiments as described herein. For example, the method may include controlling an instrument coupled to the etch tool to alter a parameter of the instrument in response to one or more output signals from the measurement device. The method may include controlling an instrument coupled to the etch tool to alter a parameter of the instrument using a feedback control technique, an in situ control technique, and/or a feedforward control technique. In addition, the method may include controlling an instrument coupled to the measurement device to alter a parameter of the instrument in response to one or more output signals from the measurement device. For example, the method may include controlling an instrument coupled to the measurement device to alter a sampling frequency of the measurement device in response to one or more output signals from the measurement device.

In an additional example, the method may include controlling the measurement device to obtain a signature characteristic of an etch process. The signature may include at least one singularity representative of an endpoint of the etch process. An endpoint of an etch process may include, but is not limited to, a predetermined thickness of a layer on the specimen. The predetermined thickness may be larger or smaller depending upon, for example, a semiconductor device being fabricated on the specimen. Subsequent to obtaining the singularity representative of the endpoint, the method may include controlling a parameter of one or more instruments coupled to the etch tool to alter a parameter of the instruments to reduce, and even end, the etch process.

An additional embodiment relates to a method for fabricating a semiconductor device, which may include disposing a specimen upon a stage. The stage may be disposed within a process chamber of an etch tool, as shown in FIG. 24. The stage may be configured to support the specimen during an etch process. A measurement device may also be coupled to the process chamber of the etch tool, as shown in FIG. 24. In this manner, the stage may be coupled to the measurement device.

The method may further include forming a portion of a semiconductor device upon the specimen. For example, forming a portion of a semiconductor device may include etching exposed regions of the specimen. During an etch process, typically, an entire specimen may be exposed to an etch chemistry. A masking material may be arranged on the specimen prior to the etch process to expose predetermined regions of the specimen to the etch chemistry. For example, portions of the masking material may be removed using a lithography process and/or an etch process to expose predetermined regions of the specimen. The exposed predetermined regions may be regions of the specimen in which features of a semiconductor device may be formed. Remaining portions of the masking material may substantially inhibit underlying regions of the specimen to be etched during the etch process. Appropriate masking materials may include, but are not limited to, a resist, a dielectric material such as silicon oxide, silicon nitride, and titanium nitride, a conductive material such polycrystalline silicon, cobalt silicide, and titanium silicide, or any combination thereof.

The method for fabricating a semiconductor device may also include directing an incident beam of light to a region of the specimen. The incident beam of light may have a known polarization state. The region of the specimen may be a region of the specimen being removed during the etch process. The method may also include detecting at least a portion of the light returned from the illuminated region of the specimen during the etch process. The method may further include generating a signal responsive to the detected light. In addition, the method may include determining a change in a polarization state of the incident beam of light returned from the specimen. The change in the polarization state of the incident beam of light returned from the specimen may vary depending on, for example, one or more characteristics of the specimen. In this manner, the method may include determining one or more characteristics of a layer on the specimen using the one or more output signals. The characteristics may include, but are not limited to, a thickness, an index of refraction, and an extinction coefficient of the layer on the specimen, a critical dimension of a feature on the specimen, or any combination thereof.

In additional embodiments, the method for fabricating a semiconductor device may include steps of any of the embodiments as described herein. For example, the method may include altering a parameter of one or more instruments coupled to the etch tool in response to one or more output signals from the measurement device. In this manner, the method may include altering a parameter of one or more instruments coupled to the etch tool using a feedback control technique, an in situ control technique, and/or a feedforward control technique. In addition, the method may include altering a parameter of one or more instruments coupled to the measurement device in response to one or more output signals from the measurement device. For example, the method may include altering a sampling frequency of the measurement device in response to one or more output signals from the measurement device.

Furthermore, the method may include obtaining a signature characteristic of an etch process. The signature may include at least one singularity representative of an endpoint of the etch process. An endpoint of an etch process may be a predetermined thickness of a layer on the specimen. In addition, the predetermined thickness may be larger or smaller depending upon, for example, the semiconductor device being fabricated on the specimen. Subsequent to obtaining the singularity representative of the endpoint, the method may include altering a parameter of one or more instruments coupled to the etch tool to reduce, and even terminate, the etch process.

Figure 25:
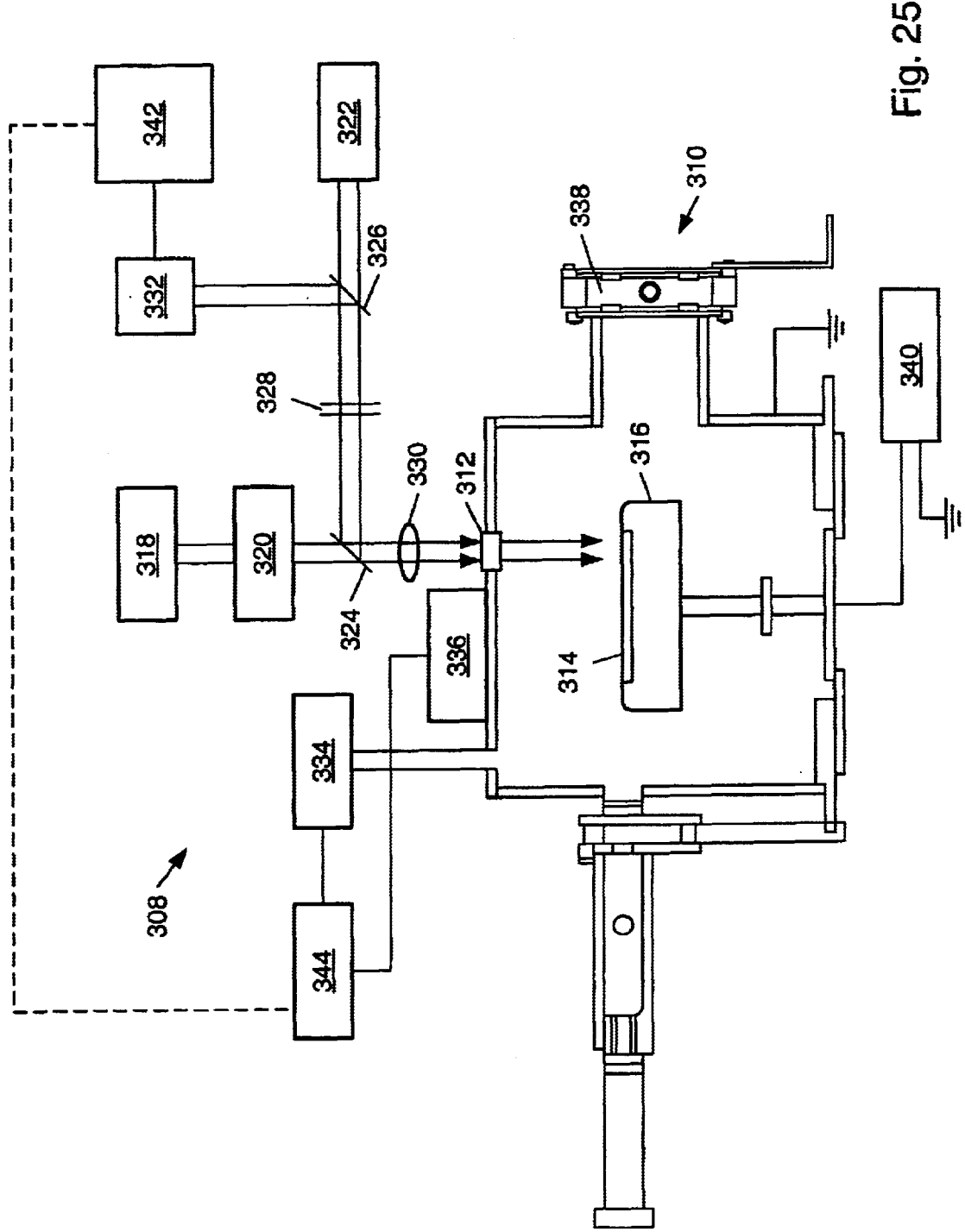
FIG. 25 depicts a schematic side view of an embodiment of a system coupled to an ion implanter.

FIG. 25 illustrates an embodiment of a system configured to evaluate an ion implantation process. In an embodiment, a system configured to evaluate an ion implantation process may include measurement device 308 coupled to ion implanter 310. Measurement device 308 may be coupled to ion implanter 310 such that measurement device 308 may be external to the ion implanter. As such, exposure of the measurement device to chemical and physical conditions within the ion implanter may be reduced, and even eliminated. Furthermore, measurement device 308 may be externally coupled to ion implanter 310 such that the measurement device does not alter the operation, performance, or control of the ion implantation process. For example, an ion implanter process chamber may include relatively small sections of a substantially transparent material 312 disposed within walls of the process chamber. A configuration of an ion implanter, however, may determine an appropriate method to couple the measurement device to the ion implanter. For example, the placement and dimensions of the substantially transparent material sections 312 within walls of the process chamber may vary depending on the configuration of the components within the process chamber. Examples of ion implanters are illustrated in U.S. Pat. No. 4,578,589 to Aitken, U.S. Pat. No. 4,587,432 to Aitken, U.S. Pat. No. 4,733,091 to Robinson et al., U.S. Pat. No. 4,743,767 to Plumb et al., U.S. Pat. No. 5,047,648 to Fishkin et al., U.S. Pat. No. 5,641,969 to Cooke et al., U.S. Pat. No. 5,886,355 to Bright et al., U.S. Pat. No. 5,920,076 to Burgin et al., U.S. Pat. No. 6,060,715 to England et al., U.S. Pat. No. 6,093,625 to Wagner et al., U.S. Pat. No. 6,101,971 to Denholm et al., and are incorporated by reference as if fully set forth herein.

In an alternative embodiment, measurement device 308 may be disposed in a measurement chamber, as described with respect to and shown in FIG. 16. The measurement chamber may be coupled to ion implanter 310, as shown in FIG. 17. For example, the measurement chamber may be disposed laterally or vertically proximate one or more process chambers of ion implanter 310. In this manner, a robotic wafer handler of ion implanter 310, stage 316, or another suitable mechanical device may be configured to move specimen 314 to and from the measurement chamber and process chambers of the ion implanter. In addition, the robotic wafer handler, the stage, or another suitable mechanical device may be configured to move specimen 314 between process chambers of the ion implanter and the measurement chamber. Measurement device 308 may be further coupled to ion implanter 310 as further described with respect to FIG. 17.

Measurement device 308 may be configured to periodically direct an incident beam of light to specimen 314 such that a region of the specimen may be periodically excited prior to, during, and/or subsequent to ion implantation. Measurement device 308 may also be configured to direct a sample beam of light to the periodically excited region of specimen 314 prior to, during, and/or subsequent to ion implantation. In addition, measurement device 308 may be configured to measure an intensity of the sample beam reflected from the periodically excited region of specimen 314 prior to, during, and/or subsequent to ion implantation. The small sections of substantially transparent material 312 may transmit the incident and sample beams from one or more illumination systems outside the process chamber to a specimen within the process chamber and the reflected sample beam from the specimen to a detection system outside the process chamber. The substantially transparent material 312 may have optical and/or material properties such that the beams may pass through the substantially transparent sections of the process chamber without undesirably altering the optical properties of the incident, sample, and reflected beam. In this manner, measurement device 308 may be coupled to stage 316 disposed within the process chamber and configured to support specimen 314.

In an embodiment, measurement device 308 may include light source 318 such as an argon laser configured to emit an incident beam of light. The light source may also be configured to generate electromagnetic radiation of other and/or multiple wavelengths including X-rays, gamma rays, infrared light, ultraviolet light, visible light, microwaves, or radio-frequencies. Light source 318 may also include any energy source that may cause a localized heated area on a surface of specimen 314 such as a beam of electrons, protons, neutrons, ions, or molecules. Such an energy source may be disposed within the process chamber of ion implanter 310. In addition, light source 318 may also include any energy source configured to cause at least some electrons of the specimen in a valence band to be excited across the band gap to a conductor band thereby creating a plurality of electron-hole pairs called a plasma. Measurement device 308 may also include modulator 320, which may be configured to chop the incident beam emitted from light source 318. The modulated incident light beam may be directed to specimen 314 to periodically excite a region of the specimen.

Measurement device 308 may also include additional light source 322 such as a helium neon laser configured to emit a sample beam of light. The measurement device may further include additional optical components such as dichroic mirror 324, polarizing beam splitter 326, quarter wave plate 328, and focusing lens 330 such as a microscopic objective. The additional optical components may be arranged within the measurement device such that the modulated incident beam and the sample beam may be directed to substantially the same region of the specimen. The additional optical components, however, may also be arranged within the measurement device such that the modulated incident beam and the sample beam may be directed to two overlapping but non-coaxial, or two laterally spaced, regions of the specimen.

Measurement device 308 may also include a tracker (not shown) coupled to each of the light sources. The trackers may be configured to control a position of the incident beam and the sample beam. For example, the tackers may be configured to alter a position of the incident beam with respect to a position of the sample beam during an ion implantation process. In addition, the trackers may be configured to control positions of the incident beam and the sample beam such that the beams may be directed to substantially different regions of the specimen during an ion implantation process. As such, the system may be configured to evaluate the ion implantation process at any number of positions on the specimen. The additional optical components may also be arranged within the measurement device such that the sample beam reflected from the surface of the specimen may be directed to a detection system of the measurement device.

In an embodiment, detection, system 332 may include a conventional photodetector that may be configured to measure intensity variations of the reflected sample beam. The intensity variations of the reflected sample beam may vary depending on, for example, periodic reflectivity changes in the periodically excited region of specimen 314. In alternative embodiments, detection system 332 may include a conventional interferometer. In this manner, the reflected sample beam may be combined with a reference beam prior to striking the interferometer. The reference beam may be a portion of the sample beam and may be directed to the interferometer by partially transmissive mirror 326. Since the sample beam reflected from the specimen and the reference beam may not be in phase, interference patterns may develop in the combined beam. Intensity variations of the interference patterns may be detected by the interferometer.

In additional embodiments, detection system 332 may include a split or bi-cell photodetector having a number of quadrants. Each quadrant of the photodetector may be configured to independently measure an intensity of the reflected sample beam. In this manner, each quadrant may detect different intensities as the reflected sample beam fluctuates across the surface of the photodetector. As such, the split photodetector may be configured to measure the extent of deflection of the reflected sample beam. For deflection measurements, the modulated incident beam and the sample beam may be directed to two overlapping but noncoaxial regions of the specimen as described above. Examples of modulated optical reflectance measurement devices are illustrated in U.S. Pat. No. 4,579,463 to Rosencwaig et al., U.S. Pat. No. 4,750,822 to Rosencwaig et al., U.S. Pat. No. 4,854,710 to Opsal et al., and U.S. Pat. No. 5,978,074 to Opsal et al. and are incorporated by reference as if fully set forth herein. The embodiments described herein may also include features of the systems and methods illustrated in these patents. In addition, each of the detectors described above may be configured to generate one or more output signals responsive to the intensity variations of the reflected sample beam.

The intensity variations of the reflected sample beam may be altered by the implantation of ions into the specimen. For example, during ion implantation processes, and especially in processes using high dosage levels, a portion of the specimen may be damaged due to the implantation of ions into the specimen. A damaged portion of the specimen may, typically, include an upper crystalline damaged layer and an intermediate layer of amorphous silicon. A lattice structure of the upper crystalline damaged layer may be substantially different than a lattice structure of the intermediate layer of amorphous silicon. The upper crystalline layer and the amorphous layer of silicon may, therefore, act as thermal and optical boundaries. For example, the two layers may have different periodic excitations due to differences in lattice structure. In addition, the different periodic excitations may cause the two layers to reflect the sample beam in a different manner. As such, the intensity variations of the reflected sample beam may depend on a thickness and a lattice structure of the upper crystalline layer and the amorphous layer.

The thickness of the upper crystalline layer and the amorphous layer may depend on a parameter of one or more coupled to the ion implanter. A parameter of one or more instruments coupled to the ion implanter may determine the process conditions of an ion implantation process. Instruments coupled to ion implanter may include, but are not limited to, gas supply 334, energy source 336, pressure valve 338, and modulator 340. Damage in the upper crystalline layer may vary depending on, for example, electronic collisions between atoms of the silicon layer and the implanted ions. Displacement damage, however, may not be produced if the ions entering the silicon layer do not have enough energy per nuclear collision to displace silicon atoms from their lattice sites. In this manner, a thickness of the upper crystalline layer may vary depending upon, for example, implant energy. Increasing the dose of ions, and in particular heavy ions, may produce an amorphous region below the upper crystalline damaged layer in which the displaced atoms per unit volume may approach the atomic density of the semiconductor. As the implant dose of an ion implantation process increases, a thickness of the amorphous layer may also increase. In this manner, the intensity variations of the reflected sample beam may be dependent upon process conditions during implantation including, but not limited to, the implant energy and dose. Therefore, processor 342 coupled to measurement device 308 may be configured to determine a parameter of an instrument coupled to ion implanter 310 from the measured intensity variations of the reflected sample beam prior to, during, and/or subsequent to ion implantation. Parameters of one or more instruments coupled to the ion implanter may define process conditions including, but not limited to, an implant energy, an implant dose, an implant species, an angle of implantation, and temperature.

In an embodiment, processor 342 coupled to measurement device 308 may be configured to determine one or more characteristics of an implanted region of specimen 314 from one or more output signals from detection system 332 prior to, during, and/or subsequent to ion implantation. The characteristics of an implanted region may include, but are limited to, a presence of implanted ions in the specimen, a concentration of implanted ions in the specimen, a depth of implanted ions in the specimen, a distribution profile of implanted ions in the specimen, or any combination thereof. Subsequent to implantation, the specimen may be annealed to electrically activate implanted regions of the specimen. Characteristics of an electrically activated implanted region such as depth and distribution profile may depend upon thicknesses of the upper crystalline layer and the amorphous layer formed during implantation and process conditions of the anneal process. As such, characteristics of an electrically activated implanted region may be determined from the determined characteristics of the implanted region. In addition, processor 342 coupled to measurement device 308 may be configured to determine a presence of defects such as foreign material on the specimen prior to, during, and/or subsequent to an implantation process from one or more output signals from detection system 332.

In an additional embodiment, processor 342 may be coupled to measurement device 308 and ion implanter 310. The processor maybe configured to interface with the measurement device and the ion implanter. For example, the processor may receive output signals from the ion implanter during an ion implantation process that may be representative of a parameter of one or more coupled to the ion implanter. The processor may also be configured to receive output signals from the detection system during an ion implantation process. In an additional embodiment, the measurement device may be configured to measure variations in output signals from the detection system during an ion implantation process. For example, the measurement device may be configured to detect the reflected sample beam substantially continuously or at predetermined time intervals during implantation. The processor may, therefore, be configured to receive output signals responsive to the detected light substantially continuously or at predetermined time intervals and to monitor variations in the one or more output signals during the ion implantation process. In this manner, processor 342 may be configured to determine a relationship between the output signals responsive to the detected light and parameters of one or more instruments coupled to an ion implanter. As such, processor 342 may be configured to alter a parameter of one or more instruments in response to the determined relationship. In addition, processor 342 may be configured to determine a parameter of one or more instruments using the relationship and output signals from the measurement device.

Furthermore, additional controller computer 344 may be coupled to ion implanter 310. Controller computer 344 may be configured to alter a parameter of one or more instruments coupled to the ion implanter. Processor 342 may also be coupled to controller computer 344. In this manner, controller computer 344 may be configured to alter a parameter of one or more instruments coupled to the ion implanter in response to one or more output signals from processor 342, which may be responsive to a determined parameter. In addition, controller computer 344 may monitor a parameter of one or more instruments coupled to the ion implanter and may send one or more output signals responsive to the monitored parameters to processor 342.

Additionally, the processor may be further configured to control the measurement device and the ion implanter. For example, the processor may be configured to alter a parameter of one or more instruments coupled to the ion implanter in response to one or more output signals from the measurement device. In this manner, the processor may be configured to alter a parameter of an instrument coupled to the ion implanter using a feedback control technique, an in situ control technique, and/or a feedforward control technique. In addition, the processor may be configured to alter a parameter of an instrument coupled to the measurement device in response to output signals from the measurement device. For example, the processing device may be configured to alter a sampling frequency of the measurement device in response to output signals from the measurement device.

By analyzing the variations in output signals from the measurement device during an ion implantation process, the processor may also generate a signature that may be representative of the implantation of the ions into the specimen. The signature may include at least one singularity that may be characteristic of an endpoint of the ion implantation process. For example, an appropriate endpoint for an ion implantation process may be a predetermined concentration of ions in the specimen. In addition, the predetermined concentration of ions may be larger or smaller depending upon a semiconductor device being fabricated on the specimen. After the processor has detected the singularity of the signature, the processor may reduce, and even terminate, the implantation of ions into the specimen by altering a parameter of one or more instruments coupled to the ion implanter.

In an embodiment, the processor nay be configured to determine appropriate process conditions for subsequent ion implantation processes of additional specimens using output signals from the measurement device. For example, a depth of implanted ions in the specimen may be determined using the output signals. The determined depth of an implanted region of the specimen may be less than a predetermined depth. The predetermined depth may vary depending on a semiconductor device being fabricated on the specimen. Before processing additional specimens, a parameter of one or more instruments coupled to the ion implanter may be altered such that an implanted depth of the additional specimens may be closer to the predetermined depth than the implanted depth of the measured specimen. For example, the implant energy of the ion implant process may be increased to drive the ions deeper into the additional specimens. In this manner, the processor may be configured to alter a parameter of one or more instruments coupled to an ion implanter in response to output signals from the measurement device using a feedback control technique.

In an additional embodiment, the processor may be configured to determine process conditions of additional semiconductor fabrication processes that may be performed subsequent to the ion implantation process using output signals from the measurement device. Additional semiconductor fabrication process may include, but are not limited to, a process to anneal implanted regions of the specimen. For example, a depth of an implanted region of a specimen may be determined using the output signals. The determined depth of the implanted region of the specimen may be greater than a predetermined depth. Current process conditions of a subsequent annealing process, however, may be optimized for the predetermined depth. Therefore, before annealing the implanted specimen, a process condition of the annealing process such as anneal time or anneal temperature may be altered. For example, an anneal time may be increased to ensure substantially complete recrystallization of the amorphous layer formed in the specimen. In this manner, the processor may be configured to alter a parameter of one or more instruments coupled to an anneal tool in response to output signals from the measurement device using a feedforward control technique. In addition, the processor may be further configured according to any of the embodiments as described herein.

In an embodiment, a method for determining a characteristic of a specimen prior to, during, and/or subsequent to an ion implantation process may include disposing the specimen upon a stage. The stage may be disposed within a process chamber of an ion implanter. The stage may also be configured according to any of the embodiments as described herein. A measurement device may be coupled to the ion implanter as described herein. As such, the stage may be coupled to the measurement device. In addition, the measurement device may be configured as described herein.

The method may include directing an incident beam of light to a region of the specimen to periodically excite a region of the specimen during the ion implantation process. The region of the specimen may be a region of the specimen being implanted during the ion implantation process. The method may also include directing a sample beam of light to the periodically excited region of the specimen during the ion implantation process. In addition, the method may include detecting at least a portion of the sample beam reflected from the periodically excited region of the specimen during the ion implantation process. The method may further include generating one or more output signals in response to the detected light. Furthermore, the method may include determining one or more characteristics of the implanted region of the specimen using the one or more output signals. The characteristics of the implanted region may include, but are not limited to, a presence of implanted ions in the specimen, a concentration of implanted ions in the specimen, a depth of implanted ions in the specimen, a distribution profile of implanted ions in the specimen, or any combination thereof.

In additional embodiments, the method for determining a characteristic of a specimen during an ion implantation process may include steps of any of the embodiments described herein. For example, the method may include altering a parameter of one or more instruments coupled to the ion implanter in response to the one or more output signals. In this manner, the method may include altering a parameter of one or more instruments coupled to the ion implanter using a feedback control technique, an in situ control technique, and/or a feedforward control technique. In addition, the method may include altering a parameter of one or more instruments coupled to the measurement device in response to the one or more output signals. For example, the method may include altering a sampling frequency of the measurement device in response to the one or more output signals.

The method may further include obtaining a signature characterizing the implantation of the ions into a specimen. The signature may include at least one singularity representative of an endpoint of the ion implantation process. For example, an endpoint for an ion implantation process may be a predetermined concentration of ions. In addition, the predetermined concentration of ions may be larger or smaller depending upon a semiconductor device being fabricated on the specimen. Subsequent to obtaining the singularity representative of the endpoint, the method may include altering a parameter of one or more instruments coupled to the ion implanter to reduce, and even terminate, the ion implantation process.

In an embodiment, a computer-implemented method may be used to control a system configured to determine a characteristic of a specimen prior to, during, and/or subsequent to an ion implantation process. The system may include a measurement device coupled to an ion implanter as described herein. The method may include controlling the measurement device to measure modulated optical reflectance of a region of a specimen during the ion implantation process. For example, controlling the measurement device may include controlling a light source to direct an incident beam of light to a region of the specimen such that the region may be periodically excited during the ion implantation process. Controlling the measurement device may also include controlling an additional light source to direct a sample beam of light to the periodically excited region of the specimen during the ion implantation process.

In addition, controlling the measurement device may include controlling a detection system to detect at least a portion of the sample beam reflected from the periodically excited region of the specimen during the ion implantation process. In addition, the method may include generating one or more output signals in response to the detected light. Furthermore, the method may include processing the one or more output signals to determine one or more characteristics of the implanted region of the specimen. The characteristics of the implanted region may include, but are not limited to, a presence of implanted ions in the specimen, a concentration of implanted ions in the specimen, a depth of implanted ions in the specimen, a distribution profile of implanted ions in the specimen, or any combination thereof.

In additional embodiments, the computer-implemented method for controlling a system to determine a characteristic of a specimen prior to, during, and/or subsequent to an ion implantation process may include steps of any of the embodiments described herein. For example, the method may include controlling an instrument coupled to the ion implanter to alter a parameter of the instrument in response to the one or more output signals. In this manner, the method may include controlling an instrument coupled to the ion implanter to alter a parameter of the instrument using a feedback control technique, an in situ control technique, and/or a feedforward control technique. In addition, the method may include controlling an instrument coupled to the measurement device to alter the parameter in response to the one or more output signals. For example, the method may include controlling an instrument coupled to the measurement device to alter a sampling frequency of the measurement device in response to the one or more output signals. Furthermore, the method may include controlling additional components of the system. For example, the method may include controlling the trackers to control lateral positions of the incident beam and the sample beam with respect to the specimen during use. In this manner, the method may include controlling the trackers to evaluate the ion implantation process at any number of positions on the specimen.

In an additional example, the method may include controlling the measurement device to obtain a signature characterizing the implantation of the ions into the specimen. The signature may include at least one singularity representative of an endpoint of the ion implantation process. For example, an endpoint for an ion implantation process may be a predetermined concentration of ions. The predetermined concentration of ions may be larger or smaller depending upon, for example, a semiconductor device being fabricated on the specimen. Subsequent to obtaining the singularity representative of the endpoint, the method may include controlling a parameter of an instrument coupled to the ion implanter to alter the parameter of the instrument thereby reducing, and even terminating, implantation of ions into the specimen.

An additional embodiment relates to a method for fabricating a semiconductor device that may include disposing a specimen upon a stage. The stage may be disposed within a process chamber of an ion implanter. The stage may be configured as described herein. A measurement device may also be coupled to the process chamber of the ion implanter. In this manner, the stage may also be coupled to the measurement device. The method may include forming a portion of the semiconductor device upon the specimen. For example, forming the portion of the semiconductor device may include implanting ions into the specimen. During an ion implantation process, typically, the entire wafer may be scanned with a beam of ions. A masking material may be arranged on the specimen to expose predetermined regions of the specimen to implantation. For example, portions of the masking material may be removed using a lithography process and/or an etch process to expose regions of the specimen to an implantation process. The exposed regions may include regions of the specimen in which features of a semiconductor device are to be formed. Appropriate masking materials may include, but are not limited to, a resist, a dielectric material such as silicon oxide, silicon nitride, and titanium nitride, a conductive material such as polycrystalline silicon, cobalt silicide, and titanium silicide, or any combination thereof.

The method for fabricating a semiconductor device may also include directing an incident beam of light to a region of the specimen. The directed incident beam of light may periodically excite a region of the specimen during the ion implantation process. The region of the specimen may be a region of the specimen implanted during the ion implantation process. The method may also include directing a sample beam of light to the periodically excited region of the specimen during the ion implantation process. In addition, the method may include detecting at least a portion of the sample beam reflected from the periodically excited region of the specimen during the ion implantation process. The method may also include generating one or more output signals in response to the detected light. Furthermore, the method may include determining one or more characteristics of the implanted region of the specimen using the one or more output signals. The characteristics of the implanted region may include, but are not limited to, a presence of implanted ions in the specimen, a concentration, a depth, and a distribution profile of implanted ions in the specimen, or any combination thereof.

In additional embodiments, the method for fabricating a semiconductor device may include steps of any of the embodiments described herein. For example, the method may include altering a parameter of an instrument coupled to the ion implanter in response to the one or more output signals. In this manner, the method may include altering a parameter of an instrument coupled to the ion implanter using a feedback control technique, an in situ control technique, and/or a feedforward control technique. In addition, the method may include altering a parameter of an instrument coupled to the measurement device in response to the one or more output signals. For example, the method may include altering a sampling frequency of the measurement device in response to the one or more output signals.

Furthermore, the method may include obtaining a signature characteristic of the implantation of the ions into the specimen. The signature may include at least one singularity representative of an endpoint of the ion implantation process. For example, an endpoint for an ion implantation process may be a predetermined concentration of ions. In addition, the predetermined concentration of ions may be larger or smaller depending upon a semiconductor device being fabricated on the specimen. Subsequent to obtaining the singularity representative of the endpoint, the method may include altering a parameter of an instrument coupled to the ion implanter to reduce, and even terminate, the implantation of ions into the specimen.

Figure 26:
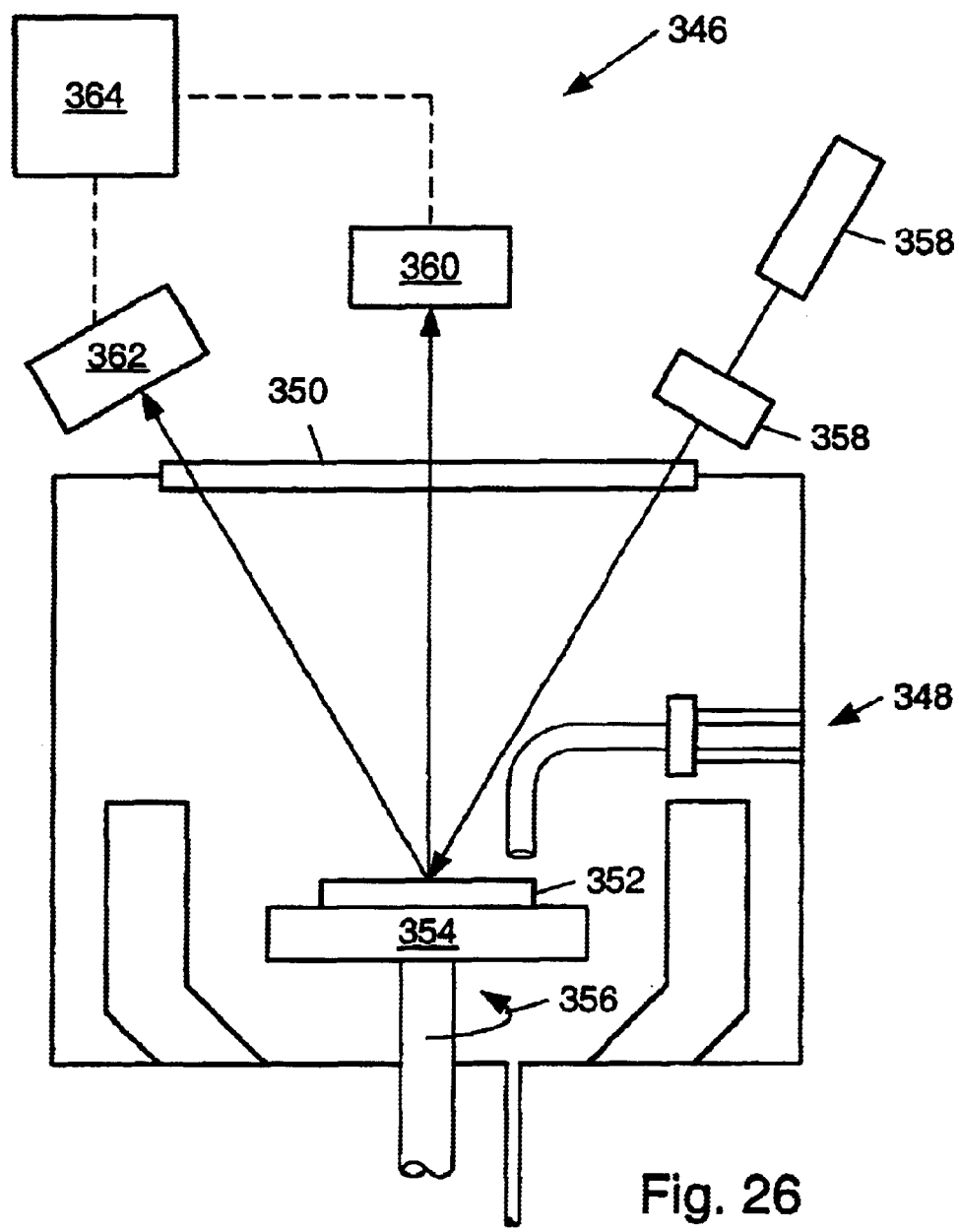
FIG. 26 depicts a schematic side view of an embodiment of a system configured to determine a characteristic of micro defects on a surface of a specimen.

FIG. 26 illustrates an embodiment of a system configured to determine at least one characteristic of micro defects on a surface of a specimen. In an embodiment, such a system may include measurement device 346 coupled to process tool 348. Process tool 348 may be configured as a process chamber of a semiconductor fabrication process tool or a semiconductor fabrication process tool. In this manner, process tool 348 may be configured to perform a step of a semiconductor fabrication process such as lithography, etch, ion implantation, chemical-mechanical polishing, plating, chemical vapor deposition, physical vapor deposition, and cleaning. For example, as shown in FIG. 26, process tool 348 may include a resist apply chamber of a process tool or a develop chamber of a process tool. As such, process tool 348 may be configured to fabricate a portion of a semiconductor device on specimen.

Measurement device 346 may be coupled to process tool 348 such that the measurement device may be external to the process tool. As such, exposure of the measurement device to chemical and physical conditions within the process tool may be reduced, and even eliminated. Furthermore, the measurement device may be externally coupled to the process tool such that the measurement device may not alter the operation, performance, or control of the process. For example, a process tool may include one or more relatively small sections of a substantially transparent material 350 disposed within walls of the process tool. The configuration of process tool 348, however, may determine an appropriate method to couple measurement device 346 to the process tool. For example, the placement and dimensions of the substantially transparent material sections 350 within the walls of the process tool may be depend on the configuration of the components within the process tool.

In an alternative embodiment, measurement device 346 may be disposed in a measurement chamber, as described with respect to and shown in FIG. 16. The measurement chamber may be coupled to process tool 348, as shown in FIG. 17. For example, the measurement chamber may be disposed laterally or vertically proximate one or more process chambers of process tool 348. In this manner, a robotic wafer handler of process tool 348, stage 354, or another suitable mechanical device may be configured to move specimen 352 to and from the measurement chamber and process chambers of the process tool. In addition, the robotic wafer handler, the stage, or another suitable mechanical device may be configured to move specimen 352 between process chambers of the process tool and the measurement chamber. Measurement device 346 may be further coupled to process tool 348 as further described with respect to FIG. 17.

In an embodiment, stage 354 may be disposed within process tool 348. Stage 354 may be configured to support specimen 352 during a process. In addition, stage 354 may also be configured according to any of the embodiments described herein. For example, the stage may include a motorized stage that may be configured to rotate in a direction indicated by vector 356. Illumination system 358 of measurement device 346 may be configured to direct light toward a surface of specimen 352. In addition, illumination system 358 may be configured to direct light toward a surface of the specimen during a process such as fabrication of a portion of a semiconductor device and during rotation of the stage. In addition, a detection system of measurement device 346 may include a first detector 360 and a second detector 362. Detectors 360 and 362 may be configured to detect light propagating from the surface of the specimen during a process such as fabrication of a portion of the semiconductor device and during rotation of the stage.

As shown in FIG. 26, first detector 360 may be configured to detect dark field light propagating along a dark field path from the surface of specimen 352. In addition, second detector 362 may be configured to detect bright field light propagating along a bright field path from the surface of specimen 352. In this manner, light detected by the measurement device may include dark field light propagating along a dark field path from the surface of the specimen and bright field light propagating along a bright field path from the surface of the specimen. In addition, the detectors may be configured to substantially simultaneously detect light propagating from a surface of the specimen.

Figure 27:
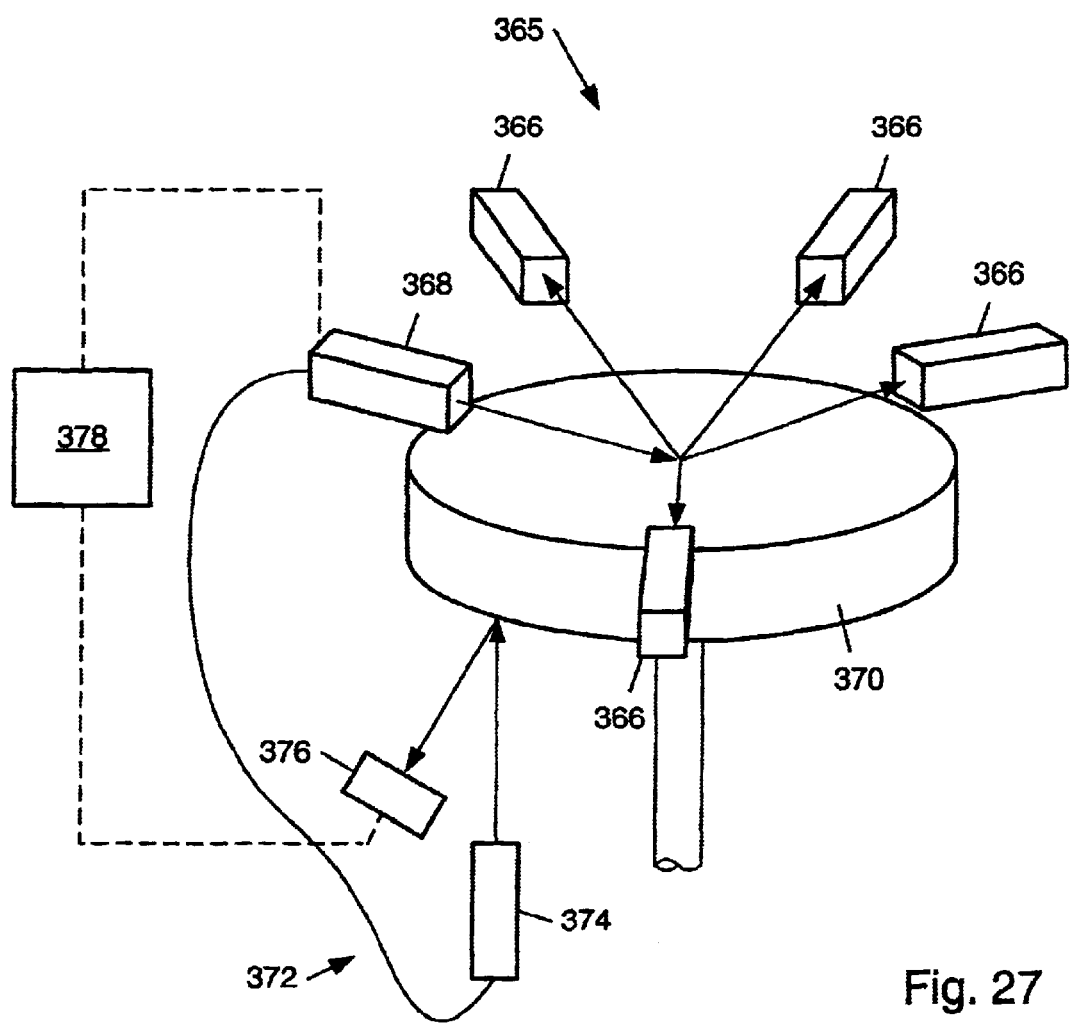
FIG. 27 depicts a schematic side view of an embodiment of a system configured to determine a characteristic of defects of multiple surfaces of a specimen.

Furthermore, detected light may include dark field light propagating along multiple dark field paths from the surface of the specimen. For example, as shown in FIG. 27, a detection system of measurement device 365 may include a plurality of detectors 366. The plurality of detectors may be positioned with respect to light source 368 such tat each of the plurality of detectors may detect dark field light propagating from the surface of the specimen. In addition, the plurality of detectors may be arranged at different radial and vertical positions with respect to light source 368. A system that includes measurement device 365 may be commonly referred to as a "pixel-based" inspection system. Examples of pixel-based inspection system. are illustrated in U.S. Pat. No. 5,887,085 to Otsuka, and U.S. Pat. No. 6,081,325 to Leslie et al., and PCT Application No. WO 00/02037 to Smilansky et al., and are incorporated by reference as if fully set forth herein. An example of an optical inspection method and apparatus utilizing a variable angle design is illustrated in PCT Application No. WO 00/77500 A1 to Golberg et al., and is incorporated by reference as if fully set forth herein.

As shown in FIG. 27, measurement device 365 may be further configured to direct light to multiple surfaces of specimen 370, which may be disposed upon a stage (not shown). The stage may be configured to move laterally and/or rotatably with respect to measurement device 365 as described herein. For example, the stage may be configured to move laterally while light from light source 368 may be configured to scan across the specimen in a direction substantially parallel to a radius of the specimen. Alternatively, the stage may be configured to move in two linear directions, which may be substantially orthogonal to one another, and optical components of measurement device 365 may be substantially stationary. The configuration of the stage with relation to the optical components of the measurement device may vary, however, depending upon, for example, space and mechanical constraints within the system Light source 368 of measurement device may include any of the light sources as described herein. In addition, fiber optic cable 372 or another suitable light cable may be coupled to light source 368 and illumination system 374 positioned below specimen 370. In this manner, the measurement device may be configured to direct light to multiple surfaces of a specimen. In an alternative embodiment, measurement device 365 may include at least two light sources. Each of the plurality of light sources may be configured to direct light to a different surface of the specimen.

Measurement device 365 may also include detector 376 coupled to illumination system 374. As shown in FIG. 27, detector 376 may be positioned with respect to illumination system 374 such that the detector may detect dark field light propagating along a dark field path. In an alternative embodiment, however, detector 376 may be positioned with respect to illumination 374 such that the detector may detect bright field light propagating along a bright field path. Measurement device 346 and measurement device 365 may be further configured as according to any of the embodiments described herein.

The measurement device may be further configured according to any of the embodiments described herein. In addition, the system may include an additional measurement device. The additional measurement device may include any of the measurement devices as described herein.

In an embodiment, processor 364 coupled to measurement device 346 may be configured to determine one or more characteristics of defects on a surface of specimen 352, as shown in FIG. 26. In addition, processor 378 coupled to measurement device 365 may be configured to determine one or more characteristics of defects on one or more surfaces of specimen 370. Processor 364 and processor 378 may be similarly configured. For example, processors 364 and 378 may be configured to receive one or more output signals from detectors 360 and 362 or 366 and 376, respectively, in response to light detected by the detectors. In addition, both processors may be configured to determine at least one characteristic of defects on at least one surface of a specimen. The defects may include macro defects and/or micro defects. For example, processor 264 and processor 378 may be configured to determine at least one characteristic of macro defects on a front side and a back side of a specimen. In addition, one or more characteristics of defects may include, but are not limited to, a presence of defects on a surface of specimen, a type of defects on a surface of a specimen, a number of defects on a surface of a specimen, and a location of defects on a surface of a specimen. In addition, processor 364 and processor 378 may be configured to determine one or more characteristics of defects substantially simultaneously or sequentially. In this manner, further description of processor 364 may be applied equally to processor 378.

In an additional embodiment, processor 364 may be coupled to measurement device 346 and process tool 348. The process tool may include, for example, a wafer cleaning tool such as a wet or dry cleaning tool, a laser cleaning tool, or a shock wave particle removal tool. An example of a laser cleaning tool is illustrated in "Chemically Assisted Laser Removal of Photoresist and Particles from Semiconductor Wafers," by Genut et al. of Oramir Semiconductor Equipment Ltd., Israel, presented at the 28$^{th}$ Annual Meeting of the Fine Particle Society, Apr. 1–3, 1998, which are incorporated by reference as if fully set forth herein. An example of a shock wave particle removal method and apparatus is illustrated in U.S. Pat. No. 5,023,424 to Vaught, which is incorporated by reference as if fully set forth herein. Processor 364 may be configured to interface with measurement device 346 and process tool 348. For example, processor 364 may receive one or more output signals from process tool 348 during a process that may be responsive to a parameter of an instrument coupled to the process tool. Processor 364 may also be configured to receive one or more output signals from measurement device 346, which may be responsive to light detected by detector 360 and detector 362 as described herein.

In an additional embodiment, the measurement device may be configured to detect light returned from the specimen during a process, as described herein. For example, the measurement device may be configured to detect light propagating from the specimen substantially continuously or at predetermined time intervals during a process. The processor may, therefore, receive output signals from the measurement device in response to the detected light and may monitor variations in the output signals during a process. In this manner, processor 364 may be configured to determine a relationship between the output signals and a parameter of one or more instruments coupled to process tool 348. As such, processor 364 may be configured to alter a parameter of an instrument coupled to the process tool in response to the determined relationship. In addition, the processor may be configured to determine a parameter of an instrument coupled to the process tool using the relationship and one or more output signals from the measurement device.

Additionally, processor 364 may be further configured to control measurement device 346 and process tool 348. For example, the processor may be configured to alter a parameter of one or more instruments coupled to the process tool in response to output signals from the measurement device. In this manner, the processor may be configured to alter a parameter of one or more instruments coupled to the process tool using a feedback control technique, an in situ control technique, and/or a feedforward control technique. In addition, the processor may be configured to alter a parameter of an instrument coupled to the measurement device in response to one or more output signals from the measurement device. For example, the processor may be configured to alter a sampling frequency of the measurement device in response to the output signals.

By analyzing the variations in the output signals from the measurement device during a process, the processor may also generate a signature that may be characteristic of the process. The signature may include at least one singularity that may be characteristic of an endpoint of the process. For example, an endpoint for a process may be a predetermined thickness of a layer. A predetermined thickness of a layer on the specimen may be larger or smaller depending upon, for example, a semiconductor device being fabricated on the specimen. After detecting the singularity, the processor may reduce, and even terminate, processing of the specimen by altering a parameter of one or more instruments coupled to the process tool.

In an embodiment, the processor may be configured to determine parameters of one or more instruments coupled to the process tool for processing of additional specimens using output signals from the measurement device. For example, a thickness of a layer on the specimen may be determined using output signals from the measurement device. The thickness of the layer on the specimen may be greater than a predetermined thickness. The predetermined thickness may vary depending on, for example, a seniconductor device being fabricated on the specimen. Before processing additional specimens, a parameter of one or more instruments coupled to the process tool may be altered such that a thickness of a layer on the additional specimens may be closer to the predetermined thickness than a thickness of the layer on the measured specimen. For example, the radio frequency power of an etch process may be increased to etch a greater thickness of the layer on the specimen. In this manner, the processor may be used to alter a parameter of one or more instruments coupled to a process tool in response to output signals from the measurement device using a feedback control technique.

In an additional embodiment, the processor may be configured to determine process conditions, of additional semiconductor fabrication processes using output signals from the measurement device. For example, the processor may be configured to alter a parameter of an instrument coupled to a stripping tool in response to output signals from the measurement device using a feedforward control technique. In addition, the processor may be further configured according to the embodiments described herein.

In an embodiment, a method for determining a characteristic of a specimen during a process may include disposing specimen 352 upon stage 354. Stage 354 may be disposed within process tool 348. The stage may also be configured according to any of the embodiments described herein. Measurement device 346 may be coupled to process tool 348 as described herein. As such, stage 354 may be coupled to measurement device 346. In addition, measurement device 346 may be configured as described herein. The method may include directing light to a surface of the specimen during a process. In addition, the method may include detecting light returned from the surface of the specimen during a process. The method may also include generating one or more output signals in response to the detected light. In this manner, the method may include determining a characteristic of the specimen being processed using the one or more output signals. The characteristic may include a presence, a number, a location, and a type of defects on at least one surface of the specimen, or any combination thereof.

In additional embodiments, the method for determining a characteristic of a specimen during a process may include steps of any of the embodiments described herein. For example, the method may include altering a parameter of an instrument coupled to the process tool in response to the one or more output signals. In this manner, the method may include altering a parameter of an instrument coupled to the process tool using a feedback control technique, an in situ control technique, and/or a feedforward control technique. In addition, the method may include altering a parameter of an instrument coupled to the measurement device in response to the one or more output signals. For example, the method may include altering a sampling frequency of the measurement device in response to the one or more output signals. Furthermore, the method may include obtaining a signature characteristic of the process. The signature may include at least one singularity representative of an endpoint of the process. Subsequent to obtaining the singularity representative of the endpoint, the method may include altering a parameter of one or more instruments coupled to the process tool to reduce, and even terminate, the process.

In an embodiment, a computer-implemented method may be used to control a system configured to determine a characteristic of a specimen during a process. The system may include a measurement device coupled to a process tool as described herein. The method may include controlling the measurement device to detect light returned from a surface of a specimen during a process. For example, controlling the measurement device may include controlling a light source to direct light to a surface of the specimen during the process. In addition, controlling the measurement device may include controlling a detector configured to detect light returned from the surface of the specimen during the process. The method may also include generating one or more output signals in response to the detected light. Furthermore, the method may include processing the one or more output signals to determine at least one characteristic of defects on at least one surface of the specimen using the one or more output signals. The characteristics may also include any of the characteristics described herein.

In additional embodiments, the computer-implemented method for controlling a system to determine a characteristic of a specimen during a process may include any steps of the embodiments described herein. For example, the method may include controlling one or more instruments coupled to the process tool to alter a parameter of the instruments in response to the one or more output signals. In this manner, the method may include controlling one or more instruments coupled to the process tool to alter a parameter of the instrument using a feedback control technique, an in situ control technique, and/or a feedforward control technique. In addition, the method may include controlling an instrument coupled to the measurement device to alter the parameter in response to the one or more output signals. For example, the method may include controlling an instrument coupled to the measurement device to alter a sampling frequency of the measurement device in response to the one or more output signals.

In an additional example, the method may include controlling the measurement device to obtain a signature characteristic of the process. The signature may include at least one singularity representative of an endpoint of the process. Subsequent to obtaining the singularity representative of the endpoint, the method may include controlling a parameter of one or more instruments coupled to the process tool to alter a parameter of an instrument to reduce, and even stop, the process.

An additional embodiment relates to a method for fabricating a semiconductor device, which may include disposing a specimen upon a stage. The stage may be disposed within a process tool. The stage may be configured as described herein. A measurement device may also be coupled to the process tool. In this manner, the stage may be coupled to the measurement device. The method may further include forming a portion of a semiconductor device upon the specimen. For example, forming a portion of a semiconductor device may include performing at least a step of a semiconductor fabrication process on the specimen. The method for fabricating a semiconductor device may also include directing light to a surface of the specimen. The method may further include detecting light returned from the surface of the specimen during the process. In addition, the method may include generating one or more output signals in response to the detected light. Furthermore, the method may include determining at least one characteristic of the specimen from the one or more output signals. The characteristic may include a presence, a number, a type, or a location of defects on at least one surface of the specimen, or any combination thereof.

In additional embodiments, the method for fabricating a semiconductor device may include any steps of the embodiments described herein. For example, the method may include altering a parameter of one or more instruments coupled to the process tool in response to the one or more output signals. In this manner, the method may include altering a parameter of one or more instruments coupled to the process tool using a feedback control technique, an in situ control technique, and/or a feedforward control technique. In addition, the method may include altering a parameter of one or more instruments coupled to the measurement device in response to the one or more output signals. For example, the method may include altering a sampling frequency of the measurement device in response to the one or more output signals. Furthermore, the method may include obtaining a signature characteristic of the process. The signature may include at least one singularity representative of an endpoint of the process. Subsequent to obtaining the singularity representative of the endpoint, the method may include altering a parameter of one or more instruments coupled to the process tool to reduce, and even terminate, the process.

In an embodiment, each of the systems describe above may be coupled to an energy dispersive X-ray spectroscopy ("EDS") device. Such a device may be configured to direct a beam of electrons to a surface of the specimen. The specimen may emit secondary electrons and a characteristic X-ray in response to the directed beam of electrons. The secondary electrons may be detected by a secondary electron detector and may be converted to electrical signals. The electrical signals may be used for brightness modulation or amplitude modulation of an image of the specimen produced by the system. The characteristic X-ray may be detected by a semiconductor X-ray detector and may be subjected to energy analysis. The X-ray spectrum may be analyzed to determine a composition of material on the specimen such as defects on a surface of the specimen. Examples of EDS systems and methods are illustrated in U.S. Pat. No. 4,559,450 to Robinson et al., U.S. Pat. No. 6,072,178 to Mizuno, and U.S. Pat. No. 6,084,679 to Steffan et al., and are incorporated by reference as if fully set forth herein.

Further Improvement

In an embodiment, each of the systems, as described herein, may be used to reduce, and even to minimize, within wafer ("WIW") variability of critical metrics of a process such as a lithography process. For example, critical metrics of a lithography process may include a property such as, but are not limited to, critical dimensions of features formed by the lidtography process and overlay misregistration. Critical metrics of a process, however, may also include any of the properties as described herein including, but not limited to, a presence of defects on the specimen, a thin film characteristic of the specimen, a flatness measurement of the specimen, an implant characteristic of the specimen, an adhesion characteristic of the specimen, a concentration of an elements in the specimen. Such systems, as described herein, may be configured to determine at least one property of a specimen at more than one position on the specimen. For example, the measurement device may be configured to measure at least the one property of the specimen at multiple positions within a field and/or at multiple positions all within at least two fields on the specimen. The measured property may be sent to a processor, or a within wafer film processor. The processor may be coupled to the measurement device and may be configured as described herein.

In addition, because at least one property of the specimen may be measured at various positions across the specimen, at least one property may be determined for each of the various positions. As such, a parameter of one or more instruments coupled to a tool or a process chamber of a process tool may also be altered, as described above, independently from field to field on the specimen. For example, many exposure process tools may be configured such that the exposure dose and focus conditions of the expose process may be varied across the specimen, i.e., from field to field. In this manner, process conditions such as exposure dose and/or post exposure bake temperature may vary across the specimen in subsequent processes in response to variations in at least one measured property from field to field across the specimen. The exposure dose and focus conditions may be determined and/or altered as described herein using a feedback or feedforward control technique. In this manner, critical metrics of a process such as a lithography process may be substantially uniform across the specimen.

In an addition, a temperature of the post exposure bake plate may be altered across the bake plate by using a number of discrete secondary heating elements disposed within a primary heating element. Secondary heating elements may be independently controlled. As such, a temperature profile across a specimen during a post exposure bake process may be altered such that individual fields on a specimen may be heated at substantially the same temperature or at individually determined temperatures. A pressure of a plating head of a chemical mechanical polishing tool may be similarly altered across the plate head in response to at least the two properties determined at multiple locations on the specimen.

In addition, at least the one parameter of a process chamber may be altered such that a first portion of a specimen may be processed with a first set of process conditions during a step of the process and such that a second portion of the specimen may be processed with a second set of process conditions during the step. For example, each portion of the specimen may be a field of the specimen. In this manner, each field of the specimen may be subjected to a different process conditions such as, but not limited to, exposure dose and focus conditions and post exposure bake temperatures. As such, because each field of a specimen may be subjected to process conditions that may vary depending upon a measured property of the specimen, within wafer variations in critical metrics of the process may be substantially reduced, or even minimized.

It is to be understood that all of the measurements described above may be used to alter a parameter of a process chamber using a feedback, a feedforward, or in situ process control technique. In addition, within wafer variations of critical metrics of a process such as a lithography process may be further reduced by using a combination of the above techniques.

A system configured to evaluate and control a process using field level analysis as described above may provide dramatic improvements over current process control methods. Measuring within wafer variability of critical metrics, or critical dimensions, may provide tighter control of the critical dimension distribution. In addition to improving the manufacturing yield, therefore, the method described above may also enable a manufacturing process to locate the distribution performance of manufactured devices closer to a higher performance level. As such, the high margin product yield may also be improved by using such a method to evaluate and control a process. Furthermore, additional variations in the process may also be minimized. For example, a process may use two different, but substantially similarly configured process chambers, to process one lot of specimens. Two process chambers may be used to perform the same process such that two specimens may be processed simultaneously in order to reduce the overall processing time. Therefore, the above method may be used to evaluate and control each process chamber separately. As such, the overall process spread may also be reduced.

Data gathered using a system, as described herein, may be analyzed, organized and displayed by any suitable means. For example, the data may be grouped across the specimen as a continuous function of radius, binned by radial range, binned by stepper field, by x-y position (or range of x-y positions, such as on a grid), by nearest die, and/or other suitable methods. The variation in data may be reported by standard deviation from a mean value, a range of values, and/or any other suitable statistical method.

The extent of the within wafer variation (such as the range, standard deviation, and the like) may be analyzed as a function of specimen, lot and/or process conditions. For example, the within wafer standard deviation of the measured CD may be analyzed for variation from lot to lot, wafer to wafer, and the like. It may also be grouped, reported and/or analyzed as a function of variation in one or more process conditions, such as develop time, photolithographic exposure conditions, resist thickness, post exposure bake time and/or temperature, pre-exposure bake time and/or temperature, and the like. It may also or instead be grouped, reported and/or analyzed as a function of within wafer variation in one or more of such processing conditions.

Data gathered using a system, as described herein, may be used not just to better control process conditions, but also where desirable to better control in situ endpointing and/or process control techniques. For example, such data may be used in conjunction with an apparatus such as that set forth in U.S. Pat. No. 5,689,614 to Gronet et al. and/or Published European Patent Application No. EP 1 066 925 A2, which are incorporated by reference as if fully set forth herein, to improve the control over localized heating of the substrate or closed loop control algorithms. Within wafer variation data may be fed forward or back to such a tool to optimize the algorithms used in control of local specimen heating or polishing, or even to optimize the tool design. In another example of such localized process control, within wafer variation data may be used to is control or optimize a process or tool such as that set forth in one or more of Published PCT Patent Applications No. WO 99/41434 or WO 99/25004 and/or Published European Patent Application No 1065567 A2, which are hereby incorporated by reference as if fully set forth herein. Again, within wafer variation data taken, for example, from stand alone and/or integrated measurement tools, may be used to better control and/or optimize the algorithms, process parameters and integrated process control apparatuses and methods in such tools or processes. Data regarding metal thickness and its within wafer variation may be derived from an x-ray reflectance tool such as that disclosed in U.S. Pat. No. 5,619,548 and/or Published PCT Application No. WO 01/09566, which are hereby incorporated by reference as if fully set forth herein, by eddy current measurements, by e-beam induced x-ray analysis, or by any other suitable method.

As shown in FIG. 9, an embodiment of system 70 may have a plurality of measurement devices. Each of the measurement devices may be configured as described herein. As described above, each of the measurement devices may be configured to determine a different property of a specimen. As such, system 70 may be configured to determine at least four properties of a specimen. For example, measurement device 72 may be configured to determine a critical dimension of a specimen. In addition, measurement device 74 may be configured to determine overlay misregistration of the specimen. In an alternative embodiment, measurement device 76 may be configured to determine a presence of defects such as macro defects on the specimen. In addition, measurement device 76 may be configured to determine a number, a location, and/or a type of defects on the specimen. Furthermore, measurement device 78 may be configured as to determine one or more thin film characteristics of the specimen and/or a layer on the specimen. Examples of thin film characteristics include, but are not limited to, a thickness, an index of refraction, and an extinction coefficient. In addition, each of the measurement devices may be configured to determine two or more properties of a specimen. For example, measurement device 72 may be configured to determine a critical dimension and a thin film characteristic of a specimen substantially simultaneously or sequentially. In addition, measurement device 72 may be configured to determine a presence of defects on the specimen. As such, system 70 may be configured to determine at least four properties of the specimen simultaneously or sequentially.

System 70 may be arranged as a cluster tool. An example of a configuration of a cluster tool is illustrated in FIG. 14. For example, each of the measurement devices described herein may be disposed in a measurement chamber. Each of the measurement chambers may be disposed proximate one another and/or coupled to each other. In addition, system 70 may include a wafer handler. The wafer handler may include any mechanical device as described herein. The system may be configured to receive a plurality of specimen to be measured and/or inspected such as a cassette of wafers. The wafer handler may be configured to remove a specimen from the cassette prior to measurement and/or inspection and to dispose a specimen into the cassette subsequent to measurement and/or inspection. The wafer handler may also be configured to dispose a specimen within each measurement chamber and to remove a specimen from each measurement chamber. In addition, the system may include a plurality of such wafer handlers. The system may be further configured as described with reference to FIG. 14. In addition, the system may be configured as a stand-alone metrology and/or inspection system. In this manner, the system may not be coupled to a process tool. Such a system may provide advantages over a similarly configured integrated tool. For example, such a system may be designed to be faster and cheaper than a similarly configured integrated tool because there may be less physical and mechanical constraints for a stand-alone system versus an integrated system. System 70 may be further configured as described herein.

In an embodiment, a system may be configured to determine at least two properties of a specimen including a thickness of a layer formed on the specimen and at least one additional property such as an index of refraction, a velocity of sound, a density, and a critical dimension, which may include a profile, of a layer or a feature formed upon the specimen. The specimen may include a structure such as single layer or multiple layers formed upon the specimen. In addition, the single layer or multiple layers formed on the specimen may include, but are not limited to, any combination of substantially transparent, semi-transparent, and opaque metal films. The specimen may also be a blanket wafer or a patterned wafer. As used herein, the term, "blanket wafer," generally refers to a wafer having at least an upper layer that may not have been subjected to a lithography process. In contrast, as used herein, the term, "patterned wafer," generally refers to a wafer having at least an upper layer that may be patterned by, for example, a lithography process and/or an etch process.

The system may be configured as described herein. For example, the system may include a processor coupled to two or more measurement devices. The processor may be configured to determine at least a thickness of the specimen and/or a layer on the specimen and at least one additional property of the specimen and/or a layer on the specimen from one or more output signals generated by the measurement devices. In addition, the processor may be configured to determine other properties of the specimen from the one or more output signals. In an embodiment, the measurement device may include, but is not limited to, a small-spot photoacoustic device, a grazing X-ray reflectometer, and a broadband small-spot spectroscopic ellipsometer. Examples of photo-acoustic devices are illustrated in U.S. Pat. No. 4,710,030 to Tauc et al., U.S. Pat. No. 5,748,318 to Maris et al., U.S. Pat. No. 5,844,684 to Maris et al., U.S. Pat. No. 5,684,393 to Maris, U.S. Pat. No. 5,959,735 to Maris et al., U.S. Pat. No. 6,008,906 to Maris, U.S. Pat. No. 6,025,918 to Maris, U.S. Pat. No. 6,175,416 to Maris et al., U.S. Pat. No. 6,191,855 to Maris, U.S. Pat. No. 6,208,418 to Maris, U.S. Pat. No. 6,208,421 to Maris et al., and U.S. Pat. No. 6,211,961 to Maris, which are incorporated by reference as if fully set forth herein. The system may also include a pattern recognition system that may be used in conjunction with the above devices.

In this manner, the measurement device may be configured to function as a single measurement device or as multiple measurement devices. Because multiple measurement devices may be integrated into a single measurement device of the system at least one element of a first measurement device, for example, may also be at least one element of a second measurement device. In addition, it may be advantageous for additional elements such as handling robots, stages, processors, and power supplies of a first measurement device to be used by a second measurement device. The system may also include an autofocus mechanism that may be configured to bring a specimen substantially into focus (i.e., to approximately a correct height) for a first measurement device, and then for a second measurement device. An example of an autofocus mechanism is shown in FIG. 11b, as autofocus sensor 124. An additional example of an autofocusing apparatus is illustrated in U.S. Pat. No. 6,172,349 to Katz et al., which is incorporated by reference as if fully set forth herein. The system, the measurement device, and the processor may be further configured as described herein.

Appropriate combinations of devices included in the measurement device may include, for example, a small-spot photo-acoustic device and a grazing X-ray reflectometer or a small-spot photo-acoustic device and a broadband small-spot spectroscopic ellipsometer. For example, a photo-acoustic device may provide measurements of layers having thickness of less than about a few hundred angstroms while a grazing X-ray reflectometer may provide measurements of layers having thicknesses in a range from about 50 angstroms to about 1000 angstrom. Ellipsometric techniques, especially broadband ellipsometry, may provide measurements of metal and semi-metallic layers having thicknesses of less than about 500 angstros because, at such thickness even metal may allow some light to pass through the layer. In addition, ellipsometric techniques may also provide measurements of transparent layers having thicknesses from about 0 angstroms to a few microns. As such, a system, as described herein, may provide measurements of layers having a broad range of thicknesses and materials.

In addition, such a system may be coupled to a chemical-mechanical polishing tool as described herein. Furthermore, the system may be coupled to or arranged proximate a chemical-mechanical polishing tool such that the system may determine at least two properties of a specimen, a layer of a specimen, and/or a feature formed on the specimen subsequent to a chemical-mechanical polishing process. For example, a feature formed on the specimen may include a relatively wide metal line. Such a relatively wide metal line may include, for example, a test structure formed on the specimen. In this manner, one or more of the determined properties of the test structure may be correlated (experimentally or theoretically) to one or more properties of a feature such as a device structure formed on the specimen. In addition, at least a portion of the specimen may include an exposed dielectric layer. Alternatively, the system may be coupled to any other process tools as described herein.

An appropriate spectroscopic ellipsometer may include a broadband light source, which may include one or a combination of light sources such as a xenon arc lamp, a quartz-halogen lamp, or a deuterium lamp. The ellipsometer may have a relatively high angle of incidence. For example, the angle of incidence may range from approximately 40 degrees to approximately 80 degrees, to the normal to the surface of the specimen. The spectroscopic ellipsometer may include an array detector such as a silicon photodiode array or a CCD array, which may be back thinned.

It may also be advantageous for the spectroscopic ellipsometer to include one or more fiber optic elements. For example, a first fiber optic element may be configured to transmit light from the light source to a fist polarizing element. For example, such a fiber may ensure that the light is randomly polarized or depolarized. The spectroscopic ellipsometer may also include a second fiber optic element configured to transmit light to a spectrometer from an analyzer assembly. In this manner, the fiber optic element may be configured to alter, or "scramble," a polarization state of light from the analyzer assembly such that the signal may not need correction for the polarization sensitivity of the spectrometer. In addition, or alternatively, the second fiber optic element may be configured to alter the polarization state of the light such that the spectrometer may be conveniently located at some distance from the specimen. The fiber optic element may, preferably, be made of fused silica or sapphire such that the fiber optic element may be transmissive at ultraviolet wavelengths.

The first polarizer may include a linear polarizing element such as a Rochon prism or a Wollaston prism and, optionally, a retarder (i.e., a compensator). The analyzer assembly may include a linear polarizing element and, optionally, a retarder. At least one of the linear polarizing elements may rotate continuously when making measurements. For calibration, at least two elements will be rotated either continuously or in a series of discrete steps.

The spectroscopic ellipsometer may further include reflective or refractive optics (or combinations thereof) configured to focus the light to a small spot on the specimen and to collect the light from the specimen. Any refractive components may, preferably, be made from fused $SiO_2$ or $CaF_2$ for relatively good ultraviolet transmission. Any reflective components may, preferably, be coated with Al for relatively good broadband transmission. Typically, a thin overcoat of $MgF_2$ or $SiO_2$ may be formed over the Al to reduce, and even eliminate, oxidation of the Al. The reflective components may be spherical or a spherical. Diamond turning may be a convenient and well-known technique for making a spheric mirrors. For vacuum conditions such as conditions suitable for ultraviolet light having wavelengths in a range of less than about 190 nm, gold or platinum may be a suitable coating material. The spectroscopic ellipsometer may be further configured as described herein.

In an embodiment, a spectroscopic ellipsometer may be coupled to a lithography track. The lithography track may be configured as illustrated in FIG. 13 and as described herein. The spectroscopic ellipsometer may be configured as in any of the embodiments described herein. A processor may be coupled to the spectroscopic ellipsometer. The processor may be configured to determine at least one property of the specimen including, but not limited to, a critical dimension, a profile, a thickness or other thin film characteristics of the specimen, a layer formed on the specimen, and/or a feature formed on the specimen from one or more output signals generated by the spectroscopic ellipsometer. In addition, the spectroscopic ellipsometer may be coupled to the lithography track as described herein. For example, the spectroscopic ellipsometer may be coupled to a process chamber of the lithography track such that the spectroscopic ellipsometer may direct light toward and detect light returned from a specimen on a support device in the process chamber. In addition, the spectroscopic ellipsometer may be configured to direct light toward and detect light returned from the specimen while the support device is spinning. Furthermore, the spectroscopic ellipsometer may be configured to direct light toward and detect light returned from the specimen during a process being performed in the process chamber. The process may include, but is not limited to, a resist apply process, a post apply bake process, and a chill process.

Alternatively, the spectroscopic ellipsometer may be disposed within the lithography track. For example, the spectroscopic ellipsometer may be disposed above a chill chamber, in an integration system, or laterally proximate or vertically proximate to a process chamber of the lithography track. An integration system may be configured to couple a lithography track to an exposure tool. For example, the integration system may be configured to receive a specimen from the lithography track and to send the specimen to the exposure tool. In addition, the integration system may be configured to receive or remove a specimen from the exposure tool and to send the specimen to the lithography track. The integration system may also include one or more chill plates and a handling robot. In this manner, the system may be configured to determine at least one property of the specimen at various points in a lithography process such as prior to an exposure step, subsequent to the exposure step, and subsequent to a develop step of the process.

The spectroscopic ellipsometer may or may not be disposed within a measurement chamber as described above. For example, in an alternative embodiment, the spectroscopic ellipsometer may be coupled to a robotic wafer handler of the lithography trace. In this manner, the spectroscopic ellipsometer may be configured to direct light toward and detect light returned from the specimen prior to or subsequent to a process such as prior to exposure, subsequent to exposure, or after develop. For example, subsequent to exposure, the spescoic ellipsometer may be configured to generate one or more output signals responsive to a critical dimension, a profile, a thickness or other thin film characteristics of a latent image formed on the specimen by the exposure process.

An environment within the track may be controlled by chemical filtration of atmospheric air or by feeding a supply of sufficiently pure gas. For example, the environment within the track may be controlled such that levels of chemical species including, but not limited to, ammonia and amine-group-containing compounds; water, carbon dioxide, and oxygen may be reduced. In addition, the environment within the track may be controlled by a controller computer such as controller computer 162, as illustrated in FIG. 14 coupled to the ISP system. The controller computer may be further configured to control additional environmental conditions within the track including, but not limited to, relative humidity, particulate count, and temperature.

The spectroscopic ellipsometer may be configured as described herein. For example, an appropriate spectroscopic ellipsometer may include a broadband light source, which may include one or a combination of light sources such as a xenon arc lamp, a quartz-halogen lamp, or a deuterium lamp. The ellipsometer may have a relatively high angle of incidence. For example, the angle of incidence may range from approximately 40 degrees to approximately 80 degrees, to the normal to the surface of the specimen. The spectroscopic ellipsometer may include an array detector such as a silicon photodiode array or a CCD array, which may be back thinned.

It may also be advantageous for the spectroscopic ellipsometer to include one or more fiber optic elements. For example, a first fiber optic element may be configured to transmit light from the light source to a first polarizing element. For example, such a fiber may ensure that the light is randomly polarized or depolarized. The spectroscopic ellipsometer may also include a second fiber optic element configured to transmit light to a spectrometer from an analyzer assembly. In this manner, the fiber optic element may be configured to alter, or "scramble," a polarization state of light from the analyzer assembly such that the signal may not need correction for the polarization sensitivity of the spectrometer. In addition, or alternatively, the second fiber optic element may be configured to alter the polarization state of the light such that the spectrometer may be conveniently located at some distance from the specimen. The fiber optic element may, preferably, be made of fused silica or sapphire such that the fiber optic element may be transmissive at ultraviolet wavelengths.

The first polarizer may include a linear polarizing element such as a Rochon prism or a Wollaston prism and, optionally, a retarder (i.e., a compensator). The analyzer assembly may include a linear polarizing element and, optionally, a retarder. At least one of the linear polarizing elements may rotate continuously when making measurements. For calibration, at least two elements will be rotated either continuously or in a series of discrete steps.

The spectroscopic ellipsometer may further include reflective or refractive optics (or combinations thereof) configured to focus the light to a small spot on the specimen and to collect the light from the specimen. Any refractive components may, preferably, be made from fused $SiO_2$ or $CaF_2$ for relatively good ultraviolet transmission. Any reflective components may, preferably, be coated with Al for relatively good broadband transmission. Typically, a thin overcoat of $MgF_2$ or $SiO_2$ may be formed over the Al to reduce, and even eliminate, oxidation of the Al. The reflective components may be spherical or aspherical. Diamond turning may be a convenient and well-known technique for making aspheric mirrors. For vacuum conditions such as conditions suitable for ultraviolet light having wavelengths in a range of less than about 190 nm, gold or platinum may be a suitable coating material. The spectroscopic ellipsometer may be further configured as described herein.

In addition, the processor may be configured to compare one or more output signals from the spectroscopic ellipsometer with one or more predetermined tables that may include expected output signals versus wavelength for different characteristics and, possibly, interpolated data between the expected output signals versus wavelength. Alternatively, the processor may be configured to perform an iteration using one or more starting guesses through (possibly approximate) equations to converge to a good fit for one or more output signals from the spectroscopic ellipsometer. Suitable equations may include, but are not limited to, any non-linear regression algorithm known in the art.

Alternatively, the spectroscopic ellipsometer may be configured to image approximately all, or an area of, a specimen onto a one-dimensional or two dimensional detector. In this manner, multiple locations on the specimen may be measured substantially simultaneously. In addition, the spectroscopic ellipsometer may be configured to measure multiple wavelengths by sequentially changing wavelength with filters, a monochromator, or by dispersing the light. For example, the light may be dispersed with a prism or grating in one dimension on a two-dimensional detector while one dimension of the specimen is being imaged in the other dimension.

In an embodiment, a system may be configured to determine at least two properties of a specimen including a thickness of the specimen and/or a layer formed on the specimen, a feature formed on the specimen and an additional property such as a lattice constant, residual stress, average grain size, crystallinity, crystal defects, an index of refraction, a velocity of sound, a density, and a critical dimension, which may include a profile, of a layer or a feature formed upon the specimen. The specimen may include a single layer or multiple layers formed upon the specimen. In addition, the single layer or multiple layers formed on the specimen may include, but are not limited to, any combination of transparent, semi-transparent, and opaque metal films. The specimen may also be a blanket wafer or a patterned wafer.

The system may be configured as described herein. For example, the system may include a processor coupled to a measurement device and configured to determine at least a thickness of the specimen and/or a layer on the specimen and an additional property of a layer on the specimen and/or a feature formed on the specimen from one or more output signals generated by the measurement device. In addition, the processor may be configured to determine other properties of the specimen from the one or more output signals. In an embodiment, the measurement device may include, but is not limited to, a grazing X-ray reflectometer, an X-ray reflectometer such as a grating X-ray reflectometer, and/or an X-ray diffractometer. The measurement device may also include a pattern recognition system that may be used in conjunction with the above devices.

An X-ray reflectometer may be configured to perform an X-ray reflectance technique as described herein.

An X-ray diffractometer may be configured to perform X-ray diffraction. X-ray diffraction involves coherent scattering of x-rays by polycrystalline materials. The x-rays are scattered by each set of lattice planes at a characteristic angle, and the scattered intensity is a function of the atoms which occupy those planes. X-ray diffraction peaks may be produced by constructive interference of a monochromatic beam scattered from each set of lattice planes at specific angles. The peak intensities are determined by atomic arrangement within the lattice planes. In this manner, the scattering from all the different sets of planes results in a pattern, which is unique to a given compound. In addition, distortions in the lattice planes due to stress, solid solution, or other effects may be measured. The scattered x-rays may be detected and one or more output signals responsive to the intensity of the scattered x-rays may be generated. The one or more output signals may be used to obtain one or more properties of a layer on a specimen or a specimen. An advantage of X-ray diffraction is that it is a substantially non-destructive technique. Commercially available X-ray diffractometers are available from, for example, Siemens, Madison, Wis. and Rigaku USA, Inc., The Woodlands, Tex.

In an embodiment, an X-ray diffractometer may be coupled to a process tool configured to grow an epitaxial layer of silicon on a specimen such as a wafer. Epitaxy is a process in which a relatively thin crystalline layer is grown on a crystalline substrate. An epitaxial layer of silicon, which may be commonly referred to as "epitaxy" or "epi," may be a layer of extremely pure silicon or silicon-germanium formed on a silicon containing substrate. The layer may be grown to form a substantially uniform crystalline structure on the wafer. In epitaxial growth, the substrate acts as a seed crystal, and the epitaxial film duplicates the structure (orientation) of the crystal. Epitaxial techniques include, but are not limited to, vapor-phase epitaxy, liquid-phase epitaxy, solid-phase epitaxy, and molecular beam epitaxy. A thickness of the epitaxial layer during an epitaxy process (i.e., a growth rate) may vary over time depending upon, for example, chemical source, deposition temperature, and mole fraction of the reactants. Examples of appropriate chemical sources include, but are not limited to, silicon tetrachloride ("$SiCl_4$"), trichlorosilane ("$SiHCl_3$"), dichlorosilane ("$SiH_2Cl_2$"), and silane ("$SiH_4$"). Examples of appropriate temperatures for an epitaxy process may range from about 950° C. to about 1250° C. An appropriate temperature may be higher or lower, however, depending upon, for example, the chemical source used for the epitaxy process. Such process tools are commercially available from Applied Materials, Inc., Santa Clara, Calif. The X-ray diffractometer may be configured as described above.

The X-ray diffractometer may be coupled to the process tool according to any of the embodiments described herein. For example, an X-ray diffractometer may be coupled to a process chamber of the epitaxial process tool or may be disposed proximate to the process chamber in a measurement chamber. In addition, a processor may be coupled to the X-ray diffractometer and the process tool. The processor may be further configured as described above.

In this manner, the measurement device may be configured to function as a single measurement device or as multiple measurement devices. Because multiple measurement devices may be integrated into a single measurement device of the system, elements of a first measurement device, for example, may also be elements of a second measurement device. In addition, it may be advantageous for additional elements such as handling robots, stages, processors, and power supplies of a first measurement device to be used by a second measurement device. The measurement device may also include an autofocus mechanism that may be configured to bring a specimen substantially into focus (i.e., to approximately a correct height) for a first measurement device, and then for a second measurement device. The system, the measurement device, the autofocus mechanism, and the processor may be further configured as described herein.

In addition, such a system may be coupled to a process tool including, but not limited to, a chemical-mechanical polishing tool, a deposition tool such as a physical vapor deposition tool, a plating tool, and an etch tool. The system may be coupled to the process tool as described herein. Furthermore, the system may be coupled to or disposed proximate to a process tool such that the system may determine at least two properties of a specimen, a layer of a specimen, and/or a feature formed on the specimen prior to, during, or subsequent to a process.

In an embodiment, a system may be configured to determine at least two properties of a specimen including an electrical property such as a capacitance, a dielectric constant, and a resistivity of the specimen and/or a layer on the specimen and a thin film characteristic of the specimen and/or a layer on the specimen. The thin film characteristic may include any of the characteristics as described herein. The specimen may include a wafer or a dielectric material disposed upon a wafer or another substrate. Examples of appropriate dielectric materials include, but are not limited to, gate dielectric materials and low-k dielectric materials. Typically, low-k dielectric materials include materials having a dielectric constant less than about 3.8, and high-k materials include materials having a dielectric constant greater than about 4.5.

The system may be configured as described herein. For example, the system may include a processor coupled to a first measurement device and a second measurement device and configured to determine at least a thin film characteristic of the specimen and/or a layer on the specimen from one or more output signals of the first measurement device and an electrical property of the specimen and/or a layer on the specimen from an output signal of the second measurement device. In addition, the processor may be configured to determine other properties of the specimen from the one or more- output signals. For example, the processor may also be used to determine additional properties of the specimen including, but not limited to, a characteristic of metal contamination on the specimen. In an embodiment, the first measurement device may include, but is not limited to, a reflectometer, a spectroscopic reflectometer, an ellipsometer, a spectroscopic ellipsometer, a beam profile ellipsometer, a photoacoustic device, an eddy current device, an X-ray reflectometer, a grazing X-ray reflectometer, and an X-ray diffractometer and a system configured to measure an electrical property of the specimen. The system, the first measurement device, and the processor may be further configured as described herein.

Such a system may be coupled to a process tool such as a deposition tool including, but not limited to, a chemical vapor deposition tool, an atomic layer deposition tool and a physical vapor deposition tool, a plating tool, a chemical-mechanical polishing tool, a thermal tool such as a furnace, a cleaning tool, and an ion implanter, as described herein. Such a system may also be coupled to an etch tool. In this manner, at least the two properties may be used to determine an amount of plasma damage caused to the specimen and/or a layer on the specimen during an etch process performed by the etch tool. For example, plasma damage may include, but is not limited to, roughness and pitting of a specimen or a layer on a specimen generated during an etch process.

The second measurement device may be configured to measure an electrical property of the specimen as illustrated, for example, in U.S. Patent Application entitled "A Method Of Detecting Metal Contamination On A Semiconductor Wafer," by Xu et al., filed May 10, 2001, which is incorporated by reference as if fully set forth herein. For example, a specimen may be placed into a wafer cassette, which may be loaded into the system. The system may include a robotic handler, which may be configured as described herein. The system may also include a pre-aligner that may be configured to alter a position of a specimen. For example, a pre-aligner may be configured to alter a position of the specimens such the orientation of each specimen may be substantially the same during processing. Alternatively, the pre-aligner may be configured to detect an alignment mark formed on a specimen and to alter a position of the specimen such that a position of the alignment mark may be substantially the same as a predetermined position.

In an embodiment, the second measurement device may also include an oven that may be used to anneal a specimen. The oven may be configured to heat the specimen to a temperature, for example, of less than approximately 1100° C. The oven may also be configured to drive the metal contamination into a dielectric material of the specimen or into a semiconductor substrate of the specimen. The second measurement device may also include a cooling device configured to reduce a temperature of the specimen subsequent to the annealing process. The cooling device may include any such device known in the art such as a chill plate.

In an embodiment, the second measurement device may include a device configured to deposit a charge on an upper surface of the specimen. The device may include, for example, a non-contact corona charging device such as a needle corona source or a wire corona source. Additional examples of non-contact corona charging devices are illustrated in U.S. Pat. No. 4,599,558 to Castellano et al., U.S. Pat. No. 5,594,247 to Verkuil et al., U.S. Pat. No. 5,644,223 to Verkuil, and U.S. Pat. No. 6,191,605 to Miller et al., which are incorporated by reference as if fully set forth herein. The deposited charge may be positive or negative depending on the parameters of the device used to deposit the charge. The device may be used to deposit a charge on predetermined regions of the specimen or on randomly determined regions of the specimen. In addition, the device may also be used to deposit a charge on a portion of the specimen or on substantially the entire specimen.

In an embodiment, the second measurement device may also include a sensor configured to measure at least one electrical property of the charged upper surface of the specimen. The sensor may be configured to operate as a non-contact work function sensor or a surface photo-voltage sensor. The non-contact work function sensor may include, e.g., a Kelvin probe sensor or a Monroe sensor. Additional examples of work function sensors, which may be incorporated into the system, are illustrated in U.S. Pat. No. 4,812,756 to Curtis et al., U.S. Pat. No. 5,485,091 to Verkuil, U.S. Pat. No. 5,650,731 to Fung, and U.S. Pat. No. 5,767,693 to Verkuil and are incorporated by reference as if fully set forth herein. The sensor may be used to measure electrical properties, which may include, but are not limited to, a tunneling voltage, a surface voltage, and a surface voltage as a function of time. The second measurement device may also include an illumination system that may be configured to direct a pulse of light toward the specimen and that may be used to generate a surface photo-voltage of the specimen. As such, an electrical property that may be measured by the sensor may also include a surface photo-voltage of the specimen. The system may further include a movable chuck configured to alter a position of the specimen under the device, under the illumination system, and under the sensor. As such, the second measurement device may be used to measure an electrical property of the specimen as a function of time and position of the specimen.

In an additional embodiment, the system may also include a processor that may be configured as described herein and may be used to monitor and control operation of the oven to heat the specimen to an anneal temperature. The processor may also be configured to monitor and control the operation of the device to deposit a charge on an upper surface of the specimen. Additionally, the processor may be further configured to monitor and control the operation of the sensor to measure an electrical property of the specimen. The measured electrical property may include a surface voltage of a dielectric material formed on the specimen, which may be measured as a function of time. The second measurement device may be configured to generate one or more output signals responsive to the measured electrical property. The processor may be configured to use one or more output signals from the second measurement device to determine at least one property of the specimen such as a resistivity of the dielectric material. The resistivity of the dielectric material may be determined by using the following equation:

$$\rho_{dielectric} = -V/[(dV/dt) \cdot \in \cdot \in_0],$$

where $\rho_{dielectric}$ is the resistivity of the dielectric material, V is the measured surface voltage of the dielectric material, t is the decay time, $\in$ is the dielectric constant of the dielectric material, and $\in_0$ is the vacuum permittivity. A characteristic of metal contamination in the dielectric material may also be a function of the resistivity of the dielectric material.

Furthermore, the processor may be used to determine a characteristic of the metal contamination in the specimen. The characteristic of the metal contamination in the specimen may be determined as a function of the measured electrical property. In addition, the processor may also be configured to monitor and control an additional device of the operating system including, but not limited to, a robotic wafer handler, a pre-aligner, a wafer chuck and/or an illumination system.

In an embodiment, each of the systems described above may be coupled to a secondary electron spectroscopy device. Such a system may be configured to determine material composition of a specimen by analyzing secondary electron emission from the specimen. An example of such a device is illustrated in PCT Application No. WO 00/70646 to Shachal et al., and is incorporated by reference as if fully set forth herein.

In an additional embodiment, more than one system described herein may be coupled to a semiconductor fabrication process tool. Each of the systems may be configured to determine at least two properties of a specimen during use. Furthermore, each of the systems may be configured to determine at least two substantially similar properties or at least two different properties. In this manner, properties of a plurality of specimens may be determined substantially simultaneously and at multiple points throughout a semiconductor fabrication process.

In a further embodiment, each of the systems described herein may be coupled to a stand alone metrology and/or inspection system. For example, each of the systems described herein may be coupled to a stand alone metrology and/or inspection system such that signals such as analog or digital signals may be sent between the coupled systems. Each of the systems may be configured as a single tool or a cluster tool that may or may not be coupled to a process tool such as a semiconductor fabrication process tool. The stand alone metrology and/or inspection system may be configured such that the stand alone system may be calibrated with a calibration standard. An appropriate calibration standard may include any calibration standard known in the art. The stand alone metrology and/or inspection system may be configured to calibrate the system coupled to the stand alone system.

In addition, the stand alone metrology and/or inspection system may be coupled to a plurality of systems as described herein. In this manner, the stand alone metrology and/or inspection system may be configured to calibrate the plurality of systems coupled to the stand alone system. For example, a plurality of systems may include single tools and/or cluster tools incorporated within the same manufacturing and/or research and development facility. Each of the plurality of systems may be configured to determine at least two characteristics of a specimen. In addition, each of the plurality of systems may be configured to determine at least two characteristics of substantially the same type of specimen such as specimens upon which a substantially similar type of semiconductor device may be forced. For example, each of the plurality of systems may be incorporated into the same type of product line in a manufacturing facility.

In addition, the stand alone metrology and/or inspection system may be configured to calibrate each of the plurality of systems using the same calibration standard. As such, a plurality of metrology and/or inspection systems in a manufacturing and/or research and development facility may be calibrated using the same calibration standard. In addition, the stand alone metrology and/or inspection system may be configured to generate a set of data. The set of data may include output signals from a measurement device of a system and characteristics of a specimen determined by a processor of the system using the output signals. The set of data may also include output signals and determined characteristics corresponding to the output signals that may be generated by using a plurality of systems as described herein. Therefore, the set of data may be used to calibrate and/or monitor the performance of a plurality of systems.

In an additional embodiment, each of the systems, as described herein, may be coupled to a cleaning tool. A cleaning tool may include any tool configured to remove unwanted material from a wafer such as a dry cleaning tool, a wet cleaning tool, a laser cleaning tool, and/or a shock wave cleaning tool. A dry cleaning tool may include a dry etch tool, which may be configured to expose a specimen to a plasma. For example, resist may be stripped from a specimen using an oxygen plasma in a plasma etch tool. An appropriate plasma may vary depending upon, for example, the type of material to be stripped from a specimen. The plasma etch tool may be further configured as described herein. Dry cleaning tools are commercially available from, for example, Applied Materials, Inc., Santa Clara, Calif. A wet cleaning tool may be configured to submerge a specimen in a chemical solution, which may include, but is not limited to, a sulfuric-acid mixture or a hydrofluoric acid mixture. Subsequent to exposure to the chemical solution, the specimen may be rinsed with de-ionized water and dried. Wet cleaning tools are commercially available from, for example, FSI International, Inc., Chaska, Minn. An example of a laser cleaning tool is illustrated in "Chemically Assisted Laser Removal of Photoresist and Particles from Semiconductor Wafers," by Genut et al. of Oramir Semiconductor Equipment Ltd., Israel, presented at the $28^{th}$ Annual Meeting of the Fine Particle Society, Apr. 1–3, 1998, which are incorporated by reference as if fully set forth herein. An example of a shock wave cleaning tool is illustrated in U.S. Pat. No. 5,023,424 to Vaught, which is incorporated by reference as if fully set forth herein.

In a further embodiment, each of the systems, as described herein, may be coupled to a thermal tool such as a tool configured for rapid thermal processing ("RTP") of a wafer. A rapid thermal processing tool may be configured to subject a specimen to a relatively brief, yet highly controlled thermal cycle. For example, the RTP tool may be configured to heat a specimen to over approximately 1000° C. in under approximately 10 seconds. RTP may be used mainly for modifying properties of a specimen or a film formed on a specimen formed by other processes. For example, RTP may be commonly used for annealing, which may activate and control the movement of atoms in a specimen after implanting. Another common use is for silicidation, which may form silicon containing compounds with metals such as tungsten or titanium. A third type of RTP application is oxidation, which may involve growing oxide on a specimen such as a silicon wafer. RTP tools are commercially available from, for example, Applied Materials, Inc., Santa Clara, Calif.

In an embodiment, each of the processors described above including a local processor, a remote controller computer, or a remote controller computer coupled to a local processor may be configured to perform a computer integrated manufacturing technique as illustrated in European Patent Application EP 1 072 967 A2 to Arackaparambil et al., which is incorporated by reference as if fully set forth herein.

In a further embodiment, each of the processors as described herein may be configured to automatically generate a schedule for wafer processing within a multichamber semiconductor wafer processing tool as illustrated in U.S. Pat. No. 6,201,999 to Jevtic, U.S. Pat. No. 6,224,638 to Jevtic, and PCT Application No. WO 98/57358 to Jevtic, which are incorporated by reference as if fully set forth herein. In addition, each of the systems as described herein may include a multiple blade wafer handler. A processor as described herein may be configured to control the multiple blade wafer handler. Each of the processors as described herein may be configured to assign a priority value to process chambers and/or measurement chambers of a cluster tool such as a process tool or a measurement and/or inspection system. One or more measurement chambers may be coupled to a process tool according to any of the embodiments as described herein. Each of the processors as described herein may also be configured to assign a priority to measurement chambers of a cluster tool such as a metrology and/or inspection system.

The processor may be configured to control the multiple blade wafer handler such that the multiple blade wafer handler may be configured to move a specimen from chamber to chamber according to the assigned priorities. The processor may also be configured to determine an amount of time available before a priority move is to be performed. If the determined amount of time is sufficient before a priority move is to be performed, the processor may control the multiple blade wafer handler to perform a non-priority move while waiting. For example, if the determined amount of time is sufficient before a process step is to be performed on a specimen, then the multiple blade wafer handler may move the specimen to a measurement chamber. In this manner, a system as described herein may be configured to determine at least two properties of a specimen while the specimen is waiting between process steps. The processor may also be configured to dynamically vary assigned priorities depending upon, for example, the availability of process and/or measurement chambers. Furthermore, the processor may assign priorities to the process and/or measurement chambers based upon, for example, a time required for a wafer handler to move the wafer in a particular sequence.

In addition, each of the processors as described herein may be configured to use "options," which may correspond to optional components of a process tool, and which may be selected by a user according to the optional components that the user desires to have as part of the process tool as illustrated in U.S. Pat. No. 6,199,157 to Dov et al., which is incorporated by reference as if fully set forth herein.

A process tool as described herein may also include multiple chill process chambers or a multi-slot chill process chamber. Such multiple or multi-slot chill process chambers allows multiple wafers to be cooled while other wafers are subjected to processing steps in other chambers. In addition, each of the processors as described herein may be configured to assign a priority level to each wafer in a processing sequence depending on its processing stage, and this priority level may be used to sequence the movement of wafers between chambers as illustrated in U.S. Pat. No. 6,201,998 to Lin et al., which is incorporated by reference as if fully set forth herein. In this manner, a system as described herein may increase an efficiency at which wafers are transferred among different processing chambers in a wafer processing facility.

In a further embodiment, each of the processors, as described herein, may be configured to determine at least a roughness of a specimen, a layer on a specimen, and/or a feature of a specimen. For example, a processor may be configured to determine a roughness from one or more output signals of a measurement device using mathematical modeling. For example, the one or more output signals may be generated by a measurement device such as a non-imaging scatterometer, a scatterometer, a spectroscopic scatterometer, and a non-imaging Linnik microscope. Appropriate mathematical models may include any mathematical models known in the art such as mathematical models that may be used to determine a critical dimension of a feature. The mathematical models may be configured to process data of multiple wavelengths or data of a single wavelength.

A system, including such a processor, may be coupled to a process tool such as a lithography tool, an atomic layer deposition tool, a cleaning tool, and an etch tool. For example, a develop process step in a lithography process may cause a significant amount of roughness to a patterned resist. In addition, a layer of material formed by atomic layer deposition may have a significant amount of roughness, particularly on sidewalls of features on a specimen. Furthermore, wet cleaning tools may tend to etch a specimen, a layer on a specimen, and/or features on a specimen, which may cause roughness on the specimen, the layer, and/or the features, respectively. The system may also be coupled to any process tool configured to perform a process that may cause roughness on a surface of a specimen. The system may be coupled to the process tool according to any of the embodiments described herein. For example, a measurement device of such a system may be coupled to a process chamber of a process tool such that the system may determine at least a roughness of a specimen, a layer on a specimen, and/or a feature on a specimen prior to and subsequent to a process. For example, the measurement device may be coupled to a process tool such that a robotic wafer handler may move below or above the measurement device. The system may be further configured as described herein.

The following references, to the extent that they provide exemplary procedural or other information or details supplementary to those set forth herein, are specifically incorporated herein by reference: U.S. patent application Ser. No. 09/310,017 filed on May 11, 1999, Ser. No. 09/396,143 filed on Sep. 15, 1999, Ser. No. 09/556,238 filed on Apr. 24, 2000, and Ser. No. 09/695,726 filed on Oct. 23, 2000.

Further modifications and alternative embodiments of various aspects of the invention may be apparent to those skilled in the art in view of this description. For example, the system may also include a stage configured to tilt in a number of angles and directions with respect to a measurement device. Accordingly, this description is to be construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

What is claimed is:

1. A system configured to a characteristic of a specimen during use, comprising:
   an ion implanter configured to direct ions toward the specimen during use;
   a measurement device coupled to the ion implanter, wherein the measurement device is configured:
      to periodically direct an incident beam of light to a region of the specimen to periodically excite the region of the specimen during use;
      to direct a sample beam of light to the periodically excited region of the specimen during use;
      to measure an intensity of the sample beam reflected from the periodically excited region of the specimen during use; and
      to generate one or more output signals responsive to the measured intensity of the reflected sample beam; and a processor coupled to the measurement device and configured to determine a characteristic of the region of the specimen from the one or more output signals during use.

2. The system of claim 1, further comprising a stage coupled to the measurement device, wherein the stage is configured to move laterally during use.

3. The system of claim 1, further comprising a stage coupled to the measurement device, wherein the stage is configured to move rotatably during use.

4. The system of claim 1, further comprising a stage coupled to the measurement device, wherein the stage is configured to move laterally and rotatably during use.

5. The system of claim 1, further comprising an additional measurement device coupled to the ion implanter, wherein the processor is further configured to determine an additional property of the specimen from one or more output signals generated by the additional measurement device.

6. The system of claim 1, wherein the characteristic is selected from the group consisting of a presence of ions in the region, a concentration of ions in the region, a depth of the region, and a distribution profile of the region.

7. The system of claim 1, wherein the processor is further configured to determine at least two characteristics of the implanted region substantially simultaneously during use.

8. The system of claim 1, wherein the measurement device is further configured to periodically direct the incident beam of light to multiple regions of the specimen substantially simultaneously during use, to direct the sample beam of light to the multiple periodically excited regions of the specimen substantially simultaneously during use, and to measure the intensity of the sample beam reflected from the multiple periodically excited regions of the specimen substantially simultaneously during use such that the characteristic of multiple regions of the specimen can be determined substantially simultaneously.

9. The system of claim 1, wherein the measurement device is further coupled to a process chamber of the ion implanter.

10. The system of claim 1, wherein the measurement device is arranged laterally proximate to a process chamber of the ion implanter.

11. The system of claim 1, wherein the measurement device is arranged laterally proximate to a process chamber of the ion implanter, and wherein the ion implanter comprises a wafer handler configured to move the specimen to a stage coupled to the measurement device during use.

12. The system of claim 1, wherein the measurement device is arranged laterally proximate to a process chamber of the ion implanter, and wherein a stage coupled to the measurement device is configured to move the specimen from the measurement device to the ion implanter during use.

13. The system of claim 1, wherein the measurement device is arranged laterally proximate to a process chamber of the ion implanter, and wherein a stage coupled to the measurement device is configured to move the specimen to the process chamber of the ion implanter during use.

14. The system of claim 1, wherein the system is further configured to determine the characteristic of the specimen while the specimen is waiting between process steps.

15. The system of claim 1, wherein the ion implanter comprises a support device configured to support the specimen during an ion implantation process step, and wherein an upper surface of the support device is substantially parallel to an upper surface of a stage coupled to the measurement device.

16. The system of claim 1, wherein the ion implanter comprises a support device configured to support the specimen during an ion implantation process step, and wherein an upper surface of the support device is substantially perpendicular to an upper surface of a stage coupled to the measurement device.

17. The system of claim 1, wherein the measurement device is disposed within a measurement chamber, and wherein the measurement chamber is arranged laterally proximate to a process chamber of the etch tool.

18. The system of claim 1, wherein the measurement device is disposed within a measurement chamber, and wherein the measurement chamber is arranged vertically proximate to a process chamber of the etch tool.

19. The system of claim 1, wherein the measurement device is further coupled to a stage disposed within a process chamber of the ion implanter, and wherein the stage is configured to support the specimen during an ion implantation process step.

20. The system of claim 1, wherein the measurement device is further coupled to a stage disposed within a process chamber of the ion implanter, and wherein the processor is further configured to determine the characteristic of the region during an ion implantation process step.

21. The system of claim 1, wherein the measurement device is further coupled to a stage disposed within a process chamber of the ion implanter, and wherein the processor is further configured to obtain a signature characterizing the implantation of ions during use, and wherein the signature comprises at least one singularity representative of an end of the implantation of ions.

22. The system of claim 1, wherein the measurement device is further coupled to a stage disposed within a process chamber of the ion implanter, wherein the processor is coupled to the ion implanter, and wherein the processor is further configured to alter a parameter of one or more instruments coupled to the ion implanter in response to the determined characteristic using an in situ control technique during use.

23. The system of claim 1, wherein the ion implanter comprises a first process chamber and a second process chamber, and wherein a stage coupled to the measurement device is configured to move the specimen from the first process chamber to the second process chamber during use.

24. The system of claim 1, wherein the ion implanter comprises a first process chamber and a second process chamber, wherein a stage coupled to the measurement device is configured to move the specimen from the first process chamber to the second process chamber during use, and wherein the processor is further configured to determine the property of the specimen as the stage is moving the specimen from the first process chamber to the second process chamber.

25. The system of claim 1, wherein the processor is further configured to compare the determined characteristic of the region and characteristics of a plurality of regions during use.

26. The system of claim 1, wherein the processor is further configured to compare the determined characteristic of the region to a predetermined range for the characteristic during use.

27. The system of claim 26, wherein the processor is further configured to generate an output signal if the determined characteristic of the region is outside of the predetermined range for the characteristic during use.

28. The system of claim 1, wherein the processor is further configured to alter a sampling frequency of the measurement device in response to the determined characteristic of the region during use.

29. The system of claim 1, wherein the processor is further configured to alter a parameter of one or more instruments coupled to the measurement device in response to the determined characteristic using a feedback control technique during use.

30. The system of claim 1, wherein the processor is further configured to alter a parameter of one or more measurements coupled to the measurement device in response to the determined characteristic using a feedforward control technique during use.

31. The system of claim 1, wherein the processor is further configured to generate a database during use, wherein the database comprises the determined characteristic of the region.

32. The system of claim 1, wherein the processor is further configured to generate a database during use, and wherein the processor is further configured to calibrate the measurement device using the database during use.

33. The system of claim 1, wherein the processor is further configured to generate a database during use, and wherein the processor is further configured to monitor output signals generated by measurement device using the database during use.

34. The system of claim 1, wherein the processor is further configured to generate a database during use, wherein the database comprises the determined characteristic of the region and characteristics of a plurality of regions, and wherein the characteristics of the plurality of regions are determined using the measurement device.

35. The system of claim 1, wherein the processor is further configured to generate a database during use, wherein the database comprises the determined characteristic of the region and characteristics of a plurality of regions, and wherein the characteristics of the plurality of regions are determined using a plurality of measurement devices.

36. The system of claim 35, wherein the processor is further coupled to the plurality of measurement devices, and wherein the processor is further configured to calibrate the plurality of measurement devices using the database during use.

37. The system of claim 35, wherein the processor is further coupled to the plurality of measurement devices, and wherein the processor is further configured to monitor output signals generated by the plurality of measurement devices using the database during use.

38. The system of claim 1, further comprising a stand alone system coupled to the system, wherein the stand alone system is configured to be calibrated with a calibration standard during use, and wherein the stand alone system is further configured to calibrate the system during use.

39. The system of claim 1, further comprising a stand alone system coupled the system and at least one additional system, wherein the stand alone system is configured to be calibrated with a calibration standard during use, and wherein the stand alone system is further configured to calibrate the system and at least the one additional system during use.

40. The system of claim 1, wherein the system is further configured to determine at least the two properties of the specimen at more than one position on the specimen, wherein the specimen comprises a wafer, and wherein the processor is configured to alter at least one parameter of one or more instruments coupled to a process tool in response to at least one of the determined properties of the specimen at the more than one position on the specimen to reduce within wafer variation of at least one of the determined properties.

41. The system of claim 1, wherein the processor is further coupled to the ion implanter.

42. The system of claim 1, wherein the processor is further coupled to the ion implanter, and wherein the processor is further configured to alter a parameter of one or more instruments coupled to the ion implanter in response to the determined characteristic using a feedback control technique during use.

43. The system of claim 1, wherein the processor is further coupled to the ion implanter, and wherein the processor is further configured to alter a parameter of one or more instruments coupled to the ion implanter in response to the determined characteristic using a feedforward control technique during use.

44. The system of claim 1, wherein the processor is further coupled to the ion implanter, and wherein the processor is further configured to monitor a parameter of one or more instruments coupled to the ion implanter during use.

45. The system of claim 1, wherein the processor is further coupled to the ion implanter, wherein the processor is further configured to monitor a parameter of one or more instruments coupled to the ion implanter during use, and wherein the processor is further configured to determine a relationship between the determined characteristic and at least one of the monitored parameters during use.

46. The system of claim 1, wherein the processor is further coupled to the ion implanter, wherein the processor is further configured to monitor a parameter of one or more instruments coupled to the ion implanter during use, wherein the processor is further configured to determine a relationship between the determined characteristic and at least one of the monitored parameters during use, and wherein the processor is further configured to alter a parameter of at least one of the instruments in response to the relationship during use.

47. The system of claim 1, wherein the processor is further coupled to a plurality of measurement devices, and wherein at least one of the plurality of measurement devices is coupled to an ion implanter.

48. The system of claim 1, wherein the processor is further coupled to a plurality of ion implanters, and wherein the processor is further configured to alter a parameter of one or more instruments coupled to the plurality of ion implanters during use.

49. The system of claim 1, wherein the processor comprises a local processor coupled to the measurement device and a remote controller computer coupled to the local processor, wherein the local processor is configured to at least partially process the one or more output signals during use, and wherein the remote controller computer is configured to further process the at least partially processed one or more output signals during use.

50. The system of claim 49, wherein the local processor is further configured to determine the characteristic of the region during use.

51. The system of claim 49, wherein the remote controller computer is further configured to determine the characteristic of the region during use.

52. A system configured to determine a characteristic of a specimen during use, comprising:
 an ion implanter configured to direct ions toward the specimen during use;
 a measurement device coupled to the ion implanter, wherein the measurement device is configured:
  to periodically direct an incident beam of light to a region of the specimen to periodically excite the region of the specimen during use;
  to direct a sample beam of light to the periodically excited region of the specimen during use;
  to measure an intensity of the sample beam reflected from the periodically excited region of the specimen during use; and
  to generate one or more output signals responsive to the measured intensity of the reflected sample beam during use;

a local processor coupled to the measurement device and configured to at least partially process the one or more output signals during use; and a remote controller computer coupled to the local processor, wherein the remote controller computer is configured to receive the at least partially processed one or more output signals and to further process the at least partially processed one or more output signals to determine a characteristic of the region of the specimen.

* * * * *

UNITED STATES PATENT AND TRADEMARK OFFICE
CERTIFICATE OF CORRECTION

PATENT NO. : 6,812,045 B1
DATED : November 2, 2004
INVENTOR(S) : Nikoonahad et al.

It is certified that error appears in the above-identified patent and that said Letters Patent is hereby corrected as shown below:

Column 157,
Line 9, please delete "measurements" and substitute therefor -- instruments --.
Line 50, after "alone system coupled" please insert -- to --.

Signed and Sealed this

Tenth Day of May, 2005

JON W. DUDAS
*Director of the United States Patent and Trademark Office*